(12) United States Patent
Macdonald et al.

(10) Patent No.: US 9,932,398 B2
(45) Date of Patent: Apr. 3, 2018

(54) RESTRICTED IMMUNOGLOBULIN HEAVY CHAIN MICE

(71) Applicant: Regeneron Pharmaceuticals, Inc., Tarrytown, NY (US)

(72) Inventors: Lynn Macdonald, White Plains, NY (US); John McWhirter, Tarrytown, NY (US); Cagan Gurer, Valhalla, NY (US); Karolina A. Meagher, Tarrytown, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 562 days.

(21) Appl. No.: 13/944,286

(22) Filed: Jul. 17, 2013

(65) Prior Publication Data

US 2013/0323791 A1 Dec. 5, 2013

Related U.S. Application Data

(62) Division of application No. 13/653,456, filed on Oct. 17, 2012.

(60) Provisional application No. 61/658,459, filed on Jun. 12, 2012, provisional application No. 61/597,969, filed on Feb. 13, 2012, provisional application No. 61/547,974, filed on Oct. 17, 2011.

(51) Int. Cl.
| | |
|---|---|
| *A01K 67/027* | (2006.01) |
| *C12N 5/10* | (2006.01) |
| *C12N 5/20* | (2006.01) |
| *C07K 16/28* | (2006.01) |
| *C12N 15/85* | (2006.01) |
| *C07K 16/00* | (2006.01) |

(52) U.S. Cl.
CPC .......... *C07K 16/28* (2013.01); *A01K 67/0278* (2013.01); *C07K 16/00* (2013.01); *C12N 15/8509* (2013.01); *A01K 2217/072* (2013.01); *A01K 2217/15* (2013.01); *A01K 2227/105* (2013.01); *A01K 2267/01* (2013.01); *C07K 2317/21* (2013.01); *C07K 2317/56* (2013.01); *C07K 2317/565* (2013.01); *C12N 2800/204* (2013.01)

(58) Field of Classification Search
CPC .......... A01K 67/0278; A01K 2227/105; A01K 2267/01; C07K 2317/24; C12N 15/8509
See application file for complete search history.

(56) References Cited

U.S. PATENT DOCUMENTS

| | | | |
|---|---|---|---|
| 5,545,807 A | 8/1996 | Surani et al. | |
| 5,633,425 A | 5/1997 | Lonberg et al. | |
| 5,770,429 A | 6/1998 | Lonberg et al. | |
| 5,939,598 A | 8/1999 | Kucherlapati et al. | |
| 6,075,181 A | 6/2000 | Kucherlapati et al. | |
| 6,150,584 A | 11/2000 | Kucherlapati et al. | |
| 6,162,963 A | 12/2000 | Kucherlapati et al. | |
| 6,586,251 B2 | 7/2003 | Economides et al. | |
| 6,596,541 B2 | 7/2003 | Murphy et al. | |
| 6,657,103 B1 | 12/2003 | Kucherlapati et al. | |
| 6,673,986 B1 | 1/2004 | Kucherlapati et al. | |
| 7,105,348 B2 | 9/2006 | Murphy et al. | |
| 7,183,076 B2 | 2/2007 | Arathoon et al. | |
| 7,501,552 B2 | 3/2009 | Lonberg et al. | |
| 7,582,298 B2 | 9/2009 | Stevens et al. | |
| 7,585,668 B2 | 9/2009 | Buelow et al. | |
| 7,910,798 B2 | 3/2011 | Tanamachi et al. | |
| 8,158,419 B2 | 4/2012 | Lonberg et al. | |
| 8,502,018 B2 | 8/2013 | Murphy et al. | |
| 8,642,835 B2 | 2/2014 | Macdonald et al. | |
| 8,697,940 B2 | 4/2014 | Macdonald et al. | |
| 8,754,287 B2 | 6/2014 | Macdonald et al. | |
| 2002/0106628 A1 | 8/2002 | Economides et al. | |
| 2002/0106629 A1 | 8/2002 | Murphy et al. | |
| 2003/0108925 A1 | 6/2003 | Dix et al. | |

(Continued)

FOREIGN PATENT DOCUMENTS

| | | |
|---|---|---|
| CN | 1203922 A | 1/1999 |
| EP | 2003960 B1 | 6/2015 |

(Continued)

OTHER PUBLICATIONS

Tiller, 2013, mAbs, 5:445-470.*
Taki et al, (1993) Science, vol. 262(5137), 1268-1271.*
Widhopf, et al., (2004) "Chronic lymphocytic leukemia B cells of more than 1% of patients express virtually identical immunoglobulins," Blood, 104:2499-2504.
Third Party Observations for European Patent Application No. 12783456.2 filed on Mar. 12, 2014.
Bendig, M. M., "Humanization of Rodent Monoclonal Antibodies by CDR Grafting," *Methods: A Companion to Methods in Enzymology*, 1995, vol. 8, pp. 83-93.
Briney, B. S., et al., "Human Peripheral Blood Antibodies with Long HCDR3s Are Established Primarily at Original Recombination Using a Limited Subset of Germline Genes," *PLoS ONE*, 2012, vol. 7, Issue 5, pp. 1-13.
Chothia, C., et al., "Structural Repertoire of the Human $V_H$ Segments," *J. Mol. Biol.*, 1992, vol. 227, pp. 799-817.

(Continued)

*Primary Examiner* — Valarie E Bertoglio
(74) *Attorney, Agent, or Firm* — Rita S. Wu; Ilona Gont; Elysa Goldberg

(57) ABSTRACT

Mice having a restricted immunoglobulin heavy chain locus are provided, wherein the locus is characterized by a single polymorphic human $V_H$ gene segment, a plurality of human $D_H$ gene segments and a plurality of $J_H$ gene segments. Methods for making antibody sequences that bind an antigen (e.g., a viral antigen) are provided, comprising immunizing a mouse with an antigen of interest, wherein the mouse comprises a single human $V_H$ gene segment, a plurality of human $D_H$ gene segments and a plurality of $J_H$ gene segments, at the endogenous immunoglobulin heavy chain locus.

17 Claims, 24 Drawing Sheets

(56) References Cited

U.S. PATENT DOCUMENTS

| | | |
|---|---|---|
| 2003/0109021 A1 | 6/2003 | Wu et al. |
| 2004/0018626 A1 | 1/2004 | Murphy et al. |
| 2006/0015957 A1 | 1/2006 | Lonberg et al. |
| 2006/0015958 A1 | 1/2006 | Kuroiwa et al. |
| 2006/0199204 A1 | 9/2006 | Dix et al. |
| 2008/0267982 A1 | 10/2008 | Kiselev et al. |
| 2009/0258392 A1 | 10/2009 | Gallo et al. |
| 2010/0146647 A1 | 6/2010 | Logtenberg et al. |
| 2011/0111406 A1 | 5/2011 | Igawa et al. |
| 2011/0195454 A1 | 8/2011 | McWhiter et al. |
| 2011/0236378 A1 | 9/2011 | Green et al. |
| 2011/0314563 A1 | 12/2011 | Craig et al. |
| 2012/0021409 A1 | 1/2012 | McWhirter et al. |
| 2012/0047585 A1 | 2/2012 | Rohrer et al. |
| 2012/0096572 A1 | 4/2012 | Macdonald et al. |
| 2012/0167237 A1 | 6/2012 | Bradley et al. |
| 2012/0204278 A1 | 8/2012 | Bradley et al. |
| 2012/0272344 A1 | 10/2012 | Tanamachi et al. |
| 2013/0096287 A1 | 4/2013 | Macdonald et al. |
| 2013/0198879 A1 | 8/2013 | McWhirter et al. |
| 2013/0243759 A1 | 9/2013 | Friedrich et al. |
| 2013/0243773 A1 | 9/2013 | Van Berkel et al. |
| 2013/0263292 A1 | 10/2013 | Liang et al. |
| 2013/0323235 A1 | 12/2013 | Craig et al. |
| 2013/0333057 A1 | 12/2013 | Macdonald et al. |
| 2014/0245468 A1 | 8/2014 | McWhirter et al. |
| 2015/0020224 A1 | 1/2015 | McWhirter et al. |
| 2015/0201589 A1 | 7/2015 | Macdonald et al. |
| 2015/0210776 A1 | 7/2015 | Macdonald et al. |
| 2015/0250152 A1 | 9/2015 | Jakobovits et al. |
| 2016/0100561 A1 | 4/2016 | McWhirter et al. |

FOREIGN PATENT DOCUMENTS

| | | |
|---|---|---|
| KR | 1020050042792 A | 10/2005 |
| WO | WO-1990/004036 A1 | 4/1990 |
| WO | 1991/000906 A1 | 1/1991 |
| WO | 1994/025585 A1 | 11/1994 |
| WO | 1998/024893 A2 | 6/1998 |
| WO | 2000/073323 A2 | 12/2000 |
| WO | 2002/012437 A2 | 2/2002 |
| WO | 2002/046237 A2 | 6/2002 |
| WO | 2002/066630 A1 | 8/2002 |
| WO | 2002/085944 A2 | 10/2002 |
| WO | 2004/049794 A2 | 6/2004 |
| WO | 2004/106375 A1 | 12/2004 |
| WO | 2005/019463 A1 | 3/2005 |
| WO | 2005/028510 A2 | 3/2005 |
| WO | 2005/038001 A2 | 4/2005 |
| WO | 2006/117699 A2 | 11/2006 |
| WO | 2007/096779 A2 | 8/2007 |
| WO | 2007/117410 A2 | 10/2007 |
| WO | 2008/151081 A1 | 12/2008 |
| WO | 2009/013620 A2 | 1/2009 |
| WO | 2009/076464 A2 | 6/2009 |
| WO | WO-2009/097006 A2 | 8/2009 |
| WO | 2009/143472 A2 | 11/2009 |
| WO | WO-2010/039900 A2 | 4/2010 |
| WO | WO-2011/004192 A1 | 1/2011 |
| WO | 2011/072204 A1 | 6/2011 |
| WO | WO-2011/158009 A1 | 12/2011 |
| WO | WO-2012/063048 A1 | 5/2012 |
| WO | WO-2012/141798 A1 | 10/2012 |
| WO | WO-2013/022782 A1 | 2/2013 |
| WO | WO-2013/041844 A2 | 3/2013 |
| WO | WO-2013/041845 A2 | 3/2013 |
| WO | WO-2013/041846 A2 | 3/2013 |
| WO | 2013/059230 A1 | 4/2013 |
| WO | WO-2013/045916 A1 | 4/2013 |
| WO | 2013/061098 A2 | 5/2013 |
| WO | WO-2013/061078 A1 | 5/2013 |
| WO | 2013/079953 A1 | 6/2013 |
| WO | 2013/144566 A2 | 10/2013 |
| WO | 2013/144567 A1 | 10/2013 |
| WO | 2013/171505 A2 | 11/2013 |
| WO | 2013/187953 A1 | 12/2013 |
| WO | 2014/130690 A1 | 8/2014 |

OTHER PUBLICATIONS

Lonberg, N., "Human antibodies from transgenic animals," *Nature Biotechnology*, 2005, vol. 23, No. 9, pp. 1117-1125.

Matsuda, F., et al., "The Complete Nucleotide Sequence of the Human Immunoglobulin Heavy Chain Variable Region Locus," *J. Exp. Med.*, 1998, vol. 188, No. 11, pp. 2151-2162.

Paul, W. E., (1993), *Fundamental Immunology, Third Edition*, New York, NY, Raven Press, pp. 292-295, under the heading "Fv Structure and Diversity in Three Dimensions."

Romo-González, T. and Vargas-Madrazo, E., "Structural analysis of substitution patterns in alleles of human immunoglobulin VH genes," *Molecular Immunology*, 2005, vol. 42, pp. 1085-1097.

Tobin, G., et al., "Subsets with restricted immunoglobulin gene rearrangement features indicate a role for antigen selection in the development of chronic lymphocytic leukemia," *Blood*, 2004, vol. 104, No. 9, pp. 2879-2885.

Adderson et al., "Restricted Ig H Chain V Gene Usage in the Human Antibody Response to Haemophilus influenzae Type b Capsular Polysaccharide," The Journal of Immunology, 147: 1667-1674, 1991.

Adderson et al., "Restricted Immunoglobulin VH Usage and VDJ Combinations in the Human Response to Haemophilus influenzae Type b Capsular Polysaccharide," J. Clin. Invest., 91: 2734-2743, 1993.

Bando et al., "Characterization of VH gene expressed in PBL from children with atopic diseases: detection of homologous VH1-69 derived transcripts from three unrelated patients," Immunology Letters, 94: 99-106, 2004.

Baseggio et al., "CD5 expression identifies a subset of splenic marginal zone lymphomas with higher lymphocytosis: a clinico-pathological, cytogenetic and molecular study of 24 cases," Haematologica, 95(4): 604-612, 2010.

Berberian et al., "A VH Clonal Deficit in Human Immunodeficiency Virus-Positive Individuals Reflects a B-Cell Maturational Arrest," Blood, 78(1): 175-179, 1991.

Brezinschek et al., "Analysis of the Heavy Chain Repertoire of Human Peripheral B Cells Using Single-Cell Polymerase Chain Reaction," Journal of Immunology, 155: 190-202, 1995.

Bruggemann et al., "A repertoire of monoclonal antibodies with human heavy chains from transgenic mice," Proc. Natl. Acad. Sci. USA, 86: 6709-6713, 1989.

Bruggemann, Marianne, "Human Antibody Expression in Transgenic Mice," Archivum Immunologiae et Therapiae Experimentalis, 49: 203-208, 2001.

Carbonari et al., "Hepatitis C Virus Drives the Unconstrained Monoclonal Expansion of VH1-69-Expressing Memory B Cells in Type II Cryoglobulinemia: A Model of Infection-Driven Lymphomagenesis," The Journal of Immunology, 174: 6532-6539, 2005.

Chan et al., "VH1-69 gene is preferentially used by hepatitis C virus-associated B cell lymphomas and by normal B cells responding to the E2 viral antigen," Blood, 97(4): 1023-1026, 2001.

Charles et al., "A flow cytometry-based strategy to identify and express IgM from VH1-69+ clonal peripheral B cells," Journal of Immunological Methods, 363: 210-220, 2011.

Communication Relating to the Results of the Partial International Search for PCT/US2013/029624, 9 pages, (May 17, 2013).

Davidkova et al., "Selective Usage of VH Genes in Adult Human B Lymphocyte Repertoires," Scand. J. Immunol., 45: 62-73, 1997.

De Wildt, R. et al., Analysis of heavy and light chain pairings indicates that receptor editing shapes the human antibody repertoire, J. Mol. Biol., 285(3):895-901 (1999).

Featherstone K. et al., The mouse immunoglobulin heavy chain V-D intergenic sequence contains insulators that may regulate ordered V(D)J recombination, The Journal of Biological Chemistry, 285(13):9327-38 (2010).

(56) References Cited

OTHER PUBLICATIONS

Han C. et al., Comprehensive analysis of reproductive ADAMs: relationship of ADAM4 and ADAM6; with an ADAM complex required for fertilization in mice, Biology of Reprodroduction, 80(5):1001-8 (2009).

Huang et al., "A Majority of Ig H Chain cDNA of Normal Human Adult Blood Lymphocytes Resembles cDNA for Fegal Ig and Natural Autoantibodies," The Journal of Immunology, 151(10): 5290-5300, 1993.

International Search Report for PCT/US2012/060487 (7 pages), dated Feb. 1, 2013.

International Search Report for PCT/US2013/029624 (9 pages), dated Aug. 2, 2013.

Johnson et al., "Ig VH1 Genes Expressed in B Cell Chronic Lymphocytic Leukemia Exhibit Distinctive Molecular Features," The Journal of Immunology, 158: 235-246, 1997.

Kantor et al., "An Unbiased Analysis of VH-D-JH Sequences from B-1a, B-1b, and Conventional B Cells," The Journal of Immunology, 158: 1175-1186, 1997.

Kunert et al., "Characterization of Molecular Features, Antigen-Binding, and in Vitro Properties of IgG and IgM Variants of 4E10, an Anti-HIV Type 1 Neutralizing Monoclonal Antibody," Aids Research and Human Retroviruses, 20(7): 755-762, 2004.

Lefranc et al., "Nomenclature of the Human Immunoglobulin Genes," Current Protocols in Immunology, A.1P.1-A.1P.37, 2000.

Mageed, R.A. et al., Rearrangement of the human heavy chain variable region gene V3-23 in transgenic mice generates antibodies reactive with a range of antigens on the basis of VHCDR3 and residues intrinsic to the heavy chain variable region, Clinical and Experimental Immunology, 123(1):1-8 (2001).

Mahmoud et al., "Limiting CDR-H3 Diversity Abrogates the Antibody Response to the Bacterial Polysaccharide x 1→3 Dextran," The Journal of Immunology, 187: 879-886, 2011.

Mahmoudi et al., "V region gene analysis of human IgM hybridoma monoclonal anti-Sm antibodies," Lupus, 6: 578-589, 1997.

Marasca et al., "Immunoglobulin Gene Mutations and Frequent Use of VH1-69 and VH4-34 Segments in Hepatitis C Virus-Positive and Hepatitis C Virus-Negative Nodal Marginal Zone B-Cell Lymphoma," American Journal of Pathology, 159(1): 253-261, 2001.

Miklos et al., "Salivary gland mucosa-associated lymphoid tissue lymphoma immunoglobulin VH genes show frequent use of V1-69 with distinctive CDR3 features," Blood, 95: 3878-3884, 2000.

Moran N., Mouse platforms jostle for slice of humanized antibody market, Nature Biotechnology, 31(4): 267-268, (2013).

Mortari et al., "Human Cord Blood Antibody Repertoire," The Journal of Immunology, 150(4): 1348-1357, 1993.

Muller et al., "B-Cell Abnormalities in AIDS: Stable and Clonally-Restricted Antibody Response in HIV-1 Infection," Scand. J. Immunol., 38: 327-334, 1993.

Perez et al., "Primary cutaneous B-cell Lymphoma is associated with somatically hypermutated immunoglobulin variable genes and frequent use of VH1-69 and VH4-59 segments," British Journal of Dermatopathology, 162: 611-618, 2010.

Pos et al., "VH1-69 germline encoded antibodies directed towards ADAMTS13 in patients with acquired thrombotic thrombocytopenic purpura," Journal of Thrombosis and Haemostatis, 7: 421-428, 2008.

Rodriguez et al., "High-efficiency deleter mice show that FLPe is an alternative to Cre-loxP," Nature Genetics, 25: 139-140, 2000.

Sasso et al., "A Fetally Expressed Immunoglobulin VH1 Gene Belongs to a Complex Set of Alleles," J. Clin. Invest., 91: 2358-2367, 1993.

Sasso et al., "Expression of the Immunoglobulin VH Gene 51p1 is Proportional to its Germline Gene Copy Number," J. Clin. Invest., 97(9): 2074-2080, 1996.

Sasso et al., "Prevalence and Polymorphism of Human VH3 Genes," The Journal of Immunology, 145(8): 2751-2757, 1990.

Schelonka et al., "A Single DH Gene Segment Creates Its Own Unique CDR-H3 Repertoire and Is Sufficient for B Cell Development and Immune Function," The Journal of Immunology, 175: 6624-6632, 2005.

Sibilia et al., "Structural Analsys of Human Antibodies to Proteinase 3 from Patients with Wegener Granulomatosis," The Journal of Immunology, 159: 712-719, 1997.

Souroujon et al., "Polymorphisms in Human H Chain V Region Genes from the VHIII Gene Family," The Journal of Immunology, 143(2): 706-711, 1989.

Suarez et al., "Rearrangement of only one human IGHV gene is sufficient to generate a wide repertoire of antigen specific antibody responses in transgenic mice," Molecular Immunology, 43(11): 1827-1835, 2006.

Sui et al., "Structural and functional bases for broad-spectrum neutralization of avian and human influenza A viruses," Nature Structural & Molecular Biology, 16(3): 265-273, 2009.

Suzuki et al., "Representation of Rearranged VH Gene Segments in the Human Adult Antibody Repertoire," The Journal of Immunology, 154: 3902-3911, 1995.

Taylor, L.D. et al., A Transgenic Mouse that Expresses a Diversity of Human Sequence Heavy and Light Chain Immunoglobulins, Nucleic Acid Research, 20(23):6287-6295 (1992).

Tuaillon et al., "Human immunoglobulin heavy-chain minilocus recombination in transgenic mice: Gene-segment use in u and y transcripts," Proc. Natl. Acad. Sci. USA, 90: 3720-3724, 1993.

Tuaillon, N., Repertoire analysis in human immunoglobulin heavy chain minilocus transgenic, [mu]MT/[mu]MT mice, Molecular Immunology, 37(5):221-231(2000).

Wagner et al., "Antibodies generated from human immunoglobulin miniloci in transgenic mice," Nucleic Acids Research, 22(8): 1389-1393, 1994.

Wagner et al., "The Diversity of Antigen-Specific Monoclonal Antibodies from Transgenic Mice Bearing Human Immunoglobulin Gene Miniloci," European Journal of Immunology, 24: 2672-2681, 1994.

Wang et al., "Universal epitopes of influenza virus hemagglutinins?," Nature Structural & Molecular Biology, 16(3): 233-234, 2009.

Written Opinion for PCT/US2012/060487 (7 pages), dated Feb. 1, 2013.

Written Opinion for PCT/US2013/029624 (12 pages), dated Aug. 2, 2013.

Xu, et al., "Diversity in the CDR3 region of VH is sufficient for most antibody specificities," Immunity, 13(1): 37-45, 2000.

Yamada et al., "Preferential Utilization of Specific Immunoglobulin Heavy Chain Diversity and Joining Segments in Adult Human Peripheral Blood B Lymphocytes," J. Exp. Med., 173: 395-407, 1991.

Choi, et al., (2004) "Characterization and comparative genomic analysis of intronless Adams with testicular gene expression," Genomics, 83(4):636-46. (Abstract Only).

Clark, et al., (2003) "A future for transgenic livestock," Nature Reviews Genetics, 4:825-833.

Edwards, et al., (2008) "The ADAM metalloproteinases," Molecular Aspects of Medicine, 29(5):258-89.

Forconi, et al., (2010) "The normal IGHV1-69—derived B-cell repertoire contains stereotypic patterns characteristic of unmutated CLL," Blood, 115(1):71-77.

Giallourakis, et al., (2010) "Elements between the IgH variable (V) and diversity (D) clusters influence antisense transcription and lineage-specific V(D)J recombination," Proceedings of the National Academy of Sciences of the USA, 107(51):22207-22212.

Hendricks, et al., (2010) "Organization of the variable region of the immunoglobulin heavy-chain gene locus of the rat," Immunogenetics, 62(7):479-86.

Kim, et al., (2006) "Expression and relationship of male reproductive ADAMs in mouse," Biology of Reproduction, 74(4):744-750.

Munoz et al., (2009) "Constraints to Progress in Embryonic Stem Cells from Domestic Species," Stem Cell Rev. and Rep, 5:6-9.

Niemann, et al., (2005) "Transgenic farm animals: present and future," Rev. sci tech Off. Int. Epiz., 24 (1):285-298.

(56) References Cited

OTHER PUBLICATIONS

Prelle, et al., (2002) "Pluripotent Stem Cells—Model of Embryonic Development, Tools for Gene Targeting, and Basis of Cell Therapy," Anat. Histol. Embryol., 31:169-186.
Ray, (1991) "Ectopic expression of a c-kitW42 minigene in transgenic mice: recapitulation of W phenotypes and evidence for c-kit function in melanoblast progenitors," Genes Dev., 5(12A):2265-73.
Seals, et al., (2003) "The ADAMs family of metalloproteases: multidomain: proteins with multiple functions," Genes and Development, 17(1):7-30.
Wagner, et al., (1996) "Antibody Expression from the Core Region of the Human IgH Locus Reconstructed in Transgenic Mice Using Bacteriophage P1 Clones," Genomics, 35:405-414.
Wheeler, et al., (2001) "Transgenic Technology and Applications in Swine," Theriogenology, 56:1345-1369.
International Search Report & Written Opinion with respect to PCT/US2012/026416, dated Jun. 25, 2012.
International Search Report & Written Opinion with respect to PCT/US2014/017427 dated Aug. 1, 2014.
Gay et al. (1993) "Receptor Editing: An Approach by Autoreactive B Cells to Escape Tolerance," J. Exp. Med., 177:999-1008.
Third Party Observations with Respect to European Patent Application No. EP12783456.2, EPO Communication submitted on Feb. 25, 2015.
Third Party Observations with Respect to European Patent Application No. EP12783456.2, EPO Communication submitted on Jun. 22, 2016.
Brüggemann (2004) "Human Monoclonal Antibodies from Translocus Mice," Molecular Biology of B Cells, Eds. Honjo, T. and Neuberger, M.S., New York, NY: Academic Press, pp. 547-561.
Defrancesco (1999) "Transgenic Mice that Produce Fully Humanized Antibodies—Abgenix Granted Patent," Bioprocess Online, 2 pages, Aug. 23, 1999.
Echelard, (2009) "Year of the ox," Nat. Biotechnol., 27(2):146-147.
Gallo et al. (2000) "The human immunoglobulin loci introduced into mice: V (D) and J gene segment usage similar to that of adult humans," Eur. J. Immunol., 30(2):534-540.
Genbank Accession AAA53514.1; GI:553403, 1 page, first referenced Jul. 30, 1993, updated Nov. 23, 1994.
Harding and Lonberg (1995) "Class switching in human immunoglobulin transgenic Mice," Ann. N Y Acad. Sci., 764:536-546.
Kuroiwa et al. (2002) "Cloned transchromosomic calves producing human immunoglobulin," Nat. Biotechnol., 20(9):889-894.
Murphy (2014) Declaration Under 37 C.F.R. §1.132, 4 pages.
Murphy PowerPoint (2009) BAC-based Modifications of the Mouse Genome: The Big and the Backward, Welcome Trust Advanced Course: Genetic Manipulation of ES Cells, 58 pages.
Ramsden et al. (1994) "Conservation of sequence in recombination signal sequence spacers," Nucleic Acids Res., 22(10):1785-1796.
Timetable for Mouse ES Cells course at Wellcome Trust Sanger Institute Oct. 26, 2009-Nov. 8, 2009 (black and white).
Timetable for Mouse ES Cells course at Wellcome Trust Sanger Institute Oct. 26, 2009-Nov. 8, 2009 (greyscale).
UniProtKB/Swiss-Prot Accession No. P23083, HV103_Human, 7 pages, integrated into UniProtKB/Swiss-Prot Nov. 1, 1991, last modified Nov. 11, 2015, last accessed Dec. 9, 2015 <http://www.uniprot.org/P23083>.
Non-Final Office Action dated Oct. 30, 2015 with Respect to U.S. Appl. No. 14/137,902.
Statement of Relatedness under MPEP 2001.06 dated Apr. 26, 2016 with Respect to U.S. Appl. No. 13/944,286.
EP1360287 Appeal Decision Mar. 10, 2016.
*Regeneron* v. *Merus B.V.* Opinion and Order Nov. 2, 2015.
Taki et al. (1993) "Targeted Insertion of a Variable Region Gene into the Immunoglobuliin Heavy Chain Locus," Science, 262:1268-1271.
UK Decision EP1360287 and EP2264163 Feb. 1, 2016.
Amit and Itskovitz-Eldor (2009) "Embryonic Stem Cells: Isolation, Characterization and Culture," Adv. Biochem. Eng. Biotechnol., 114:173-184.
Astellas Negotiates $295M License Extension to Regeneron's VelocImmune mAb Platform, Genetic Engineering & Biotechnology News, Jul. 28, 2010, 2 pages.
Brouwers et al. (2015) "Unexpected Phenotypes in Mouse Models Carrying the Human Growth Hormone Minigene to Enhance Transgene Expression," Journal of Steroids & Hormonal Science, 6(2):1-2.
Brüggemann and Neuberger (1996) "Strategies for expressing human antibody repertoires in transgenic mice," Review Immunology Today, 192(17):391-397.
Butler, (1998) "Immunoglobulin diversity, B-cell and antibody repertoire development in large farm animals," Rev. Sco. Tech. Off. Int. Epiz., 17(1):43-70.
Cheval et al. (2012) Of Mice and Men: Divergence of Gene Expression Patterns in Kidney, PLoS One, 7(10): e46876 (12 pages).
Choi et al. (2011) "Expression of the metabotropic glutamate receptor 5 (mGluR5) induces melanoma in transgenic mice," PNAS, 108(37):15219-15224.
Glick and Pasternak (2002) Molekulyarnaya biotekhnologiya. Printsipy i primeneniye, Moscow Mir., 45-47.
Hoiruchi and Blobel (2005) Studies from Adam Knockout Mice, in Hooper and Lendeckel, The ADAM Family of proteases, Netherlands 2005, Springer (37 pages).
Kong et al. (2009) "Transgene expression is associated with copy number and cytomegalovirus promoter methylation in transgenic pigs," PLoS One 4(8):1-10.
Kuroiwa et al. (2004) "Sequential targeting of the genes encoding immunoglobulin-µ and prion protein in cattle," Nature Genetics, 36:775-780.
Lee et al. (2014) "Complete humanization of the mouse immunoglobulin loci enables efficient therapeutic antibody discovery," Nature Biotechnology, 32(4):356.
Lin et al. (1990) "Research of Immune Globulin in Mice," Guangzhou Medical Journal, 1:49-50.
Liu et al. (2014) "Primary Genetic Investigation of a Hyperlipidemia Model: Molecular Characteristics and Variants of the Apolipoprotein E Gene in Mongolian Gerbil," Biomed. Research International, (9 pages).
Lovell-Badge (2007) "Many ways to pluripotency," Nature Biotechnology, 25:1114-1116.
Macdonald et al. (2006) "Velocigene Technology Extended to Humanization of Several Megabases of complex Gene Loci," First International MUGEN Conference of Animal Models for Human Immunological Disease, Sep. 10-13, 2006—Athens, Greece, Abstract 21 and Poster, 2 pages.
Manis et al. (2002) "Mechanism and control of class-switch recombination," TRENDS in Immunology, 23(1):31-39.
McGoldrick et al. (2013) "Rodent models of amyotrophic lateral sclerosis," Biochimica et Biophysica Acta, 1832:1421-1436.
Murphy and Silha (2000) "Unexpected and unexplained phenotypes in transgenic models," Growth Hormone & IGF Research, 10:233-235.
Nagle, Regeneron helps make Sanofi VelocImmune to its "weak pipeline". <http://www.outsourcing-pharma.com> Published Dec. 3, 2007.
Osborn et al. (2013) "High-Affinity IgG Antibodies Develop Naturally in Ig-Knockout Rats Carrying Germline Human IgH/Igκ/Igλ Loci Bearing the Rat CH Region," J. Immunol., 190:1481-1490.
Pasqualini and Arap (2004) "Hybridoma-free generation of monoclonal antibodies," Proceedings of the National Academy of Sciences USA, 101(1):257-259.
Rudikoff et al. (1982) "Single amino acid substitution altering antigen-binding specificity," PNAS 79:1979-1983.
Schulze et al. (2006) "Derivation, Maintenance, and Characterization of Rat Embryonic Stem Cells in Vitro," Methods in Molecular Biology, 329:45-58.
Shmerling et al. (2005) "Strong and ubiquitous expression of transgenes targeted into the β-actin locus by Cre/lox cassette replacement," Genesis, 42(5):229-235.
Sigmund (2000) "Viewpoint: Are Studies in Genetically Altered Mice Out of Control?" Arterioscler. Thomb. Vasc. Biol., 20(6):1425-1429.

(56) References Cited

OTHER PUBLICATIONS

Stevens et al. (2006) "Velocimmune: Humanization of Immunoglobulin Loc Using Velocigene Technology," First International MUGEN Conference of Animal Models for Human Immunological Disease, Sep. 10-13, 2016—Athens, Greece, Abstract 4 and Poster (2 pages).

Tong et al. (2010) "Production of p53 gene knockout rats by homologous recombination in embryonic stem cells," Nature Letters, 467:211-215.

Yantha et al. (2010) "Unexpected Acceleration of Type 1 Diabetes by Transgenic Expression of B7-H1 in NOD Mouse Peri-Islet Glia," Diabetes, 59:2588-2596.

Zou et al. (1994) Cre-IoxP-mediated gene replacement: a mouse strain producing humanized antibodies, Current Biology, 4:1099-1103.

Canadian Office Action for Application No. 2,820,824, 3 pages, dated Aug. 5, 2014.

Extended European Search Report with respect to EP 14754019.9 dated Aug. 28, 2015.

Statement of Relatedness under MPEP 2001.06 dated Feb. 17, 2017 with Respect to U.S. Appl. No. 13/944,286.

Glick and Pasternak (2002) Molekulyarnaya biotekhnologiya. Printsipy i primeneniye, Moscow Mir., 45-47, Including English translation.

Lin et al. (1990) "Research of Immune Globulin in Mice," Guangzhou Medical Journal, 1:49-50, including English translation.

Adkins et al. (2004) "Neonatal Adaptive Immunity Comes of Age," Nature Reviews Immunol., 4:553-564.

Dennis (2002) "Welfare issues of genetically modified animals," ILAR Journal, 43(2):100-109.

Vakil et al. (1991) "Antigen-Independent Selection of T15 Idotype During B-Cell Ontogeny in Mice," Developmental Immunology, 1:203-212.

Zhou et al., (2009) "Developing tTA transgenic rats for inducible and reversible gene expression," International Journal of Biological Sciences, 5:171-181.

PCT/US2013/029624 Invitation to Pay Additional Fees and Where Applicable, Protest Fee dated May 17, 2013, 9 pages.

\* cited by examiner

```
              10        20        30        40        50        60        70
VH1-69*01  CAGGTgCAGCTGGTGCAGTCTGGGGCTGAGGTGAAGAAGCCTGGGTCCTCGGTGAAGGTCTCCTGCAAGGCTTCT
VH1-69*02  CAGGTCCAGCTGGTGCAaTCTGGGGCTGAGGTGAAGAAGCCTGGGTCCTCGGTGAAGGTCTCCTGCAAGGCTTCT
VH1-69*03  CAGGTgCAGCTGGTGCAGTCTGGGGCTGAGGTGAAGAAGCCTGGGTCCTCGGTGAAGGTCTCCTGCAAGGCTTCT
VH1-69*04  CAGGTCCAGCTGGTGCAGTCTGGGGCTGAGGTGAAGAAGCCTGGGTCCTCGGTGAAGGTCTCCTGCAAGGCTTCT
VH1-69*05  CAGGTCCAGCTGGTGCAGTCTGGGGCTGAGGTGAAGAAGCCTGGGTCCTCGGTGAAGGTCTCCTGCAAGGCTTCT
VH1-69*06  CAGGTgCAGCTGGTGCAGTCTGGGGCTGAGGTGAAGAAGCCTGGGTCCTCGGTGAAGGTCTCCTGCAAGGCTTCT
VH1-69*07  -----------------------------------AGAAGCCTGGGTCCTCGGTGAAGGTCTCCTGCAAGGCTTCT
VH1-69*08  CAGGTCCAGCTGGTGCAaTCTGGGGCTGAGGTGAAGAAGCCTGGGTCCTCGGTGAAGGTCTCCTGCAAGGCTTCT
VH1-69*09  CAGGTgCAGCTGGTGCAGTCTGGGGCTGAGGTGAAGAAGCCTGGGTCCTCGGTGAAGGTCTCCTGCAAGGCTTCT
VH1-69*10  CAGGTCCAGCTGGTGCAGTCTGGGGCTGAGGTGAAGAAGCCTGGGTCCTCaGTGAAGGTCTCCTGCAAGGCTTCT
VH1-69*11  CAGGTCCAGCTGGTGCAGTCTGGGGCTGAGGTGAAGAAGCCTGGGTCCTCGGTGAAGGTCTCCTGCAAGGCTTCT
VH1-69*12  CAGGTCCAGCTGGTGCAGTCTGGGGCTGAGGTGAAGAAGCCTGGGTCCTCGGTGAAGGTCTCCTGCAAGGCTTCT
VH1-69*13  CAGGTCCAGCTGGTGCAGTCTGGGGCTGAGGTGAAGAAGCCTGGGTCCTCaGTGAAGGTCTCCTGCAAGGCTTCT
           CAGGTCCAGCTGGTGCAGTCTGGGGCTGAGGTGAAGAAGCCTGGGTCCTCGGTGAAGGTCTCCTGCAAGGCTTCT 80        90       100       110       120       130       140       150
VH1-69*01  GGAGGCACCTTCAGCAGCTATGCTATCAGCTGGGTGCGACAGGCCCCTGGACAAGGGCTTGAGTGGATGGGAGGG
VH1-69*02  GGAGGCACCTTCAGCAGCTATaCTATCAGCTGGGTGCGACAGGCCCCTGGACAAGGGCTTGAGTGGATGGGAaGG
VH1-69*03  GGAGGCACCTTCAGCAGCTATGCTATCAGCTGGGTGCGACAGGCCCCTGGACAAGGGCTTGAGTGGATGGGAGGG
VH1-69*04  GGAGGCACCTTCAGCAGCTATGCTATCAGCTGGGTGCGACAGGCCCCTGGACAAGGGCTTGAGTGGATGGGAaGG
VH1-69*05  GGAGGCACCTTCAGCAGCTATGCTATCAGCTGGGTGCGACAGGCCCCTGGACAAGGGCTTGAGTGGATGGGAGGG
VH1-69*06  GGAGGCACCTTCAGCAGCTATGCTATCAGCTGGGTGCGACAGGCCCCTGGACAAGGGCTTGAGTGGATGGGAGGG
VH1-69*07  GGAGGCACCTTCAGCAGCTATGCTATCAGCTGGGTGCGACAGGCCCCTGGACAAGGGCTTGAGTGGATGGGAaGG
VH1-69*08  GGAGGCACCTTCAGCAGCTATaCTATCAGCTGGGTGCGACAGGCCCCTGGACAAGGGCTTGAGTGGATGGGAaGG
VH1-69*09  GGAGGCACCTTCAGCAGCTATGCTATCAGCTGGGTGCGACAGGCCCCTGGACAAGGGCTTGAGTGGATGGGAaGG
VH1-69*10  GGAGGCACCTTCAGCAGCTATGCTATCAGCTGGGTGCGACAGGCCCCTGGACAAGGGCTTGAGTGGATGGGAGGG
VH1-69*11  GGAGGCACCTTCAGCAGCTATGCTATCAGCTGGGTGCGACAGGCCCCTGGACAAGGGCTTGAGTGGATGGGAaGG
VH1-69*12  GGAGGCACCTTCAGCAGCTATGCTATCAGCTGGGTGCGACAGGCCCCTGGACAAGGGCTTGAGTGGATGGGAGGG
VH1-69*13  GGAGGCACCTTCAGCAGCTATGCTATCAGCTGGGTGCGACAGGCCCCTGGACAAGGGCTTGAGTGGATGGGAGGG
           GGAGGCACCTTCAGCAGCTATGCTATCAGCTGGGTGCGACAGGCCCCTGGACAAGGGCTTGAGTGGATGGGAGGG 160       170       180       190       200       210       220
VH1-69*01  ATCATCCCTATCTTTGGTACAGCAAACTACGCACAGAAGTTCCAGGGCAGAGTCACGATTACCGCGGACGAATCC
VH1-69*02  ATCATCCCTATCcTTGGTAtAGCAAACTACGCACAGAAGTTCCAGGGCAGAGTCACGATTACCGCGGACaAATCC
VH1-69*03  ATCATCCCTATCTTTGGTACAGCAAACTACGCACAGAAGTTCCAGGGCAGAGTCACGATTACCGCGGACGAATCC
VH1-69*04  ATCATCCCTATCcTTGGTAtAGCAAACTACGCACAGAAGTTCCAGGGCAGAGTCACGATTACCGCGGACaAATCC
VH1-69*05  ATCATCCCTATCTTTGGTACAGCAAACTACGCACAGAAGTTCCAGGGCAGAGTCACGATTACCaCGGACGAATCC
VH1-69*06  ATCATCCCTATCTTTGGTACAGCAAACTACGCACAGAAGTTCCAGGGCAGAGTCACGATTACCGCGGACGAATCC
VH1-69*07  ATCATCCCTATCTTTGGTACAGCAAACTACGCACAGAAGTTCCAGGGCAGAGTCACGATTACCGCGGACGAATCC
VH1-69*08  ATCATCCCTATCcTTGGTACAGCAAACTACGCACAGAAGTTCCAGGGCAGAGTCACGATTACCGCGGACaAATCC
VH1-69*09  ATCATCCCTATCTTTGGTAtAGCAAACTACGCACAGAAGTTCCAGGGCAGAGTCACGATTACCGCGGACaAATCC
VH1-69*10  ATCATCCCTATCcTTGGTAtAGCAAACTACGCACAGAAGTTCCAGGGCAGAGTCACGATTACCGCGGACaAATCC
VH1-69*11  ATCATCCCTATCcTTGGTACAGCAAACTACGCACAGAAGTTCCAGGGCAGAGTCACGATTACCGCGGACGAATCC
VH1-69*12  ATCATCCCTATCcTTGGTACAGCAAACTACGCACAGAAGTTCCAGGGCAGAGTCACGATTACCGCGGACGAATCC
VH1-69*13  ATCATCCCTATCTTTGGTACAGCAAACTACGCACAGAAGTTCCAGGGCAGAGTCACGATTACCGCGGACGAATCC
           ATCATCCCTATCTTTGGTACAGCAAACTACGCACAGAAGTTCCAGGGCAGAGTCACGATTACCGCGGACGAATCC 230       240       250       260       270       280       290
VH1-69*01  ACGAGCACAGCCTACATGGAGCTGAGCAGCCTGAGATCTGAGGACACGGCCGTGTATTACTGTGCGAGAGAA
VH1-69*02  ACGAGCACAGCCTACATGGAGCTGAGCAGCCTGAGATCTGAGGACACGGCCGTGTATTACTGTGCGAGA---
VH1-69*03  ACGAGCACAGCCTACATGGAGCTGAGCAGCCTGAGATCTGAtGACACGGC----------------------
VH1-69*04  ACGAGCACAGCCTACATGGAGCTGAGCAGCCTGAGATCTGAGGACACGGCCGTGTATTACTGTGCGAGAGAA
VH1-69*05  ACGAGCACAGCCTACATGGAGCTGAGCAGCCTGAGATCTGAGGACACGGCCGTGTATTACTGTGCGAGA---
VH1-69*06  ACGAGCACAGCCTACATGGAGCTGAGCAGCCTGAGATCTGAGGACACGGCCGTGTATTACTGTGCGAGAGAA
VH1-69*07  ACGAGCACAGCCTACATGGAGCTGAGCAGCCTGAGATCTGAG-----------------------------
VH1-69*08  ACGAGCACAGCCTACATGGAGCTGAGCAGCCTGAGATCTGAGGACACGGCCGTGTATTACTGTGCGAGAGAA
VH1-69*09  ACGAGCACAGCCTACATGGAGCTGAGCAGCCTGAGATCTGAGGACACGGCCGTGTATTACTGTGCGAGAGAA
VH1-69*10  ACGAGCACAGCCTACATGGAGCTGAGCAGCCTGAGATCTGAGGACACGGCCGTGTATTACTGTGCGAGAGAA
VH1-69*11  ACGAGCACAGCCTACATGGAGCTGAGCAGCCTGAGATCTGAGGACACGGCCGTGTATTACTGTGCGAGAGAA
VH1-69*12  ACGAGCACAGCCTACATGGAGCTGAGCAGCCTGAGATCTGAGGACACGGCCGTGTATTACTGTGCGAGAGAA
VH1-69*13  ACGAGCACAGCCTACATGGAGCTGAGCAGCCTGAGATCTGAGGACACGGCCGTGTATTACTGTGCGAGAGAA
           ACGAGCACAGCCTACATGGAGCTGAGCAGCCTGAGATCTGAGGACACGGCCGTGTATTACTGTGCGAGAGA
```

FIG. 13

|          | 10         | 20         | 30         | 40         | 50         | 60     |
|----------|------------|------------|------------|------------|------------|--------|
| VH1-69*01 | QVQLVQSGAEVKKPGS | SVKVSCKASG | GTFSSYA | ISWVRQAPGQGLEWMGG | IIPIFGTANY |
| VH1-69*02 | QVQLVQSGAEVKKPGS | SVKVSCKASG | GTFSSYA | ISWVRQAPGQGLEWMGr | IIPIlGiANY |
| VH1-69*03 | QVQLVQSGAEVKKPGS | SVKVSCKASG | GTFSSYA | ISWVRQAPGQGLEWMGr | IIPIFGTANY |
| VH1-69*04 | QVQLVQSGAEVKKPGS | SVKVSCKASG | GTFSSYA | ISWVRQAPGQGLEWMGG | IIPIFGTANY |
| VH1-69*05 | QVQLVQSGAEVKKPGS | SVKVSCKASG | GTFSSYA | ISWVRQAPGQGLEWMGG | IIPIFGTANY |
| VH1-69*06 | QVQLVQSGAEVKKPGS | SVKVSCKASG | GTFSSYA | ISWVRQAPGQGLEWMGr | IIPIFGTANY |
| VH1-69*07 | -------KPGS | SVKVSCKASG | GTFSSYt | ISWVRQAPGQGLEWMGr | IIPIlGiANY |
| VH1-69*08 | QVQLVQSGAEVKKPGS | SVKVSCKASG | GTFSSYt | ISWVRQAPGQGLEWMGr | IIPIlGiANY |
| VH1-69*09 | QVQLVQSGAEVKKPGS | SVKVSCKASG | GTFSSYA | ISWVRQAPGQGLEWMGG | IIPIlGiANY |
| VH1-69*10 | QVQLVQSGAEVKKPGS | SVKVSCKASG | GTFSSYA | ISWVRQAPGQGLEWMGr | IIPIlGiANY |
| VH1-69*11 | QVQLVQSGAEVKKPGS | SVKVSCKASG | GTFSSYA | ISWVRQAPGQGLEWMGG | IIPIFGTANY |
| VH1-69*12 | QVQLVQSGAEVKKPGS | SVKVSCKASG | GTFSSYA | ISWVRQAPGQGLEWMGG | IIPIFGTANY |
| VH1-69*13 | QVQLVQSGAEVKKPGS | SVKVSCKASG | GTFSSYA | ISWVRQAPGQGLEWMGG | IIPIFGTANY |

|          | 70         | 80         | 90         | 100  |
|----------|------------|------------|------------|------|
| VH1-69*01 | AQKFQGRVTITADEST | STAYMELSSLRSEDTAVYY | CARR |
| VH1-69*02 | AQKFQGRVTITADEST | STAYMELSSLRSEDTAVYY | CARR |
| VH1-69*03 | AQKFQGRVTITADkST | STAYMELSSLRSEDTAVYY | CARR |
| VH1-69*04 | AQKFQGRVTITADkST | STAYMELSSLRSEDTAVYY | CARR |
| VH1-69*05 | AQKFQGRVTITtDEST | STAYMELSSLRSDDT--- | CARR |
| VH1-69*06 | AQKFQGRVTITADkST | STAYMELSSLRSEDTAVYY | CARR |
| VH1-69*07 | AQKFQGRVTITADkST | STAYMELSSLRSEDTAVYY | CARR |
| VH1-69*08 | AQKFQGRVTITADEST | STAYMELSSLRSE----- | CARR |
| VH1-69*09 | AQKFQGRVTITADkST | STAYMELSSLRSEDTAVYY | CARR |
| VH1-69*10 | AQKFQGRVTITADkST | STAYMELSSLRSEDTAVYY | CARR |
| VH1-69*11 | AQKFQGRVTITADEST | STAYMELSSLRSEDTAVYY | CARR |
| VH1-69*12 | AQKFQGRVTITADEST | STAYMELSSLRSEDTAVYY | CARR |
| VH1-69*13 | AQKFQGRVTITADEST | STAYMELSSLRSEDTAVYY | CAR  |

FIG. 14

| V$_H$1-69 Allele | 01 | 02 | 03 | 04 | 05 | 06 | 07 | 08 | 09 | 10 | 11 | 12 | 13 |
|---|---|---|---|---|---|---|---|---|---|---|---|---|---|
| 01 | 100 | 94.9 | 91.8 | 95.9 | 99 | 99 | 77.6 | 95.9 | 95.9 | 96.9 | 98 | 100 | 100 |
| 02 | 95.9 | 100 | 86.7 | 99 | 93.9 | 95.9 | 74.5 | 99 | 99 | 98 | 96.9 | 94.9 | 94.9 |
| 03 | 92.9 | 88.8 | 100 | 87.8 | 90.8 | 90.8 | 82.4 | 87.8 | 87.8 | 88.8 | 89.8 | 91.8 | 91.8 |
| 04 | 95.9 | 100 | 88.8 | 100 | 94.9 | 96.9 | 75.5 | 98 | 100 | 99 | 98 | 95.9 | 95.9 |
| 05 | 100 | 95.9 | 92.9 | 95.9 | 100 | 98 | 76.5 | 94.9 | 94.9 | 95.9 | 96.9 | 99 | 99 |
| 06 | 99.0 | 96.9 | 91.8 | 96.9 | 99 | 100 | 76.5 | 96.9 | 96.9 | 98 | 96.9 | 99 | 99 |
| 07 | 77.6 | 75.5 | 83.5 | 75.5 | 77.6 | 76.5 | 100 | 75.5 | 75.5 | 74.5 | 77.6 | 77.6 | 77.6 |
| 08 | 96.9 | 99 | 89.8 | 99 | 96.9 | 98 | 76.5 | 100 | 98 | 96.9 | 98 | 95.9 | 95.9 |
| 09 | 95.9 | 99 | 88.8 | 100 | 95.9 | 96.9 | 75.5 | 99 | 100 | 99 | 98 | 95.9 | 95.9 |
| 10 | 96.9 | 98 | 89.8 | 99 | 96.9 | 98 | 74.5 | 98 | 99 | 100 | 96.9 | 96.9 | 96.9 |
| 11 | 98 | 96.9 | 90.8 | 98 | 98 | 96.9 | 77.6 | 99 | 98 | 96.9 | 100 | 98 | 98 |
| 12 | 100 | 95.9 | 92.9 | 95.9 | 100 | 99 | 77.6 | 96.9 | 95.9 | 96.9 | 98 | 100 | 100 |
| 13 | 100 | 95.9 | 92.9 | 95.9 | 100 | 99.0 | 77.6 | 96.9 | 95.9 | 96.9 | 98 | 100 | 100 |

% Identity (upper) / % Similarity (lower), V$_H$1-69 Allele

|           | 10 | 20 | 30 | 40 | 50 |
|---|---|---|---|---|---|
| VH1-2*01 | QVQLVQSGAEVKKPGASVKVSCKAS | GYTFTGYYM | HWVRQAPGQGLEWMGr |
| VH1-2*02 | QVQLVQSGAEVKKPGASVKVSCKAS | GYTFTGYYM | HWVRQAPGQGLEWMGW |
| VH1-2*03 | QVQLVQSGAEVKKlGASVKVSCKAS | GYTFTGYYM | HWVxQAPGQGLEWMGW |
| VH1-2*04 | QVQLVQSGAEVKKPGASVKVSCKAS | GYTFTGYYM | HWVRQAPGQGLEWMGW |
| VH1-2*05 | QVQLVQSGAEVKKPGASVKVSCKAS | GYTFTGYYM | HWVRQAPGQGLEWMGr |

|           | 60 | 70 | 80 | 90 |
|---|---|---|---|---|
| VH1-2*01 | INPNSGGT | NYAQKFQGRVTsTRDTSISTAYMELSRLRSDDTVVYYCAR |
| VH1-2*02 | INPNSGGT | NYAQKFQGRVTMTRDTSISTAYMELSRLRSDDTAVYYCAR |
| VH1-2*03 | INPNSGGT | NYAQKFQGRVTMTRDTSISTAYMELSRLRSDDTAVYYCAR |
| VH1-2*04 | INPNSGGT | NYAQKFQGwVTMTRDTSISTAYMELSRLRSDDTVVYYCAR |
| VH1-2*05 | INPNSGGT | NYAQKFQGRVTMTRDTSISTAYMELSRLRSDDTAVYYCAR |

FIG. 17

| $V_H$1-2 Allele | % Identity $V_H$1-2 Allele | | | | |
|---|---|---|---|---|---|
| | 01 | 02 | 03 | 04 | 05 |
| 01 | 100 | 96.9 | 94.9 | 95.9 | 99.0 |
| 02 | 96.9 | 100 | 98.0 | 99.0 | 98.0 |
| 03 | 94.9 | 98.0 | 100 | 96.9 | 95.9 |
| 04 | 95.9 | 99.0 | 96.9 | 100 | 96.9 |
| 05 | 99.0 | 98.0 | 95.9 | 96.9 | 100 |
| % Similarity | | | | | |

FIG. 18

RESTRICTED IMMUNOGLOBULIN HEAVY CHAIN MICE

CROSS-REFERENCE TO RELATED APPLICATIONS

This application is a divisional of U.S. patent application Ser. No. 13/653,456, filed Oct. 17, 2012, which claims the benefit under 35 USC § 119(e) of U.S. Provisional Application Ser. No. 61/658,459, filed Jun. 12, 2012, U.S. Provisional Application Ser. No. 61/597,969, filed Feb. 13, 2012 and U.S. Provisional Application Ser. No. 61/547,974, filed Oct. 17, 2011, which applications are hereby incorporated by reference in their entirety.

FIELD

Non-human animals that are genetically engineered at an immunoglobulin heavy chain variable (V) region locus (or in a transgene) to make antibodies from a restricted number of immunoglobulin heavy chain variable ($V_H$) segments (or a single $V_H$ segment) and/or variants thereof. Non-human animals that have a human heavy chain variable domain derived from a single immunoglobulin heavy chain variable gene segment, e.g., human immunoglobulin $V_H$1-69 gene segment or human $V_H$1-2 gene segment. Methods for making antibody sequences in non-human animals that are useful for binding pathogens, including human pathogens.

BACKGROUND

Non-human animals, e.g., mice, have been genetically engineered to be useful tools in methods for making antibody sequences for use in antibody-based human therapeutics. Mice with humanized variable region loci (e.g., $V_H$, $D_H$, and $J_H$ genes, and $V_L$ and $J_L$ genes) are used to generate cognate heavy and light chain variable domains for use in antibody therapeutics. Other mice are available that generate fully human antibodies with cognate heavy and light chains.

Human antibody therapeutics are engineered based on desired characteristics with respect to certain pre-selected antigens. Humanized mice are immunized with the pre-selected antigens, and the immunized mice are used to generate antibody populations from which to identify high-affinity cognate heavy and light variable domains with desired binding characteristics. Some humanized mice, such as those having a humanization of just variable regions at endogenous mouse loci, generate populations of B cells that are similar in character and number to wild-type mouse B cell populations. As a result, an extremely large and diverse population of B cells is available in these mice from which to screen antibodies, reflecting a large number of different immunoglobulin rearrangements, to identify heavy and light variable domains with the most desirable characteristics.

But not all antigens provoke an immune response that exhibits a very large number of rearrangements from a wide selection of variable (V) segments. That is, the human humoral immune response to certain antigens is apparently restricted. The restriction is reflected in clonal selection of B cells that express only certain V segments that bind that particular antigen with sufficiently high affinity and specificity. Some such antigens are clinically significant, i.e., a number are well-known human pathogens. A presumption arises that the V segment expressed in the human immune response is a V segment that, in combination with a human D and a human J segment, is more likely to generate a useful high affinity antibody than a randomly selected V segment that has not been observed in a human antibody response to that antigen.

It is hypothesized that natural selection, over millennia, has selected the most efficient foundation or base from which to design a most effective weapon for neutralizing human pathogens—a clonally selected V segment. There is a need in the art for more and superior antibodies that bind and/or neutralize antigens such as the pathogens discussed above. There is a need to more rapidly generate useful sequences from selected V segments, including polymorphic and/or somatically mutated selected V segments and to more rapidly generate useful populations of B cells having rearrangements of the V segments with various D and J segments, including somatically mutated versions thereof, and in particular rearrangements with unique and useful CDR3s. There is a need for biological systems, e.g., non-human animals (such as, e.g., mice, rats, rabbits, etc.) that can generate therapeutically useful antibody variable region sequences from pre-selected V segments in increased number and diversity than, e.g., can be achieved in existing modified animals. There is a need for biological systems engineered to have a committed humoral immune system for clonally selecting antibody variable sequences derived from restricted, pre-selected V segments, including but not limited to cognate human heavy and light chain variable domains, useful in the manufacture of human antibody-based therapeutics against selected antigens, including certain human pathogens.

There is a need in the art for therapeutic antibodies that are capable of neutralizing viral antigens, e.g., HIV and HCV, including antigen-specific antibodies containing heavy chains derived from a single human variable segment, and for a system that produces a diverse source of antibodies from which to select therapeutic antibody sequences. There is also a need for further methods and non-human animals for making useful antibodies, including antibodies that comprise a repertoire of heavy chains derived from a single human $V_H$ segment and having a diverse set of CDR sequences, and including such heavy chains that express with cognate human light chain variable domains. Methods are needed for selecting CDRs for immunoglobulin-based binding proteins that provide an enhanced diversity of binding proteins from which to choose, and enhanced diversity of immunoglobulin variable domains, including compositions and methods for generating somatically mutated and clonally selected immunoglobulin variable domains for use, e.g., in making human therapeutics.

SUMMARY

Genetically modified immunoglobulin loci are provided that comprise a restricted number of different heavy chain variable region gene segments (i.e., V genes, $V_H$ genes, $V_H$ gene segments, or V gene segments), e.g., no more than one, two, or three different V genes; or no more than one V gene segment family member present, e.g., in a single copy or in multiple copies and/or comprising one or more polymorphisms.

Loci are provided that are capable of rearranging and forming a gene encoding a heavy chain variable domain that is derived from a $V_H$ gene repertoire that is restricted, e.g., that is a single $V_H$ gene segment or selected from a plurality of polymorphic variants of the single $V_H$ gene segment. Modified immunoglobulin loci include loci that comprise human immunoglobulin sequences are provided, e.g., a human V segment operably linked to a human or (or human/non-human chimeric) non-human immunoglobulin constant sequence (and in operable linkage with, e.g., a D and/or a J segment). Modified loci that comprise multiple copies of a single $V_H$ gene segment, including wherein one or more of the copies comprises a polymorphic variant, are provided. Modified loci that comprise multiple copies of a single $V_H$ segment, operably linked with one or more D segments and one or more J segments, operably linked to a non-human immunoglobulin constant sequence, e.g., a mouse or rat sequence, are provided. Non-human animals comprising such humanized loci are also provided.

Non-human animals are provided that have a reduced immunoglobulin heavy chain variable gene segment complexity (i.e., a limited number of heavy chain variable gene segments, or a limited heavy chain variable gene repertoire), wherein the reduced immunoglobulin heavy chain variable gene segment complexity is characterized by the presence of no more than one or no more than two heavy chain variable gene segments, and wherein the heavy chain variable genes present are operably linked to a human or non-human constant region sequence.

Non-human animals are provided that have a reduced immunoglobulin heavy chain variable gene segment complexity (e.g., a single $V_H$ gene segment, or a limited number of $V_H$ gene segments that are polymorphic variants of a single $V_H$ gene segment), wherein the reduced immunoglobulin heavy chain variable gene segment complexity is characterized by the presence of a single $V_H$ gene segment or a plurality of $V_H$ gene segments that are polymorphic forms of a single $V_H$ gene segment (e.g., $V_H$ gene segments associated with high copy number and/or polymorphism in humans), and wherein the heavy chain variable genes present are operably linked to a human or non-human constant region sequence. In various embodiments, the heavy chain variable genes present are operably linked to one or more D and/or one or more J gene segments in the germline of the non-human animal.

Non-human animals are provided that comprise an immunoglobulin heavy chain variable locus (e.g., on a transgene or as an insertion or replacement at an endogenous non-human animal heavy chain variable locus) that comprises a single $V_H$ segment operably linked to a D and/or J gene segment. In various embodiments, the single $V_H$ gene segment is operably linked to one or more D and/or one or more J gene segments at the endogenous immunoglobulin heavy chain variable gene locus of the non-human animal.

Non-human animals are provided that are modified at their immunoglobulin heavy chain variable region loci to delete all or substantially all (e.g., all functional segments, or nearly all functional segments) endogenous immunoglobulin $V_H$ segments and that comprise a human $V_H$1-69 segment (or a human $V_H$1-2 segment) operably linked to a D and J segment or a J segment at the endogenous immunoglobulin heavy chain variable region locus of the non-human animal.

Non-human animals are also provided that are modified at their immunoglobulin heavy chain variable region loci to render the endogenous variable region loci incapable of rearranging to form a functional heavy chain comprising endogenous variable region gene segments; wherein the non-human animals comprise a single human variable gene segment (a human $V_H$1-2 or a human $V_H$1-69 gene segment) operably linked to a D and a J segment or a J segment at the endogenous immunoglobulin heavy chain variable region locus of the non-human animal.

Non-human animals are provided that comprise a restricted number (e.g., no more than one, or no more than two) of heavy chain gene segments operably linked to a human or non-human constant region sequence. In one embodiment, the no more than one or no more than two heavy chain gene segments linked to the constant region sequence are on a transgene, e.g., are at a position other than an endogenous heavy chain locus.

Methods are provided for making human immunoglobulin sequences in non-human animals. In various embodiments, the human immunoglobulin sequences are derived from a repertoire of immunoglobulin V sequences that consist essentially of a single human V segment, e.g., $V_H$1-69 or $V_H$1-2, and one or more D and J segments or one or more J segments. Methods for making human immunoglobulin sequences in non-human animals, tissues, and cells are provided, wherein the human immunoglobulin sequences bind a pathogen.

Methods are provided for making mice characterized by a restricted immunoglobulin heavy chain locus, wherein the restriction is with respect to the number of immunoglobulin $V_H$ gene segments. In various aspects, the restriction is to one or no more than two, or a single $V_H$ gene family member (e.g., one or more $V_H$ alleles, variants, or polymorphic variants thereof). In various aspects, the heavy chain locus further comprises one or more $D_H$ gene segments and one or more $J_H$ gene segments. In various aspects, the $V_H$, $D_H$ and $J_H$ gene segments are human. In various aspects, the $V_H$, $D_H$ and $J_H$ gene segments are operably linked to a non-human constant region (e.g., an IgM and/or an IgG). In various aspects, the constant region is a mouse or rat constant region.

In one aspect, a method for making a mouse having a restricted immunoglobulin heavy chain locus is provided, comprising introducing a nucleic acid construct as described herein into a mouse embryonic stem (ES) cell, and isolating or identifying a mouse ES cell that comprises the nucleic acid construct.

In one embodiment, the nucleic acid construct comprises a single human $V_H$ gene segment, one or more human $D_H$ gene segments, and one or more human $J_H$ gene segments. In one embodiment, the nucleic acid construct comprises one or more site-specific recombination sites (e.g., a loxP or a Frt site).

In one aspect, a mouse made using a targeting vector, nucleic acid sequence, or cell as described herein is provided. In various embodiments, the targeting vector, nucleic acid sequence or cell comprises a DNA sequence that contains a single human $V_H$ gene segment (or polymorphic variants thereof), one or more human $D_H$ gene segments, and one or more human $J_H$ gene segments operably linked to a non-human constant gene.

In one aspect, a method for making a mouse comprising a restricted immunoglobulin heavy chain locus is provided, comprising replacing a mouse immunoglobulin heavy chain locus with a human genomic sequence comprising a single human $V_H$ gene segment (or polymorphic variants thereof), one or more human $D_H$ gene segments, and one or more human JH gene segments, wherein the human $V_H$, $D_H$ and $J_H$ gene segments are capable of rearranging to form a chimeric heavy chain that contains a human variable domain operably linked to a non-human constant region. In one embodiment, the non-human constant region is a mouse or rat constant region.

In various aspects, the non-human animals are rodents. In various aspects, the rodents are mice and/or rats.

In one aspect, a modified immunoglobulin heavy chain locus is provided that comprises a heavy chain V segment repertoire that is restricted with respect to the identity of the V segment, and that comprises one or more D segments and one or more J segments, or one or more J segments. In one embodiment, the heavy chain V segment is a human segment. In one embodiment, the one or more D segments are human D segments. In one embodiment, the one or more J segments are human J segments. In one embodiment, the one or more D segments and one or more J segments are human D and human J segments.

In one embodiment, the modified locus is a non-human locus. In one embodiment, the non-human locus is modified with at least one human immunoglobulin sequence.

In one embodiment, the restriction is to one V segment family member. In one embodiment, the one V segment family member is present in two or more copies. In one embodiment, the one V segment family member is present as two or more variants (e.g., two or more polymorphic forms of the V segment family member). In one embodiment, the one V segment is a human V segment family member. In one embodiment, the one V segment family member is present in a number of variants as is observed in the human population with respect to that variant. In one embodiment, the V segment family member is selected from Table 1. In one embodiment, the V segment family member is present in a number of variants as shown, for each V segment, in a number of alleles from 1 allele to the number of alleles shown in the right column of Table 1.

In one embodiment, the restriction is to a human $V_H1$-69 gene segment. In one embodiment, the human $V_H1$-69 gene segment is present in two or more copies. In one embodiment, the human $V_H1$-69 gene segment is present as two or more variants (e.g., two or more polymorphic forms the human $V_H1$-69 gene). In one embodiment, the human $V_H1$-69 gene segment is present in a number of variants as is observed in the human population with respect to the human $V_H1$-69 gene segment. In one embodiment, the human $V_H1$-69 gene segment is selected from Table 2. In one embodiment, the human $V_H1$-69 gene segment is present in a number of variants as shown, for each $V_H1$-69 gene segment, in a number of alleles from one allele to the number of alleles shown in Table 2.

In one embodiment, the restriction is to a human $V_H1$-2 gene segment. In one embodiment, the human $V_H1$-2 gene segment is present in two or more copies. In one embodiment, the human $V_H1$-2 gene segment is present as two or more variants (e.g., two or more polymorphic forms the human $V_H1$-2 gene). In one embodiment, the human $V_H1$-2 gene segment is present in a number of variants as is observed in the human population with respect to the human $V_H1$-2 gene segment. In one embodiment, the human $V_H1$-2 gene segment is selected from Table 3. In one embodiment, the human $V_H1$-2 gene segment is present in a number of variants as shown, for each $V_H1$-2 gene segment, in a number of alleles from one allele to the number of alleles shown in Table 3.

In one aspect, a heavy chain immunoglobulin locus is provided that comprises a single functional human V segment. In one embodiment, the single functional human V segment is selected from a $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, and a $V_H7$-81 segment. In one embodiment, the single functional human V segment is a $V_H1$-69 segment; in a specific embodiment, the single functional human V segment is present in 1, 2, 3, 4, 5, 6, 7, 8, 9, 10, 11, 12, or 13 polymorphic forms found in the human population. In one embodiment, the single functional human V segment is a $V_H1$-2 segment; in a specific embodiment, the single functional human V segment is present in 1, 2, 3, 4, or 5 polymorphic forms found in the human population.

In one embodiment, the heavy chain immunoglobulin locus is a modified locus of a non-human animal. In one embodiment, the modified non-human immunoglobulin heavy chain locus is present in the non-human animal at a position in the genome in which the corresponding unmodified non-human locus is found in the wild-type non-human animal. In one embodiment, the modified non-human immunoglobulin heavy chain locus is present on a transgene in a non-human animal.

In one embodiment, the single functional human V gene segment is a $V_H1$-69 gene segment. In one embodiment, the $V_H1$-69 gene segment comprises SEQ ID NO: 34. In one embodiment, the $V_H1$-69 gene segment is derived from SEQ ID NO: 34. In one embodiment, the $V_H1$-69 gene segment is at least 80%, at least 85%, at least 90%, at least 95%, or at least 98% identical to SEQ ID NO: 34.

In one embodiment, the single functional human V gene segment is encoded by the nucleotide sequence of SEQ ID NO: 34.

In one embodiment, the single functional human V gene segment is a $V_H1$-2 gene segment. In one embodiment, the $V_H1$-2 gene segment comprises SEQ ID NO: 60. In one embodiment, the $V_H1$-2 gene segment is derived from SEQ ID NO: 60. In one embodiment, the $V_H1$-2 gene segment is at least 80%, at least 85%, at least 90%, at least 95%, or at least 98% identical to SEQ ID NO: 60.

In one embodiment, the single functional human V gene segment is encoded by the nucleotide sequence of SEQ ID NO: 60.

In one embodiment, the single functional human V segment is operably linked to one or more D segments and one or more J segments, or one or more J segments. In one embodiment, the V segment and one or more D and/or J segments are operably linked to an immunoglobulin heavy chain constant region sequence. In one embodiment the immunoglobulin heavy chain constant region sequence is selected from a $C_H1$, a hinge, a $C_H2$, a $C_H3$ sequence, and a combination thereof. In one embodiment, the $C_H1$, hinge, $C_H2$, $C_H3$, or combination thereof are each non-human endogenous constant sequences. In one embodiment, at least one of the $C_H1$, hinge, $C_H2$, $C_H3$, or combination thereof is a human sequence. In a specific embodiment, the $C_H1$ and/or hinge are human sequences.

In one aspect, a modified endogenous non-human immunoglobulin heavy chain locus is provided, comprising a replacement of all functional V gene segments with a single human V gene segment (or a single human V gene segment present in multiple polymorphic forms or copy number), wherein the non-human immunoglobulin heavy chain locus is incapable of rearrangement to form a heavy chain variable gene that is derived from a V gene segment other than the single human V gene segment (or one of the polymorphic forms or copies).

In one embodiment, the single human V gene segment is $V_H1$-69. In one embodiment, the single human V gene segment is $V_H1$-2.

In one embodiment, the locus comprises at least one human or non-human $D_H$ gene segment, and one human or non-human $J_H$ gene segment. In a specific embodiment, the locus comprises a human $D_H$ gene segment and a human $J_H$ gene segment. In a specific embodiment, the locus comprises a human $J_H$ gene segment. In another specific embodiment, the locus comprises a human $V_H1$-69 gene segment (present as a single copy or multiple copies of different polymorphic variants), all functional human $D_H$ gene segments, and all functional human $J_H$ gene segments. In another specific embodiment, the locus comprises a human $V_H1$-2 gene segment (present as a single copy or multiple copies of different polymorphic forms), all functional human $D_H$ gene segments, and all functional human $J_H$ gene segments. In one embodiment, the human V, D, and J gene segments (or V and J gene segments) are operably linked to a mouse constant region gene at an endogenous mouse heavy chain locus. In a specific embodiment, the mouse heavy chain locus comprises a wild-type repertoire of mouse immunoglobulin constant region sequences.

In one aspect, a genetically modified non-human animal is provided, wherein the only functional immunoglobulin heavy chain V gene segment of the non-human animal is selected from a human $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, and $V_H7$-81 gene segment. In one embodiment, the heavy chain V gene segment is a human $V_H1$-69 gene segment. In one embodiment, the heavy chain V gene segment is a human $V_H1$-2 gene segment.

In one aspect, a genetically modified non-human animal is provided, wherein the non-human animal comprises a single functional human $V_H$ gene segment (present as a single copy or multiple copies of different polymorphic forms), and wherein the non-human animal is substantially incapable of forming a rearranged immunoglobulin heavy chain variable domain gene that lacks the single functional human $V_H$ gene segment (or one of the polymorphic forms or copies).

In one aspect, a genetically modified non-human animal is provided, wherein the only immunoglobulin heavy chain variable region expressed in the non-human animal is derived from one of a human segment selected from a human $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, and $V_H7$-81 gene segment. In one embodiment, the human segment is a $V_H1$-69 segment. In one embodiment, the human segment is a $V_H1$-2 segment. In one embodiment, the only immunoglobulin heavy chain variable region expressed by the mouse is derived from a single V segment family member, and in one embodiment the only immunoglobulin heavy chain variable region is derived from a polymorphic variant of the single V segment family member.

In one aspect, a non-human animal comprising a restricted immunoglobulin heavy chain V gene segment repertoire is provided, wherein the non-human animal further comprises one or more human immunoglobulin κ light chain variable segments (Vκ). In one embodiment, the one or more Vκ segments are operably linked to one or more human J segments. In a specific embodiment, the J segments are human Jκ segments. In another specific embodiment, the non-human animal does not express an immunoglobulin λ light chain. In another specific embodiment, the non-human animal does not comprise a functional human or functional endogenous immunoglobulin λ light chain variable locus.

In one embodiment, the non-human animal is a rodent. In one embodiment, the rodent is a mouse.

In one embodiment, the non-human animal comprises a replacement at the endogenous non-human immunoglobulin Vκ locus of all or substantially all functional endogenous Vκ segments with one or more functional human Vκ segments. In a further specific embodiment, the replacement is with all or substantially all functional human immunoglobulin Vκ segments.

In one embodiment, the non-human animal comprises a replacement at the endogenous non-human immunoglobulin Vκ locus of all or substantially all functional endogenous Vκ gene segments with human Vκ gene segments selected from Vκ4-1, Vκ5-2, Vκ7-3, Vκ2-4, Vκ1-5, Vκ1-6, Vκ3-7, Vκ1-8, Vκ1-9, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, Vκ2-40, and a combination thereof.

In one embodiment, the non-human animal comprises a replacement at the endogenous non-human immunoglobulin Jκ locus of all or substantially all functional endogenous non-human immunoglobulin Jκ segments with one or more functional human immunoglobulin Jκ segments. In a further specific embodiment, the replacement is with all or substantially all functional human immunoglobulin Jκ segments.

In one embodiment, the non-human animal comprises a replacement at the endogenous non-human immunoglobulin Jκ locus of all or substantially all functional endogenous non-human immunoglobulin Jκ gene segments with human Jκ gene segments selected from Jκ1, Jκ2, Jκ3, Jκ4, Jκ5, and a combination thereof.

In a specific embodiment, the non-human animal comprises an immunoglobulin heavy chain variable region locus that comprises a repertoire of V segments consisting essentially of a single V segment and/or polymorphic variants thereof. In one embodiment, the single immunoglobulin heavy chain V segment is a human $V_H1$-69 segment, and the non-human animal further comprises a replacement of all functional non-human $D_H$ segments with all functional human $D_H$ segments, and further comprises a replacement of all functional non-human $J_H$ segments with all functional human $J_H$ segments, and wherein the immunoglobulin heavy chain variable region locus is operably linked to a human or non-human constant region gene sequence. In a specific embodiment, the constant region gene sequence is an endogenous non-human constant region gene sequence. In a specific embodiment, the non-human animal rearranges segments at the non-human immunoglobulin heavy chain locus to form a gene encoding heavy chain variable region comprising a human $V_H1$-69 sequence, a human $D_H$ sequence, a human $J_H$ sequence, and a mouse constant region sequence.

In a specific embodiment, the non-human animal comprises an immunoglobulin heavy chain variable region locus that comprises a repertoire of V segments consisting essentially of a single V segment and/or polymorphic variants thereof. In one embodiment, the single immunoglobulin heavy chain V segment is a human $V_H1$-2 segment, and the non-human animal further comprises a replacement of all functional non-human $D_H$ segments with all functional human $D_H$ segments, and further comprises a replacement of all functional non-human $J_H$ segments with all functional human $J_H$ segments, and wherein the immunoglobulin heavy chain variable region locus is operably linked to a human or non-human constant region gene sequence. In a specific embodiment, the constant region gene sequence is an endogenous non-human constant region gene sequence. In a specific embodiment, the non-human animal rearranges segments at the non-human immunoglobulin heavy chain locus to form a gene encoding heavy chain variable region comprising a human $V_H1$-2 sequence, a human $D_H$ sequence, a human $J_H$ sequence, and a mouse constant region sequence.

In one embodiment, a B cell is provided that comprises the rearranged gene. In a specific embodiment, the B cell is from a mouse as described that has been immunized with an antigen of interest, and the B cell encodes an antibody that specifically binds the antigen of interest. In one embodiment, the antigen of interest is a pathogen. In a specific embodiment, the pathogen is selected from an influenza virus, a hepatitis virus (e.g., hepatitis B or hepatitis C virus), and a human immunodeficiency virus. In a specific embodiment, the B cell encodes a somatically mutated, high affinity (e.g., about $10^{-9}$ $K_D$ or lower) antibody comprising a human light chain variable region (e.g., a human κ light chain variable region) that specifically binds the antigen of interest.

In one aspect, a non-human animal comprising a restricted immunoglobulin heavy chain V segment repertoire is provided, wherein the non-human animal comprises one or more human λ light chain variable (Vλ) segments. In one embodiment, the one or more human Vλ segments are operably linked to one or more human J segments. In a specific embodiment, the J segments are human Jλ segments. In another specific embodiment, the non-human animal does not express a κ light chain. In another specific embodiment, the non-human animal does not comprise a functional human or non-human κ light chain variable locus.

In one embodiment, the non-human animal comprises a replacement of all or substantially all functional non-human immunoglobulin Vλ segments with one or more functional human immunoglobulin Vλ segments. In a further specific embodiment, the replacement is with all or substantially all functional human immunoglobulin Vλ segments.

In one embodiment, the non-human animal comprises a replacement of all or substantially all functional non-human Vλ segments with a fragment of cluster A of the human λ light chain locus. In a specific embodiment, the fragment of cluster A of the human λ light chain locus comprises human Vλ gene segments Vλ3-27 through Vλ3-1.

In one embodiment, the non-human animal comprises a replacement of all or substantially all functional non-human Vλ segments with a fragment of cluster B of the human λ light chain locus. In a specific embodiment, the fragment of cluster B of the human λ light chain locus comprises human Vλ gene segments Vλ5-52 through Vλ1-40.

In one embodiment, the non-human animal comprises a replacement of all or substantially all functional non-human Vλ segments with a fragment of cluster A and a fragment of cluster B of the human λ light chain locus, wherein as a result of the replacement comprise human Vλ gene segments Vλ5-52 through Vλ3-1.

In one embodiment, the non-human animal comprises a replacement of all or substantially all functional non-human Vλ segments with at least 12 human Vλ gene segments, at least 28 human Vλ gene segments, or at least 40 human Vλ gene segments.

In one embodiment, the non-human animal comprises a replacement of all or substantially all functional non-human immunoglobulin Jλ gene segments with one or more functional human immunoglobulin Jλ gene segments. In a further specific embodiment, the replacement is with all or substantially all functional human immunoglobulin Jλ gene segments. In various embodiments, the functional human Jλ gene segments include Jλ1, Jλ2, Jλ3 and Jλ7.

In a specific embodiment, the non-human animal comprises an immunoglobulin heavy chain variable ($V_H$) region locus that comprises only a single $V_H$ segment, wherein the single $V_H$ segment is a human $V_H1$-69 segment or a human $V_H1$-2 segment, and further comprises a replacement of all functional non-human $D_H$ segments with all functional human $D_H$ segments, and further comprises a replacement of all functional non-human $J_H$ segments with all functional human $J_H$ segments, and wherein the $V_H$ region locus is operably linked to a human or non-human constant region gene sequence. In a specific embodiment, the constant region gene sequence is a non-human constant region gene sequence, e.g., an endogenous non-human constant gene sequence. In a specific embodiment, the non-human animal rearranges segments at the non-human immunoglobulin heavy chain locus to form a gene encoding an immunoglobulin heavy chain variable region comprising a human $V_H1$-69 sequence (or a human $V_H1$-2 sequence), a human $D_H$ sequence, a human $J_H$ sequence, and an endogenous non-human constant region sequence.

In one embodiment, a B cell is provided that comprises the rearranged gene. In a specific embodiment, the B cell is from a non-human animal as described that has been immunized with an antigen of interest, and the B cell encodes an antibody that specifically binds the antigen of interest. In one embodiment, the antigen is a human protein selected from a ligand, a cell surface receptor and an intracellular protein. In one embodiment, the antigen of interest is a pathogen. In a specific embodiment, the pathogen is selected from an influenza virus, a hepatitis virus (e.g., hepatitis B or hepatitis C virus), and a human immunodeficiency virus. In a specific embodiment, the B cell encodes a somatically mutated, high affinity (e.g., about $10^{-9}$ $K_D$ or lower) antibody comprising a human light chain variable region (e.g., a human λ light chain variable region) that specifically binds the antigen of interest.

In one aspect, a non-human animal comprising a restricted immunoglobulin $V_H$ segment repertoire is provided, wherein the non-human animal comprises a human $V_H1$-69 segment (or a human $V_H1$-2 segment) on a transgene, wherein the human $V_H1$-69 segment is operably linked on the transgene to a human or non-human $D_H$ segment, and/or a human or non-human J segment, and the transgene further comprises a human or non-human constant region gene, or a chimeric human/non-human constant region (e.g., a $C_H1$, hinge, $C_H2$, $C_H3$ or combination thereof wherein at least one sequence is non-human, e.g., selected from hinge, $C_H2$, and $C_H3$ and/or hinge). In one embodiment, the non-human animal is a mouse or rat and the non-human D, J, and/or constant region gene is a mouse or rat gene or chimeric human/mouse or rat.

In one embodiment, the non-human animal comprises a transgene that comprises an immunoglobulin light chain variable region locus that comprises one or more human immunoglobulin Vλ gene segments and Jλ gene segments, or one or more human immunoglobulin Vκ gene segments and Jκ gene segments, and a human immunoglobulin κ or λ light chain constant region gene, such that the transgene rearranges in the non-human animal to form a rearranged immunoglobulin κ or λ light chain gene. In various embodiments, the human Vκ and Jκ gene segments are those described herein. In various embodiments, the human Vλ and Jλ gene segments are those described herein.

In a specific embodiment, the non-human animal comprises a transgene having an immunoglobulin heavy chain variable locus that comprises a single V segment that is a human $V_H1$-69 segment (or a human $V_H1$-2 segment), one or more human D segments, one or more human J segments, and a human constant gene operably linked to the heavy chain variable locus, such that the mouse expresses from the transgene a fully human antibody derived from the $V_H1$-69 segment (or the $V_H1$-2 segment). In one embodiment, the non-human animal does not comprise a functional endogenous immunoglobulin heavy chain variable region locus. In a specific embodiment, the non-human animal comprises a nonfunctional endogenous immunoglobulin heavy chain variable region locus that comprises a deletion of an endogenous non-human $D_H$ and/or endogenous non-human $J_H$ segment, such that the non-human animal is incapable of rearranging the endogenous immunoglobulin heavy chain variable region locus to form a rearranged non-human antibody gene. In a specific embodiment, the non-human animal comprises a deletion of a switch sequence operably linked to an endogenous mouse heavy chain constant region. In a specific embodiment, the switch sequence is a non-human (e.g., mouse) μ switch sequence. In another embodiment, the non-human animal further comprises a lack of a functional endogenous light chain variable locus selected from an immunoglobulin κ locus and an immunoglobulin λ locus. In a specific embodiment, the non-human animal comprises a deletion of a Jκ and/or a Jλ sequence, such that the non-human animal is incapable of rearranging an endogenous non-human immunoglobulin κ light chain and/or an endogenous non-human immunoglobulin λ light chain variable region to form a rearranged endogenous non-human immunoglobulin κ light chain and/or a rearranged endogenous non-human immunoglobulin λ light chain gene.

In one embodiment, the non-human animal comprises a deletion of an endogenous non-human immunoglobulin κ light chain sequence that results in a functional knockout of the endogenous non-human immunoglobulin κ light chain. In one embodiment, the non-human animal comprises a deletion of an endogenous non-human immunoglobulin λ light chain sequence that results in a functional knockout of the endogenous non-human immunoglobulin λ light chain.

In one aspect, the non-human animal comprises a functionally silenced endogenous immunoglobulin heavy chain variable gene locus, and comprises a restricted repertoire of human heavy chain variable gene segments (e.g., no more than one, or no more than two). In one embodiment, the functional silencing comprises a modification of an endogenous non-human heavy chain variable gene locus selected from a deletion, an insertion, an inversion, and a combination thereof.

In one aspect, a rodent is provided that comprises an immunoglobulin $V_H$ repertoire derived from no more than one human $V_H$ segment or one or more polymorphs thereof, from a D segment selected from a repertoire of one or more D segments, and from a J segment derived from a repertoire of one or more J segments. In one embodiment, the rodent rearranges the human $V_H$ segment, a human D segment, and a human J segment and forms a rearranged human heavy chain sequence that is operably linked to a human or a rodent constant region sequence. In one embodiment, the human and/or rodent constant region sequence is selected from a $C_H1$, a hinge, a $C_H2$, a $C_H3$, and a combination thereof. In one embodiment, the rodent expresses an immunoglobulin light chain that comprises a human variable domain, wherein the light chain is cognate with a human heavy chain domain derived from the rearranged human heavy chain sequence. In one embodiment, the rodent does not express a polypeptide sequence selected from a non-human heavy chain variable domain, a non-human light chain variable domain, and a combination thereof.

In one embodiment, the human $V_H$ segment is present in 1, 2, 3, 4, 5, 6, 7, 8, 9, 10, 11, 12, 13, 14, 15, 16, 17, 18, or 19 or more polymorphic variants, wherein each polymorphic variant is operably linked to a D and/or J segment such that each polymorphic variant is capable for rearranging and forming a rearranged heavy chain variable domain with any of the one or more D segments and any of the one or more J segments. In one embodiment, the rodent is a mouse or a rat. In one embodiment, the repertoire of D segments comprises two or more D segments. In one embodiment, the repertoire of J segments comprises two or more J segments. In one embodiment, the D and/or J segments are human segments.

In one aspect, a nucleic acid construct is provided that comprises a sequence encoding a single human immunoglobulin $V_H$ segment and/or polymorphic variants thereof and one or more $D_H$ and one or more J sequences, wherein the construct comprises at least one homology arm homologous to a non-human immunoglobulin heavy chain variable locus, or a recombinase recognition site (e.g., a lox site). In one embodiment, the V segment is a $V_H1$-69 segment or a $V_H1$-2 segment.

In one aspect, a nucleic acid construct is provided; comprising a nucleic acid sequence encoding a single human immunoglobulin heavy chain V segment, wherein the single $V_H$ segment is a $V_H1$-69 (or $V_H1$-2) segment. In one embodiment, the construct comprises a site-specific recombinase recognition site. In one embodiment, the construct comprises a first mouse homology arm upstream of the $V_H1$-69 (or $V_H1$-2) segment and a second mouse homology arm downstream of the $V_H1$-69 (or $V_H1$-2) segment, and wherein the first mouse homology arm is homologous to a region of a mouse chromosome immediately upstream of a mouse immunoglobulin heavy chain variable region but not including a functional mouse immunoglobulin heavy chain variable segment. In one embodiment, the construct comprises SEQ ID NO: 3. In one embodiment, the construct comprises SEQ ID NO: 70.

In one aspect, the restricted single $V_H$ segment is in a non-human animal, or the restricted $V_H$ segment is at a non-human immunoglobulin heavy chain locus (e.g., in situ or in a transgene), and the non-human animal or non-human immunoglobulin heavy chain locus is selected from a mouse, rat, rabbit, pig, bovine (e.g., cow, bull, buffalo), deer, sheep, goat, chicken, cat, dog, ferret, primate (e.g., marmoset, rhesus monkey) locus or animal. In a specific embodiment, the non-human animal or locus is a mouse or a rat locus.

In one aspect, a cell or tissue is provided, wherein the cell or tissue is derived from a non-human animal as described herein, and comprises a restricted $V_H$ segment repertoire. In one embodiment, the $V_H$ segment repertoire is restricted to a single $V_H$ segment family member and/or polymorphic variants thereof. In a specific embodiment, the single $V_H$ segment is a human $V_H1$-69 segment or a human $V_H1$-2 segment. In one embodiment, the cell or tissue is derived from spleen, lymph node or bone marrow of the non-human animal.

In one embodiment, the cell is an ES cell. In one embodiment, the cell is a B cell. In one embodiment, the cell is a germ cell.

In one embodiment, the tissue is selected from connective, muscle, nervous and epithelial tissue. In a specific embodiment, the tissue is reproductive tissue.

In one embodiment, the cell and/or tissue derived from a mouse as described herein are isolated for use in one or more ex vivo assays. In various embodiments, the one or more ex vivo assays include measurements of physical, thermal, electrical, mechanical or optical properties, a surgical procedure, measurements of interactions of different tissue types, the development of imaging techniques, or a combination thereof.

In one embodiment, the non-human animal is a mouse.

In one aspect, a non-human embryo is provided comprising a restricted heavy chain $V_H$ segments as described herein. In one embodiment, the embryo comprises an ES donor cell that comprises the restricted $V_H$ segment, and host embryo cells.

In one embodiment, the non-human animal is a mouse.

In one aspect, a non-human cell comprising a chromosome or fragment thereof of a non-human animal as described herein. In one embodiment, the non-human cell comprises a nucleus of a non-human animal as described herein. In one embodiment, the non-human cell comprises the chromosome or fragment thereof as the result of a nuclear transfer.

In one aspect, a nucleus derived from a non-human animal as described herein is provided. In one embodiment, the nucleus is from a diploid cell that is not a B cell.

In one aspect, a pluripotent, induced pluripotent, or totipotent cell derived from a non-human animal as described herein is provided. In a specific embodiment, the cell is a mouse embryonic stem (ES) cell.

In one aspect, a non-human induced pluripotent cell comprising a restricted $V_H$ segment repertoire is provided. In one embodiment, the induced pluripotent cell is derived from a non-human animal as described herein.

In one aspect, a hybridoma or quadroma is provided, derived from a cell of a non-human animal as described herein. In one embodiment, the non-human animal is a mouse or rat.

In one aspect, a lymphocyte of a non-human animal as described herein is provided. In one embodiment, the lymphocyte is a B cell.

In one aspect, mouse cells and mouse embryos are provided, including but not limited to ES cells, pluripotent cells, and induced pluripotent cells, that comprise genetic modifications as described herein. Cells that are XX and cells that are XY are provided. Cells that comprise a nucleus containing a modification as described herein are also provided, e.g., a modification introduced into a cell by pronuclear injection.

In one aspect, an antibody variable domain sequence made in a non-human animal as described herein is provided.

In one aspect, a human therapeutic is provided, comprising an antibody variable domain comprising a sequence derived from a non-human animal as described herein.

In one aspect, a method of obtaining an antibody variable region sequence from a non-human animal is provided, wherein the antibody variable region sequence is derived from a human $V_H$1-69 segment or a $V_H$1-2 segment, wherein the method comprises (a) immunizing a non-human animal with an antigen of interest, wherein the non-human animal comprises a replacement at the endogenous immunoglobulin heavy chain locus of all or substantially all non-human variable segments with a single human variable segment, wherein the single human variable segment is a $V_H$1-69 segment or a $V_H$1-2 segment, and wherein the non-human animal is substantially incapable of forming a immunoglobulin heavy chain variable region sequence that is not derived from a human $V_H$1-69 segment or a $V_H$1-2 segment; (b) allowing the non-human animal to mount an immune response with respect to the antigen of interest; and, (c) identifying or isolating an immunoglobulin heavy chain variable region sequence of the non-human animal, wherein the antibody binds the antigen of interest.

In one embodiment, the single human variable segment is a $V_H$1-69 segment.

In one embodiment, the antibody variable region sequence is derived from SEQ ID NO: 34. In one embodiment, the antibody variable region sequence is at least 75%, at least 80%, at least 85%, at least 90%, at least 95%, or at least 98% identical to SEQ ID NO: 34. In one embodiment, the antibody variable region sequence comprises SEQ ID NO: 34.

In one embodiment, the single human variable segment is a $V_H$1-2 segment.

In one embodiment, the antibody variable region sequence is derived from SEQ ID NO: 60. In one embodiment, the antibody variable region sequence is at least 75%, at least 80%, at least 85%, at least 90%, at least 95%, or at least 98% identical to SEQ ID NO: 60. In one embodiment, the antibody variable region sequence comprises SEQ ID NO: 60.

In one embodiment, the immune response to the antigen is characterized by an antibody titer that is about $6 \times 10^4$ to about $5 \times 10^5$ times greater than two times background as determined in an ELISA assay. In a specific embodiment, the antibody titer is about $1 \times 10^5$ to about $2 \times 10^5$ times greater than two times background as determined in an ELISA assay. In a specific embodiment, the antibody titer is about $1.5 \times 10^5$ times greater than two times background as determined in an ELISA assay. In one embodiment, the antigen is a human cell surface receptor.

In one aspect, a method for generating a repertoire of human antibody variable regions in a non-human animal is provided, wherein the human heavy chain variable regions of the repertoire are derived from the same $V_H$ gene family member and one of a plurality of $D_H$ segments and one of a plurality of $J_H$ segments, wherein the repertoire is characterized by having heavy chain immunoglobulin FR1 (framework 1), CDR1, FR2, CDR2, and FR3 sequences from a single $V_H$ gene family member. In one embodiment, the repertoire is further characterized by having a plurality of different CDR3+FR4 sequences.

In one embodiment, the single $V_H$ gene family is selected from $V_H$ family 1, 2, 3, 4, 5, 6, and 7. In a specific embodiment, the single $V_H$ gene family is $V_H$ family 1. In one embodiment, the single $V_H$ gene family member is selected from $V_H$1-2, $V_H$1-69, $V_H$2-26, $V_H$2-70, and $V_H$3-23. In a specific embodiment, the single $V_H$ gene family member is $V_H$1-69. In a specific embodiment, the single $V_H$ gene family member is $V_H$1-2.

In one embodiment, the repertoire comprises heavy chain FR1, CDR1, FR2, CDR2 and FR3 sequences derived from a $V_H$1-69 segment. In a specific embodiment, the repertoire comprises heavy chain FR1, CDR1, FR2, CDR2 and FR3 sequences derived from SEQ ID NO: 35. In a specific embodiment, the repertoire comprises heavy chain FR1, CDR1, FR2, CDR2 and FR3 sequences of SEQ ID NO: 35.

In one embodiment, the repertoire comprises heavy chain FR1, CDR1, FR2, CDR2 and FR3 sequences derived from a $V_H$1-2 segment. In a specific embodiment, the repertoire comprises heavy chain FR1, CDR1, FR2, CDR2 and FR3 sequences derived from SEQ ID NO: 61. In a specific embodiment, the repertoire comprises heavy chain FR1, CDR1, FR2, CDR2 and FR3 sequences of SEQ ID NO: 61.

In one aspect, a biological (i.e., in vivo) system is provided for generating a plurality of different human CDR3 sequences reflecting a plurality of rearrangements of a single human $V_H$ gene segment with a plurality of human D and J segments, wherein the system generates human heavy chain variable domains characterized by having human FR1-CDR1-FR2-CDR2-FR3 sequences that are identical but for somatic hypermutations, wherein the heavy chain variable domains are characterized by being somatically hypermutated and derived from a single human $V_H$ gene segment and a plurality of human D and J segments; wherein the system comprises a genetically modified non-human animal (e.g., a rodent, e.g., a mouse or rat) as described herein.

In one embodiment, the single human $V_H$ gene segment is selected from $V_H1$-2, $V_H1$-69, $V_H2$-26, $V_H2$-70, and $V_H3$-23. In one embodiment, the single human $V_H$ gene segment is $V_H1$-69. In one embodiment, the single human $V_H$ gene segment is $V_H1$-2. In one embodiment, the single human $V_H$ gene segment is identified in Table 1. In one embodiment, the single human $V_H$ gene segment is identified in Table 2. In one embodiment, the single human $V_H$ gene segment is identified in Table 3.

In one aspect, an in vivo method for generating a plurality of heavy chain CDR sequences derived from rearrangements of a single human $V_H$ gene segment with a plurality of human D and J segments is provided, wherein the method generates human heavy chain variable domains characterized by having human FR1-CDR1-FR2-CDR2-FR3 sequences that are identical but for somatic hypermutations, wherein the heavy chain variable domains are characterized by being somatically hypermutated and derived from a single human $V_H$ gene segment and a plurality of human D and J segments; wherein the system comprises a genetically modified non-human animal (e.g., a rodent, e.g., a mouse or rat) as described herein.

In one embodiment, the method comprises exposing a non-human animal as described herein to an antigen of interest, allowing the non-human animal to develop an immune response to the antigen, wherein the immune response generates the plurality of heavy chain CDR sequences derived from rearrangements of the single human $V_H$ gene segment with one of the human D and one of the human J segments, and identifying a set of heavy chain CDRs that bind the antigen. In one embodiment, the method comprises isolating from the animal a nucleic acid sequence that encodes a human $V_H$ domain that comprises the heavy chain CDRs.

In one embodiment, the heavy chain CDR sequences are derived from a rearrangement of a human $V_H1$-69 gene segment. In one embodiment, the heavy chain CDR sequences are derived from a rearrangement of a human $V_H1$-2 gene segment.

In one aspect, a method for generating a plurality of different CDR3 and FR4 sequences in a non-human animal is provided, comprising exposing a non-human animal that comprises an immunoglobulin heavy chain variable gene locus with a $V_H$ segment repertoire restricted to a single $V_H$ segment family member to an antigen of interest, allowing the non-human animal to develop an immune response to the antigen, wherein the immune response generates a B cell repertoire whose heavy chain variable domains are each derived from the single $V_H$ segment family member and that comprise a plurality of different CDR3 and FR4 sequences.

In one embodiment, the singe $V_H$ segment family member is human. In one embodiment, the non-human animal is selected from a mouse, a rat, and a rabbit. In one embodiment, the antigen of interest is selected from a ligand, a receptor, an intracellular protein and a secreted protein. In one embodiment, the antigen of interest is a human pathogen as described herein.

In one embodiment, the single human $V_H$ gene family member is selected from $V_H1$-2, $V_H1$-69, $V_H2$-26, $V_H2$-70, and $V_H3$-23. In one embodiment, the single human $V_H$ gene family member is $V_H1$-69. In one embodiment, the single human $V_H$ gene family member is $V_H1$-2. In one embodiment, the single human $V_H$ gene family member is identified in Table 1. In one embodiment, the single human $V_H$ gene family member is identified in Table 2. In one embodiment, the single human $V_H$ gene family member is identified in Table 3.

In one aspect, a nucleotide sequence encoding an immunoglobulin variable region made in a non-human animal as described herein is provided.

In one aspect, an immunoglobulin heavy chain or immunoglobulin light chain variable region amino acid sequence of an antibody made in a non-human animal as described herein is provided.

In one aspect, an immunoglobulin heavy chain or immunoglobulin light chain variable region nucleotide sequence encoding a variable region of an antibody made in a non-human as described herein is provided.

In one aspect, an antibody or antigen-binding fragment thereof (e.g., Fab, F(ab)$_2$, scFv) made in a non-human animal as described herein is provided.

In one aspect, a mouse having a restricted immunoglobulin heavy chain locus characterized by the presence of a single human $V_H$ gene segment, one or more human $D_H$ gene segments, and one or more human $J_H$ gene segments is provided, wherein the single human $V_H$ gene segment is at an endogenous mouse locus and the $V_H$ gene segment is operably linked to the one or more human $D_H$ gene segments, the one or more human $J_H$ gene segments, and to an endogenous immunoglobulin heavy chain constant gene.

In one embodiment, the mouse further comprises a humanized immunoglobulin light chain locus comprising one or more human $V_L$ gene segments, and one or more human $J_L$ gene segments, wherein the human $V_L$ gene segments and the human $J_L$ gene segments are operably linked to a non-human immunoglobulin light chain constant region gene. In a specific embodiment, the human $V_L$ and $J_L$ gene segments are at an endogenous mouse light chain locus, and wherein the non-human immunoglobulin light chain constant region gene is a mouse gene.

In one embodiment, the humanized immunoglobulin light chain locus is on a transgene, and the constant region gene is selected from mouse, rat, and human.

In one embodiment, the human $V_L$ and $J_L$ gene segments are Vκ and Jκ gene segments. In one embodiment, the human $V_L$ and $J_L$ gene segments are Vλ and Jλ gene segments In one aspect, a non-human animal is provided, wherein the non-human animal has a B cell repertoire that expresses immunoglobulin heavy chain variable domains derived from a single V segment family member. In one embodiment, at least 10%, at least 20%, at least 30%, at least 40%, at least 50%, at least 60%, at least 70%, at least 80%, at least 90, or at least 95% of the B cell repertoire of the non-human animal immunoglobulin heavy chain variable domain expressed in the B cell repertoire is derived from the same V segment family member. In a specific embodiment, the percentage is at least 90%. In one embodiment, the B cell repertoire consists essentially of peripheral (blood) B cells. In one embodiment, the B cell repertoire consists essentially of splenic B cells. In one embodiment, the B cell repertoire consists essentially of bone marrow B cells. In one embodiment, the B cell repertoire consists essentially of peripheral B cells, splenic B cells, and bone marrow B cells.

In one aspect, a genetically modified non-human animal is provided, wherein more than 10%, 20%, 30%, 40%, 50%, 60%, 70%, 80%, or more than 90% of the B cells of the non-human animal that express a heavy chain immunoglobulin variable domain express a heavy chain immunoglobulin variable domain derived from a single $V_H$ gene segment family member. In one embodiment, at least 75% of the B cells of the non-human animal that express an immunoglobulin heavy chain variable domain express an immunoglobulin heavy chain variable domain derived from the single $V_H$ gene segment family member. In a specific embodiment, the percentage is at least 90%. In one embodiment, all of the B cells that express a heavy chain domain that is derived from the single $V_H$ gene family member.

In one aspect, a genetically modified mouse is provided that makes an antigen-specific B cell population in response to immunization with an antigen of interest, wherein at least 10%, 20%, 30%, 40%, 50%, 60%, 70%, 80%, or more than 90%, of said antigen-specific B cell population expresses immunoglobulin heavy chains that are all derived from the same $V_H$ gene segment. In one embodiment, at least 75% of the antigen-specific B cell population expresses immunoglobulin heavy chains derived from the same $V_H$ gene segment. In one embodiment, all of the antigen-specific B cells express a heavy chain that is derived from the same $V_H$ gene segment.

In one aspect, a non-human animal comprising a restricted $V_H$ gene segment repertoire is provided, wherein the restriction is to a human $V_H$1-69 gene segment or a $V_H$1-69 gene segment that is at least about 75.5%, 76.5%, 86.7%, 87.8%, 94.9%, 96.9%, 98%, or 99% identical to a $V_H$1-69*01 gene segment. In a specific embodiment, the restricted repertoire is selected from one or more of the $V_H$1-69 variants of FIG. 15.

In one aspect, a non-human animal comprising a restricted $V_H$ gene segment repertoire is provided, wherein the restriction is to a human $V_H$1-2 gene segment or a $V_H$1-2 gene segment that is at least about 94.9%, 95.9%, 96.9%, 98%, or 99% identical to a $V_H$1-2 gene segment. In a specific embodiment, the restricted repertoire is selected from one or more of the $V_H$1-2 variants of FIG. 18.

In one embodiment, the non-human animal is a mouse.

In one embodiment, the mouse exhibits an immunophenotype having a characteristic of a higher ratio of mature B cells to immature B cells as compared to a wild type mouse. In a specific embodiment, the ratio is calculated from B cells harvested from spleen. In one embodiment, the mouse exhibits a population of mature B cells of about 1×10$^7$. In one embodiment, the mouse exhibits a population of immature B cells of about 0.5×10$^7$. In one embodiment, the mouse exhibits a ratio of mature B cells to immature B cells in the spleen of the mouse that is about 1.5-fold to about 2-fold higher than exhibited by a wild type mouse.

In one embodiment, the ratio is calculated from B cells harvested from bone marrow. In a specific embodiment, the mouse exhibits a population of mature B cells of about 3×10$^5$. In one embodiment, the mouse exhibits a population of immature B cells of about 7×10$^5$. In one embodiment, the mouse exhibits a ratio of mature B cells to immature B cells in the bone marrow of the mouse that is about 3-fold, or about 3.3-fold higher than exhibited by a wild type mouse.

In one embodiment, the mouse exhibits an immunophenotype having a characteristic of a higher number of pro B cells in the bone marrow as compared to a wild type mouse. In a specific embodiment, the mouse exhibits a population of pro B cells in the bone marrow of the mouse that is about 2.5-fold to about 3-fold higher than exhibited in the bone marrow of a wild type mouse. In a specific embodiment, the mouse exhibits a population of pro B cells in the bone marrow of the mouse that is about 2.75-fold higher than exhibited in the bone marrow of a wild type mouse.

In one embodiment, the mouse exhibits an immunophenotype having a characteristic selected from the group consisting of a CD19$^+$ splenic B cell population that is about 80% of a wild-type B cell, a CD3$^+$ splenic T cell population that is about the same as a wild type mouse, and a combination thereof.

In one embodiment, the mouse comprises a lymphocyte population whose % CD19$^+$ B cells in spleen are about the same as a wild-type mouse. In one embodiment, the number of CD19$^+$ B cells per spleen of the mouse is at least about 50% of the number of CD19$^+$ B cells per spleen of a wild-type mouse.

In one embodiment, the non-human animal comprises at least about 75% to about 80% of CD19$^+$ B cells in bone marrow as compared with a wild-type mouse.

In one embodiment, the total number of CD19$^+$ bone cells per femur of the mouse is non less than about 30%, 40%, 50%, 60%, or 75% of the total number of CD19+ bone marrow cells in a wild-type mouse.

In one embodiment, the mouse expresses IgD and IgM at about the same level as observed in a wild-type mouse.

In one aspect, a mouse comprising a restricted human $V_H$ segment repertoire is provided, further comprising a humanized immunoglobulin light chain variable segment locus, wherein the ratio of λ to κ light chains expressed in the mouse is about the same as in a wild-type mouse.

In one aspect, a mouse is provided, comprising a restricted immunoglobulin heavy chain locus characterized by the presence of a single $V_H$ gene segment, one or more $D_H$ gene segments, and one or more $J_H$ gene segments, wherein the single $V_H$ gene segment is a polymorphic $V_H$ gene segment.

In one embodiment, the polymorphic $V_H$ gene segment is a human $V_H$ gene segment that is associated with a high copy number in human populations. In one embodiment, the human $V_H$ gene segment is selected from $V_H$1-2, $V_H$1-69, $V_H$2-26, $V_H$2-70, $V_H$3-23, or a polymorphic variant thereof. In a specific embodiment, the human $V_H$ gene segment is a $V_H$1-69 gene segment. In another specific embodiment, the human $V_H$ gene segment is a $V_H$1-2 gene segment.

In one embodiment, the single $V_H$ gene segment is operably linked to a human, mouse, or chimeric human/mouse immunoglobulin constant region gene. In a specific embodiment, the immunoglobulin constant region gene is a mouse constant region gene. In one embodiment, the immunoglobulin constant gene comprises a human sequence selected from a human $C_H$1, a human hinge, a human $C_H$2, a human $C_H$3, and a combination thereof. In one embodiment, the mouse constant gene is at an endogenous immunoglobulin heavy chain locus.

In one embodiment, the mouse further comprises a human immunoglobulin $V_L$ gene segment operably linked to a J gene segment and a light chain constant gene. In a specific embodiment, the $V_L$ gene segment and/or the J gene segment are selected from a human κ gene segment and a human λ gene segment. In one embodiment, the $V_L$ and/or J gene segments are human κ gene segments.

In various embodiments, the mouse comprises a deletion of all or substantially all endogenous $V_H$ gene segments.

In various embodiments, the non-human animal comprises an inactivated endogenous heavy chain variable gene locus. In various embodiments, the inactivated endogenous heavy chain variable gene locus is not operably linked to an endogenous heavy chain constant region gene.

In one aspect, a mouse is provided, wherein the mouse is characterized by the expression of serum immunoglobulin, wherein greater than 80% of the serum immunoglobulin comprises a human heavy chain variable domain and a cognate human light chain variable domain, wherein the human heavy chain variable domain is derived from a $V_H$ gene segment repertoire consisting essentially of a single human $V_H$ gene segment and/or polymorphic variants thereof.

In one embodiment, the single human $V_H$ gene segment is a human $V_H$1-69 gene segment and/or polymorphic variants thereof. In one embodiment, the single human $V_H$ gene segment is a human $V_H$1-2 gene segment and/or polymorphic variants thereof.

In one aspect, a mouse is provided, comprising, in its germline, a replacement at an endogenous immunoglobulin heavy chain locus of all or substantially all endogenous $V_H$ gene segments with a single human $V_H$ gene segment and/or polymorphic variants thereof. In one embodiment, the single human $V_H$ gene segment is a human $V_H$1-69 gene segment and/or polymorphic variants thereof. In one embodiment, the single human $V_H$ gene segment is a human $V_H$1-2 gene segment and/or polymorphic variants thereof.

In one embodiment, the mouse further comprises a replacement at an endogenous immunoglobulin light chain locus of all or substantially all endogenous $V_L$ gene segments with one or more human $V_L$ gene segments. In a specific embodiment, the mouse further comprises one or more human $J_L$ gene segments operably linked to the human $V_L$ gene segments.

In one aspect, use of a mouse as described herein to make an immunoglobulin variable region nucleotide sequence is provided. In one embodiment, the sequence comprises a rearranged $V_H$1-69 gene segment. In one embodiment, the sequence comprises a rearranged $V_H$1-2 gene segment.

In one embodiment, the immunoglobulin variable region nucleotide sequence is at least 80%, at least 85%, at least 90%, at least 95%, or at least 98% identical with a human $V_H$1-69 gene segment. In a specific embodiment, the immunoglobulin variable region nucleotide sequence is at least 80%, at least 85%, at least 90%, at least 95%, or at least 98% identical with SEQ ID NO: 34. In various embodiments, the human $V_H$1-69 gene segment is identified from Table 2.

In one embodiment, the immunoglobulin variable region nucleotide sequence encodes an amino acid sequence that is at least 80%, at least 85%, at least 90%, at least 95%, or at least 98% identical with SEQ ID NO: 35.

In one embodiment, the immunoglobulin variable region nucleotide sequence is at least 80%, at least 85%, at least 90%, at least 95%, or at least 98% identical with a human $V_H$1-2 gene segment. In a specific embodiment, the immunoglobulin variable region nucleotide sequence is at least 80%, at least 85%, at least 90%, at least 95%, or at least 98% identical with SEQ ID NO: 60. In various embodiments, the human $V_H$1-2 gene segment is identified from Table 3.

In one embodiment, the immunoglobulin variable region nucleotide sequence encodes an amino acid sequence that is at least 80%, at least 85%, at least 90%, at least 95%, or at least 98% identical with SEQ ID NO: 61.

In one aspect, use of a mouse as described herein to make a fully human Fab or a fully human F(ab)$_2$ is provided. In one embodiment, the fully human Fab or fully human F(ab)2 comprises a heavy chain variable region that comprises a rearranged human $V_H$1-69 gene segment. In one embodiment, the fully human Fab or fully human F(ab)2 comprises a heavy chain variable region that comprises a rearranged human $V_H$1-2 gene segment.

In one aspect, use of a mouse as described herein to make an immortalized cell line is provided.

In one aspect, use of a mouse as described herein to make a hybridoma or quadroma is provided.

In one aspect, use of a mouse as described herein to make a phage library containing human heavy chain variable regions and human light chain variable regions is provided.

In one embodiment, the human heavy chain variable regions are derived from a human $V_H$1-69 gene segment that comprises a sequence selected from SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56 and SEQ ID NO: 58.

In one embodiment, the human heavy chain variable regions are derived from a human $V_H$1-69 gene segment that comprises a sequence selected from SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57 and SEQ ID NO: 59.

In one embodiment, the human heavy chain variable regions are all derived from a human $V_H$1-2 gene segment that comprises a sequence selected from SEQ ID NO: 60, SEQ ID NO: 62, SEQ ID NO: 64, SEQ ID NO: 66 and SEQ ID NO: 68.

In one embodiment, the human heavy chain variable regions are derived from a human $V_H$1-2 gene segment that comprises a sequence selected from SEQ ID NO: 61, SEQ ID NO: 63, SEQ ID NO: 65, SEQ ID NO: 67 and SEQ ID NO: 69.

In one aspect, use of a mouse as described herein to generate a variable region sequence for making a human antibody is provided, comprising (a) immunizing a mouse as described herein with an antigen of interest, (b) isolating a lymphocyte from the immunized mouse of (a), (c) exposing the lymphocyte to one or more labeled antibodies, (d) identifying a lymphocyte that is capable of binding to the antigen of interest, and (e) amplifying one or more variable region nucleic acid sequence from the lymphocyte thereby generating a variable region sequence.

In one embodiment, the lymphocyte is derived or isolated from the spleen of the mouse. In one embodiment, the lymphocyte is derived or isolated from a lymph node of the mouse. In one embodiment, the lymphocyte is derived or isolated from the bone marrow of the mouse. In one embodiment, the lymphocyte is derived or isolated from the blood of the mouse.

In one embodiment, the labeled antibody is a fluorophore-conjugated antibody. In one embodiment, the one or more fluorophore-conjugated antibodies are selected from an IgM, an IgG, and/or a combination thereof.

In one embodiment, the lymphocyte is a B cell.

In one embodiment, the one or more variable region nucleic acid sequence comprises a heavy chain variable region sequence. In one embodiment, the one or more variable region nucleic acid sequence comprises a light chain variable region sequence. In a specific embodiment, the light chain variable region sequence is an immunoglobulin κ light chain variable region sequence. In one embodiment, the one or more variable region nucleic acid sequence comprises a heavy chain and a κ light chain variable region sequence.

In one embodiment, use of a mouse as described herein to generate a heavy and a κ light chain variable region sequence for making a human antibody is provided, comprising (a) immunizing a mouse as described herein with an antigen of interest, (b) isolating the spleen from the immunized mouse of (a), (c) exposing B lymphocytes from the spleen to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and κ light chain variable region sequences.

In one embodiment, use of a mouse as described herein to generate a heavy and a κ light chain variable region sequence for making a human antibody is provided, comprising (a) immunizing a mouse as described herein with an antigen of interest, (b) isolating one or more lymph nodes from the immunized mouse of (a), (c) exposing B lymphocytes from the one or more lymph nodes to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and κ light chain variable region sequences.

In one embodiment, use of a mouse as described herein to generate a heavy and a κ light chain variable region sequence for making a human antibody is provided, comprising (a) immunizing a mouse as described herein with an antigen of interest, (b) isolating bone marrow from the immunized mouse of (a), (c) exposing B lymphocytes from the bone marrow to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and κ light chain variable region sequences. In various embodiments, the one or more labeled antibodies are selected from an IgM, an IgG, and/or a combination thereof.

In various embodiments, the antigen of interest is a pathogen that afflicts human subjects including, e.g., a viral antigen. Exemplary viral pathogens include, e.g., mainly those of the families of Adenoviridae, bacteria Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Such exemplary viruses typically range between 20-300 nanometers in length. In various embodiments, the antigen of interest is a viral antigen selected from a hepatitis virus (e.g., HCV, HBV, etc.), a human immunodeficiency virus (HIV), or an influenza virus (e.g., H1N1).

In various embodiments, use of a mouse as described herein to generate a heavy and κ light chain variable region sequence for making a human antibody is provided, further comprising fusing the amplified heavy and light chain variable region sequences to human heavy and light chain constant region sequences, expressing the fused heavy and light chain sequences in a cell, and recovering the expressed heavy and light chain sequences thereby generating a human antibody.

In various embodiments, the human heavy chain constant regions are selected from IgM, IgD, IgA, IgE and IgG. In various specific embodiments, the IgG is selected from an IgG1, an IgG2, an IgG3 and an IgG4. In various embodiments, the human heavy chain constant region comprises a $C_H1$, a hinge, a $C_H2$, a $C_H3$, a $C_H4$, or a combination thereof. In various embodiments, the light chain constant region is an immunoglobulin κ constant region. In various embodiments, the cell is selected from a HeLa cell, a DU145 cell, a Lncap cell, a MCF-7 cell, a MDA-MB-438 cell, a PC3 cell, a T47D cell, a THP-1 cell, a U87 cell, a SHSY5Y (human neuroblastoma) cell, a Saos-2 cell, a Vero cell, a CHO cell, a GH3 cell, a PC12 cell, a human retinal cell (e.g., a PER.C6™ cell), and a MC3T3 cell. In a specific embodiment, the cell is a CHO cell.

In one aspect, a method for generating a reverse-chimeric rodent-human antibody specific against an antigen of interest is provided, comprising the steps of immunizing a mouse as described herein with the antigen, isolating at least one cell from the mouse producing a reverse-chimeric mouse-human antibody specific against the antigen, culturing at least one cell producing the reverse-chimeric mouse-human antibody specific against the antigen, and obtaining said antibody.

In one embodiment, the reverse-chimeric mouse-human antibody comprises a human heavy chain variable domain fused with a mouse or rat heavy chain constant gene, and a human light chain variable domain fused with a mouse or rat or human light chain constant gene. In a specific embodiment, the human heavy chain variable domain contains a rearranged human $V_H1$-69 or human $V_H1$-2 gene segment.

In one embodiment, culturing at least one cell producing the reverse-chimeric rodent-human antibody specific against the antigen is performed on at least one hybridoma cell generated from the at least one cell isolated from the mouse.

In one embodiment, the antigen of interest is a pathogen that afflicts human subjects as described herein.

In one aspect, a method for generating a fully human antibody specific against an antigen of interest is provided, comprising the steps of immunizing a mouse as described herein with the antigen, isolating at least one cell from the mouse producing a reverse-chimeric rodent-human antibody specific against the antigen, generating at least one cell producing a fully human antibody derived from the reverse-chimeric rodent-human antibody specific against the antigen, and culturing at least one cell producing the fully human antibody, and obtaining said fully human antibody.

In various embodiments, the at least one cell isolated from the mouse producing a reverse-chimeric rodent-human antibody specific against the antigen is a splenocyte or a B cell.

In various embodiments, the antibody is a monoclonal antibody.

In various embodiments, the antibody comprises a heavy chain variable domain that contains a rearranged human $V_H1$-69 or human $V_H1$-2 gene segment.

In various embodiments, immunization with the antigen of interest is carried out with protein, DNA, a combination of DNA and protein, or cells expressing the antigen. In one embodiment, the antigen of interest is a pathogen that afflicts human subjects as described herein.

In one aspect, use of a mouse as described herein to make a nucleic acid sequence encoding an immunoglobulin variable region or fragment thereof is provided. In one embodiment, the nucleic acid sequence is used to make a human antibody or antigen-binding fragment thereof. In one embodiment, the mouse is used to make an antigen-binding protein selected from an antibody, a multi-specific antibody (e.g., a bi-specific antibody), an scFv, a bi-specific scFv, a diabody, a triabody, a tetrabody, a V-NAR, a $V_{HH}$, a $V_L$, a F(ab), a F(ab)$_2$, a DVD (i.e., dual variable domain antigen-binding protein), a an SVD (i.e., single variable domain antigen-binding protein), or a bispecific T-cell engager (BiTE).

In one aspect, a method for making a human antigen-binding protein is provided, comprising exposing a genetically modified non-human animal as described herein to an antigen of interest, allowing the genetically modified non-human animal to mount an immune response to the antigen, obtaining from the genetically modified non-human animal a heavy chain variable domain nucleic acid sequence encoding a human heavy chain variable domain that specifically binds the antigen of interest, cloning the heavy chain variable domain nucleic acid sequence to a human constant region sequence, and expressing in a mammalian cell an antibody comprising the human heavy chain variable domain sequence and the human constant region sequence. In one embodiment, the mammalian cell is a CHO cell. In one embodiment the genetically modified non-human animal comprises a human $V_H$ gene segment repertoire that consists essentially of a single human $V_H$ gene segment, optionally present in two or more polymorphic variants thereof, operably linked to one or more human D and/or J segments. In one embodiment, the human $V_H$ gene segment repertoire is at an endogenous non-human $V_H$ segment locus. In one embodiment, the human $V_H$ gene segment repertoire is at a locus that is not an endogenous $V_H$ segment locus. In one embodiment, the human $V_H$ gene segment rearranges with a human D segment and a human J segment to form a rearranged human VDJ gene operably linked to a constant region sequence, wherein the constant region sequence is selected from a human sequence and a rodent sequence (e.g., a mouse or rat or hamster sequence). In one embodiment, the constant region sequence comprises a sequence selected from a $C_H1$, a hinge, a $C_H2$, a $C_H3$, and a combination thereof; in a specific embodiment, the constant region sequence comprises a $C_H1$, a hinge, a $C_H2$, and a $C_H3$. In one embodiment, the human variable domain and the constant sequence are expressed in the mammalian cell with a cognate human light chain variable domain obtained from the same mouse (e.g., sequence obtained from the same B cell as the human variable domain sequence); in one embodiment the sequence encoding the human light chain variable domain obtained from the mouse is then fused with a sequence encoding a human light chain constant sequence, and the light chain sequence and the heavy chain sequence are expressed in the mammalian cell.

In one embodiment, the antigen of interest is a pathogen that afflicts human subjects as described herein.

In one aspect, a method for making an antibody heavy chain variable domain that binds an antigen of interest is provided, comprising expressing in a single cell (a) a first $V_H$ sequence of an immunized non-human animal as described herein, wherein the first $V_H$ sequence is fused with a $C_H$ gene sequence; and (b) a $V_L$ gene sequence of an immunized non-human animal as described herein, wherein the $V_L$ gene sequence is fused with a human $C_L$ gene sequence; maintaining the cell under conditions sufficient to express an antibody; and, isolating the antibody heavy chain variable domain. In one embodiment, the $V_L$ gene sequence is cognate with the first $V_H$ sequence.

In one embodiment, the cell comprises a second $V_H$ gene sequence of an immunized non-human animal as described herein, wherein the second $V_H$ gene sequence is fused with a $C_H$ gene sequence, wherein the first $V_H$ gene sequence encodes a $V_H$ domain that specifically binds a first epitope, and the second $V_H$ gene sequence encodes a $V_H$ domain that specifically binds a second epitope, wherein the first epitope and the second epitope are not identical.

In one embodiment, the constant region sequences are all human constant region sequences. In one embodiment, the antigen of interest is a pathogen that afflicts human subjects as described herein.

In one aspect, a method for making a human bispecific antibody is provided, comprising making the bispecific antibody using human variable region gene sequences of B cells of a non-human animal as described herein.

In one embodiment, the method comprises (a) identifying a clonally selected lymphocyte of the non-human animal, wherein the non-human animal has been exposed to an antigen of interest and allowed to develop an immune response to the antigen of interest, and wherein the lymphocyte expresses an antibody that specifically binds the antigen of interest, (b) obtaining from the lymphocyte or the antibody a nucleotide sequence that encodes a human heavy chain variable region that specifically binds the antigen of interest, and (c) employing the nucleotide sequence that encodes the human heavy chain variable region that specifically binds the antigen of interest in making the bispecific antibody. In a specific embodiment, the human heavy chain variable region comprises a rearranged $V_H1$-2 or $V_H1$-69 gene segment.

In one embodiment, steps (a) through (c) are performed a first time for a first antigen of interest to generate a first human heavy chain variable region sequence, and steps (a) through (c) are performed a second time for a second antigen of interest to generate a second human heavy chain variable region sequence, and wherein the first human heavy chain variable region sequence is expressed fused with a first human heavy chain constant region to form a first human heavy chain, the second human heavy chain variable region sequence is expressed fused with a second human heavy chain constant region to form a second human heavy chain, wherein the first and the second human heavy chains are expressed in the presence of a single human light chain expressed from a rearranged human Vκ1-39 or a human Vκ3-20 gene segment. In a specific embodiment, the single human light chain comprises a germline sequence.

In one embodiment, the method comprises (a) cloning heavy chain variable regions from B cells of a non-human animal as described herein which has been exposed to a first antigen of interest, and the same non-human animal, or a different non-human animal which is genetically the same and has been exposed to a second antigen of interest; and (b) expressing in a cell the heavy chain variable regions of (a) with the same heavy chain constant region and the same light chain to make a bispecific antibody.

In one aspect, a use of a non-human animal as described herein is provided, to obtain a nucleic acid sequence that encodes a human heavy chain variable domain. In one embodiment, the heavy chain variable domain comprises a rearranged human $V_H$ gene segment selected from $V_H1$-2 and $V_H1$-69.

In one aspect, a use of a non-human animal as described herein is provided, to obtain a cell that encodes a human heavy chain variable domain. In one embodiment, the heavy chain variable domain comprises a rearranged human $V_H$ gene segment selected from $V_H1$-2 and $V_H1$-69.

In one aspect, use of a non-human animal as described herein to make a human antibody variable domain is provided. In one embodiment, the variable domain comprises a rearranged human $V_H$ gene segment selected from $V_H1-2$ and $V_H1-69$.

In one aspect, use of a non-human animal as described herein to make a human antibody is provided, comprising making the antibody using human variable region gene sequences of B cells of a non-human animal as described herein. In one embodiment, the human antibody is a human bispecific antibody. In a specific embodiment, the bispecific antibody comprises one heavy chain variable domain derived from a rearranged human $V_H1-2$ or $V_H1-69$ gene segment. In one embodiment, the human variable region gene sequences comprise a rearranged human $V_H1-2$ or $V_H1-69$ gene segment.

In one aspect, use of a non-human animal as described herein is provided to select a human immunoglobulin heavy chain variable domain. In one embodiment, the heavy chain variable domain comprises a rearranged human $V_H$ gene segment selected from $V_H1-2$ and $V_H1-69$.

In one aspect, use of the mouse as described herein for the manufacture of a medicament (e.g., an antigen-binding protein), or for the manufacture of a sequence encoding a variable sequence of a medicament (e.g., an antigen-binding protein), for the treatment of a human disease or disorder is provided. In one embodiment, the variable sequence of a medicament comprises a polymorphic human $V_H$ gene segment. In one embodiment, the variable sequence of a medicament comprises a human $V_H1-69$ gene segment. In one embodiment, the variable sequence of a medicament comprises a human $V_H1-2$ gene segment.

In one aspect, a nucleic acid construct encoding an immunoglobulin variable domain made in a mouse as described herein is provided. In one embodiment, the variable domain is a heavy chain variable domain. In a specific embodiment, the heavy chain variable domain comprises a rearranged human $V_H$ gene segment selected from $V_H1-2$, $V_H1-69$, $V_H2-26$, $V_H2-70$, or $V_H3-23$. In another specific embodiment, the heavy chain variable domain comprises a rearranged human $V_H1-2$ gene segment. In another specific embodiment, the heavy chain variable domain comprises a rearranged human $V_H1-69$ gene segment.

In one embodiment, the variable domain is a light chain variable domain. In a specific embodiment, the variable domain is a κ light chain variable domain that is cognate with a human heavy chain variable domain that comprises a rearranged human $V_H1-69$ gene segment. In a specific embodiment, the variable domain is a κ light chain variable domain that is cognate with a human heavy chain variable domain that comprises a rearranged human $V_H1-2$ gene segment.

In one aspect, use of a mouse as described herein to make a nucleic acid construct encoding a human immunoglobulin variable domain is provided. In one embodiment, the variable domain is a light chain variable domain. In one embodiment, the variable domain is a κ light chain variable domain that comprises a rearranged human Vκ gene segment selected from Vκ4-1, Vκ5-2, Vκ7-3, Vκ2-4, Vκ1-5, Vκ1-6, Vκ3-7, Vκ1-8, Vκ1-9, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, and Vκ2-40.

In one embodiment, the variable domain is a heavy chain variable domain. In a specific embodiment, the heavy chain variable domain comprises a rearranged human $V_H$ gene segment selected from $V_H1-2$, $V_H1-69$, $V_H2-26$, $V_H2-70$, or $V_H3-23$. In a specific embodiment, the heavy chain variable domain comprises a rearranged human $V_H1-69$ gene segment. In a specific embodiment, the heavy chain variable domain comprises a rearranged human $V_H1-2$ gene segment.

In one aspect, use of a mouse as described herein to make a human immunoglobulin variable domain is provided. In one embodiment, the variable domain is a light chain variable domain. In one embodiment, the variable domain is a κ light chain variable domain that comprises a rearranged human Vκ gene segment selected from Vκ4-1, Vκ5-2, Vκ7-3, Vκ2-4, Vκ1-5, Vκ1-6, Vκ3-7, Vκ1-8, Vκ1-9, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, and Vκ2-40.

In one embodiment, the variable domain is a heavy chain variable domain. In a specific embodiment, the heavy chain variable domain comprises a rearranged human $V_H$ gene segment selected from $V_H1-2$, $V_H1-69$, $V_H2-26$, $V_H2-70$, or $V_H3-23$. In a specific embodiment, the heavy chain variable domain comprises a rearranged human $V_H1-69$ gene segment. In a specific embodiment, the heavy chain variable domain comprises a rearranged human $V_H1-2$ gene segment.

In one aspect, use of a non-human animal as described herein to make a nucleic acid sequence encoding a human heavy chain variable domain is provided. In one embodiment, the human heavy chain variable domain is characterized by having human FR1-CDR1-FR2-CDR2-FR3 sequences that are derived from a polymorphic human $V_H$ gene segment. In a specific embodiment, the human $V_H$ gene segment is selected from a human $V_H1-2$, $V_H1-69$, $V_H2-26$, $V_H2-70$, or $V_H3-23$ gene segment. In one embodiment, the human $V_H$ gene segment is a human $V_H1-69$ gene segment. In one embodiment, the human $V_H$ gene segment is a human $V_H1-2$ gene segment.

In one aspect, a method for making a nucleic acid sequence encoding a human $V_H$ domain is provided, the method comprising immunizing a non-human animal as described herein with an antigen of interest, allowing the non-human animal to mount an immune response to the antigen of interest, and obtaining therefrom a nucleic acid sequence encoding a human $V_H$ domain that binds the antigen of interest. In one embodiment, the method further comprises making a nucleic acid sequence encoding a human $V_L$ domain that is cognate with the human $V_H$ domain, comprising isolating a B cell encoding the human $V_H$ domain and the human $V_L$ domain, and obtaining therefrom the sequence of the heavy and light chain variable domains. In various embodiments, the human $V_H$ domain is derived from a rearranged human $V_H1-69$ or human $V_H1-2$ gene segment. In various embodiments, the human $V_L$ domain is selected from a human Vκ or a human Vλ domain.

In one aspect, use of a non-human animal as described herein to make a human therapeutic is provided, comprising immunizing the non-human animal with an antigen of interest, allowing the non-human animal to mount an immune response, and obtaining from the animal a nucleic acid sequence encoding an immunoglobulin variable domain that binds the antigen of interest, and employing the immunoglobulin variable domain in a human therapeutic. In one embodiment, the variable domain is a heavy chain variable domain. In a specific embodiment, the heavy chain variable domain is derived from a rearranged human $V_H1-69$ or a human $V_H1-2$ gene segment. In one embodiment, the variable domain is a light chain variable domain. In a specific embodiment, the light chain variable domain is derived from a rearranged human Vκ or human Vλ gene segment.

In one aspect, a method for making a human therapeutic is provided, comprising immunizing a non-human animal as described herein with an antigen of interest, allowing the non-human animal to mount an immune response, and obtaining from the animal a nucleic acid sequence encoding an immunoglobulin variable domain that binds the antigen of interest, and employing the immunoglobulin variable domain in a human therapeutic. In one embodiment, the variable domain is a heavy chain variable domain. In a specific embodiment, the heavy chain variable domain is derived from a rearranged human $V_H$1-69 or a human $V_H$1-2 gene segment. In one embodiment, the variable domain is a light chain variable domain. In a specific embodiment, the light chain variable domain is derived from a rearranged human Vκ or human Vλ gene segment.

In one aspect, a method for making a human antigen-binding protein is provided, comprising immunizing a non-human animal as described herein with an antigen of interest, allowing the animal to mount an immune response, obtaining from the mouse a nucleic acid sequence encoding an immunoglobulin variable domain that specifically binds the antigen of interest, cloning the nucleic acid sequence in a vector suitable for expression of the nucleic acid, wherein the nucleic acid sequence is cloned in frame with a nucleic acid sequence encoding a human immunoglobulin constant region or functional fragment thereof, and inserting the vector in a mammalian cell, and maintaining the cell under conditions suitable for expressing an antigen-binding protein that comprises the immunoglobulin variable domain and the immunoglobulin constant region or functional fragment thereof. In one embodiment, the antigen-binding protein is a human antibody. In a specific embodiment, the antibody comprises a heavy chain variable domain and a light chain variable domain obtained from a mouse as described herein. In a specific embodiment, the antibody comprises a heavy chain variable domain obtained from a mouse as described herein. In various embodiments, the heavy chain variable domain is derived from a rearranged human $V_H$1-69 or a human $V_H$1-2 gene segment.

In one aspect, a nucleic acid sequence encoding a human antigen-binding domain made in a non-human animal as described herein is provided. In one embodiment, the nucleic acid sequence encodes a human immunoglobulin $V_H$ domain. In one embodiment, the nucleic acid sequence encodes a human immunoglobulin $V_H$ domain and a cognate human $V_L$ domain. In various embodiments, the human $V_H$ domain is derived from a rearranged human $V_H$1-69 or a human $V_H$1-2 gene segment.

In one aspect, a method for preparation of a human antibody is provided, comprising immunizing a non-human animal as described herein with an antigen of interest, allowing the non-human animal to mount an immune response, harvesting a lymphocyte (e.g., a B cell) from the immunized animal, fusing the lymphocyte with a myeloma cell to form a hybridoma cell, obtaining from the hybridoma cell a nucleic acid sequence that encodes a human $V_H$ domain and a human $V_L$ domain, cloning the nucleic acid sequence in frame (i.e., in operable linkage) with a human constant region sequence to create an immunoglobulin heavy chain and an immunoglobulin light chain, and expressing the heavy and light chains in a cell capable of expressing the fully human antibody. In one embodiment, the cell is a CHO cell. In various embodiments, the human $V_H$ domain is derived from a rearranged human $V_H$1-69 gene segment or a human $V_H$1-2 gene segment.

In one aspect, a method for preparation of a human antibody is provided, comprising immunizing a non-human animal as described herein with an antigen of interest, allowing the non-human animal to mount an immune response, harvesting a lymphocyte (e.g., a B cell) from the immunized animal, obtaining from the lymphocyte a nucleic acid sequence that encodes a human $V_H$ domain and a human $V_L$ domain, cloning the nucleic acid sequence in frame (i.e., in operable linkage) with a human constant region sequence to create an immunoglobulin heavy chain and an immunoglobulin light chain, and expressing the heavy and light chains in a cell capable of expressing the fully human antibody. In one embodiment, the lymphocyte is derived from the spleen of the non-human animal. In one embodiment, the cell is a CHO cell. In various embodiments, the human $V_H$ domain is derived from a rearranged human $V_H$1-69 gene segment or a human $V_H$1-2 gene segment.

In various aspects, the antigen of interest is a pathogen that afflicts human subjects as described herein. In various aspects, the antigen of interest is a virus that is capable of infecting a human. Exemplary antigens that can be employed in the methods and uses described herein include microbes or microorganisms such as a virus, bacterium, prion, or fungus or any other pathogen that causes disease in humans. A person of skill, upon reading the disclosure, will appreciate those human pathogens that will be applicable for the methods and uses described herein. The various aspects and embodiments are capable of use together, unless expressly noted otherwise or the context clearly prohibits use together.

BRIEF DESCRIPTION OF FIGURES

FIG. 13 shows the nucleotide alignment of the second exon for each of thirteen reported alleles for the human $V_H$1-69 gene. Lower case bases indicate germline nucleotide differences among the alleles. Complementary determining regions (CDRs) are indicated with boxes around the sequence. Dashes indicate artificial gaps for proper sequence alignment. $V_H$1-69*01 (SEQ ID NO: 34); $V_H$1-69*02 (SEQ ID NO: 36); $V_H$1-69*03 (SEQ ID NO: 38); $V_H$1-69*04 (SEQ ID NO: 40); $V_H$1-69*05 (SEQ ID NO: 42); $V_H$1-69*06 (SEQ ID NO: 44); $V_H$1-69*07 (SEQ ID NO: 46); $V_H$1-69*08 (SEQ ID NO: 48); $V_H$1-69*09 (SEQ ID NO: 50); $V_H$1-69*10 (SEQ ID NO: 52); $V_H$1-69*11 (SEQ ID NO: 54); $V_H$1-69*12 (SEQ ID NO: 56); $V_H$1-69*13 (SEQ ID NO: 58).

FIG. 14 shows the protein alignment of the mature heavy chain variable gene sequence for each of thirteen reported alleles for the human $V_H$1-69 gene. Lower case amino acids indicate germline differences among the alleles. Complementary determining regions (CDRs) are indicated with boxes around the sequence. Dashes indicate artificial gaps for proper sequence alignment. $V_H$1-69*01 (SEQ ID NO: 35); $V_H$1-69*02 (SEQ ID NO: 37); $V_H$1-69*03 (SEQ ID NO: 39); $V_H$1-69*04 (SEQ ID NO: 41); $V_H$1-69*05 (SEQ ID NO: 43); $V_H$1-69*06 (SEQ ID NO: 45); $V_H$1-69*07 (SEQ ID NO: 47); $V_H$1-69*08 (SEQ ID NO: 49); $V_H$1-69*09 (SEQ ID NO: 51); $V_H$1-69*10 (SEQ ID NO: 53); $V_H$1-69*11 (SEQ ID NO: 55); $V_H$1-69*12 (SEQ ID NO: 57); $V_H$1-69*13 (SEQ ID NO: 59).

FIG. 15 shows a percent identity/percent similarity matrix for the aligned protein sequences of the mature variable gene for each of thirteen reported alleles for the human $V_H$1-69 gene. Percent identity among the $V_H$1-69 alleles is indicated above the shaded boxes and percent similarity is indicated below the shaded boxes. Scores for percent identity and percent similarity were scored by a ClustalW (v1.83) alignment tool using MacVector software (MacVector, Inc., North Carolina).

FIG. 16 shows the nucleotide alignment of the second exon for each of five reported alleles for the human $V_H$1-2 gene. Lower case bases indicate germline nucleotide differences among the alleles. Complementary determining regions (CDRs) are indicated with boxes around the sequence. Dashes indicate artificial gaps for proper sequence alignment. $V_H$1-2*01 (SEQ ID NO: 60); $V_H$1-2*02 (SEQ ID NO: 62); $V_H$1-2*03 (SEQ ID NO: 64); $V_H$1-2*04 (SEQ ID NO: 66); $V_H$1-2*05 (SEQ ID NO: 68).

FIG. 17 shows the protein alignment of the mature heavy chain variable gene sequence for each of five reported alleles for the human $V_H$1-2 gene. Lower case amino acids indicate germline differences among the alleles. Complementary determining regions (CDRs) are indicated with boxes around the sequence. Dashes indicate artificial gaps for proper sequence alignment. $V_H$1-2*01 (SEQ ID NO: 61); $V_H$1-2*02 (SEQ ID NO: 63); $V_H$1-2*03 (SEQ ID NO: 65); $V_H$1-2*04 (SEQ ID NO: 67); $V_H$1-2*05 (SEQ ID NO: 69).

FIG. 18 shows a percent identity/percent similarity matrix for the aligned protein sequences of the mature variable gene for each of five reported alleles for the human $V_H$1-2 gene.

Percent identity among the $V_H$1-2 alleles is indicated above the shaded boxes and percent similarity is indicated below the shaded boxes. Scores for percent identity and percent similarity were scored by a ClustalW (v1.83) alignment tool using MacVector software (MacVector, Inc., North Carolina).

Figure 19:
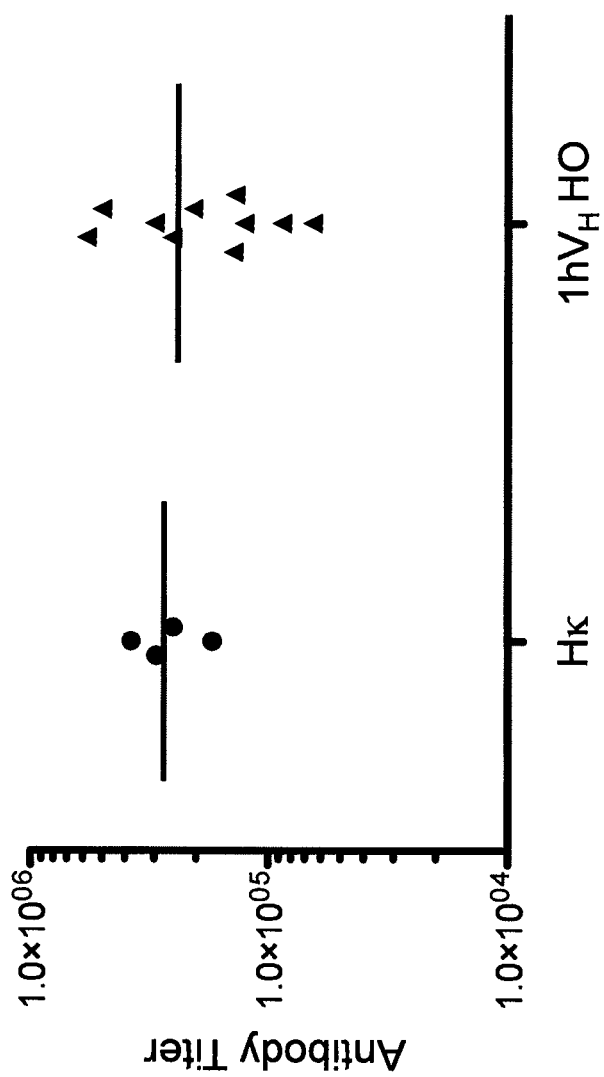

FIG. 19 shows the antibody titer from mice homozygous for human heavy and human κ light chain variable gene loci (Hκ; n=4) and mice homozygous for a single human $V_H$1-69 gene segment, twenty-seven human $D_H$ and six human $J_H$ gene segments at the endogenous immunoglobulin heavy chain locus (1h$V_H$HO; n=10) that were immunized with a human cell surface receptor (Antigen A).

Figure 20:
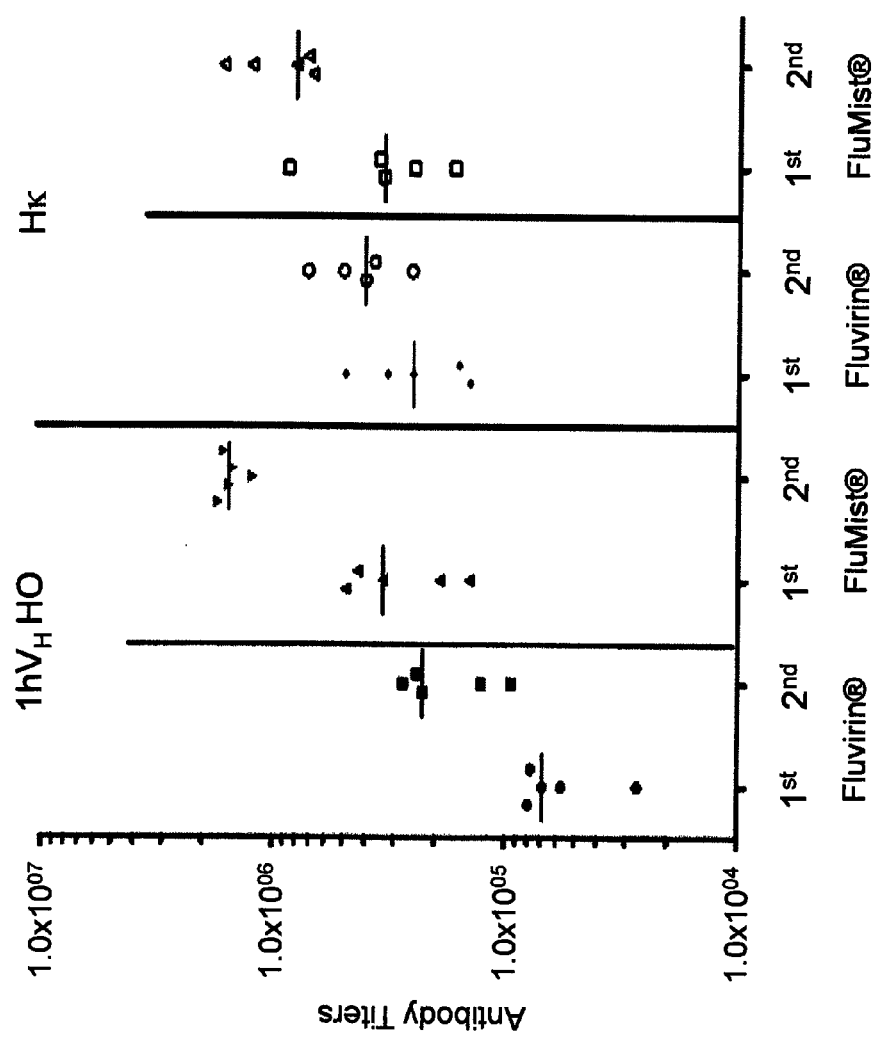

FIG. 20 shows the antibody titer from mice homozygous for human heavy and human κ light chain variable gene loci (Hκ; n=5) and mice homozygous for a single human $V_H$1-69 gene segment, twenty-seven human $D_H$ and six human $J_H$ gene segments at the endogenous immunoglobulin heavy chain locus (1 h$V_H$HO; n=5) that were immunized with two different influenza vaccines.

Figure 21:
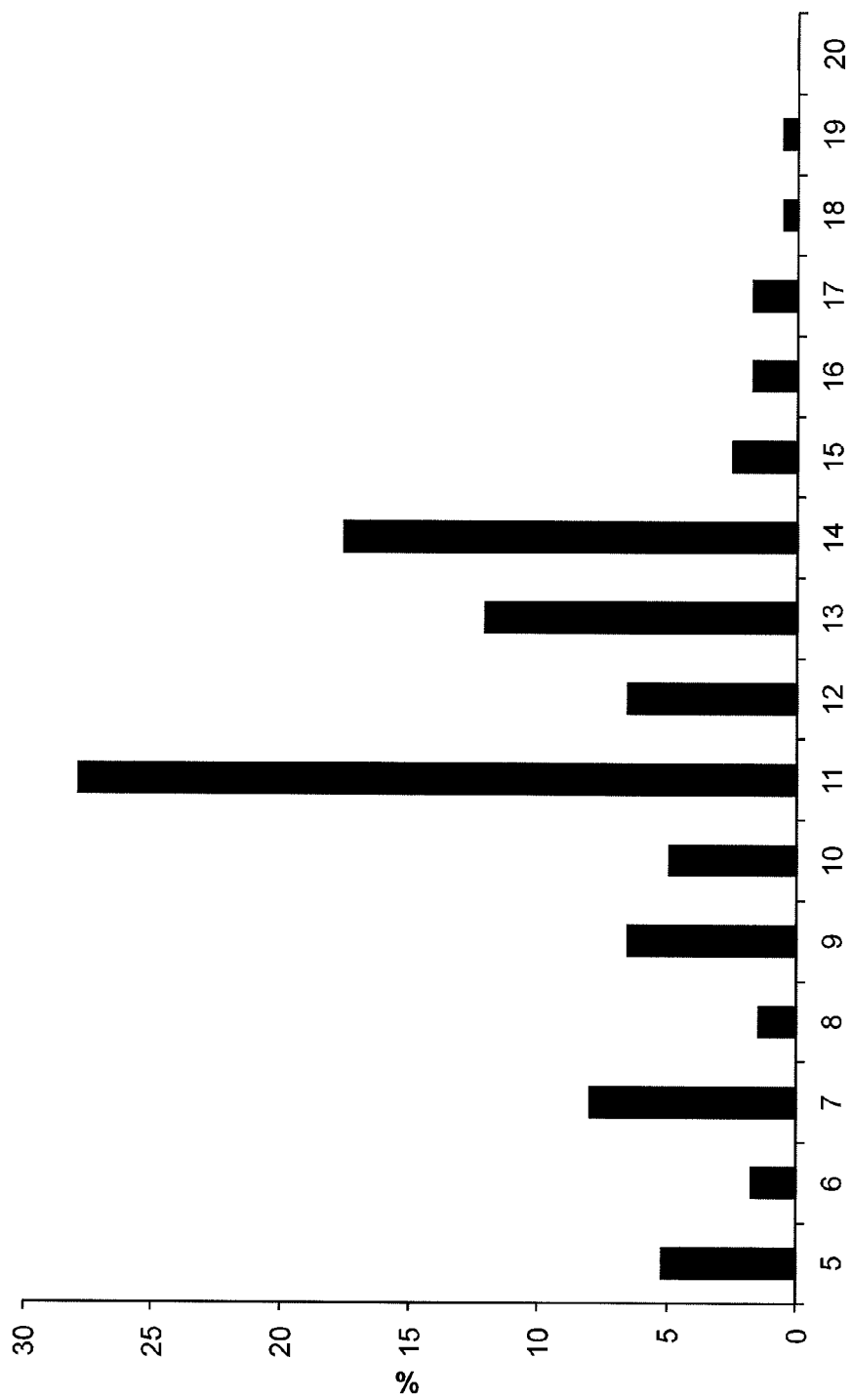

FIG. 21 shows the percentage (y-axis) of IgM-primed heavy chains having a specified amino acid length for the $V_H$ CDR3 region (x-axis) from mice homozygous for a single human $V_H$1-69 gene segment, twenty-seven human $D_H$ and six human $J_H$ gene segments at the endogenous immunoglobulin heavy chain locus and homozygous for a replacement of the endogenous κ light chain variable loci with human κ light chain variable loci that were immunized with a human cell surface receptor (Antigen A).

Figure 22:
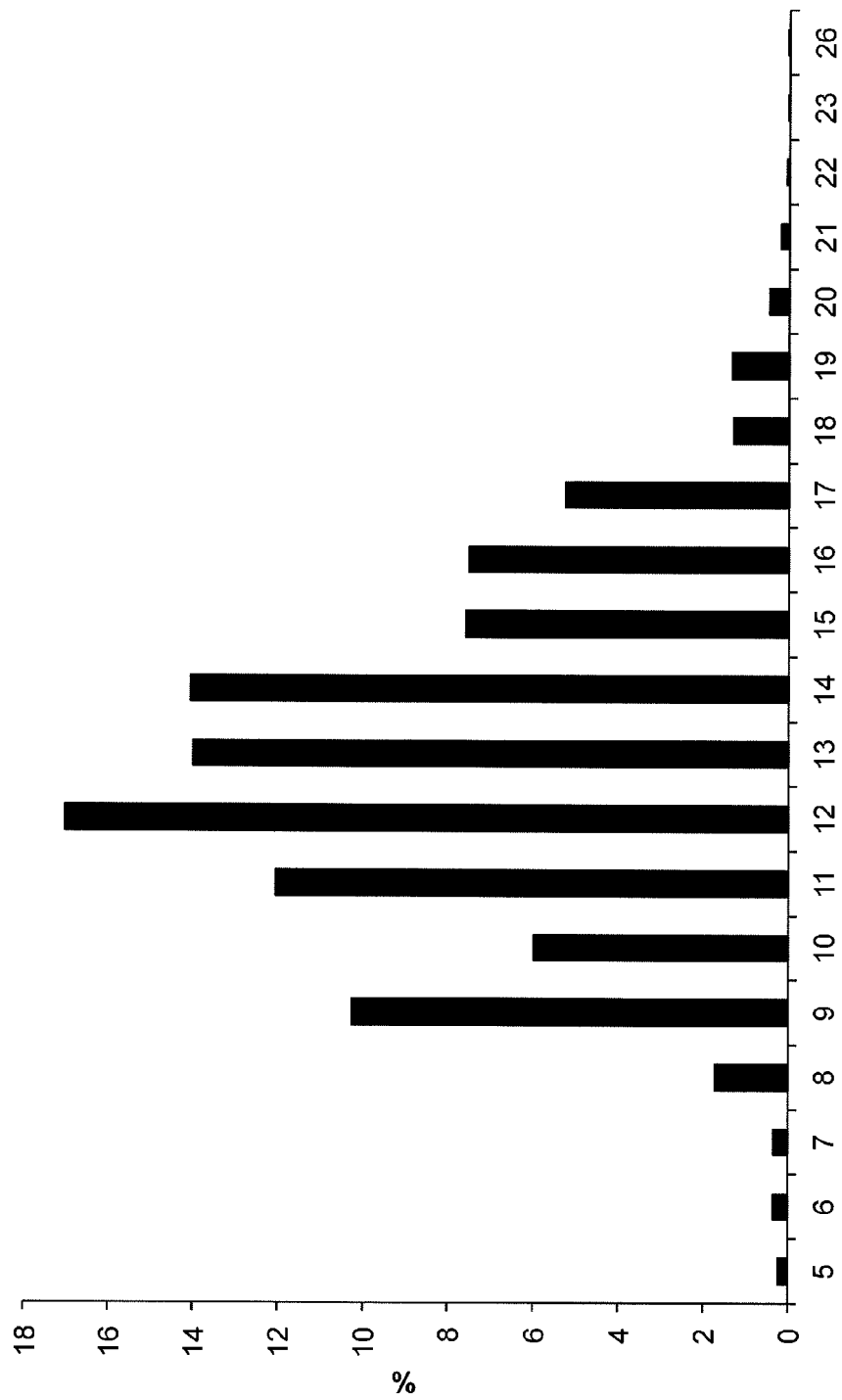

FIG. 22 shows the percentage (y-axis) of IgG-primed heavy chains having a specified amino acid length for the $V_H$ CDR3 region (x-axis) from mice homozygous for a single human $V_H$1-69 gene segment, twenty-seven human $D_H$ and six human $J_H$ gene segments at the endogenous immunoglobulin heavy chain locus and homozygous for a replacement of the endogenous κ light chain variable loci with human κ light chain variable loci that were immunized with a human cell surface receptor (Antigen A).

DETAILED DESCRIPTION

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference.

The phrase "substantial" or "substantially" when used to refer to an amount of gene segments (e.g., "substantially all" V gene segments) includes both functional and non functional gene segments and include, in various embodiments, e.g., 80% or more, 85% or more, 90% or more, 95% or more 96% or more, 97% or more, 98% or more, or 99% or more of all gene segments; in various embodiments, "substantially all" gene segments includes, e.g., at least 95%, 96%, 97%, 98%, or 99% of functional (i.e., non-pseudogene) gene segments.

The term "replacement" includes wherein a DNA sequence is placed into a genome of a cell in such a way as to replace a sequence within the genome with a heterologous sequence (e.g., a human sequence in a mouse), at the locus of the genomic sequence. The DNA sequence so placed may include one or more regulatory sequences that are part of source DNA used to obtain the sequence so placed (e.g., promoters, enhancers, 5'- or 3'-untranslated regions, appropriate recombination signal sequences, etc.). For example, in various embodiments, the replacement is a substitution of an endogenous sequence for a heterologous sequence that results in the production of a gene product from the DNA sequence so placed (comprising the heterologous sequence), but not expression of the endogenous sequence; the replacement is of an endogenous genomic sequence with a DNA sequence that encodes a protein that has a similar function as a protein encoded by the endogenous genomic sequence (e.g., the endogenous genomic sequence encodes an immunoglobulin gene or domain, and the DNA fragment encodes one or more human immunoglobulin genes or domains). In various embodiments, an endogenous gene or fragment thereof is replaced with a corresponding human gene or fragment thereof. A corresponding human gene or fragment thereof is a human gene or fragment that is an ortholog of, a homolog of, or is substantially identical or the same in structure and/or function, as the endogenous gene or fragment thereof that is replaced.

Figure 1:
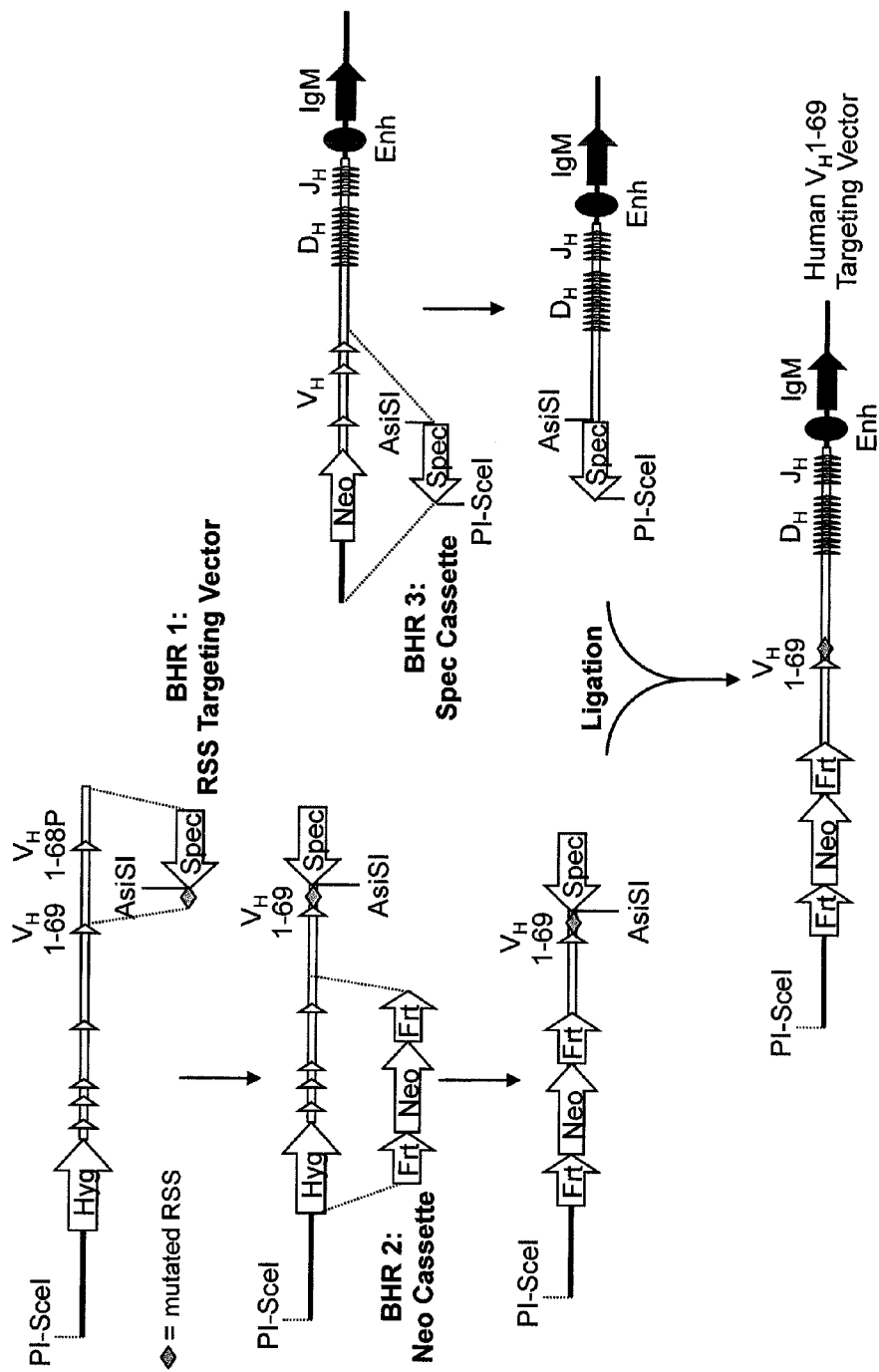
FIG. 1 shows a general illustration, not to scale, of a series of targeting and molecular engineering steps employed to make a targeting vector for construction of a modified heavy chain locus containing a single human $V_H$1-69 gene segment, twenty-seven human $D_H$ and six human $J_H$ gene segments at an endogenous immunoglobulin heavy chain locus.
Figure 2:
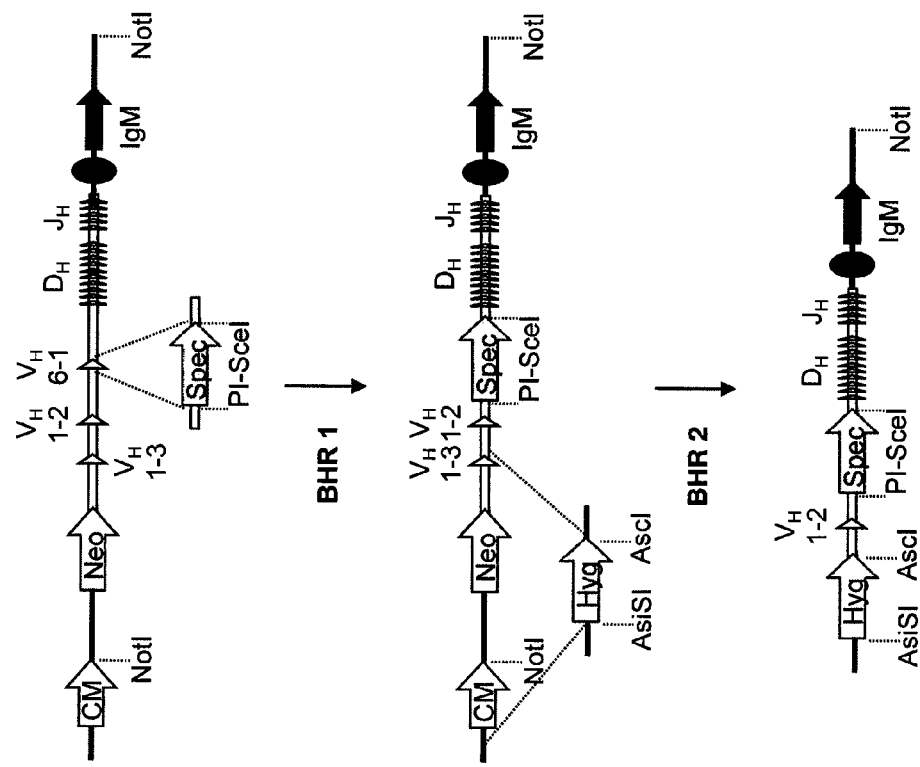
FIG. 2 shows a general illustration, not to scale, of a series of targeting and molecular engineering steps employed to make a targeting vector for construction of a modified heavy chain locus containing a single human $V_H$1-2 gene segment, twenty-seven human $D_H$ and six human $J_H$ gene segments at an endogenous immunoglobulin heavy chain locus.
Figure 3:
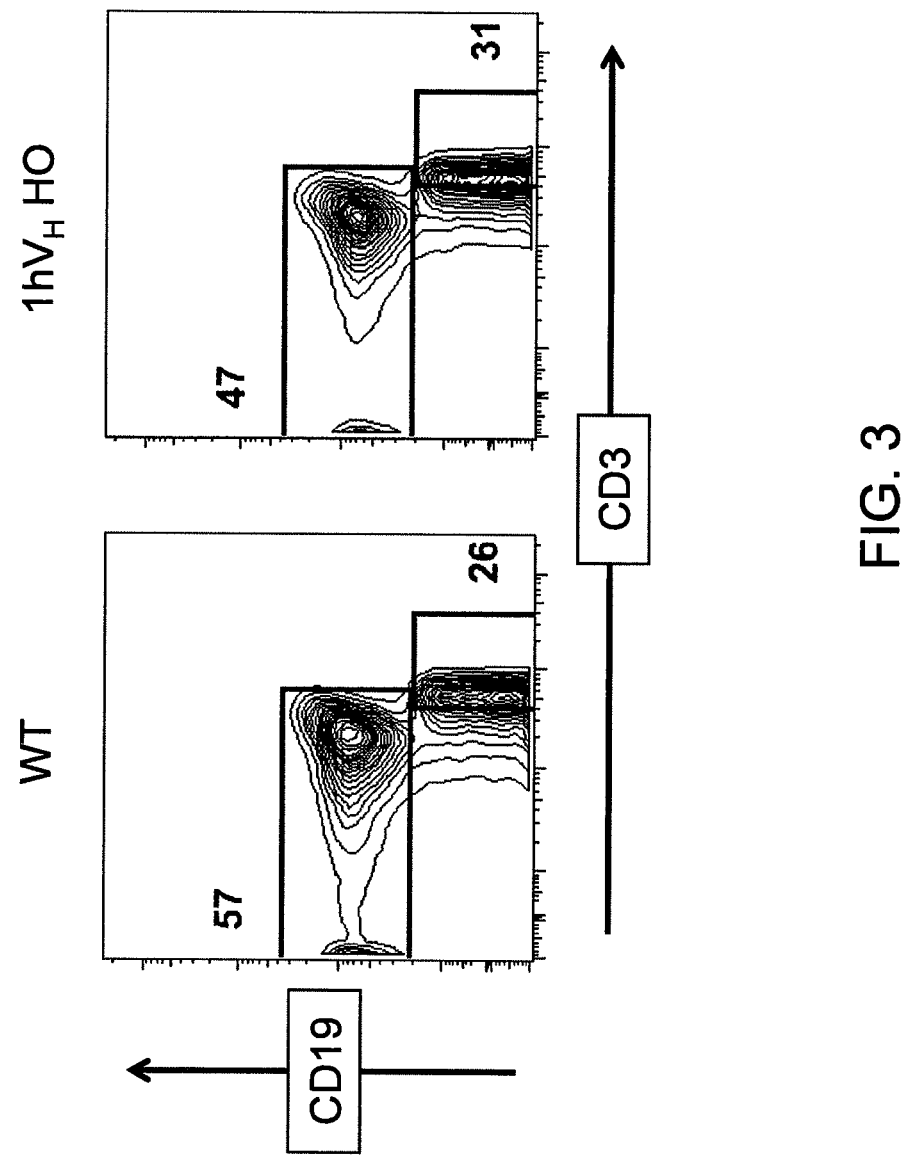
FIG. 3 shows contour plots of splenocytes gated on single lymphocytes and stained for CD19 (B cell) and CD3 (T cell) from a wild type mouse (WT) and a mouse homozygous for a single human $V_H$ gene segment, twenty-seven human $D_H$ and six human $J_H$ gene segments at the endogenous immunoglobulin heavy chain locus (1h$V_H$ HO).
Figure 4A:
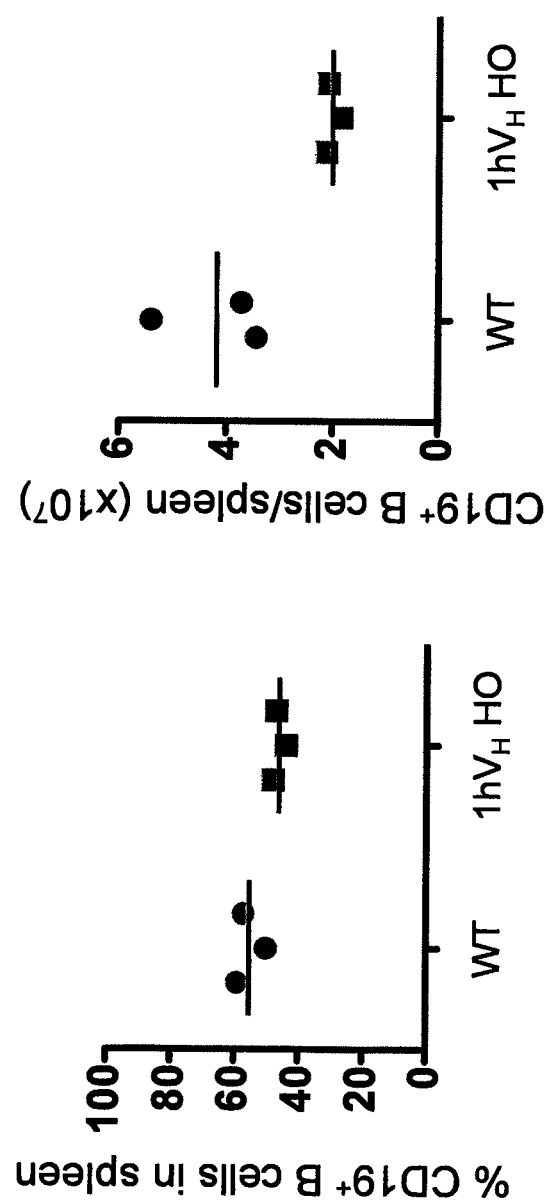
FIG. 4A shows, on the left, the percent of CD19$^+$ B cells in spleens harvested from wild type mice (WT) and mice homozygous for a single human $V_H$ gene segment, twenty-seven human $D_H$ and six human $J_H$ gene segments at the endogenous immunoglobulin heavy chain locus (1 h$V_H$ HO). On the right, the number of CD19$^+$ B cells per spleen is shown for both wild type mice (WT) and mice homozygous for a single human $V_H$ gene segment, twenty-seven human $D_H$ and six human $J_H$ gene segments at the endogenous immunoglobulin heavy chain locus (1h$V_H$ HO).
Figure 4B:
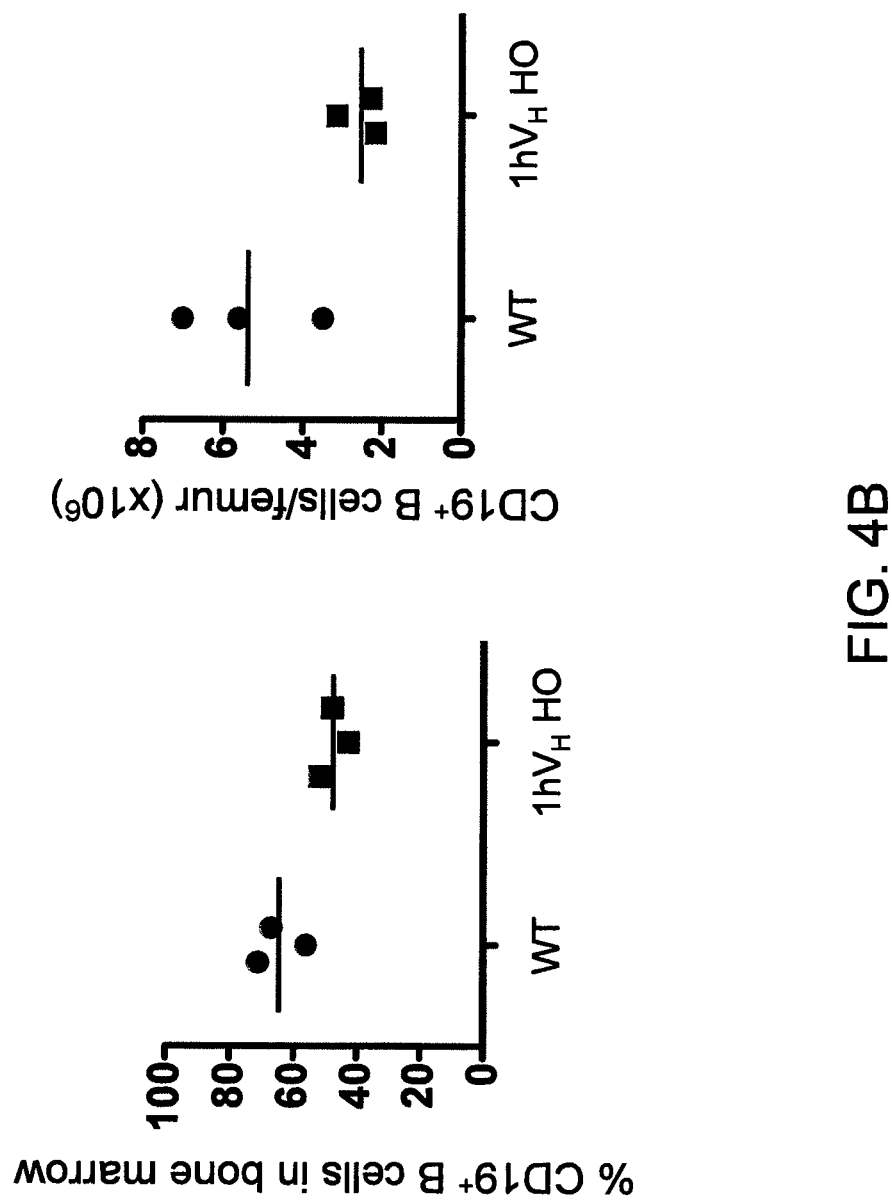
FIG. 4B shows, on the left, the percent of CD19$^+$ B cells in bone marrow harvested from femurs of wild type mice (WT) and mice homozygous for a single human $V_H$ gene segment, twenty-seven human $D_H$ and six human $J_H$ gene segments at the endogenous immunoglobulin heavy chain locus (1 h$V_H$ HO). On the right, the number of CD19+ B cells per femur is shown for both wild type mice (WT) and mice homozygous for a single human $V_H$ gene segment, twenty-seven human $D_H$ and six human $J_H$ gene segments at the endogenous immunoglobulin heavy chain locus (1 h$V_H$ HO).
Figure 5:
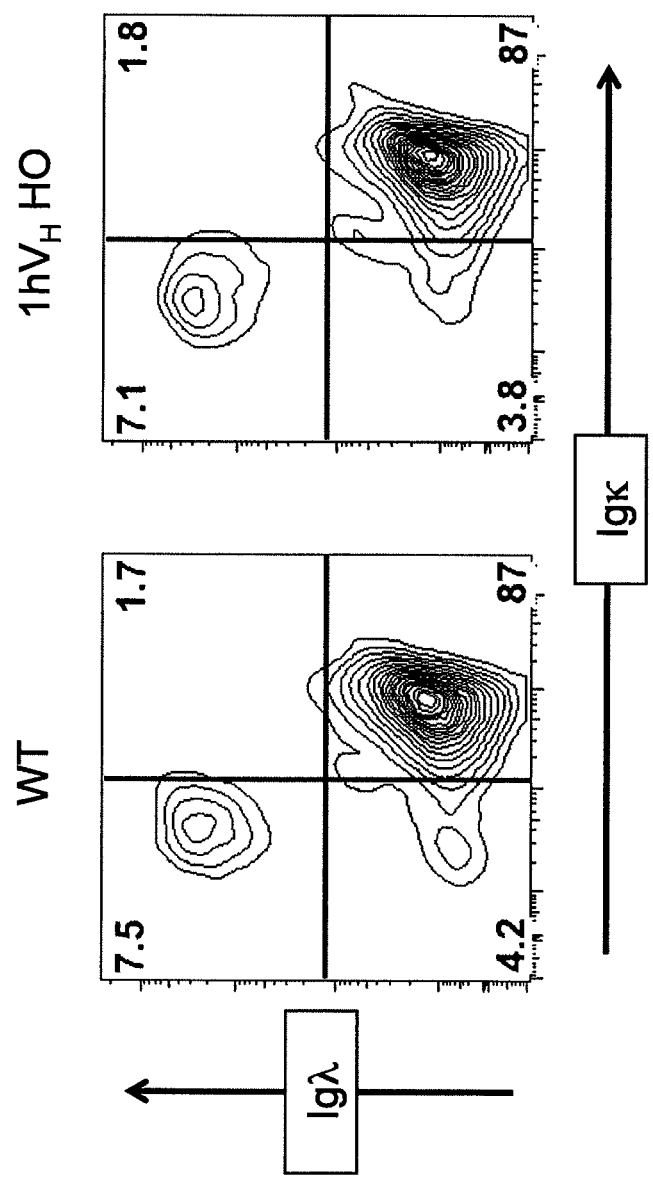
FIG. 5 shows contour plots of splenocytes gated on CD19+ B cells and stained for Igλ+ and Igκ+ expression from a wild type mouse (WT) and a mouse homozygous for a single human $V_H$ gene segment, twenty-seven human $D_H$ and six human $J_H$ gene segments at the endogenous immunoglobulin heavy chain locus (1h$V_H$ HO).
Figure 6:
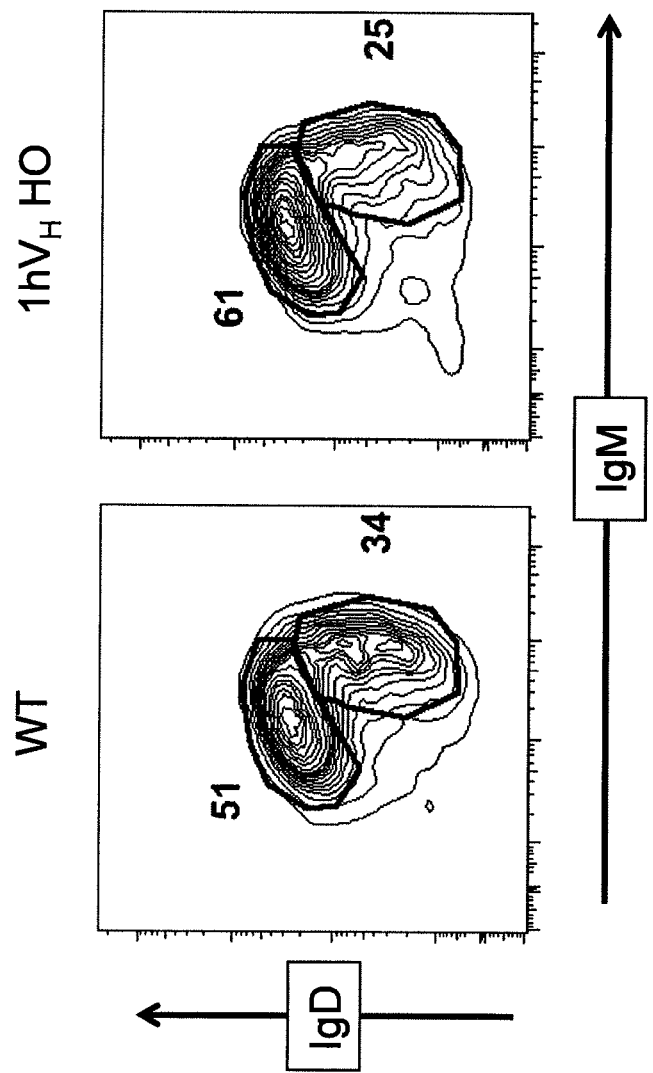
FIG. 6 shows contour plots of splenocytes gated on CD19+ B cells and stained for immunoglobulin D (IgD) and immunoglobulin M (IgM) from a wild type mouse (WT) and a mouse homozygous for a single human $V_H$ gene segment, twenty-seven human $D_H$ and six human $J_H$ gene segments at the endogenous immunoglobulin heavy chain locus (1h$V_H$ HO).
Figure 7:
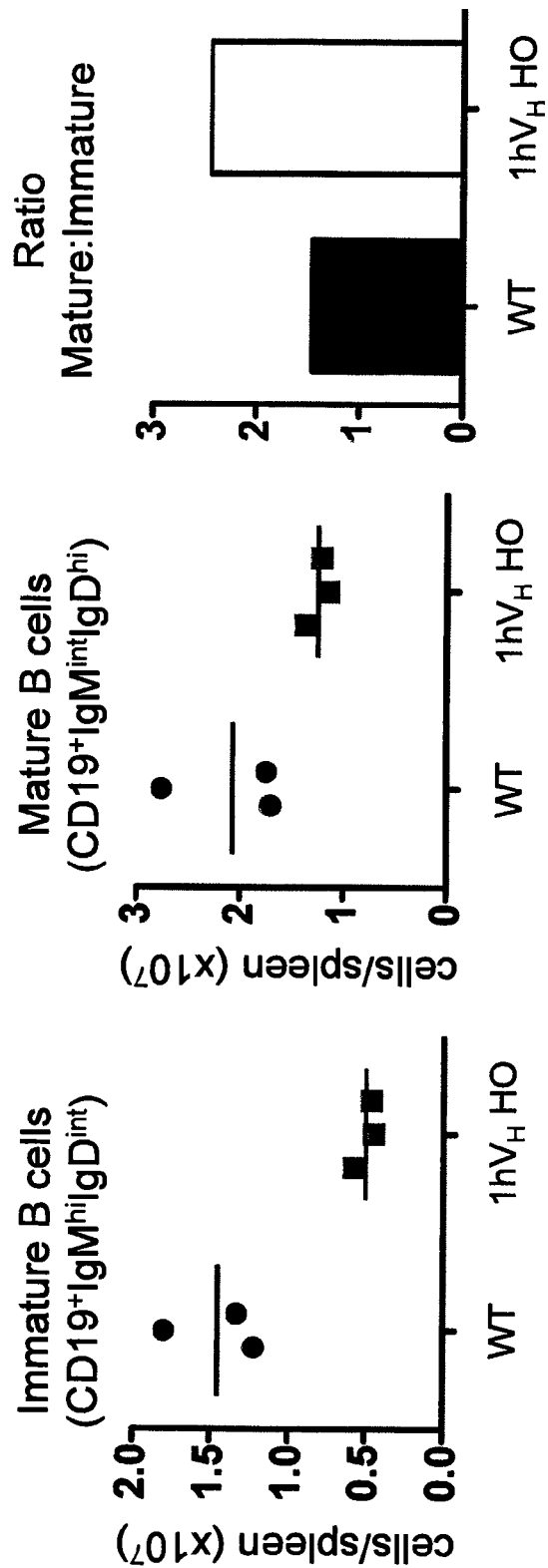
FIG. 7 shows the total number of transitional B cells (CD19+IgM$^{hi}$IgD$^{int}$), mature B cells (CD19+IgM$^{int}$IgD$^{hi}$), and the ratio of mature to immature B cells in harvested spleens from wild type mice (WT) and mice homozygous for a single human $V_H$ gene segment, twenty-seven human $D_H$ and six human $J_H$ gene segments at the endogenous immunoglobulin heavy chain locus (1 h$V_H$ HO).
Figure 8:
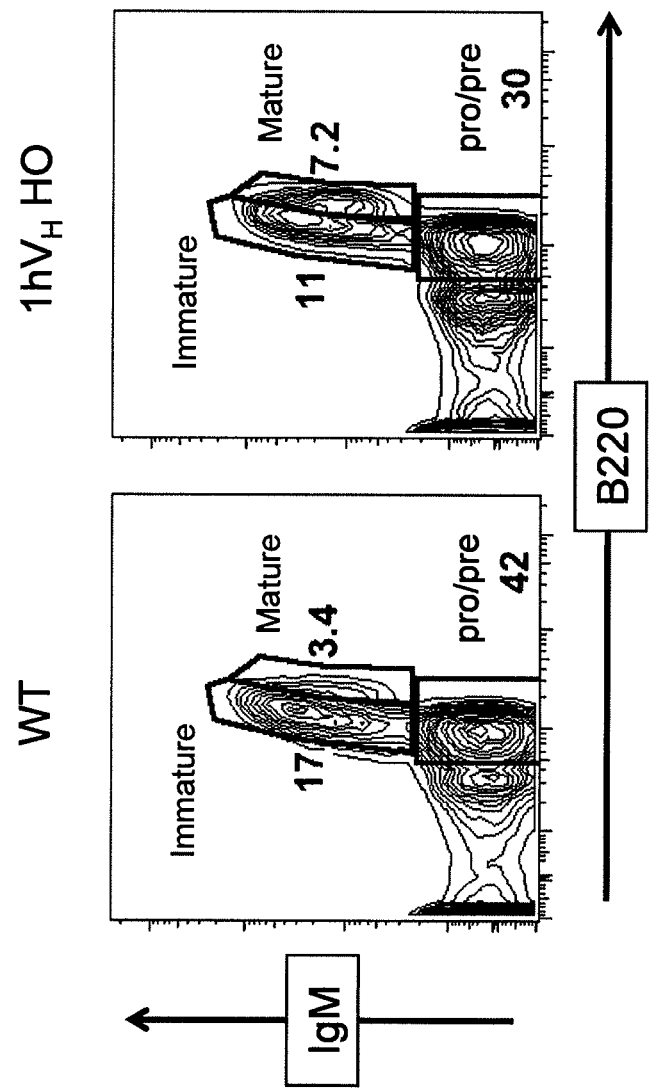
FIG. 8 shows contour plots of bone marrow gated on singlets stained for immunoglobulin M (IgM) and B220 from a wild type mouse (WT) and a mouse homozygous for a single human $V_H$ gene segment, twenty-seven human $D_H$ and six human $J_H$ gene segments at the endogenous immunoglobulin heavy chain locus (1h$V_H$ HO).
Figure 9:
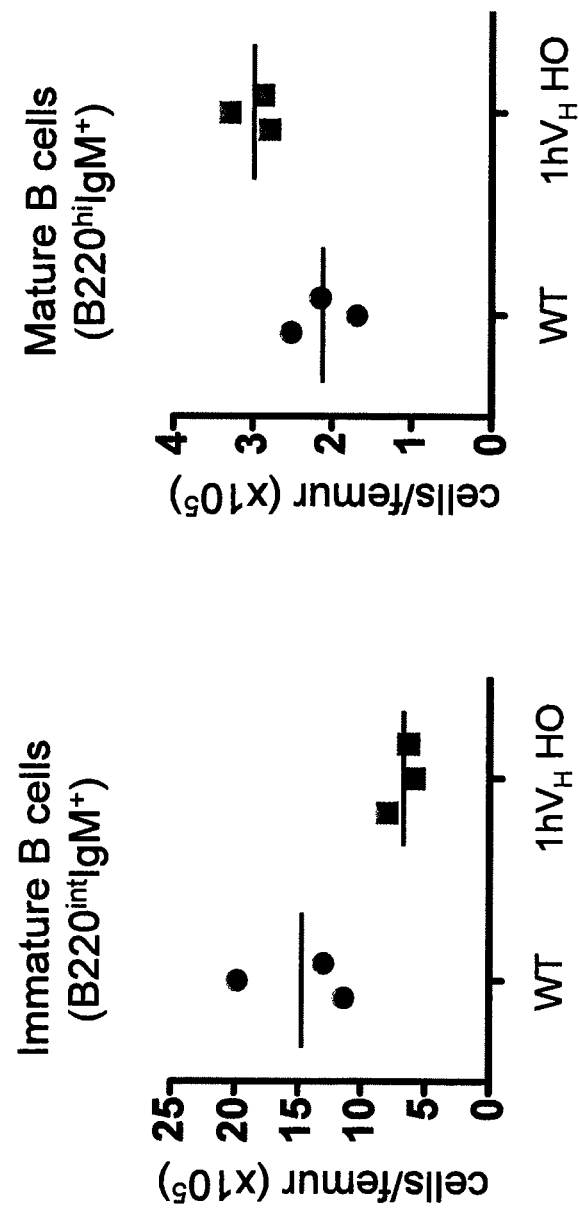
FIG. 9 shows the total number of immature (B220$^{int}$IgM+) and mature (B220$^{hi}$IgM+) B cells in bone marrow isolated from the femurs of wild type mice (WT) and mice homozygous for a single human $V_H$ gene segment, twenty-seven human $D_H$ and six human $J_H$ gene segments at the endogenous immunoglobulin heavy chain locus (1h$V_H$ HO).
Figure 10:
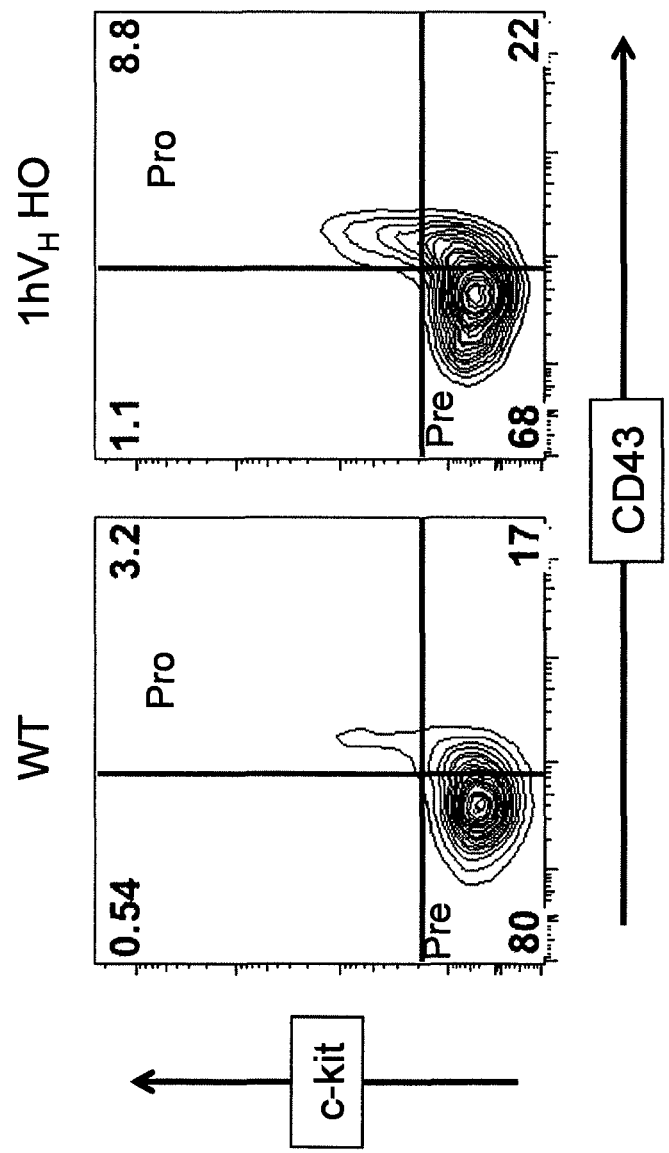
FIG. 10 shows contour plots of bone marrow gated on CD19+ B cells and stained for ckit+ and CD43+ from a wild type mouse (WT) and a mouse homozygous for a single human $V_H$ gene segment, twenty-seven human $D_H$ and six human $J_H$ gene segments at the endogenous immunoglobulin heavy chain locus (1h$V_H$ HO).
Figure 11A:
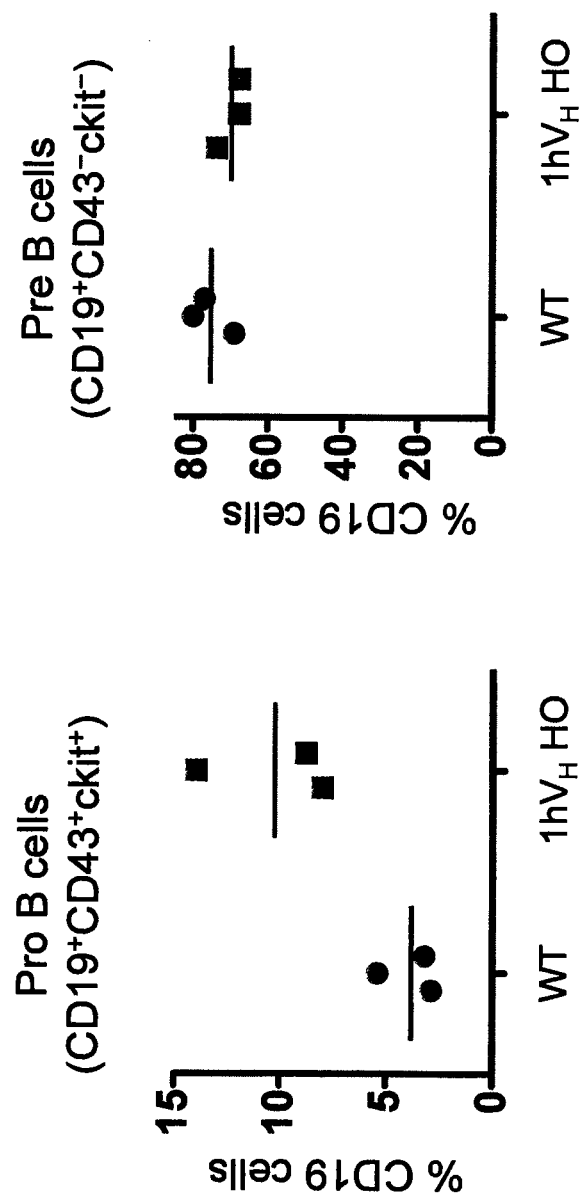
FIG. 11A shows the percent of CD19+ cells in populations of pro B (CD19+CD43+ckit+) and pre B (CD19+CD43$^-$ ckit$^-$) cells in bone marrow harvested from the femurs of wild type mice (WT) and mice homozygous for a single human $V_H$ gene segment, twenty-seven human $D_H$ and six human $J_H$ gene segments at the endogenous immunoglobulin heavy chain locus (1h$V_H$ HO).
Figure 11B:
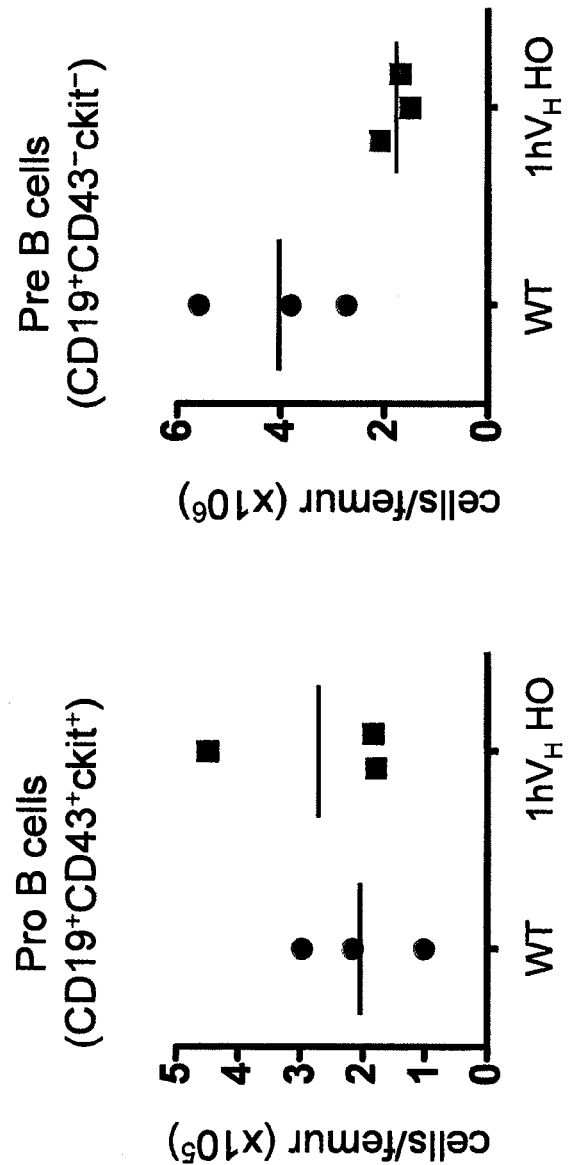
FIG. 11B shows the absolute number of cells per femur in populations of pro B (CD19+CD43+ckit+) and pre B (CD19+ CD43$^-$ckit$^-$) cells in bone marrow harvested from wild type mice (WT) and mice homozygous for a single human $V_H$ gene segment, twenty-seven human $D_H$ and six human $J_H$ gene segments at the endogenous immunoglobulin heavy chain locus (1 h$V_H$ HO).

A precise, in situ replacement of six megabases of the variable regions of the mouse heavy chain immunoglobulin loci ($V_H$-$D_H$-$J_H$) with a restricted human immunoglobulin heavy chain locus was performed, while leaving the flanking mouse sequences intact and functional within the hybrid loci, including all mouse constant chain genes and locus transcriptional control regions (FIG. 1 and FIG. 2). Specifically, a single human $V_H$, 27 $D_H$, and six $J_H$ gene segments were introduced through chimeric BAC targeting vectors into mouse ES cells using VELOCIGENE® genetic engineering technology (see, e.g., U.S. Pat. No. 6,586,251 and Valenzuela et al., 2003, High-throughput engineering of the mouse genome coupled with high-resolution expression analysis, *Nat Biotechnol* 21:652-659).

Non-Human Animals with Restricted Immunoglobulin $V_H$ Gene Segments

Non-human animals comprising immunoglobulin loci that comprise a restricted number of $V_H$ genes, and one or more D genes and one or more J genes, are provided, as are methods of making and using them. When immunized with an antigen of interest, the non-human animals generate B cell populations with antibody variable regions derived only from the restricted, pre-selected $V_H$ gene or set of $V_H$ genes (e.g., a pre-selected $V_H$ gene and variants thereof). In various embodiments, non-human animals are provided that generate B cell populations that express human antibody variable domains that are human heavy chain variable domains, along with cognate human light chain variable domains. In various embodiments, the non-human animals rearrange human heavy chain variable gene segments and human light chain variable gene segments from modified endogenous mouse immunoglobulin loci that comprise a replacement or insertion of the non-human unrearranged variable region sequences with human unrearranged variable region sequences.

Early work on the organization, structure, and function of the immunoglobulin genes was done in part on mice with disabled endogenous loci and engineered to have transgenic loci (randomly placed) with partial human immunoglobulin genes, e.g., a partial repertoire of human heavy chain genes linked with a human constant gene, randomly inserted into the genome, in the presence or absence of a human light chain transgene. Although these mice were somewhat less than optimal for making useful high affinity antibodies, they facilitated certain functional analyses of immunoglobulin loci. Some of these mice had as few as two or three, or even just a single, heavy chain variable gene.

Mice that express fully human immunoglobulin heavy chains derived from a single human $V_H5$-51 gene and 10 human $D_H$ genes and six human $J_H$ genes, with human μ and γ1 constant genes, on a randomly inserted transgene (and disabled endogenous immunoglobulin loci) have been reported (Xu and Davis, 2000, Diversity in the CDR3 Region of $V_H$ Is Sufficient for Most Antibody Specificities, *Immunity* 13:37-45). The fully human immunoglobulin heavy chains of these mice are mostly expressed with one of just two fully mouse λ light chains derived from the endogenous mouse λ light chain locus (Vλ1-Jλ1 or Vλ2-Jλ2 only), and can express no κ light chain (the mice are Igκ$^{-/-}$). These mice exhibit severely abnormal dysfunction in B cell development and antibody expression. B cell numbers are reportedly 5-10% of wild-type, IgM levels 5-10% of wild-type, and IgG1 levels are only 0.1-1% of wild-type. The observed IgM repertoire revealed highly restricted junctional diversity. The fully human heavy chains display largely identical CDR3 length across antigens, the same $J_H$ ($J_H2$) usage across antigens, and an initial junctional Q residue, thus reflecting a certain lack of CDR3 diversity. The fully mouse λ light chains nearly all had a W96L substitution in Jλ1 as initial junctional residue. The mice are reportedly unable to generate any antibodies against bacterial polysaccharide. Because the human variable domains couple with mouse light chains, the utility of the human variable regions is highly limited.

Other mice that have just a single human $V_H3$-23 gene, human $D_H$ and $J_H$ genes, and mouse light chain genes have been reported, but they exhibit a limited diversity (and thus a limited usefulness) due in part to mispairing potential between human $V_H$ and mouse $V_L$ domains (see, e.g., Mageed et al., 2001, Rearrangement of the human heavy chain variable region gene V3-23 in transgenic mice generates antibodies reactive with a range of antigens on the basis of $V_H$CDR3 and residues intrinsic to the heavy chain variable region, *Clin. Exp. Immunol.* 123:1-5). Similarly, mice that bear two $V_H$ genes (3-23 and 6-1) along with human $D_H$ and $J_H$ genes in a transgene containing the human μ constant gene (Bruggemann et al., 1991, Human antibody production in transgenic mice: expression from 100 kb of the human IgH locus, *Eur. J. Immmunol.* 21:1323-1326) and express them in human IgM chains with mouse light chains may exhibit a repertoire limited by mispairing (Mackworth-Young et al., 2003, The role of antigen in the selection of the human V3-23 immunoglobulin heavy chain variable region gene, *Clin. Exp. Immunol.* 134:420-425).

Other transgenic mice that express $V_H$-restricted fully human heavy chains from a human transgene randomly inserted in the genome, with a limited human λ repertoire expressed from a fully human randomly inserted transgene, have also been reported (see, e.g., Taylor et al., 1992, A transgenic mouse that expresses a diversity of human sequence heavy and light chain immunoglobulins, *Nucleic Acids Res.* 20(23):6287-6295; Wagner et al., 1994, Antibodies generated form human immunoglobulin miniloci in transgenic mice, *Nucleic Acids Res.* 22(8):1389-1393). However, transgenic mice that express fully human antibodies from transgenes randomly integrated into the mouse genome, and that comprise damaged endogenous loci, are known to exhibit substantial differences in immune response as compared with wild-type mice that affect the diversity of the antibody variable domains obtainable from such mice.

Useful non-human animals that generate a diverse population of B cells that express human antibody variable domains from a restricted $V_H$ gene repertoire and one or more D genes and one or more J genes will be capable of generating, preferably in some embodiments, repertoires of rearranged variable region genes that will be sufficiently diverse. In various embodiments, diversity includes junctional diversity, somatic hypermutation, and polymorphic diversity in $V_H$ gene sequence (for embodiments where $V_H$ genes are present in polymorphic forms). Combinatorial diversity occurs in the pairing of the $V_H$ gene with one of a plurality of cognate human light chain variable domains (which, in various embodiments, comprise junctional diversity and/or somatic hypermutations).

Non-human animals comprising a restricted human $V_H$ gene repertoire and a complete or substantially complete human $V_L$ gene repertoire will in various embodiments generate populations of B cells that reflect the various sources of diversity, such as junctional diversity (e.g., VDJ, VJ joining, P additions, N additions), combinatorial diversity (e.g., cognate $V_H$-restricted human heavy, human light), and somatic hypermutations. In embodiments comprising a restriction of the $V_H$ repertoire to one human $V_H$ gene, the one human $V_H$ gene can be present in two or more variants. In various embodiments, the presence of two or more polymorphic forms of a $V_H$ gene will enrich the diversity of the variable domains of the B cell population.

Variations in the germline sequences of gene segments (e.g., V genes) contribute to the diversity of the antibody response in humans. The relative contribution to diversity due to V gene sequence differences varies among V genes. The degree of polymorphism varies across gene families, and is reflected in a plurality of haplotypes (stretches of sequence with coinherited polymorphisms) capable of generating further diversity as observed in $V_H$ haplotype differences between related and unrelated individuals in the human population (see, e.g., Souroujon et al., 1989, Polymorphisms in Human H Chain V Region Genes from the $V_H$III Gene Family, *J. Immunol.* 143(2):706-711). Some have suggested, based on data from particularly polymorphic human $V_H$ gene families, that haplotype diversity in the germline is a major contributor to $V_H$ gene heterogeneity in the human population, which is reflected in the large diversity of different germline $V_H$ genes across the human population (see, Sasso et al., 1990, Prevalence and Polymorphism of Human $V_H3$ Genes, *J. Immunol.* 145(8):2751-2757).

Although the human population displays a large diversity of haplotypes with respect to the $V_H$ gene repertoire due to widespread polymorphism, certain polymorphisms are reflected in prevalent (i.e., conserved) alleles observed in the human population (Sasso et al., 1990). $V_H$ polymorphism can be described in two principle forms. The first is variation arising from allelic variation associated with differences among the nucleotide sequence between alleles of the same gene segment. The second arises from the numerous duplications, insertions, and/or deletions that have occurred at the immunoglobulin heavy chain locus. This has resulted in the unique situation in which $V_H$ genes derived by duplication from identical genes differ from their respective alleles by one or more nucleotide substitutions. This also directly influences the copy number of $V_H$ genes at the heavy chain locus.

Polymorphic alleles of the human immunoglobulin heavy chain variable gene segments ($V_H$ genes) have largely been the result of insertion/deletion of gene segments and single nucleotide differences within coding regions, both of which have the potential to have functional consequences on the immunoglobulin molecule. Table 1 sets forth the functional $V_H$ genes listed by human $V_H$ gene family and the number of identified alleles for each $V_H$ gene in the human immunoglobulin heavy chain locus. There are some findings to suggest that polymorphic $V_H$ genes have been implicated in susceptibility to certain diseases such as, for example, rheumatoid arthritis, whereas in other cases a linkage between $V_H$ and disease has been less clear. This ambiguity has been attributed to the copy number and presence of various alleles in different human populations. In fact, several human $V_H$ genes demonstrate copy number variation (e.g., $V_H1-2$, $V_H1-69$, $V_H2-26$, $V_H2-70$, and $V_H3-23$). In various embodiments, humanized mice as described herein with restricted $V_H$ repertoires comprise multiple polymorphic variants of an individual $V_H$ family member (e.g., two or more polymorphic variants of $V_H1-2$, $V_H1-69$, $V_H2-26$, $V_H2-70$, or $V_H3-23$, replacing all or substantially all functional mouse $V_H$ segments at an endogenous mouse locus). In a specific embodiment, the two or more polymorphic variants of mice described herein are in number up to and including the number indicated for the corresponding $V_H$ family member in Table 1 (e.g., for $V_H1-69$, 13 variants; for $V_H1-2$, five variants; etc.).

Commonly observed variants of particular human $V_H$ genes are known in the art. For example, one of the most complex polymorphisms in the $V_H$ locus belongs to the $V_H1-69$ gene. The human $V_H1-69$ gene has 13 reported alleles (Sasso et al., 1993, A fetally expressed immunoglobulin $V_H1$ gene belongs to a complex set of alleles, *Journal of Clinical Investigation* 91:2358-2367; Sasso et al., 1996, Expression of the immunoglobulin $V_H$ gene 51p1 is proportional to its germline gene copy number, *Journal of Clinical Investigation* 97(9):2074-2080) and exists in at least three haplotypes that carry duplications of the $V_H1-69$ gene, which results in multiple copies of the $V_H$ gene at a given locus. These polymorphic alleles include differences in the complementarity determining regions (CDRs), which may dramatically influence antigen specificity. Table 2 sets for the reported alleles for human $V_H1-69$ and the SEQ ID NOs for the DNA and protein sequences of the mature heavy chain variable regions. Table 3 sets forth the reported alleles for human $V_H1-2$ genes and the SEQ ID NOs for the DNA and protein sequences of the mature heavy chain variable regions.

Figure 16:
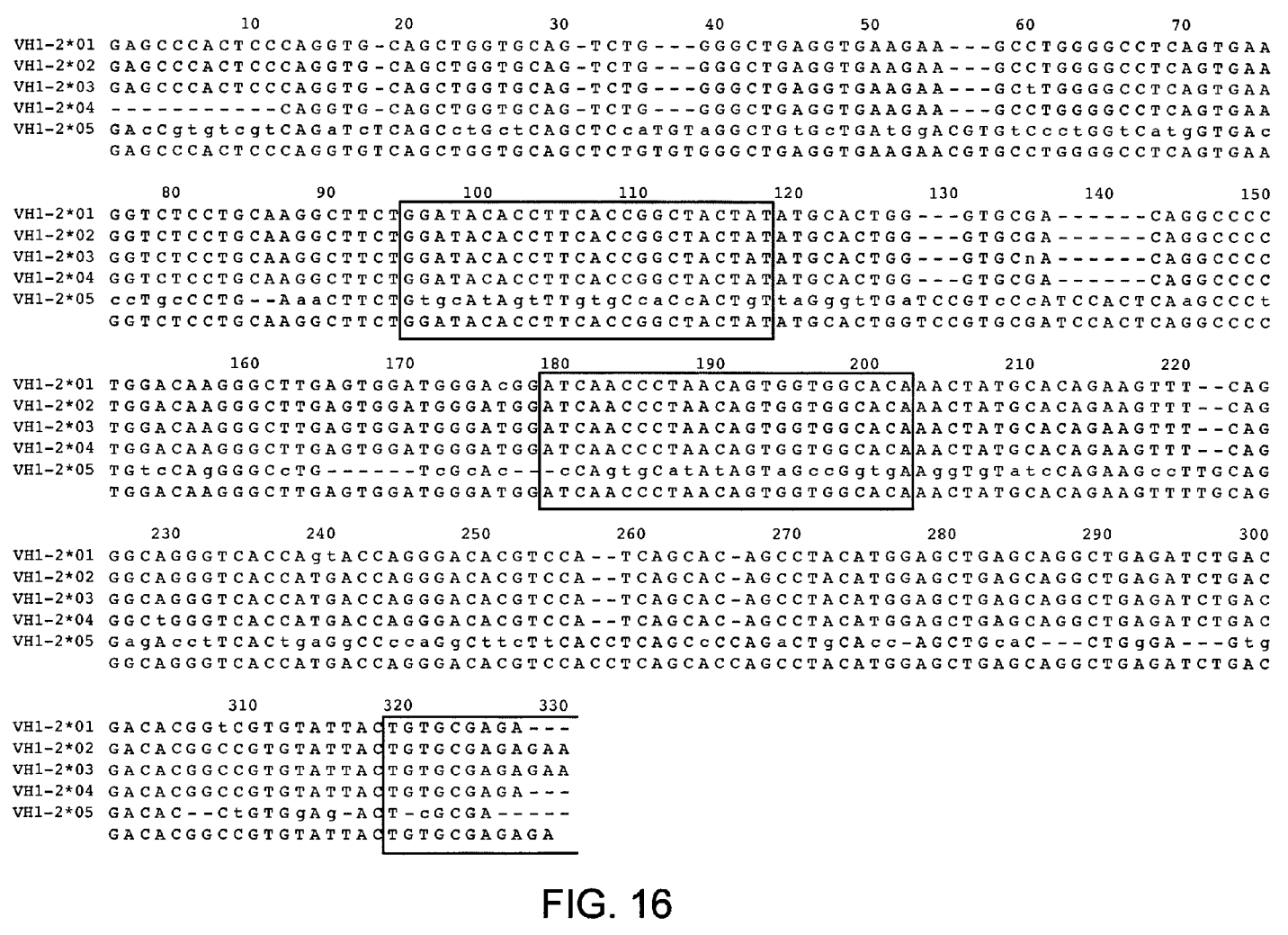

Representative genomic DNA and full-length protein sequences of a $V_H1-69$ gene are set forth in SEQ ID NO: 1 and SEQ ID NO: 2, respectively. FIG. 13 and FIG. 14 set forth DNA and protein alignments of thirteen reported $V_H1-69$ alleles, respectively. Representative DNA and protein sequences of a $V_H1-2$ gene are set forth in SEQ ID NO: 60 and SEQ ID NO: 61, respectively. FIG. 16 and FIG. 17 set forth DNA and protein alignments of five reported $V_H1-2$ alleles, respectively. FIG. 15 and FIG. 18 set forth a percent identity/similarity matrix for aligned protein sequences corresponding to thirteen reported human $V_H1-69$ alleles and five reported human $V_H1-2$ alleles, respectively. In various embodiments, the modified locus of the invention comprises a $V_H$ gene selected from Table 1, present in two or more copy number, wherein the copy number includes up to and including the number of alleles shown in Table 1. In one embodiment, the modified locus of the invention comprises a $V_H1-69$ gene selected from Table 2, present in two or more copy number, wherein the copy number includes up to and including the number of alleles shown in Table 1. In one embodiment, the modified locus of the invention comprises a $V_H1-2$ gene selected from Table 3, present in two or more copy number, wherein the copy number includes up to and including the number of alleles shown in Table 1.

Although embodiments employing a restricted human $V_H$ repertoire in a mouse are extensively discussed, other non-human animals that express a restricted human $V_H$ repertoire are also provided. Such non-human animals include any of those which can be genetically modified to express a restricted human $V_H$ repertoire as disclosed herein, including, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. Methods for modifying a non-human animal genome (e.g., a pig, cow, rodent, chicken, etc. genome) include, e.g., employing a zinc finger nuclease (ZFN) or a transcription activator-like effector nuclease (TALEN) to modify a genome to include a restricted human $V_H$ repertoire. Thus, in one embodiment a method is provided for editing a non-human animal genome to include a restricted human $V_H$ repertoire, comprising a step of editing the genome employing a ZFN or a TALEN to include no more than one, or no more than two, human $V_H$ gene segments (or polymorphic variants thereof), wherein the no more than one or no more than two human $V_H$ gene segments are operably linked to an immunoglobulin constant gene sequence. In one embodiment, the constant gene sequence is selected from a human heavy chain constant sequence and a non-human heavy chain constant sequence. In one embodiment, the constant sequence is non-human and the no more than one or no more than two human $V_H$ gene segments are operably linked to non-human constant gene sequence at an endogenous non-human immunoglobulin locus.

In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae, In one embodiment, the non-human animal is a rodent that is a mouse of a C57BL strain. In one embodiment, the C57BL strain is selected from C57BL/A, C57BL/An, C57BL/GrFa, C57BL/KaLwN, C57BL/6, C57BL/6J, C57BL/6ByJ, C57BL/6N, C57BL/6NJ, C57BL/10, C57BL/10ScSn, C57BL/10Cr, and C57BL/Ola. In another embodiment, the mouse is a 129 strain. In one embodiment, the 129 strain is selected from the group consisting of 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al. (2000) Establishment and Chimera Analysis of 129/SvEv- and C57BL/6-Derived Mouse Embryonic Stem Cell Lines). In one embodiment, the genetically modified mouse is a mix of an aforementioned 129 strain and an aforementioned C57BL strain (e.g., a C57BL/6 strain). In another embodiment, the mouse is a mix of aforementioned 129 strains, or a mix of aforementioned C57BL/6 strains. In one embodiment, the 129 strain of the mix is a 129S6 (129/SvEvTac) strain. In another embodiment, the mouse is a mix of a 129/SvEv- and a C57BL/6-derived strain. In a specific embodiment, the mouse is a mix of a 129/SvEv- and a C57BL/6-derived strain as described in Auerbach et al. 2000 BioTechniques 29:1024-1032. In another embodiment, the mouse is a BALB strain, e.g., BALB/c strain. In another embodiment, the mouse is a mix of a BALB strain (e.g., BALB/c strain) and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more of a strain selected from the group consisting of Wistar, LEA, Sprague Dawley, Fischer, F344, F6, and Dark Agouti.

TABLE 1

| $V_H$ Family | $V_H$ Gene | Alleles |
|---|---|---|
| $V_H1$ | 1-2 | 5 |
| | 1-3 | 2 |
| | 1-8 | 2 |
| | 1-18 | 3 |
| | 1-24 | 1 |
| | 1-45 | 3 |
| | 1-46 | 3 |
| | 1-58 | 2 |
| | 1-69 | 13 |
| $V_H2$ | 2-5 | 10 |
| | 2-26 | 1 |
| | 2-70 | 13 |
| $V_H3$ | 3-7 | 3 |
| | 3-9 | 2 |
| | 3-11 | 4 |
| | 3-13 | 4 |
| | 3-15 | 8 |
| | 3-16 | 2 |
| | 3-20 | 1 |
| | 3-21 | 4 |
| | 3-23 | 5 |
| | 3-30 | 19 |
| | 3-30-3 | 2 |
| | 3-30-5 | 1 |
| | 3-33 | 6 |
| | 3-35 | 1 |
| | 3-38 | 2 |
| | 3-43 | 2 |
| | 3-48 | 4 |
| | 3-49 | 5 |
| | 3-53 | 4 |
| | 3-64 | 5 |
| | 3-66 | 4 |
| | 3-72 | 2 |
| | 3-73 | 2 |
| | 3-74 | 3 |
| $V_H4$ | 4-4 | 7 |
| | 4-28 | 6 |
| | 4-30-1 | 1 |
| | 4-30-2 | 5 |

TABLE 1-continued

| $V_H$ Family | $V_H$ Gene | Alleles |
|---|---|---|
| | 4-30-4 | 6 |
| | 4-31 | 10 |
| | 4-34 | 13 |
| | 4-39 | 7 |
| | 4-59 | 10 |
| | 4-61 | 8 |
| $V_H5$ | 5-51 | 5 |
| $V_H6$ | 6-1 | 2 |
| $V_H7$ | 7-4-1 | 5 |
| | 7-81 | 1 |

TABLE 2

| IgHV1-69 Allele | Accession Number | SEQ ID NO: (DNA/Protein) |
|---|---|---|
| IgHV1-69*01 | L22582 | 34/35 |
| IgHV1-69*02 | Z27506 | 36/37 |
| IgHV1-69*03 | X92340 | 38/39 |
| IgHV1-69*04 | M83132 | 40/41 |
| IgHV1-69*05 | X67905 | 42/43 |
| IgHV1-69*06 | L22583 | 44/45 |
| IgHV1-69*07 | Z29978 | 46/47 |
| IgHV1-69*08 | Z14309 | 48/49 |
| IgHV1-69*09 | Z14307 | 50/51 |
| IgHV1-69*10 | Z14300 | 52/53 |
| IgHV1-69*11 | Z14296 | 54/55 |
| IgHV1-69*12 | Z14301 | 56/57 |
| IgHV1-69*13 | Z14214 | 58/59 |

TABLE 3

| IgHV1-2 Allele | Accession Number | SEQ ID NO: (DNA/Protein) |
|---|---|---|
| IgHV1-2*01 | X07448 | 60/61 |
| IgHV1-2*02 | X62106 | 62/63 |
| IgHV1-2*03 | X92208 | 64/65 |
| IgHV1-2*04 | Z12310 | 66/67 |
| IgHV1-2*05 | HM855674 | 68/69 |

Antigen-Dependent $V_H$ Gene Usage

Antigen-dependent preferential usage of $V_H$ genes can be exploited in the development of human therapeutics targeting clinically significant antigens. The ability to generate a repertoire of antibody variable domains using a particular $V_H$ gene can provide a significant advantage in the search for high-affinity antibody variable domains to use in human therapeutics. Studies on naive mouse and human $V_H$ gene usage in antibody variable domains reveal that most heavy chain variable domains are not derived from any particular single or dominantly used $V_H$ gene. On the other hand, studies of antibody response to certain antigens reveal that in some cases a particular antibody response displays a biased usage of a particular $V_H$ gene in the B cell repertoire following immunization.

Although the human $V_H$ repertoire is quite diverse, by some estimates the expected frequency of usage of any given $V_H$ gene, assuming random selection of $V_H$ genes, is about 2% (Brezinschek et al., 1995, Analysis of the Heavy Chain Repertoire of Human Peripheral B Cells Using Single-Cell Polymerase Chain Reaction, J. Immunol. 155: 190-202). But $V_H$ usage in peripheral B cells in humans is skewed. In one study, functional V gene abundance followed the pattern $V_H3>V_H4>V_H1>V_H2>V_H5>V_H6$ (Davidkova et al., 1997, Selective Usage of $V_H$ Genes in Adult Human Lymphocyte Repertoires, Scand. J. Immunol. 45:62-73).

One early study estimated that $V_H3$ family usage frequency was about 0.65, whereas $V_H1$ family usage frequency was about 0.15; these and other observations suggest that the germline complexity of the human $V_H$ repertoire is not precisely reflected in the peripheral B cell compartment in humans that have a normal germline $V_H$ repertoire, a situation that is similar to that observed in the mouse—i.e., $V_H$ gene expression is non-stochastic (Zouali and These, 1991, Probing $V_H$ Gene-Family Utilization in Human Peripheral B Cells by In Situ Hybridization, *J. Immunol.* 146(8):2855-2864). According to one report, $V_H$ gene usage in humans, from greatest to least, is $V_H3>V_H4>V_H1>V_H5>V_H2>V_H6$; rearrangements in peripheral B cells reveal that $V_H3$ family usage is higher than to be expected based on the relative number of germline $V_H3$ genes (Brezinschek et al., 1995). According to another report $V_H$ usage in humans follows the pattern $V_H3>V_H5>V_H2>V_H1>V_H4>V_H6$, based on analysis of pokeweed mitogen-activated peripheral small immunocompetent B cells (Davidkova et al., 1997, Selective Usage of $V_H$ Genes in Adult Human B Lymphocyte Repertoires, *Scand. J. Immunol.* 45:62-73). One report asserts that among the most frequently used $V_H3$ family members are 3-23, 3-30 and 3-54 (Brezinschek et al., 1995). In the $V_H4$ family, member 4-59 and 4-4b were found relatively more frequently (Id.), as well as 4-39 and 4-34 (Brezinscheck et al., 1997, Analysis of the Human $V_H$ Gene Repertoire, *J. Clin. Invest.* 99(10):2488-2501). Others postulate that the activated heavy chain repertoire is skewed in favor of high $V_H5$ expression and lower $V_H3$ expression (Van Dijk-Hard and Lundkvist, 2002, Long-term kinetics of adult human antibody repertoires, *Immunology* 107:136-144). Other studies assert that the most commonly used $V_H$ gene in the adult human repertoire is $V_H4$-59, followed by $V_H3$-23 and $V_H3$-48 (Arnaout et al., 2001, High-Resolution Description of Antibody Heavy-Chain Repertoires in Humans, *PLoS ONE* 6(8):108). Although usage studies are based on relatively small sample numbers and thus exhibit high variance, taken together the studies suggest that V gene expression is not purely stochastic. Indeed, studies with particular antigens have established that—in certain cases—the deck is firmly stacked against certain usages and in favor of others.

Over time, it became apparent that the observed repertoire of human heavy chain variable domains generated in response to certain antigens is highly restricted. Some antigens are associated almost exclusively with neutralizing antibodies having only certain particular $V_H$ genes, in the sense that effective neutralizing antibodies are derived from essentially only one $V_H$ gene. Such is the case for a number of clinically important human pathogens.

$V_H1$-69-derived heavy chains have been observed in a variety of antigen-specific antibody repertoires of therapeutic significance. For instance, $V_H1$-69 was frequently observed in heavy chain transcripts of an IgE repertoire of peripheral blood lymphocytes in young children with atopic disease (Bando et al., 2004, Characterization of $V_H\epsilon$ gene expressed in PBL from children with atopic diseases: detection of homologous $V_H1$-69 derived transcripts from three unrelated patients, *Immunology Letters* 94:99-106). $V_H1$-69-derived heavy chains with a high degree of somatic hypermutation also occur in B cell lymphomas (Perez et al., 2009, Primary cutaneous B-cell lymphoma is associated with somatically hypermutated immunoglobulin variable genes and frequent use of $V_H1$-69 and $V_H4$-59 segments, *British Journal of Dermatology* 162:611-618), whereas some $V_H1$-69-derived heavy chains with essentially germline sequences (i.e., little to no somatic hypermutation) have been observed among autoantibodies in patients with blood disorders (Pos et al., 2008, $V_H1$-69 germline encoded antibodies directed towards ADAMTS13 in patients with acquired thrombotic thrombocytopenic purpura, *Journal of Thrombosis and Haemostasis* 7:421-428).

Further, neutralizing antibodies against viral antigens such as HIV, influenza and hepatitis C (HCV) have been found to utilize germline and/or somatically mutated $V_H1$-69-derived sequences (Miklos et al., 2000, Salivary gland mucosa-associated lymphoid tissue lymphoma immunoglobulin $V_H$ genes show frequent use of V1-69 with distinctive CDR3 features, *Blood* 95(12):3878-3884; Kunert et al., 2004, Characterization of molecular features, antigen-binding, and in vitro properties of IgG and IgM variants of 4E10, an anti-HIV type I neutralizing monoclonal antibody, *Aids Research and Human Retroviruses* 20(7):755-762; Chan et al., 2001, $V_H1$-69 gene is preferentially used by hepatitis C virus-associated B cell lymphomas and by normal B cells responding to the E2 viral antigen, *Blood* 97(4):1023-1026; Carbonari et al., 2005, Hepatitis C virus drives the unconstrained monoclonal expansion of $V_H1$-69-expressing memory B cells in type II cryoglobulinemia: A model of infection-driven lymphomagenesis, *Journal of Immunology* 174:6532-6539; Wang and Palese, 2009, Universal epitopes of influenza virus hemagglutinins?, *Nature Structural & Molecular Biology* 16(3):233-234; Sui et al., 2009, Structural and functional bases for broad-spectrum neutralization of avian and human influenza A viruses, *Nature Structural & Molecular Biology* 16(3):265-273; Marasca et al., 2001, Immunoglobulin Gene Mutations and Frequent Use of $V_H1$-69 and $V_H4$-34 Segments in Hepatitis C Virus-Positive and Hepatitis C Virus-Negative Nodal Marginal Zone B-Cell Lymphoma, *Am. J. Pathol.* 159(1):253-261).

$V_H$ usage bias is also observed in the humoral immune response to *Haemophilus influenzae* type b (Hib PS) in humans. Studies suggest that the $V_H$III family (the $V_H$IIIb subfamily in particular, $V_H9.1$) exclusively characterizes the human humoral response to Hib PS, with diverse D and J genes (Adderson et al., 1991, Restricted Ig H Chain V Gene Usage in the Human Antibody Response to *Haemophilus influenzae* Type b Capsular Polysaccharide, *J. Immunol.* 147(5):1667-1674; Adderson et al., 1993, Restricted Immunoglobulin $V_H$ Usage and VDJ Combinations in the Human Response to *Haemophilus influenzae* Type b Capsular Polysaccharide, *J. Clin. Invest.* 91:2734-2743). Human $J_H$ genes also display biased usage; $J_H4$ and $J_H6$ are observed at about 38-41% in peripheral B cells in humans (Brezinschek et al., 1995).

$V_H$ usage in HIV-1-infected humans is reportedly biased against $V_H3$ usage and in favor of $V_H1$ and $V_H4$ gene families (Wisnewski et al., 1996, Human Antibody Variable Region Gene Usage in HIV-1 Infection, *J. Acquired Immune Deficiency Syndromes & Human Retrovirology* 11(1):31-38). However, cDNA analysis of bone marrow from affected patients' revealed significant $V_H3$ usage not expressed in the functional B cell repertoire, where Fabs reflecting the $V_H3$ usage exhibited effective in vitro neutralization of HIV-1 (Id.). It might be postulated that the humoral immune response to HIV-1 infection is possibly attenuated due to the $V_H$ restriction; modified non-human animals as described herein (not infectable by HIV-1) might thus be useful for generating neutralizing antibody domains derived from particular $V_H$ genes present in the genetically modified animals described herein, but derived from different $V_H$ genes than those observed in the restricted repertoire of affected humans.

Thus, the ability to generate high affinity human antibody variable domains in $V_H$-restricted mice, e.g., (restricted, e.g., to a $V_H3$ family member and polymorph(s) thereof) immunized with HIV-1 might provide a rich resource for designing effective HIV-1-neutralizing human therapeutics by thoroughly mining the restricted (e.g., restricted to a $V_H3$ family member or variant(s) thereof) repertoire of such an immunized mouse.

Restriction of the human antibody response to certain pathogens may reduce the likelihood of obtaining antibody variable regions from affected humans that can serve as springboards for designing high affinity neutralizing antibodies against the pathogen. For example, the human immune response to HIV-1 infection is clonally restricted throughout HIV-1 infection and into AIDS progression (Muller et al., 1993, B-cell abnormalities in AIDS: stable and clonally restricted antibody response in HIV-1 infection, Scand. J. Immunol. 38:327-334; Wisnewski et al., 1996). Further, $V_H$ genes are in general not present in all polymorphic forms in any particular individual; certain individuals in certain populations possess one variant, whereas individuals in other populations possess a different variant. Thus, the availability of a biological system that is restricted to a single $V_H$ gene and its variants will in various embodiments provide a hitherto unexploited source of diversity for generating antibody variable regions (e.g., human heavy and light cognate domains) based on a restricted $V_H$ gene. Thus, in one aspect, a genetically modified non-human animal is provided that comprises a plurality of polymorphic variants of no more than one, or no more than two, human $V_H$ gene segment family member. In one embodiment, the no more than one, or no more than two, human $V_H$ gene segments are operably linked to one or more human $D_H$ gene segments, one or more human $J_H$ gene segments, and a human or non-human constant region gene segment. In one embodiment the constant region is at an endogenous non-human immunoglobulin constant gene locus. In one embodiment, the non-human animal further comprises a nucleic acid sequence derived from a human $V_L$ sequence, e.g., a rearranged or unrearranged human $V_L$ gene segment or a rearranged human $V_L/J_L$ sequence. In one embodiment, the nucleic acid sequence derived from the human $V_L$ sequence is at an endogenous non-human $V_L$ gene locus; in one embodiment, the nucleic acid sequence derived form the human $V_L$ sequence is on a transgene. In a specific embodiment, the non-human animal is incapable of expressing an immunoglobulin light chain variable domain that itself comprises an endogenous $V_L$ or $J_L$ gene segment, and comprises no more than one, or no more than two, light chain genes that encode rearranged human $V_L$ domains (i.e., from no more than one, or no more than two, rearranged human $V_L/J_L$ sequences).

Genetically modified mice that express human heavy chain variable regions with restricted $V_H$ gene segment usage are useful to generate a relatively large repertoire of junctionally diverse, combinatorially diverse, and somatically mutated high affinity human immunoglobulin heavy chain variable regions from an otherwise restricted repertoire. A restricted repertoire, in one embodiment, refers to a predetermined limitation in the number and/or identity of germline genes that results in the mouse being unable to form a rearranged heavy chain gene that is derived from any V gene other than a preselected V gene. In embodiments that employ a preselected V gene but not a preselected D and/or J gene, the repertoire is restricted with respect to the identity of the V gene but not the D and/or J gene (e.g., the repertoire consists essentially of no more than one, or no more than two, $V_H$ gene segments (and/or polymorphs thereof); and a plurality of D gene segments and a plurality of J gene segments)). The identity of the preselected V gene (and any preselected D and/or J genes) is not limited to any particular V gene.

Designing a mouse so that it rearranges a single $V_H$ gene (present as a single segment or a set of variants) with a variety of human D and J gene segments (e.g., $D_H$ and $J_H$ segments) provides an in vivo junctional diversity/combinatorial diversity/somatic hypermutation permutation machine that can be used to iterate mutations in resulting rearranged heavy chain variable region sequences (e.g., V/D/J or V/J, as the case may be). In such a mouse, the clonal selection process operates to select suitable variable regions that bind an antigen of interest that are based on a single preselected $V_H$ gene (or variants thereof). Because the mouse's clonal selection components are dedicated to selection based on the single preselected $V_H$ gene segment, background noise (e.g., a wide variety of non antigen-binding $V_H$ domains derived from many germline gene segments) is largely eradicated. With judicious selection of the $V_H$ gene segment, a relatively larger number of clonally selected, antigen-specific antibodies can be screened in a shorter period of time than with a mouse with a large diversity of V segments.

Preselecting limited repertoire and restricting a mouse to a single V segment provides a system for permuting V/D/J junctions at a rate that is in various embodiments higher than that observed in mice that otherwise have up to 40 or more V segments to recombine with D and J regions. Removal of other V segments frees the locus to form more V/D/J combinations for the preselected V segment than otherwise observed. The increased number of transcripts that result from the recombination of the preselected V with one of a plurality of D and one of a plurality of J segments will feed those transcripts into the clonal selection system in the form of pre-B cells, and the clonal selection system is thus dedicated to cycling B cells that express the preselected V region. In this way, more unique V region rearrangements derived from the preselected V segment can be screened by the organism than would otherwise be possible in a given amount of time.

In various aspects, mice are described that enhance the junctional diversity of V/D/J recombinations for the preselected V region, because all or substantially all recombinations of the immunoglobulin heavy chain variable locus will be of the preselected V segment and the D and J segments that are placed in such mice. Therefore, the mice provide a method for generating a diversity of CDR3 segments using a base, or restricted $V_H$ gene repertoire.

In one aspect, a non-human animal is provided, wherein the B cell population of the non-human animal expresses immunoglobulin heavy chains that are derived from no more than one, or no more than two human $V_H$ gene segments. In one embodiment, each of the no more than one, or no more than two, human $V_H$ gene segments are present in two or more polymorphic forms. In one embodiment, the human $V_H$ gene segment is present in three, four, five, six, seven, eight, nine, 10, 11, 12, 13, 14, 15, 16, 17, 18, 19 or 20 polymorphic forms. In one embodiment, the non-human animal expresses a human light chain variable domain derived from a human $V_L$ gene segment.

In one aspect, a method is provided for generating a B cell population in a non-human animal, wherein the B cell population expresses human heavy chains derived from a single germline human $V_H$ gene segment and two or more human D gene segments and two or more human J gene segments; the method comprising a step of immunizing a non-human animal as described herein with an antigen of interest, and allowing the non-human animal to mount an immune response to the antigen of interest, wherein the immune response comprises expressing the human heavy chains on the surface of B cells in the B cell population. In one embodiment, the non-human animal is a rodent (e.g., a mouse or rat). In one embodiment, the human $V_H$ gene segment, human $D_H$ segment, and human $J_H$ segment are operably linked to a non-human constant region gene. In one embodiment, the non-human animal further comprises a nucleic acid sequence encoding a human $V_L$ domain. In one embodiment, the nucleic acid sequence encoding the human $V_L$ domain is linked to a non-human light chain constant region gene sequence.

In one aspect, a method for making a non-human animal that expresses an immunoglobulin population characterized by the immunoglobulins having heavy chains that are derived from a plurality of rearrangements of a single human $V_H$ gene segment (or sing human $V_H$ gene family member) and one of a plurality of $D_H$ gene segments and one of a plurality of $J_H$ gene segments, is provided. In one embodiment, the human $V_H$ gene segment is a human $V_H$1-69 gene segment. In one embodiment, the human $V_H$ gene segment is a human $V_H$1-2 gene segment.

In one aspect, a method is provided for generating a population of human immunoglobulin heavy chain variable domains whose CDR1 and CDR2 are derived from the same germline $V_H$ gene segment, and whose CDR3 are derived from the germline gene segment and two or more human D segments, and two or more human J segments; the method comprising immunizing a non-human animal as described herein with an antigen of interest, and allowing the non-human animal to mount an immune response to the antigen of interest, wherein the immune response comprises expressing the human heavy chain variable domains in the context of a light chain variable domain. In one embodiment, the non-human animal is a rodent (e.g., a mouse or rat). In one embodiment, the human $V_H$ gene segment, human D segment, and human J segment are operably linked to a non-human constant region gene. In one embodiment, the non-human animal further comprises a nucleic acid sequence encoding a human $V_L$ domain. In one embodiment, the nucleic acid sequence encoding the human $V_L$ domain is linked to a non-human light chain constant region gene sequence.

In one aspect, a genetically modified non-human animal is provided, wherein the non-human animal is incapable of expressing a non-human $V_H$ domain, and wherein each immunoglobulin heavy chain of the heavy chain population expressed in the animal comprises a human $V_H$ domain comprising a CDR1 and a CDR2 that are identical but for one or more somatic hypermutations, and wherein the heavy chain population comprises a plurality of CDR3 sequences derived from a plurality of rearrangements with a plurality of D and J gene segments.

In one aspect, a biological system for generating variation in CDR3 identity and length is provided, comprising a genetically modified non-human animal as described herein, wherein the non-human animal comprises no more than or no more than two human $V_H$ gene segments, and two or more D gene segments and one or more J gene segments, wherein the non-human animal further comprises a humanized immunoglobulin light chain locus. In various embodiments, the non-human animal in response to immunization with an antigen of interest generates an immune response that comprises expressing an immunoglobulin heavy chain population characterized by each heavy chain having CDR1s and CDR2s that differ only by somatic hypermutation, and CDR3s that differ by rearrangement and somatic hypermutation. In one embodiment, the biological system is a mouse that is genetically modified as described herein. In one embodiment, the human $V_H$ gene segment and the human $V_L$ gene segment are at endogenous mouse heavy and light immunoglobulin loci, respectively. In one embodiment, one or more of the human $V_H$ gene segment and the human $V_L$ gene segment are on transgenes (i.e., at a locus other than an endogenous immunoglobulin locus).

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric. In the foregoing Examples, when the use of kits and/reagents from various suppliers is indicated, all procedures were carried out according to manufacturer's specifications.

Example 1 Construction of Restricted Heavy Chain Loci

A uniquely engineered human heavy chain locus containing a single human $V_H$ gene segment located upstream of all the human $D_H$ and $J_H$ gene segments was created by a series of homologous recombination reactions in bacterial cells (BHR) using Bacterial Artificial Chromosome (BAC) DNA. Several targeting constructs for creation of a single $V_H$ containing heavy chain locus were constructed using VELOCIGENE® genetic engineering technology (see, e.g., U.S. Pat. No. 6,586,251 and Valenzuela, D. M. et al. (2003) High-throughput engineering of the mouse genome coupled with high-resolution expression analysis. *Nature Biotechnology* 21(6): 652-659).

Construction of a Human $V_H$1-69 Restricted Heavy Chain Locus.

Briefly, four modifications were performed using human BAC DNA to create a targeting construct containing a human $V_H$1-69 gene segment with all the human $D_H$ and $J_H$ segments (FIG. 1). In the first modification, a modified human BAC containing multiple distal (5') human $V_H$ gene segments, including $V_H$1-69, an upstream hygromycin selection cassette and a 5' mouse homology arm was targeted with a second spectinomycin cassette, which also contained a modified recombination signal sequence (RSS; BHR 1, FIG. 1, top left). This modified recombination signal sequence (RSS) introduced two point mutations (T to A and G to A) in the 3' RSS region of the human $V_H$1-69 gene changing the RSS nonamer to the optimal consensus sequence. Thus, the first modification (BHR 1) created a human genomic fragment containing the human $V_H$1-69 gene segment with a modified 3' RSS, a unique AsiSI restriction site about 180 bp downstream of the RSS and a spectinomycin cassette (FIG. 1, middle left).

The second modification (BHR 2) included the use of a neomycin (Neo) cassette flanked by Frt sites to delete the hygromycin cassette and 5' human $V_H$ gene segments upstream of the $V_H$1-69 gene segment. This modification was targeted 5' to the human $V_H$1-69 gene segment to leave intact about 8.2 kb of the promoter region of human $V_H$1-69 and the 5' mouse homology arm (FIG. 1, bottom left).

The third modification (BHR 3) included another spectinomycin cassette flanked by uniquely engineered 5' PI-SceI and 3' AsiSI sites targeted to a human genomic fragment containing the first three functional human $V_H$ gene segments and all the human $D_H$ and $J_H$ gene segments (FIG. 1, middle right). The human genomic fragment was previously targeted with a neomycin cassette and contained 5' and 3' homology arms containing the mouse genomic sequence 5' and 3' of the endogenous heavy chain locus including the 3' intronic enhancer and the IgM gene. This modification deleted the 5' mouse genomic sequence and human $V_H$ gene segments, leaving about 3.3 kb of the $V_H$-$D_H$ intergenic region upstream of the human $D_H$1-1 gene segment, all of the human $D_H$ and $J_H$ segments, and the 3' mouse genomic fragment containing the 3' intronic enhancer and the IgM gene (FIG. 1, bottom right).

The fourth modification was achieved by employing the unique PI-SceI and AsiSI sites (described above) to ligate the two modified BACs from BHR 2 and BHR 3 (FIG. 1, bottom center), which yielded the final targeting construct. The final targeting construct for the creation of a modified heavy chain locus containing a single human $V_H$ gene segment and all the human $D_H$ and $J_H$ gene segments in ES cells contained, from 5' to 3', a 5' homology arm containing about 20 kb of mouse genomic sequence upstream of the endogenous heavy chain locus, a 5' Frt site, a neomycin cassette, a 3' Frt site, about 8.2 kb of the human $V_H$1-69 promoter, the human $V_H$1-69 gene segment with a modified 3' RSS, 27 human $D_H$ gene segments, six human $J_H$ segments, and a 3' homology arm containing about 8 kb of mouse genomic sequence downstream of the mouse $J_H$ gene segments including the 3' intronic enhancer and IgM gene (FIG. 1, bottom). The Human $V_H$1-69 Targeting Vector (SEQ ID NO: 3) was linearized and electroporated into mouse ES cells heterozygous for a deletion of the endogenous heavy chain locus.

Construction of a Human $V_H$1-2 Restricted Heavy Chain Locus.

Using the steps described above, other polymorphic $V_H$ gene segments in the context of mouse heavy chain constant regions are employed to construct a series of mice having a restricted number immunoglobulin heavy chain V segments (e.g., 1, 2, 3, 4, or 5), wherein the V segments are polymorphic variants of a V gene family member. Exemplary polymorphic $V_H$ gene segments are derived from human $V_H$ gene segments including, e.g., $V_H$1-2, $V_H$2-26, $V_H$2-70 and $V_H$3-23. Such human $V_H$ gene segments are obtained, e.g., by de novo synthesis (e.g., Blue Heron Biotechnology, Bothell, Wash.) using sequences available on published databases. Thus, DNA fragments encoding each $V_H$ gene are, in some embodiments, generated independently for incorporation into targeting vectors, as described herein. In this way, multiple modified immunoglobulin heavy chain loci comprising a restricted number of $V_H$ gene segments are engineered in the context of mouse heavy chain constant regions. An exemplary targeting strategy for creating a restricted humanized heavy chain locus containing a human $V_H$1-2 gene segment, 27 human $D_H$ gene segments, and six human $J_H$ gene segments is shown in FIG. 2.

Briefly, a modified human BAC clone containing three human $V_H$ gene segments ($V_H$6-1, $V_H$1-2, $V_H$1-3), 27 human $D_H$ gene segments, and six human $J_H$ gene segments (see U.S. Ser. No. 13/404,075; filed 24 Feb. 2012, herein incorporated by reference) is used to create a restricted humanized heavy chain locus containing a human $V_H$1-2 gene segment. This modified BAC clone functionally links the aforementioned human heavy chain gene segments with the mouse intronic enhancer and the IgM constant region. The restricted human $V_H$1-2 based heavy chain locus is achieved by two homologous recombinations using the modified human BAC clone described above.

For the first homologous recombination, 205 bp of the human $V_H$6-1 gene segment (from about 10 bp upstream (5') of the $V_H$6-1 start codon in exon 1 to about 63 bp downstream (3') of the beginning of exon 2) in the modified human BAC clone is deleted by bacterial homologous recombination using a spectinomycin (aadA) cassette flanked by unique PI-SceI restriction sites (FIG. 2, BHR 1). This allows for subsequent removal of the aadA cassette without disrupting other human gene segments within the restricted heavy chain locus.

For the second homologous recombination, the 5' end of the modified human BAC clone including the entire human $V_H$1-3 gene segment and about 60 bp downstream (3') of the gene segment is deleted by homologous recombination using a hygromycin cassette containing flanking 5' AsiSI and 3' Ascl restriction sites (FIG. 2, BHR 2). As described above, the spectinomycin cassette is optionally removed after confirmation of the final targeting vector including deletion of the two human $V_H$ gene segments flanking the human $V_H$1-2 gene segment (FIG. 2, bottom). An exemplary human $V_H$1-2 targeting vector is set forth in SEQ ID NO: 70.

Employing polymorphic $V_H$ gene segments in a restricted immunoglobulin heavy chain locus represents a novel approach for generating antibodies, populations of antibodies, and populations of B cells that express antibodies having heavy chains with diverse CDRs derived from a single human $V_H$ gene segment. Exploiting the somatic hypermutation machinery of the host animal along with combinatorial association with rearranged human immunoglobulin light chain variable domains results in the engineering of unique heavy chains and unique $V_H$/$V_L$ pairs that expand the immune repertoire of genetically modified animals and enhance their usefulness as a next generation platform for making human therapeutics, especially useful as a platform for making neutralizing antibodies specific for human pathogens.

Thus, using the strategy outlined above for incorporation of additional and/or other polymorphic $V_H$ gene segments into the mouse immunoglobulin heavy chain locus allows for the generation of novel antibody repertoires for use in neutralizing human pathogens that might otherwise effectively evade the host immune system.

Targeted ES cells described above were used as donor ES cells and introduced into an 8-cell stage mouse embryo by the VELOCIMOUSE® method (supra). Mice bearing a humanized heavy chain locus containing a single human $V_H$ gene segment, all the human $D_H$ and $J_H$ gene segments operably linked to the mouse immunoglobulin constant region genes were identified by genotyping using a modification of allele assay (Valenzuela et al., supra) that detected the presence of the neomycin cassette, the human $V_H$ gene segment and a region within the human $D_H$ and $J_H$ gene segments as well as endogenous heavy chain sequences. Table 4 sets forth the primers and probes used in this assay to confirm mice harboring a restricted heavy chain locus containing a single human $V_H$1-69 gene segment, 27 human $D_H$ gene segments and six human $J_H$ gene segments.

Mice bearing an engineered heavy chain locus that contains a single human $V_H$ gene segment can be bred to a FLPe deletor mouse strain (see, e.g., Rodriguez, C. I. et al. (2000) High-efficiency deleter mice show that FLPe is an alternative to Cre-loxP. *Nature Genetics* 25: 139-140) in order to remove any Frt'ed neomycin cassette introduced by the targeting vector that is not removed, e.g., at the ES cell stage or in the embryo. Optionally, the neomycin cassette is retained in the mice.

Pups are genotyped and a pup heterozygous for a humanized heavy chain locus containing a single human $V_H$ gene segment, all the human $D_H$ and $J_H$ segments operably linked to the endogenous mouse immunoglobulin constant genes is selected for characterizing the immunoglobulin heavy chain repertoire.

ences), PE-Igλ (RML-42, BIOLEGEND®), PeCy7-IgM (II/41, EBIOSCIENCE®), PerCP-Cy5.5-IgD (11-26c.2a, BIOLEGEND®), Pacific Blue-CD3 (17A2, BIOLEGEND®), APC-B220 (RA3-6B2, EBIOSCIENCE®), APC-H7-CD19 (ID3, BD Biosciences). Bone marrow: immature B cells (B220$^{int}$IgM$^+$), mature B cells (B220$^{hi}$IgM$^+$), pro B cells (CD19$^+$ckit$^+$CD43$^+$), pre B cells (CD19$^+$ckit$^-$CD43$^-$), immature Igκ$^+$ B cells (B220$^{int}$IgM$^+$Igκ$^+$Igλ$^-$), immature Igλ$^+$ B cells (B220$^{int}$IgM$^+$Igκ$^-$Igλ$^+$), mature Igκ$^+$ B cells

TABLE 4

| Name (Region Detected) | | Sequence (5'-3') | SEQ ID NO: |
|---|---|---|---|
| hyg (hygromycin cassette) | Forward: | TGCGGCCGAT CTTAGCC | 4 |
| | Reverse: | TTGACCGATT CCTTGCGG | 5 |
| | Probe: | ACGAGCGGGT TCGGCCCATT C | 6 |
| neo (neomycin cassette) | Forward: | GGTGGAGAGG CTATTCGGC | 7 |
| | Reverse: | GAACACGGCG GCATCAG | 8 |
| | Probe: | TGGGCACAAC AGACAATCGG CTG | 9 |
| h1gH9T (human $D_H$-$J_H$ genomic sequence) | Forward: | TCCTCCAACG ACAGGTCCC | 10 |
| | Reverse: | GATGAACTGA CGGGCACAGG | 11 |
| | Probe: | TCCCTGGAAC TCTGCCCCGA CACA | 12 |
| 77h3 (human $V_H$1-69 gene segment) | Forward: | CTCTGTGGAA AATGGTATGG AGATT | 13 |
| | Reverse: | GGTAAGCATA GAAGGTGGGT ATCTTT | 14 |
| | Probe: | ATAGAACTGT CATTTGGTCC AGCAATCCCA | 15 |
| m1gHA7 (mouse $D_H$-$J_H$ genomic sequence) | Forward: | TGGTCACCTC CAGGAGCCTC | 16 |
| | Reverse: | GCTGCAGGGT GTATCAGGTG C | 17 |
| | Probe: | AGTCTCTGCT TCCCCCTTGT GGCTATGAGC | 18 |
| 88710T (mouse 3' $V_H$ genomic sequence) | Forward: | GATGGGAAGA GACTGGTAAC ATTTGTAC | 19 |
| | Reverse: | TTCCTCTATT TCACTCTTTG AGGCTC | 20 |
| | Probe: | CCTCCACTGT GTTAATGGCT GCCACAA | 21 |
| m1gHd10 (mouse 5' $V_H$ genomic sequence) | Forward: | GGTGTGCGAT GTACCCTCTG AAC | 22 |
| | Reverse: | TGTGGCAGTT TAATCCAGCT TTATC | 23 |
| | Probe: | CTAAAAATGC TACACCTGGG GCAAAACACC TG | 24 |
| m1gHp2 (mouse $J_H$ genomic sequence) | Forward: | GCCATGCAAG GCCAAGC | 25 |
| | Reverse: | AGTTCTTGAG CCTTAGGGTG CTAG | 26 |
| | Probe: | CCAGGAAAAT GCTGCCAGAG CCTG | 27 |

Example 2 Characterization of Mice Expressing Heavy Chains Derived from a Single Human $V_H$ Gene Segment Mice homozygous for a single human $V_H$ gene segment at the endogenous heavy chain locus as described in Example 1 were evaluated for expression and B cell development using flow cytometry.

Briefly, spleens and bone marrow was harvested from wild type (n=3 per group; six weeks old, male and female) and mice homozygous for a single human $V_H$ gene segment, all human $D_H$ and $J_H$ gene segments operably linked to mouse heavy chain constant regions. Red blood cells from spleens were lysed with ACK lysis buffer (Lonza Walkersville), followed by washing with complete RPMI medium.

Flow Cytometry.

Cells (1×10$^6$) were incubated with anti-mouse CD16/CD32 (2.4G2, BD PHARMINGEN™) on ice for 10 minutes, followed by labeling with the following antibody panels for 30 minutes on ice. Bone marrow panel: anti-mouse FITC-CD43 (1B11, BioLegend), PE-ckit (2B8, BIOLEGEND®), PeCy7-IgM (II/41, EBIOSCIENCE®), PerCP-Cy5.5-IgD (11-26c.2a, BIOLEGEND®), APC-eFluor 780-B220 (RA3-6B2, EBIOSCIENCE®), APC-CD19 (MB19-1, EBIOSCIENCE®). Bone marrow and spleen panel: anti-mouse FITC-Igκ (187.1, BD Biosci- (B220$^{hi}$IgM$^+$Igκ$^+$Igλ$^-$), mature Igλ$^+$ B cells (B220$^{hi}$IgM$^+$Igκ$^-$Igλ$^+$). Spleen: B cells (CD19$^+$), mature B cells (CD19$^+$IgD$^{hi}$IgM$^{int}$), transitional/immature B cells (CD19$^+$IgD$^{in}$-IgM$^{hi}$). Bone marrow and spleen: Igκ$^+$ B cells (CD19$^+$Igκ$^+$Igλ$^-$), Igλ$^+$ B cells (CD19$^+$Igκ$^-$Igλ$^+$).

Following staining, cells were washed and fixed in 2% formaldehyde. Data acquisition was performed on a LSRII flow cytometer and analyzed with FLOWJO™ software (Tree Star, Inc.). Results for the splenic compartment are shown in FIGS. 3, 4A and 5-7. Results for the bone marrow compartment are shown in FIGS. 4B and 8-11B.

Human $V_H$ Expression.

Expression of the human $V_H$1-69 gene segment was determined for mice heterozygous and homozygous for a human $V_H$1-69 gene segment, all human $D_H$ and $J_H$ gene segments operably linked to mouse heavy chain constant regions by a quantitative PCR assay using TAQMAN® probes.

Figure 12:
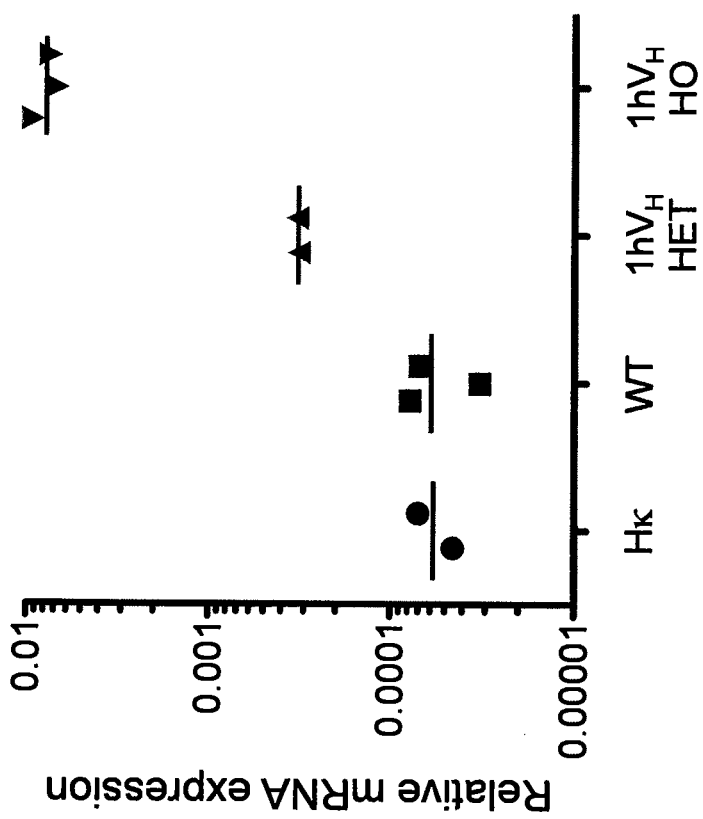
FIG. 12 shows the relative mRNA expression (y-axis) in purified splenic B cells of $V_H$1-69-derived heavy chains in a quantitative PCR assay using a probe specific for the human $V_H$1-69 gene segment in mice homozygous for a replacement of the endogenous heavy chain $V_H$, $D_H$, $J_H$, and a replacement of the endogenous light chain Vκ and Jκ gene segments with human $V_H$, $D_H$, $J_H$, Vκ and Jκ gene segments (Hκ), wild type mice (WT), mice heterozygous for a single human $V_H$ gene segment, twenty-seven human $D_H$ and six human $J_H$ gene segments at the endogenous immunoglobulin heavy chain locus (1h$V_H$ HET) and mice homozygous for a single human $V_H$ gene segment, twenty-seven human $D_H$ and six human $J_H$ gene segments at the endogenous immunoglobulin heavy chain locus (1h$V_H$ HO). Signals are normalized to expression of mouse Cκ.

Briefly, CD19$^+$ B cells were purified from the spleens of groups of mice (n=3 per group) using mouse CD19 microbeads (Miltenyi Biotec) according to manufacturer's specifications. Total RNA was purified using the RNEASY™ Mini kit (Qiagen) and genomic RNA was removed using an RNase-free DNase on-column treatment (Qiagen). About 200 ng mRNA was reverse-transcribed into cDNA using the First Stand cDNA Synthesis kit (Invitrogen), followed by amplification with the TAQMAN® Universal PCR Master Mix (Applied Biosystems) using the ABI 7900 Sequence Detection System (Applied Biosystems). Unique primer/probe combinations were employed to specifically determine expression of human $V_H$1-69-derived heavy chains (Table 5). Relative expression was normalized to the mouse κ constant region (mCκ). The results are shown in FIG. 12.

TABLE 5

| Name | | Sequence (5'-3') | SEQ ID NO: |
|---|---|---|---|
| hIgHV1-69 | Sense: | AACTACGCAC AGAAGTTCCA GG | 28 |
| | Anti-sense: | GCTCGTGGAT TTGTCCGC | 29 |
| | Probe: | CAGAGTCACG ATTACC | 30 |
| mCκ | Sense: | TGAGCAGCAC CCTCACGTT | 31 |
| | Antisense: | GTGGCCTCAC AGGTATAGCT GTT | 32 |
| | Probe: | ACCAAGGACG AGTATGAA | 33 |

Example 3 Humoral Immune Response in Mice Expressing Heavy Chains Derived from a Single Human $V_H$ Gene Segment The humoral immune response was determined for mice homozygous for human heavy and κ light chain variable gene loci (HK) and mice homozygous for a single human $V_H$ gene segment, all human $D_H$ and $J_H$ gene segments operably linked to mouse heavy chain constant regions (1 h$V_H$ HO) by comparative immunization using a human cell surface receptor (Antigen A).

Immunization.

Serum was collected from groups of mice prior to immunization with the above antigen. Antigen (2.35 μg each) was administered in an initial priming immunization mixed with 10 μg of CpG oligonucleotide (Invivogen) and 25 μg of Adju-phos (Brenntag) as adjuvants. The immunogen was administered via footpad (f.p.) in a volume of 25 μl per mouse. Subsequently, mice were boosted via f.p. with 2.3 μg of antigen along with 10 μg CpG and 25 μg Adju-Phos as adjuvants on days 3, 6, 11, 13, 17, and 20 for a total of six boosts. Mice were bled on days 15 and 22 after the fourth and sixth boosts, respectively, and antisera were assayed for antibody titers to Antigen A.

Antibody titers were determined in sera of immunized mice using an ELISA assay. Ninety six-well microtiter plates (Thermo Scientific) were coated with Antigen A (1 μg/ml) in phosphate-buffered saline (PBS, Irvine Scientific) overnight at 4° C. The following day, plates were washed with phosphate-buffered saline containing 0.05% Tween 20 (PBS-T, Sigma-Aldrich) four times using a plate washer (Molecular Devices). Plates were then blocked with 250 μl of 1% bovine serum albumin (BSA, Sigma-Aldrich) in PBS and incubated for one hour at room temperature. The plates were then washed four times with PBS-T. Sera from immunized mice and pre-immune sera were serially diluted tenfold in 0.1% BSA PBS-T starting at 1:100 and added to the blocked plates in duplicate and incubated for one hour at room temperature. The last two wells were left blank to be used as secondary antibody control. The plates were again washed four times with PBS-T in a plate washer. A 1:5000 dilution of goat anti-mouse IgG-Fc-Horse Radish Peroxidase (HRP, Jackson Immunoresearch) conjugated secondary antibody was added to the plates and incubated for one hour at room temperature. Plates were again washed eight times with PBS-T and developed using TMB/$H_2O_2$ as substrate. The substrate was incubated for twenty minutes and the reaction stopped with 1N $H_2SO_4$ (VWR). Plates were read on a spectrophotometer (Victor, Perkin Elmer) at 450 nm. Antibody titers were calculated using GRAPHPAD PRISM™ (GraphPad Software, Inc).

Serum titer was calculated as serum dilution within experimental titration range at the signal of antigen binding equivalent to two times above background. Antibody titer for the humoral immune response against a human cell surface receptor (Antigen A) is set forth in FIG. 19.

In a similar experiment, humoral immune responses were determined for mice homozygous for human heavy and κ light chain variable gene loci (HK) and mice homozygous for a single human $V_H$ gene segment, all human $D_H$ and $J_H$ gene segments operably linked to mouse heavy chain constant regions (1 h$V_H$ HO) by comparative immunization using influenza viral vaccines FLUVIRIN® (Novartis Vaccines) and FLUMIST® (MedImmune LLC).

Briefly, serum was collected from groups of mice prior to immunization with the above antigen (as described above). Mice (n=5) homozygous for a single human $V_H$ gene segment ($V_H$1-69), all human $D_H$ and $J_H$ gene segments operably linked to mouse heavy chain constant regions (1 h$V_H$ HO) were immunized intra-nasally (i.n.) with FLUMIST® (live attenuated influenza vaccine) at ⅓ the normal dose/mouse. One normal dose of FLUMIST® contains $10^{6.5-7.5}$ FFU (fluorescent focus units) of live attenuated influenza vaccine. Therefore, each mouse was primed with 70 μl FLUMIST® on day 1 followed by i.n. boost on days 3, 6, 11, 13, 17, 20 for a total of 6 boosts. No adjuvants were employed in this immunization. The mice were bled on days 15 and 22 after 4th and 6th boosts respectively and antiserum assayed for antibody titers to FLUMIST® (as described above).

In a similar manner, in immunizations with FLUVIRIN®, pre-immune serum was collected from mice prior to initiation of immunization. Mice (n=5) homozygous for a single human $V_H$ gene segment ($V_H$1-69), all human $D_H$ and $J_H$ gene segments operably linked to mouse heavy chain constant regions (1h$V_H$ HO) were immunized with FLUVIRIN® (trivalent inactivated influenza vaccine) via footpad (f.p.) with 0.75 μg each of hemagglutinin/mouse/boost. Mice were primed on day 1 followed by f.p. boost on days 3, 6, 11, 13, 17, 20 for a total of 6 boosts. No adjuvants were employed in this immunization. The mice were bled on days 15 and 22 after 4th and 6th boosts respectively and antiserum assayed for antibody titers to FLUVIRIN® (as described above).

Serum titer was calculated as serum dilution within experimental titration range at the signal of antigen binding equivalent to two times above background. Antibody titer for the humoral immune response against FLUVIRIN® and FLUMIST® is set forth in FIG. 20.

As shown in this Example, antibody titers generated in 1 h$V_H$ HO mice were comparable to those generated in mice having a plurality of human $V_H$ gene segments (Hκ) for both a human cell surface receptor and a viral antigen (e.g., influenza). Thus, mice having immunoglobulin heavy chain loci restricted to a single $V_H$ gene segment are capable of mounting a robust immune response to antigen in a manner comparable to mice having immunoglobulin heavy chain loci containing a plurality of human $V_H$ gene segments (e.g., 80 $V_H$).

Example 4 Analysis of Antibody Gene Usage and CDR3 Length in Mice Having a Restricted Immunoglobulin Heavy Chain Locus Splenocytes harvested from mice homozygous for a single human $V_H$ gene segment at the endogenous heavy chain locus and homozygous for a replacement of the endogenous κ light chain variable loci with human κ light chain variable loci immunized with a human cell surface receptor (Antigen A) were analyzed for heavy and light chain gene segment usage by reverse-transcriptase polymerase chain reaction (RT-PCR) on mRNA from splenic B cells.

Briefly, spleens were harvested and homogenized in 1×PBS (Gibco) using glass slides. Cells were pelleted in a centrifuge (500×g for 5 minutes), and red blood cells were lysed in ACK Lysis buffer (Gibco) for 3 minutes. Cells were washed with 1×PBS and filtered using a 0.7 μm cell strainer. B-cells were isolated from spleen cells using MACS magnetic positive selection for CD19 (Miltenyi Biotec). Total RNA was isolated from pelleted B-cells using the RNeasy Plus Kit (Qiagen). PolyA⁺ mRNA was isolated from total RNA using the OLIGOTEX® Direct mRNA mini kit (Qiagen).

Double-stranded cDNA was prepared from splenic B cell mRNA by 5' RACE using the SMARTER™ Pico cDNA Synthesis Kit (Clontech) with substitution of the supplied reverse transcriptase and dNTPs with SUPERSCRIPT® II and dNTPs (Invitrogen). $V_H$ and Vκ antibody repertoires were amplified from the cDNA using primers specific for IgM, IgG, or Igκ constant regions and the SMARTER™ 5' RACE primer (Table 6). PCR products were purified using a QIAQUICK® PCR Purification Kit (Qiagen). A second round of PCR was done using the same 5' RACE primer and a nested 3' primer specific for the IgM, IgG, or Igκ constant regions (Table 7). Second round PCR products were purified using a SIZESELECT™ E-Gel® system (Invitrogen). A third PCR was performed with primers that added 454 adapters and barcodes. Third round PCR products were purified using AGENCOURT® AMPURE® XP Beads (Beckman Coulter). Purified PCR products were quantified by SYBR® qPCR using a KAPA Library Quantification Kit (KAPA Biosystems). Pooled libraries were subjected to emulsion PCR (emPCR) using a 454 GS Junior Titanium Series Lib-A emPCR Kit (Roche Diagnostics) and bidirectional sequencing using Roche 454 GS Junior instrument according to manufacturer's specifications.

Bioinformatic Analysis.

The 454 sequences were sorted based on the sample barcode perfect match and trimmed for quality. Sequences were annotated based on alignment of rearranged immunoglobulin sequences to human germline V(D)J segment database using local installation of Igblast (NCBI, v2.2.25+). A sequence was marked as ambiguous and removed from analysis when multiple best hits with identical score were detected. A set of perl scripts was developed to analyze results and store data in mysql database. CDR3 region was defined between conserved C codon and FGXG motif for light and WGXG motif for heavy chains. CDR3 length was determined using only productive antibodies. From the nucleic acid sequences and predicted amino acid sequences of the antibodies, gene usage was identified for IgM-primed (15,650), IgG-primed (18,967), and Igκ-primed (26,804) sequences. Results are shown in Table 8, Table 9, FIG. 21 and FIG. 22.

Table 8 sets forth the percentage of observed human $D_H$ and $J_H$ gene segments used among IgM-primed (15,650 sequences) and IgG-primed (18,967 sequences) $V_H$1-69 derived heavy chain variable region sequences. Human $D_H$4-4/$D_H$4-11 and human $D_H$5-5/$D_H$5-18 gene segments are presented in Table 8 together due to identical sequence identity between the respective pairs of $D_H$ gene segments. Table 9 sets forth the percentage of human Vκ and Jκ gene segments observed among light chains (26,804 sequences) cognate with $V_H$1-69 derived heavy chain variable regions. Percentages in Tables 8 and 9 represent rounded values and in some cases may not equal 100% when added together.

Amino acid length of the CDR3 region of IgM-primed $V_H$1-69-derived heavy chains is shown in FIG. 21. Amino acid length of the CDR3 region of IgG-primed $V_H$1-69-derived heavy chains is shown in FIG. 22.

As shown in Tables 8 and 9, mice according to the invention generate antigen-specific antibodies containing $V_H$1-69-derived heavy chains, which demonstrate a variety of rearrangements of a human $V_H$1-69 gene segment with a variety of human $D_H$ segments and human $J_H$ segments. Further, the antigen-specific antibodies contain cognate human light chains containing human Vκ domains resulting from a variety of rearrangements of human Vκ and Jκ gene segments.

TABLE 6

| Primer | Sequence (5'-3') |
|---|---|
| 3' Cg1 outer | GGAAGGTGTG CACACCGCTG GAC (SEQ ID NO: 71) |
| 3' Cg2ac outer | GGAAGGTGTG CACACCACTG GAC (SEQ ID NO: 72) |
| 3' Cg2b outer | GGAAGGTGTG CACACTGCTG GAC (SEQ ID NO: 73) |
| 3' Cg3 outer | AGACTGTGCG CACACCGCTG GAC (SEQ ID NO: 74) |
| 3' mIgM CH1 outer | TCTTATCAGA CAGGGGGCTC TC (SEQ ID NO: 75) |
| 3' mIgκC outer | AAGAAGCACA CGACTGAGGC AC (SEQ ID NO: 76) |

TABLE 7

| Primer | Sequence (5'-3') |
|---|---|
| 3' mIgG1/2b CH1 inner | AGTGGATAGA CWGATGGGGG TG (SEQ ID NO: 77) |
| 3' mIgG2a/2c CH1 inner | AGTGGATAGA CCGATGGGGC TG (SEQ ID NO: 78) |
| 3' mIgG3 CH1 inner | AAGGGATAGA CAGATGGGGC TG (SEQ ID NO: 79) |
| 3' mIgM CH1 inner | GGAAGACATT TGGGAAGGAC TG (SEQ ID NO: 80) |
| 3' mIgκC-2 inner | GGAAGATGGA TACAGTTGGT GC (SEQ ID NO: 81) |

TABLE 8

|  | IgM | IgG |
|---|---|---|
| Human $D_H$ |  |  |
| 1-1 | 1.2 | 6.0 |
| 1-7 | 39.9 | 9.0 |
| 1-14 | 0.5 | 2.3 |
| 1-20 | 2.3 | 1.4 |
| 1-26 | 3.5 | 5.7 |
| 2-2 | 1.1 | 3.2 |
| 2-8 | 0.7 | 0.6 |
| 2-15 | 0.3 | 1.2 |

TABLE 8-continued

| | IgM | IgG |
|---|---|---|
| 2-21 | 0.7 | 0.3 |
| 3-3 | 6.3 | 5.2 |
| 3-9 | 0.6 | 0.6 |
| 3-10 | 0.9 | 10.3 |
| 3-16 | 0.9 | 2.0 |
| 3-22 | 5.1 | 2.7 |
| 4-4/4-11 | 1.5 | 4.0 |
| 4-17 | 1.5 | 4.7 |
| 4-23 | 11.5 | 2.4 |
| 5-12 | 1.1 | 1.8 |
| 5-5/5-18 | 1.3 | 3.2 |
| 5-24 | 0.3 | 3.3 |
| 6-6 | 1.8 | 4.5 |
| 6-13 | 6.1 | 7.4 |
| 6-19 | 3.0 | 5.1 |
| 6-25 | 0.1 | 0.6 |
| 7-27 | 3.3 | 7.3 |
| Human $J_H$ | | |
| 1 | 7.5 | 1.5 |
| 2 | 3.3 | 4.2 |
| 3 | 22.2 | 12.8 |
| 4 | 51.5 | 36.4 |
| 5 | 10.5 | 9.5 |
| 6 | 4.9 | 29.4 |

TABLE 9

| | % Observed |
|---|---|
| Human Vκ | |
| 1-5 | 3.4 |
| 1-6 | 1.3 |
| 1-8 | 0 |
| 1-9 | 1.3 |
| 1-12 | 1.0 |
| 1-13 | 0 |
| 1-16 | 2.5 |
| 1-17 | 3.6 |
| 1-22 | 0 |
| 1-27 | 0.5 |
| 1-32 | 0 |
| 1-33 | 14.3 |
| 1-35 | 0 |
| 1-37 | 0 |
| 1-39 | 1.6 |
| 2-4 | 0 |
| 2-10 | 0 |
| 2-14 | 0 |
| 2-18 | 0 |
| 2-19 | 0 |
| 2-23 | 0 |
| 2-24 | 0.7 |
| 2-26 | 0 |
| 2-28 | 0 |
| 2-29 | 0 |
| 2-30 | 1.9 |
| 2-36 | 0 |
| 2-38 | 0 |
| 2-40 | 1.5 |
| 3-7 | 0 |
| 3-11 | 2.7 |
| 3-15 | 3.9 |
| 3-20 | 41.2 |
| 3-25 | 0 |
| 3-31 | 0 |
| 3-34 | 0 |
| 4-1 | 13.2 |
| 5-2 | 0.1 |
| 6-21 | 0 |
| 7-3 | 0 |
| Human Jκ | |
| 1 | 28.1 |
| 2 | 25.3 |
| 3 | 12.1 |
| 4 | 22.5 |
| 5 | 11.1 |

We claim:

1. A method of making a nucleic acid encoding a human immunoglobulin heavy chain variable domain, comprising
amplifying a nucleic acid from a lymphocyte of a non-human animal or a hybridoma produced from the lymphocyte,
wherein the nucleic acid comprises a rearranged human immunoglobulin variable gene sequence that encodes a human immunoglobulin heavy chain variable domain, wherein the non-human animal comprises in its germline genome a restricted immunoglobulin heavy chain locus characterized by the presence of a single human unrearranged $V_H$1-69 gene segment or a polymorphic variant thereof, one or more human unrearranged $D_H$ gene segments, and one or more human unrearranged $J_H$ gene segments operably linked to a non-human immunoglobulin constant region comprising at least a non-human IgM gene at an endogenous heavy chain locus of the non-human animal, wherein the restricted immunoglobulin heavy chain locus is capable of (1) rearranging in a lymphocyte and (2) forming a plurality of distinct rearranged human heavy chain variable region gene sequences, each of which (a) is derived from the single human unrearranged $V_H1$-69 gene segment or polymorphic variant thereof, one of the human D segments, and one of the human J segments, and (b) encodes a different heavy chain variable domain, wherein the non-human animal further comprises a population of mature $IgM^{int}IgD^{hi}$ B cells in its spleen, each B cell comprising one of the plurality of distinct rearranged human heavy chain variable region gene sequences, and wherein the rearranged human immunoglobulin variable gene sequence is one of the plurality of rearrangements.

2. The method of claim 1, wherein the single human unrearranged $V_H$ gene segment comprises a sequence that is at least 90%, at least 95%, or at least 98% identical to a sequence selected from the group consisting of SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56 and SEQ ID NO: 58.

3. The method of claim 1, wherein the single human unrearranged $V_H$ gene segment comprises a sequence selected from the group consisting of SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, and a polymorphic variant thereof.

4. The method of claim 1, wherein the human immunoglobulin heavy chain variable domain is at least 90%, at least 95%, or at least 98% identical with SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, or SEQ ID NO: 59.

5. The method of claim 1, wherein the non-human animal further comprises one or more human immunoglobulin $V_L$ and one or more human immunoglobulin $J_L$ gene segments operably linked to a non-human light chain constant region.

6. The method of claim 1, wherein the lymphocyte is a B cell.

7. The method of claim 5, wherein the non-human animal comprises
(a) a deletion of an endogenous immunoglobulin heavy chain variable locus and a deletion of an endogenous κ light chain variable locus, or
(b) a deletion of an endogenous immunoglobulin heavy chain variable locus and a deletion of an endogenous λ light chain variable locus.

8. The method of claim 1, wherein the lymphocyte specifically binds an antigen of interest.

9. The method of claim 1, wherein the amplified rearranged human immunoglobulin $V_H$ region gene sequence comprises at least one somatic hypermutation.

10. The method of claim 1, wherein the non-human animal is a rodent.

11. The method of claim 10, wherein the rodent is a rat or a mouse.

12. The method of claim 1, wherein the non-human animal comprises a higher ratio of mature $IgD^{hi}IgM^{int}$ B cells to immature $IgD^{int}IgM^{hi}$ B cells in the spleen as compared to a control ratio of mature $IgD^{hi}IgM^{int}$ B cells to immature $IgD^{int}IgM^{hi}$ B cells in the spleen of a control mouse comprising a plurality of human $V_H$ gene segments.

13. The method of claim 12, wherein the ratio is about 1.5-fold to about 2-fold higher than the control ratio.

14. The method of claim 1, wherein the non-human animal exhibits a population of mature $IgD^{hi}IgM^{int}$ B cells of at least $1\times10^7$ cells.

15. The method of claim 1, wherein the number of CD19$^+$ cells in the population of mature $IgD^{hi}IgM^{int}$ B cells in the spleen is within an order of magnitude of a number of CD19$^+$ cells in a population of mature $IgD^{hi}IgM^{int}$ B cells in a spleen of a control non-human animal comprising a plurality of human $V_H$ gene segments.

16. The method of claim 1, wherein the non-human animal is a rat.

17. The method of claim 1, wherein the non-human animal is a mouse.

* * * * *

UNITED STATES PATENT AND TRADEMARK OFFICE
CERTIFICATE OF CORRECTION

PATENT NO. : 9,932,398 B2
APPLICATION NO. : 13/944286
DATED : April 3, 2018
INVENTOR(S) : Lynn Macdonald et al.

Page 1 of 1

It is certified that error appears in the above-identified patent and that said Letters Patent is hereby corrected as shown below:

In the Specification

Column 4, Line 39:
"IoxP" should be --loxP--

Column 16, Line 57:
"segments" should be --segments.--

Column 18, Line 29:
"non" should be --not--

Column 33, Line 49:
"Immmunol." should be --Immunol.--

Column 33, Line 63:
"form" should be --from--

Column 36, Line 60:
"Muridae," should be --Muridae.--

Signed and Sealed this
Twenty-first Day of August, 2018

Andrei Iancu
*Director of the United States Patent and Trademark Office*

UNITED STATES PATENT AND TRADEMARK OFFICE
CERTIFICATE OF CORRECTION

Page 1 of 2

PATENT NO. : 9,932,398 B2
APPLICATION NO. : 13/944286
DATED : April 3, 2018
INVENTOR(S) : Lynn Macdonald et al.

It is certified that error appears in the above-identified patent and that said Letters Patent is hereby corrected as shown below:

In the Specification

Column 4, Line 39:
"IoxP" should be --loxP--

Column 16, Line 57:
"segments" should be --segments.--

Column 18, Line 29:
"non" should be --not--

Column 33, Line 49:
"Immmunol." should be --Immunol.--

Column 33, Line 63:
"form" should be --from--

Column 36, Line 60:
"Muridae," should be --Muridae.--

Column 39, Line 25:
"Brezinscheck" should be --Brezinschek--

Column 41, Line 42:
"form" should be --from--

This certificate supersedes the Certificate of Correction issued August 21, 2018.

Signed and Sealed this
Thirteenth Day of November, 2018

Andrei Iancu
*Director of the United States Patent and Trademark Office*

CERTIFICATE OF CORRECTION (continued)
U.S. Pat. No. 9,932,398 B2

In the Claims

Column 304 (Line 39) Claim 16, Line 2:
"animal is a rat." should be --animal is a rat or a mouse.--

UNITED STATES PATENT AND TRADEMARK OFFICE
CERTIFICATE OF CORRECTION

PATENT NO. : 9,932,398 B2  
APPLICATION NO. : 13/944286  
DATED : April 3, 2018  
INVENTOR(S) : Lynn Macdonald et al.

Page 1 of 1

It is certified that error appears in the above-identified patent and that said Letters Patent is hereby corrected as shown below:

On the Title Page

(72) Inventors: "Lynn Macdonald, White Plains, NY (US); John McWhirter, Tarrytown, NY (US); Cagan Gurer, Valhalla, NY (US); Karolina A. Meagher, Tarrytown, NY (US); Andrew J. Murphy, Croton-on-Hudson, NY (US)" should read --Lynn Macdonald, White Plains, NY (US); John McWhirter, Tarrytown, NY (US); Andrew J. Murphy, Croton-on-Hudson, NY (US)--.

Signed and Sealed this  
Twentieth Day of August, 2019

Andrei Iancu  
*Director of the United States Patent and Trademark Office*

SEQUENCE LISTING

<160> NUMBER OF SEQ ID NOS: 81

<210> SEQ ID NO 1
<211> LENGTH: 872
<212> TYPE: DNA
<213> ORGANISM: Homo sapiens
<220> FEATURE:
<223> OTHER INFORMATION: synthetic

<400> SEQUENCE: 1

```
gcaggattta gggcttggtc tctcagcatc ccacacttgt acagctgatg tggcatctgt      60
gttttctttc tcatcgtaga tcaggctttg agctgtgaaa taccctgcct catgcatatg     120
caaataacct gaggtcttct gagataaata tagatatatt ggtgccctga gagcatcaca     180
taacaaccac attcctcctc taaagaagcc cctgggagca cagctcatca ccatggactg     240
gacctggagg ttcctctttg tggtggcagc agctacaggt aagggcttc ctagtcctaa      300 ggctgaggaa gggatcctgg tttagttaaa gaggatttta ttcaccctg tgtcctctcc      360 acaggtgtcc agtcccaggt gcagctggtg cagtctgggg ctgaggtgaa gaagcctggg     420
tcctcggtga aggtctcctg caaggcttct ggaggcacct tcagcagcta tgctatcagc     480
tgggtgcgac aggcccctgg acaagggctt gagtggatgg gagggatcat ccctatcttt     540
ggtacagcaa actacgcaca gaagttccag ggcagagtca cgattaccgc ggacgaatcc     600
```

```
acgagcacag cctacatgga gctgagcagc ctgagatctg aggacacggc cgtgtattac    660
tgtgcgagag acacagtgtg aaaacccaca tcctgagagt gtcagaaacc ctgagggaga    720
aggcagctgt gccgggctga ggagatgaca gggtttatta ggtttaaggc tgtttacaaa    780
atgggttata tatttgagaa aaaaagaaca gtagaaacaa gtacatactc ctctaatttt    840
aagataatta ttccattcaa gagtcgtaat at                                  872

<210> SEQ ID NO 2
<211> LENGTH: 118
<212> TYPE: PRT
<213> ORGANISM: Homo sapiens
<220> FEATURE:
<223> OTHER INFORMATION: synthetic

<400> SEQUENCE: 2

Met Asp Trp Thr Trp Arg Phe Leu Phe Val Val Ala Ala Ala Thr Gly
 1               5                  10                  15

Gly Val Gln Ser Gln Val Gln Leu Val Gln Ser Gly Ala Glu Val Lys
            20                  25                  30

Lys Pro Gly Ser Ser Val Lys Val Ser Cys Lys Ala Ser Gly Gly Thr
        35                  40                  45

Phe Ser Ser Tyr Ala Ile Ser Trp Val Arg Gln Ala Pro Gly Gln Gly
    50                  55                  60

Leu Glu Trp Met Gly Gly Ile Ile Pro Ile Phe Gly Thr Ala Asn Tyr
65                  70                  75                  80

Ala Gln Lys Phe Gln Gly Arg Val Thr Ile Thr Ala Asp Glu Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Arg
        115

<210> SEQ ID NO 3
<211> LENGTH: 99294
<212> TYPE: DNA
<213> ORGANISM: Artificial Sequence
<220> FEATURE:
<223> OTHER INFORMATION: synthetic

<400> SEQUENCE: 3
aagcttatct ctctgttgct cagactcatc taggaatttc agaaatttct gttctagcat     60
ctcttccagc ttttgtctcc aaccctcatt ctcttcttcc tttttttttt taaattatat    120
gttctctgtc ttttaaaaa acttttaaa attaggtatt tatgtcattt acatttccaa      180
tgctatccca aaagtcccac ccacgctccc aacccacta tcccaccac ccactcccac      240 ttcttggccc tggcattcac agtgtactga acatataaa gtttgcacaa ccaatgggcc    300
tctctttcca ctgatggccg actaggccat cttctgatac atatgcagct agagacacga    360
gattctgggg gtactggtta gttcatattg ttgttccacc tatagggttg cagatccttt    420
tagctccttg ggtactttct ctagctcctc cattgggggc cctgtgatcc atccaatagc    480
tgactgtgag catccacttc tgtgtttgct aggcccagaa tagtctcaca agagacagct    540
atatctgggt cctttcagca aaatcttgct agtgtatgca acggtgtcag agtttggaag    600
ctgattatgg gatggatccc cggatatggc attctctagt tggttcatcc ttttgtctca    660 gctccaaaact ttgtctctgt aactccttcc atgggtgttt gttcccagt tctaaggagg    720
```

```
ggcaaagtat ccacactttg gtcttcattc ttcttgagtt tcatgtgttt tgcaaattgt    780
atcttatatc ttgggtattc taagtttctg ggctaatatc cacttatcag tgagtacaca    840
ttgtgtgagt tcttttgtga ttgggttacc tcactcagta tgatgccctc caggtccatc    900
catttgccta ggaatttcat aaattcattc tttttaatag ctcagtagta ctccattgtg    960
tagatgtacc acattttctg tattcattcc tctgttgagg ggcatctggg ttcttttccag   1020 cttctggcta ttataaataa ggctgctatg aacatagtgg agcatgtgac cttcttaccg    1080
gttgggacat cttctggata tatgcccagg agaggtattg ctggatcttc cggtagtact    1140
atgtccaatt ttctgaggaa ctgacaaact gatttccaga gtggttagta ccagcttgca    1200
atcccaccaa caatgagagg agtgttcgtc tttctccaca tcctcaccag catgctgctg    1260
tcacctgaat ttttgatgct tagccattct gactggtgtg aggtggaatc tcagggttgt    1320
tttgatttgt atttccctga tgattaagga tgctgaacat tttctcaggt gcttctcagc    1380
cattcagtat tctttaggtg agaattcttt gtttagctct aagccccatt tttttaatgg    1440
ggttatttga ttttctggag tccaccttct tgagtttttt tttccatttt ttattacata    1500
atttcctcaa ttacatttcc aatgctatcc caaaagtccc ccataccctc cccccccaa    1560 ttccctaccc accccttccc attttttttgg ccctggcgtt ccctgtact ggggcatata    1620 aagtttgtgt gtccaatggg cttctctttc cagtgatggc tgactaggcc atcttttgat    1680
acatatgcag ctagagtcaa gagctcccgg gtactggtta gttcataatg ttgttccacc    1740 tataggggttg cagatccctt tagcttcttg ggtactttct ctagctcctc cattgggagc    1800
cctgtgatcc atccaaatagc tgactgtgag catccacttc tgtgtttgct aggcccggc    1860 atagtctcac aagagacagc tacatctggg tccttttgat aaaatcttgc tagtgtatgc    1920
aagggtgtca gcatttggaa gctgattatg gggtggatcc ctggatatgg cagtctctac    1980
atggtccatc cttttgtctc agctccaaac tttgtctctg taacttcttc catgagtgtt    2040
ttgttcccaa ttctaaggag gggcatagtg tccacacttc attcttcatt cttcttgagt    2100
ttcatgtgtt tagcaaattg tatcttatat cttgggtatc ctaggttttg ggctaatatc    2160
cacttatcag tgagtacata ttgtgtgagt tcctttgtaa atgtgttacc tcactcagga    2220
tgacgccctc caggtccatc catttggcta ggaatttcat aaattcattc tttttaatag    2280
ctgagtagta ctccattgtg taaatgtacc acattttctg tactcattcc tctgttgagg    2340
ggcatctggg ttcttttatag gttctggcta ttataaataa ggttgctatg aacatagtgg    2400
agcatgtgtc cttcttaccg gttgagacat cttctggata tatgcccagg cgaggtattg    2460
ctggatcctc cggtagtact atgtccaatt ttctgaggaa ctgccagact gatttccaga    2520
gtggttgtac aagcctgcac tctcaccaac aatggaggag tgttcctctt tctccacatc    2580
cacgccagca tctgctgtca cctgaatttt tgatcttagc cattctgact ggtgtgaggt    2640
ggaatctcag ggttgttttg atttgcattt ccctgatgat taaggatgtt gaacattttt    2700
ttcaggtgct tctctgccat tcggtattcc tcaggtgaga attctttgtt cagttctgag    2760
ccccattttt taatggggtt atttgatttt ctgaagtcca ccttcttgag ttctttatat    2820
atgttggata ttagtcccct atctgattta cgataggtaa agatcctttc ccaatctgtt    2880
ggtggtcttt ttctcttatt gacggtgtct tttgccttgc agaaactttg gagtgagttc    2940
tttatatata ttggatatta gtcccctatc tgatttagga taggtaaaga tcctttccca    3000
atctgttggt gacctttttg tcttattgac ggtgtctttt gccttgcaga atctttgcaa    3060
ttttatgagg tcgcatttgt caattctcga tcttacagca caagtcattg ctgttctgtt    3120
```

```
caggaatttt tcctctgtgc ccatatcttc gaggctttta cctgcttcct cctctatatg    3180
tttgagtgtc tctggtttaa tgtggagttc cttaatccac ttagatttga ccttagtaca    3240
aggagatagg aatggatcaa ttcgcattct tctacatgat aaccgctagt tgtgccagca    3300
ccatttgttg ataatgctgt cttttttcca ctggatggtt tttgctccct tgtctaagat    3360
caagtgacca taggtgtgtg ggttcatttc tgggtcttca attctatttc attggtctac    3420
ttgtctgttg ttataccagt accatgcaga ttttatcaca attgctctgt agtagagttt    3480
taggtcaggc atggtgatta caccagaggt ttttttatc cttgagcaga gtttttgcta    3540
tcctaggttt tgtgttattt cagatgaatt tgcagattgc cctttccagt tcgttgaaga    3600
attgagttgg aattttgatg gggattgcat tgaatctgta gattgctttg gcaatatagc    3660
catttttact atattgatcc tgccaatcca tgagcatggg agatcttcc atcttctcaa    3720 atcttcttta atttctttct tcagagactt gaagttcttg tcatacagat ctttcacttc    3780
cttagttaga gtcacgctaa ggtattttat attatttgtg actattgaga agggtgttgt    3840
ttccctaatt tctttctcag cctgtttatc ctttgtgtac agaaaagcca ttgacttgtg    3900
ttagttaatc tcatatccag ctacttcact gaagcggttt atcaggttta ggagttctct    3960
ggtgtaattt ttagggtcac tcatatatac tatcatatca tctgcaaaaa gtgacatttt    4020
gacttcttcc tttccaattt gtatccccttt gatctccttt tgttgtcgaa ttgctctggc    4080
aaggacatca agtactatat tgaataggta gggagaaaat cggcacccctt gtctagtccc    4140 tgattttagt aggattgctt caagtttctc accatttact ttgatgttgg ctactggttt    4200
gctgttgaat gctttttatc atgtttaggt atgggccttg aattcctgat cttttccaaga    4260 cttttatcat gaaagggtgt tggattttgt caaatgcttt ctccagcctt tcattctgag    4320
gttgtgtctg tctttttccc tgagatgggg ttcctgtaag cagcaaaatg ttgggtcctg    4380
tttgtgtagc ccgtctgtta ttctatgtct ttttattggg gagttgagtc cattgatatt    4440
aagatatatt aaggaaaagt aattgttgct tcctattatt tttgttttta aagttggcat    4500
tctgttcttg tggctgtctt cttttaggtt tgttgaagga ttccttttctt gcttttctta    4560 ggtcgtggtt tccatccttg tattcatttt tttctgtta ttatcctttg aaggactgga    4620
ttcatggata gataatgtgt gaatttggtt ttgtcttgga atacttttgt ttctccatct    4680
acggtaattg agagtttggc tgggtatagt agcctgggct ggcaattgtg ttgtcttagt    4740
gtctatataa tgtctgtcca ggatcttctg gctttcatag tctgtggtga aaaatctggt    4800
gtaattctga taggcttgcc tttatatgtt acttgaattt ttcacttact gcttttaata    4860 ttctttctt atttagtgca tttgttgttc tgattattat gtgtcgggag gaatttcttt    4920
tctggtccag tctatttgga gttctgtagg cttcttgtat gttcacgggc atctcttctt    4980
ttaggtttgg gaagttttct tctataattt tgttgaagat atttgctggc ccttcaagtt    5040
gaaaatgttc attctcatct actcctatta ttcgtatggt tggtcttctc attgtgtcct    5100
ggatttcctg gatgttttga gttaggatct tttgcattt tccatttct ttgattgttg    5160 tgcagatgtt ctctatggaa tcttctgcac ctgatattct ctcttccatc tcttgtagtc    5220
tgttgctgat gctcgcatct atggttccag atttcttcc tagggtttct atctccagtg    5280
ttgccccact ttgggttttc tgtatagtgt ctacttccct ttttagatct agtatggttt    5340
tgttcatttc catcacctgt ttgggtgtgt tttcctgttt ttctttaaag acttgcaact    5400
ctttagcaga gttctcctgt atttaagtga gttattaaag tccttcttga tgtccagtac    5460
```

```
cataattgtg agatatgcct ttaaatccaa gtctaggttt ttgggtgtgt tggggtgccc    5520
tggactggct gagttgggag tgctgcattc tgatgatggt gagtggtctt ggtttctgct    5580
agtaagattc ttacatctgc ctttcgccat ctggtaatct ctggagtcag ttgttaaagt    5640
tgtctctggt taaagcttgt tcctctcgtg attctgttat tctcttccag cagacctggg    5700
agactagctc tttcctgagt ttcagtggtc agagcactct ctgcaggcag gatttcctct    5760
ttcagggaag gtgcacagat atctggtgtt cagatttgcc tcctggcaga agatgatggc    5820
ctgaaacagg acctgtccca gaagctgtta gcttctgtag tcaacactgt cacctgtgca    5880
gactagtctc ggtggagtcc gggaaccaag atgtctcctg cagatgctct ggcattccct    5940
tctgggccgg gtgatcacct ctcctctggc agggaaggtg ccctggtgtc tggaacccga    6000 aaaggggggct gcctcagaag ctctgtggct actgcctgtc ccagaagctg ttagcttctg    6060
tagtccacac tctcacctgt gcagactagt cttggtggag tctgggaacc aagatgtctc    6120
ccgcagatgc tccagccatt ctcctctttc tgttgcttat tttgacctat gaaatcctgg    6180
acatatagtt ctagtgttgc ttgtaatctc ttttctaagc caaggaattt ttttttatcta    6240 gggcacaatc ttttgagaag acatattaaa tcaagagaat aaatattgca agaccaataa    6300
atgataaggt atctattttc tttaaatcca tcgctgtcaa accattcaaa atatcctcac    6360
ataaagccaa aaagatattt attgtgtttc ccatcttagt tgagttcaag tcaatatttt    6420
ggtgccattt tgttgcagta aatctctaac acaaatatgc ctgggcaatg aaaacacaac    6480
tcagttaata tgaatacaga ttgttcagat ctaccactac actaccatct tcttcatcta    6540 agagaccccct tagaacttgc agtttctcca ggccttgtgc ttctgcgctg cttttcttct    6600
tcttcctctt ctacattgct tctctcataa acctacttct tttttttccct ccttctgttc    6660 catcttccct tttatctgcc caatcattag ctctcctttta ttttacaaat taaggtgtga    6720
agccggtttc taggaaatca cctgagtgct gacttgttcc ttgttcagag ccacgcacag    6780
gagaacagaa ttaacatcaa atataattat ccccagggct atccacaaca cgtgcatcct    6840
ataagatcac cacggactaa tgctggtctt caattacaac ataaacaaca aaaccccac    6900 atatatgtgg aaacaaatcg aactatacaa agaatcaatg aaaccaggag cttgttcttt    6960
gagaaaaatc aacaagatag ataaacccct tagccagacta accagagggc acagagacag    7020
tatccaaatt aataaagtca gaaatgaaag gaagacataa caatgaaata tatcttaaaa    7080
taattaatct gtttgtagac tattagcagt tgaaaatatt aaaatcatgt tctacaaacg    7140
tggaattatt attgataatt ttctcactgt gcttgaaatt agcatttttct taatgtttaa    7200 cttcaaagag ttttttgctat tttgaaatat taaacatata cttactgata aaataatttc    7260
cctcctaaca acactgataa tcttttttta agtaaactga ttattagaca atgtacacag    7320
atatataatg tgttttaaat actctcccac tgtcaggtgg tatcatatag ggcctttgaa    7380
tatattttta aatgtattat ttgtaatatt ttatggtctc tcctatgctt atttctgaaa    7440 gaatatttg tatgttttga aacaatttag tatttaacat tagatatagg atcctcagtt    7500
atggatagta ttaaatattc attaatgata tttttaaggt ataaaggat atgaatataa    7560 aagtttaaca aattttatgt attatttgat tctaaaaata ctcaatatta ttaatatgtt    7620
tgatgtttaa aatgcatttta aataataaaa acatttaaaa aaataaaatc aagaaatgag    7680
gttctaagca gaggtcaagg aaaatgagga atagaaaaat agtaaaaatc aatatgtcca    7740
tttattcaag gaaagctcct acatagacat tgcaccagat tagcaaatat tatggtcctc    7800
atattagttt aagttaggag actatgctta tgttatctat ttacattcta aggagcctag    7860
```

```
acatttgtga atggattaca ttataagagg aggatgtcta cttaagtagg catgaacgcc    7920
tgtgcattgc accctatgag ttccatcagc attccatgat tggagtatga agaacagcat    7980
tatagacatt acccagaacc ttagtggttc tagaatgcca agataaaaca atctaacctt    8040
ctggatagta gggataaatg ttcctatatc atcagaattc actggtgccc tgaggatgtt    8100
accctgctaa ctgacaattc acaggacatc acatggattc tgataagttg cagaaaagag    8160
gagatgcatt caattggtcc tcctccttct aagctgcaat attaggtgca tccaatttgt    8220
gaacttcaat ttagattaca atagacatga ataatctgaa ttcatgtagt acatattttt    8280
gttttaatat gagttaccat tgttcagaaa attaaataca catgatcaca tattcctaca    8340
tagtgctgtt agttttttcac atctctggga caatattcca aatatctcct tcattagtga    8400
aaatatcaac tactgtaaag cttagctaac atgcctttgc aggaataaga acatcctgga    8460
ttgaaagcta cacagggaga tgtaaaactt tctaagcaca cacattctcc atccattagg    8520
atcatggtcc atgagatttt tctctctctc ttcttcccat aaatgcatg tacatgcagg    8580 ttgggaaaca gattgtgttg cagaatacat ttgcttgatt tccacttcct tctcaatgca    8640
aatatttttg aagtgttaat tttgctgtga gtaccacagt ggttcttgct ctttctgttg    8700
actcctgtct gtgaatgttc caggaattca cacatggaca cacgtggggc tgcatctgag    8760
ctccagactc actgttgtcc ttctgtcctc agctgctctg gcccaggcac agcctcgtga    8820
attcaacaaa gaccctgatc tctcttgttt acacctcatt acaaatggga actgttagag    8880
gtggacccaa ctgcatttcc atgaggaaag cacatgagtt tgagagggtc gttgatgata    8940
aggtagaaac aactttaatt cataggctga gatatcagtc atcacctcca gataaacaag    9000
agccatttct tcctgcatct gagccctgta agcacactag ctttaggaat atgttactgc    9060
tgaagtcaga ttgggcaact tcatagtata caatagaaaa tctacctgca gatgagttca    9120
gaaccagcag ggggcacaat ggggccaaga atccctagca gagagatgtg gtgtgtgtgc    9180 agggggactct gcatcctctg tggtttcctt tcttaactta catgtacctg tagtgattga    9240
catgtaacgt ttccacgctc aaacactgtg aagatacttt gctaaacact tcaaagattt    9300
atgttttctt gatgtgtgca tgtgtgtatt ctttttttgtt tttagacaca gggtttctct    9360
gtgtagtcct ggctgccctg gaactcactc tgtagaccag gctggcctcg aactcagaaa    9420
tctgcctgct tctgcctccc aagtgctgaa gttaaagaca tgtgccacca ttgcctggcc    9480
atgtgtgtat tcttgatgca ctcttctgtt gacagataca cagtttattt ccataattta    9540
tttattgtga tggtgctgca ataatcactt atgtacaaat gtttctgaag tatatttagt    9600
tttggtcatt tgggtgatta ttttttttctt tctagtatat agcattttgg aaaggtagat    9660
attaattgta tgtatgggaa ggaggctgta aattctaata acttagctgc ttttgaaatt    9720
tgtcctcaat tctatcatcc ttgtaaccac cttaaatcca tctattagcc ttgtcacaag    9780
tgagccactg tctcaggctg caaatctttt tatagattag gtcgtgatgt tacatccaca    9840
gcctctgcac aatgctcagg ggtgggatat gggatgaatt ccctcagaca gcattaggac    9900
ttggatctca gcagactgat tcttgaccca aatgtctctt cttctctagc aggagtaagt    9960
ccttatctaa gatgtactct gctcatgaat atgcaaatca attgagtcta tggtggtaaa   10020
tatagggatg tctacacccc tcaaaaactt aagatcactg tcgtcttcac agtcacagga   10080
gtacacagga catcaccatg tgttggagct gtatcatcct cttcctgtta gcaacagctg   10140
cacgtaaggg gcttacagta gcaggcttga ggtctggcca tacactcatg tgacaatgac   10200
```

```
atccactctg tccttccctt cacaggtgtg cactcccagg tccagctgca gcagtctggg    10260
gctgagctgg tgaggcctgg ggcctcagtg aagatttcct gcaaggcttt tggctacacc    10320
ttcacaaacc atcatataaa ctgggtgaag cagaggcctg acagggcct ggactggatt     10380 ggatatatta atccttataa tgattatact agctacagaa ccagaagttc aagggcaagg    10440
ccacattgac tgtagacaaa tcctccagca cagcctatat ggagcttagc agcctgacat    10500
ctgaggactc tgcagtctat tactgtgcaa gacacagtgc tacaaacaca tcctgagtgt    10560
gtcagaaacc ctggaggaga agcaagcaga gctggaatgg agatgacaga aagattatca    10620
tttagacttg ctcagaaaga gaaattttga atgcccattt attgcctctt ccttacagta    10680
ctatagtgcc tgttttgtt gacattttca aactaatttc caaagtcact accacaattt     10740
acaatcacat aaaaagcaag caaggataac attattttct gtgcttactt gccatttata    10800
ttcttgctta ttctcatctc actgaggtca tattgggaca ttaaatttct ggggttactt    10860
tttattaaaa attttcatt attcattcac tttacatcct tctagtcttc ctctcacaca     10920
tgccctatcc ctttctcctc tgagaggatg gagccctccc taccctcgta tcccttacc     10980 caggcacatc aagtgtctgc agtactagga atattctctg tcaatgctgc cagacaaggc    11040
agacaagtta ggggatcagg attcacagga aggcaacagc ttgagggaca gccccactg     11100 aagttattgg tggattcaca tgaagactga gttgcacatc tgctacatat attcaggggt    11160
cctatttaca gctcaagtag actcttgttg gtggtttagt ctcttagaac cccaagtgtc    11220
caggttagtt gactctgtgg gtcttccttt ggagttccta tcccctccag atccctcagt    11280
tcttctccca actcttccat aagacacccg taggtccatc caatgtttgg ttttgggttt    11340
ttctgcatct gcttcagtca gctgctgggt ggagcatctc tgaggataat tatgagaagc    11400
tcttatgtgc aagcataaca ggatatcatt attagtgtca gggactggtg cttggccatg    11460
ggatgggtct caagtttggt cagttatttg gccattccca cagtctctga taatctttgt    11520
ccctgcattt cttgtagaca ggaaaaatat tgggttgaaa gttttgtggg tgggttggcg    11580
tctctattgc tccactgggc ttctttctgg atataggagt ttgcctcttc aggttccata    11640
ttcccaaagt agtgtgtcac actaaggtca ctcccataca gagggacact cattctcttg    11700
ccacgtctct gtccaccttc attggacctg aggttcctga atcatacaga actgcatgtg    11760
tgcaaccaca cagaacaagg ctatctatca gaggcctacc ataccaggac catcaaggtt    11820
caccttactc ccaatactga ctacaaaaag aacatcaagg accaatgcag tctatatgga    11880
taaacacact tgaaagaaca caaacaagat tgagggcaac atgacacctc caaagcatac    11940
ctaaccgagt acagcatgcc ctggatatcc taacacaatc aaaacacaag aaagttacct    12000
taaatccagt cttataaagg tgatgaaggc ctttaaatag gaaatgaatt aatccttagg    12060
ataatacagg acaatacatt cgaacagata gaggtcttta ggaggaaaga aataaatccc    12120
tcaaagacat acatgaaaat acaattaaac aggtgaaagt aataactaca atggtgtaag    12180
acctaaaaat ggaaatagaa gcaataaagt aacacaaact tagaatcttg aaggtggaaa    12240
acctagagaa caggaatact agatgcaagg atgatatctt ctaggtccat ccatttgctt    12300
gcacaattta tcatgtcctt gcttttaata gttgaacagt atttcattgt ttaaatgaac    12360
cacatgttct gtctccattc tctggatgag ggggtgagca agttttcca cattctggct     12420 attacaaata gagctgctat gaacctagta gaaaacatat cctgtgtatg gtggagagtt    12480
ttggagtata tcaccaagag tgttatagct gggtcttcat gtagaactat tcctaatttt    12540
ctgagaaatc ccaagtcaga tttctagaat ggttgttcaa gtgttcactc caaccatcaa    12600
```

```
tggaggactg ttttccttgc cagcatgtgc tgtattttga gttttttgatc ctagccagtt    12660 ttatcctgca tttcacactt agatatggac tatggtacag gacagagaga aaccaacctt    12720
ctactcacca ggatattcta cctgctacca atttatttat ttatttattt atttatttat    12780
ttatttattt atttatttat attagagaac aacaccatgc agtttagaag aagtactaag    12840
acgtcagtga tgttatactg tgcctaacct tgcattgtac aatctcagct ttcaggtaag    12900
acagtgcatg actcttatgc agtgccaact gttttctgat tgtatttatg gtctattgcc    12960
taggaatgac ctcctctcaa ataaacatgg tcaaaagccc atggcctgag atgacagagc    13020
ccctagtaga ccctagttgt atttctgaag tttagatatc ataatgactt ataaatactt    13080
atgtttatac aatagattag agctgctctc agccatgacc aaggagcttc tgtgttcaat    13140
gaataatgat tgatgcagac attcgtgagt ggtcaaagtg gtgagaatga ttagagagtc    13200
ctcagccaca caagcgttaa tgatatgaac tttccaatat attaactgta ttaatgaata    13260
aatgcagaca tcatatgaga tctcattagt agttcttagg tattgcattt ttatatacaa    13320
ttatgcatat cagtacatta tagtgtataa aggaaattgt ctagcataat agagaaaaat    13380
aggacagtca agaaacaaaa gagtagaaat tatgggtgaa atatgcagtg tgaaatattt    13440
acatgaaaat tttaaccata tgtaaaattg ttattttttgt ttttcagaat gagtttgctc    13500
attctttgac attttttattc ctgtgtgaaa tatatcagga tcatatgtat cccattctga    13560
tggtctgact tccactggga atttccaata tatctcttcc aactaactga ccagtttctt    13620 ttttttcttat tttctctctt tctcgttttg ttttgctttg ttttgttttt caagacaggg    13680
tttctctgtg tagctctggc tgtcctggaa ctcactttgt agatcaggct ggcttcgagc    13740
tcataaatcc acttgcctct gcctcctgag tgctgggatt aaaggagtgg ctaccacgcc    13800
cggctagttt ttttttttct tataagaaca acatttactg gatggtcact tacatattca    13860
gaggttcagt caattattat caaggcagaa gcatggcagt ggtccagtag tcatggcact    13920
ggggaaggag ctgagagatc tacatcttgc tccaaaggga aagaggaata gtctgacttc    13980
catgtgtttc agaggagggt ttcatttccc accccccacag tgacacactt cctccaacac    14040
ggccacacct cctaatattg ccactcttgg atcaagcata ttcacaccac aaaggaaagt    14100
ttagagataa acattaagaa aattaatgaa gtcatttat cttatatgct caacatgact    14160
agtacttaaa accataattt tacatgtaca atatttcatg gcataacata ttttttatat    14220
ttttattaga tattttctttt atttatattt caaatgtgat acccttccc aattcccctc    14280 caaaaatccc ctatgccttc ccctcatagc cagctcccaa acccacccac tcctgctttc    14340
tggtcctggc attcccctat actggggcat aaaaccttca caggaccaag tgcctcttct    14400
ccattgatgg ccaattaggc catcctctgc tacatatgca gctagagcca tgagttccac    14460
catgtgtttt ctttgattgg tggtttagtt ccagggagct ctgggggtat tggttagttc    14520
atattgttcc tcctatgggg ctgcaaaccc tttcagcccc ttgggtattt tttctagctc    14580
cttcattggg gaccctgtgc tccatccaat ggatgagtga gcctccactt ttgtatttgt    14640
caggaactgg cagagtctct caggagacaa ttatatcagg ctcctgtcag caaaatctcg    14700
ttggcatctg caatagtgtc tgggtttggt ggttgtttat gggatggatt tctgggtggg    14760
gcagtctctg gattgtcatt cctttagtct ctgcttccac ctttgtcttt gtaactccat    14820
ccatgggtat tttgttcccc cttcaaagaa ggatcaaaat atccacactt tagtcttcct    14880
tcttcttgag tctcatgtgt ttttcaaatt gtatcttggg tattctgagc ttctaggcta    14940
```

```
atatccactt atcagtgagt gattatcatg tctgttcttt tgtgattgag ttacctcact    15000
tagcatgata tcctccaggt ctatccattt gtctaagaat ttcataaagt cattgtcttt    15060
aatagctgca tcgtactcaa ttgtgtaaat gcaccacatt ttctttatcc attcctctgt    15120
tgagggacac ttggttttc ccagcttctg gttattataa ataaggctgc tatgaacata    15180
gtggaacatg tgtccttagt acatgttgga acatcttctg ggtatatgcc caggagtggt    15240
attgctggat cttctggtgg tactatgtcc aaattttgg ggaaccatca aactgatttc    15300
ctgagtggtt gtacaagctt gcaatcccac accagcaata gtggaatgtt catctttgtc    15360
caagtccttg ccagcatctg ctgtcacctg agtttttgat cttagccatt cttactggtg    15420
tgaggtggaa tcttggggtt gttttgattt gcatttccct gatgtttaag ggttttgaac    15480
atttttaggt gcttattaga catttggtat tcctcagttt agaaatcttt gtttagctct    15540
gtaccacatt tttgaatagg gttatttggt tttctggagt ctaacttctt gagttctttg    15600
tacatattgg atattagccc tctatcagat ttagaattag taaggatctt tccccaaact    15660
gttggtggtt cttttgtctt attgacagtg tactttgcct tagagaagct ttgcaatttt    15720
atgaggtccc atttgtcaat tcttgatctt atagtacaag ccattggtct tttgttcagg    15780
aatttttccc atgtgtccat atgttcaagg catttcccca ctttctccac tacaagtttt    15840
agtgtctctg gttttatgtg gaggtccttg atccacttag atttgagctt tgtacaagga    15900
gataagaatg gatagattca cattcttcta catgctctct gccagttgag ctagcaccat    15960
ttgttgaaaa tgctgtcttt ttttcccc actggatggt tttagctct tttggccaag    16020 atcaagtgac cattggtgtg tgggttcatt tcttggtctt caattctagt tcactgactt    16080
acctgtttgt cactgtacaa ggaccatgca gctttttca caattgctct gtagtacagc    16140
ttgaggtctg ggatggtgat tctaccagag agattcttt actgttgtga ataattttg    16200 ctatcatagg atatttttt atttcagatg aatttacaaa ttgctctttc taactctgtg    16260
aacaattgag ttggaattt gattgtgatt gctttgaata ctcaagatat aatttacaaa    16320
acacatgaaa cttaacaagg actactaaag tgcagatact tcgatccttc ttagaagggg    16380
gaacaaaata cccatagatg gagttacaga gacaaagttc ggagcagaga ctataggaac    16440
gaccatccag aggtccacct ggggatccat catgtaaaca accacccaaa acagacacta    16500
ttgtggatgc caagaagaac ttgctgacag gagtctgata tagctgtctc ttgagaggct    16560
ctgccagggc ctcagaaagt ggaggctcac agccatccat tggatggagc acagggtccc    16620
caatgaagga gctagagaaa gtactcaagg agctgaaggg gtttgcagcc ccataggagg    16680
aacaacaata tgaactaacc agtaccccca gagctccctg ggactaaacc accaatcaaa    16740
gaaaacacat ggagggactt gaagctcttg ctgcatttat agcagaggat ggcctagatg    16800
gtcatcaatg ggaggagagg tcaatggtcc tgggaaggtt ccatgcccca gtataggga    16860 atgccagggc caggaagcag gagtgggtgg gctgggatc agggaggggg agatgatagg    16920
gcattttcag tggggaaact aggaaagagg ataacattta aaatataaat aaagaaaata    16980
tctaattaaa aaggattacc tatgtgcatg ggagctcatg agcagcaggg gtcactctaa    17040
ggccaataat ccacatagag cgatgagctg tgtgtgaaca ggactctgta tcctctgtgg    17100
tttcctttct taagtgtatt aactgatctg tccagctgtg attgacatgt gatgtctcca    17160
tgctcaagcc cagtaaagat tctctgttaa ataccttaca gacttatgtt tacttgtttt    17220
tatttgcttt tcatatttt ttaaaaagtc atacaatgta ttctaataac tcattctccc    17280
atctccaatt tattctaagt ttttcttaac tcatccaacc acacactttt taattctgat    17340
```

```
aaagcaccec ccccccaaa aaaaaaccca accaaccaaa aaaaaaaaaa gccaaggaat    17400 ttaaagggg  attgaaagca aataaaaact aaacaaaaaa gtaaaaacta cacacacaca    17460
cacacacaca cacacacaca cacacacaca cacacactca cacacacaca cacacaccac    17520
acacacacac acccatgcac gaacacacac acacacacac acacacacac acacacacac    17580
acacacacac acacatggaa tccagtaaaa ccacaactct ttacccatga tacacaggaa    17640
aatataagtc aaacaaacag aatggaagaa ggtggtatta taaaaatgtc tgcacaaata    17700
ccattaagtt cattttcttg ttggctacca actgctaagc ctgtctccct tgattaattg    17760
tgcttatcat cccctatgaa ctccattgga ggacactaat ttttccttct gtctccagga    17820
attgaagtgt tgcagaactc tcagtagctt tatttacctg cacaatacag cctctaatcc    17880
aaccagtgaa aattaccaca tgagagactt ccaaatgaaa gaacaggtaa agttgtctac    17940
tggcaagctt agtaatatca tgtaaatgcc ttagaattta atgacatatg tcatcctctg    18000 aggtaataa  atccattttg gtgcatatat accctgaact caccactaac ataatacaac    18060
aattaaaaaa ttccaacatg gatgcagagg aatccctgag ggacatttgt tgatttgtga    18120
gcacaatata attattttt gggggggaaa tgtctgaatg ttaactcttt accagtgata    18180
atctattcta ttaatgtgta cataggtagc actaattaaa atcactgtgt tatcaggtaa    18240
tgaaacagag gaagtaggat gctgggaaac agacttttgg aaggtcccaa gggaaaccac    18300
agggacctag tggtgataga ttatggtgag agtcctgaga gtggtcatag attatagcat    18360
atttcatatg caattgaaaa tttcaaagaa tgaaaatcct tatgaaatat agaaataaca    18420
actttactta tgtacatata cttcatagta caatttttac actgtgcata tttctcctgt    18480
aacatctggt tcctcctatt ttcctttatt ctcctagaca atttcactga tacaatctca    18540
tgtttttgta taaatagttg tatataacta ttaaatacat aagctgttaa tgagtcttca    18600
ttaatgtctg tgatttttt attgtcttaa ttaatactat tatctctaat tgcatccaca    18660
ttttcaaaag caatgtaaat ttcttactca tttctgttca aaaacttctg ttgttgtatc    18720
attaccatgc cttagtgata aaatcctttc ttgacacatc tatagctatt gctataattt    18780
agttattgat gatcctcctg caataatcat tgataggtaa atattttaag cacttttact    18840
tttagtcatt ttagtgagat ttgaagtagt atataacctg ttggaaaggc aaatattaat    18900
tccatatatg tgaaagaaga cgctaaaact aaaaacatta gccactttta gatatcttct    18960
ccttcttctt cttcttcttc ttcttcttct tcttcttctt cttcttcttc ttcttcttct    19020
tcttcttctt cttcttttct tcttcttctt ctccttctcc ttctccttct ccttctcctt    19080
ctcctcttcc tcctccttcc ttccttcctt ccttccttcc ttccttcctt ccttccttcc    19140
ttccttcctt ccttccttcc ttccttcctt ccttccttcc ttccttcctt ccttccttcc    19200
ttcctttctt tctttctttc tttctttctt tctttctttc tttctttctt tctttctttc    19260
tttctttctt tctttctttc tttctttctt ctcctcctcc ttctttttcc ttctccttcc    19320
ccttcacctt ccccttcctt cctctttccc ttcccttcct ccttctcctc aatctacaat    19380
ctgttaacat attaacatgt cccagagtag agcaacagac tcaggtcaaa catctactga    19440
gaaatttgcc catgtagtta acatctacag catctgtcta ggggttacaa aaagtctatg    19500
ggatacaatt cctcagaaag gaataggatt tggacctgag catactgctg cctaacacat    19560
gaaatggcag ttcttctcca gctggactag gtccttaact aagaaatgca ctgctcatga    19620
atatgcaaat tacccaagtc tatggcagta aatacagaga tgtccacacc ctgaagacaa    19680
```

```
cctatgaaca atgttctctc cacagtccct gaagacactg attctaggac cgaagttcct   19740
attccgaagt tcctattctc tagaaagtat aggaacttct cgcgcgtctg gcctccgagg   19800
cctccgcgcc gggttttggc gcctcccgcg ggcgccccc  tcctcacggc gagcgctgcc   19860
acgtcagacg aagggcgcag cgagcgtcct gatccttccg cccggacgct caggacagcg   19920
gcccgctgct cataagactc ggccttagaa ccccagtatc agcagaagga cattttagga   19980
cgggacttgg gtgactctag gcactggtt  ttctttccag agagcggaac aggcgaggaa   20040
aagtagtccc ttctcggcga ttctgcggag ggatctccgt ggggcggtga acgccgatga   20100
ttatataagg acgcgccggg tgtggcacag ctagttccgt cgcagccggg atttgggtcg   20160
cggttcttgt ttgtggatcg ctgtgatcgt cacttggtga gtagcgggct gctgggctgg   20220
ccggggcttt cgtggccgcc gggccgctcg gtgggacgga agcgtgtgga gagaccgcca   20280
agggctgtag tctgggtccg cgagcaaggt tgccctgaac tgggggttgg ggggagcgca   20340
gcaaaatggc ggctgttccc gagtcttgaa tggaagacgc ttgtgaggcg ggctgtgagg   20400
tcgttgaaac aaggtggggg gcatggtggg cggcaagaac ccaaggtctt gaggccttcg   20460
ctaatgcggg aaagctctta ttcgggtgag atgggctggg gcaccatctg gggaccctga   20520
cgtgaagttt gtcactgact ggagaactcg gtttgtcgtc tgttgcgggg gcggcagtta   20580
tggcggtgcc gttgggcagt gcacccgtac cttt gggagc gcgcgccctc gtcgtgtcgt   20640
gacgtcaccc gttctgttgg cttataatgc agggtgggc  cacctgccgg taggtgtgcg   20700
gtaggctttt ctccgtcgca ggacgcaggg ttcgggccta gggtaggctc tcctgaatcg   20760
acaggcgccg gacctctggt gagggaggg  ataagtgagg cgtcagtttc tttggtcggt   20820
tttatgtacc tatcttctta agtagctgaa gctccggttt tgaactatgc gctcggggtt   20880
ggcgagtgtg ttttgtgaag ttttttaggc acctttgaa  atgtaatcat ttgggtcaat   20940
atgtaatttt cagtgttaga ctagtaaatt gtccgctaaa ttctggccgt ttttggcttt   21000
tttgttagac gtgttgacaa ttaatcatcg gcatagtata tcggcatagt ataatacgac   21060
aaggtgagga actaaaccat gggatcggcc attgaacaag atggattgca cgcaggttct   21120
ccggccgctt gggtggagag gctattcggc tatgactggg cacaacagac aatcggctgc   21180
tctgatgccg ccgtgttccg gctgtcagcg caggggcgcc cggttctttt tgtcaagacc   21240
gacctgtccg gtgccctgaa tgaactgcag gacgaggcag cgcggctatc gtggctggcc   21300
acgacgggcg ttccttgcgc agctgtgctc gacgttgtca ctgaagcggg aagggactgg   21360
ctgctattgg gcgaagtgcc ggggcaggat ctcctgtcat ctcaccttgc tcctgccgag   21420
aaagtatcca tcatggctga tgcaatgcgg cggctgcata cgcttgatcc ggctacctgc   21480
ccattcgacc accaagcgaa acatcgcatc gagcgagcac gtactcggat ggaagccggt   21540
cttgtcgatc aggatgatct ggacgaagag catcaggggc tcgcgccagc cgaactgttc   21600
gccaggctca aggcgcgcat gcccgacggc gatgatctcg tcgtgaccca tggcgatgcc   21660
tgcttgccga atatcatggt ggaaaatggc cgcttttctg gattcatcga ctgtggccgg   21720
ctgggtgtgg cggaccgcta tcaggacata gcgttggcta cccgtgatat tgctgaagag   21780
cttggcggcg aatgggctga ccgcttcctc gtgctttacg gtatcgccgc tcccgattcg   21840
cagcgcatcg ccttctatcg ccttcttgac gagttcttct gagggga tcc gctgtaagtc   21900
tgcagaaatt gatgatctat taaacaataa agatgtccac taaaatggaa gttttttcctg   21960
tcatactttg ttaagaaggg tgagaacaga gtacctacat tttgaatgga aggattggag   22020
ctacggggg  tgggggt ggg tgggattaga taaatgcctg ctctttactg aaggctcttt   22080
```

```
actattgctt tatgataatg tttcatagtt ggatatcata atttaaacaa gcaaaaccaa    22140
attaagggcc agctcattcc tcccactcat gatctataga tctatagatc tctcgtggga    22200
tcattgtttt tctcttgatt cccactttgt ggttctaagt actgtggttt ccaaatgtgt    22260
cagtttcata gcctgaagaa cgagatcagc agcctctgtt ccacatacac ttcattctca    22320
gtattgtttt gccaagttct aattccatca gacctcgacc tgcagcccct agagaagttc    22380
ctattccgaa gttcctattc tctagaaagt ataggaactt cctagggttt caccggttaa    22440
atggcatgtc ccctgttagt ggttcatgca agcagaagct gtatcctgtt tgacaaagat    22500
tcagcatgaa aggtcctgct acctaaaaaa aaatagacag atgagattta attaacctaa    22560
ataatttttt tcacaacaac agagtgaata cgcaatttac agaatgacag aaaacttttg    22620
cacactttgc ctgtgacagg gaactaatat gaagaatttg caaggaactc aaacaactct    22680
acaacaacaa cagcaacaag aaccaaataa ctccgttaaa atgagcaaag acatgagta    22740 gacattttca aaagaacaca tagaaatgga taataaatat ataaacaata ctcaacatca    22800
ctaaccatca gggaaatgca aattaaaacc acaataagat atcatcttcc accagtcaca    22860
atgactatta ctaaaaactc aaataatatc agatgttgct gaggatggga aatgaaggca    22920
actcttagac attgttgatg aggatgtaga tgagtacaac ctctgtggaa aatggtatgg    22980
agatttccca gaaaactaga aatagaactg tcatttggtc cagcaatccc actactgggt    23040
aactacccaa aggaaaataa actattattt caaaagata cccaccttct atgcttacca    23100
taaaactact ctcaatagca catatgtcaa actgagtgtc tgccaaccga tgattttata    23160
aaagaatata gcatgtatgc acaattcaat actagtcagc cacaataagg aatgaaactg    23220
tgtcttttgc agcaagatgc atagaagtgg gggacaatat aattagtgaa ctaactcaca    23280
aacagaatgt cacatgtcac acattattac ttgtaagtgg gaggtaaaca gcgtgtacac    23340
aaggatttgt agagagaaat tacacacatt ggagacttac aaggatgggc gggcagaagg    23400
tgggagcatg atgagtcatt acataacagg cacaatataa aataattaag aattgaccaa    23460
tgatcttaaa attaaaatgt agaatatgat caataaatga acttgatatt agttgacctc    23520
attaaattta aaaacttttt ctactcaaat gactgtaaga aaatgaatgc ccggttacag    23580
atgagaaact gtttgcgagt caaataacca ccaatgtaac tataataaga aacttcagaa    23640
ctcaactgtg aataaaaaag aaacaactga tggataaatt aggcaagggt ttctacagac    23700
atttcgtcaa agaagatgtg cagatgacac tgaagcatat aaacaggatc tcaacaggat    23760
tttccgttag agaaattcaa atcaagcccg caaagagaca ccactgtaca ctttttaaaa    23820
tggctgaaat taagaagaaa tacagataac atcaatgctg gtgagcatac caggttgcta    23880
gaggctaaaa cattgctaac aggaatgcaa aatgaaacag atactcagga aataattt    23940 tagttttctc taaaatcaaa catacccta acacctgaat atttgcatca gagaaaaaca    24000
atcttacatt cacgcataac ttctattcaa atattcaaga tatcgtgtgt atgtgtgtta    24060
gaaagtaaaa ataacataaa tgtctcaaaa tttgaatagg tgaagaacta ggaagcatct    24120
ataaattgaa taccaccagc aataaaaaaa taacaagtga ccgatacata aactattaca    24180
ggtgaactcc agacattgtg ctaagtgaga gaagccagtc tcaaagatca aagggacaca    24240
gctgtaagca ccacggtcat cctcaggtgt cagtggtttg ggctggactt tctgtgtctc    24300
tttcctgacc agacccagat attgagctcc accacttgca gatggaaaat cctattttca    24360
accatgcagt gaggtttgaa ctgcttcaca gactgaacga aacaaacacg ggctcctttg    24420
```

| | | | | | |
|---|---|---|---|---|---|
| aacagcgtcc | ggcatttgtt | ccaaccacaa | gagaacgtcc | ctcagctctc | ccacctcctc 24480 |
| ggttctctcc | tgcaagccag | cagccctgca | gtttagcctg | catctcccgt | gcatccaccc 24540 |
| atctccctcc | aagcaccttc | ccccacaccc | tccactgttt | ctgagagcac | aggcaggctt 24600 |
| tgaactttc | cgcattctgt | tgttattgaa | gttaggatgt | ttaggaccaa | cttaaggatc 24660 |
| atattttatg | actgaattcc | agtgcccctt | ctctcctggg | acagagtgca | taaccaagtt 24720 |
| tctgcaggtg | gagacgaagt | tgagcttttt | tcttcctcag | cctaggagat | gagcgctaat 24780 |
| tggagggttg | gcagaagctt | cccaccatcc | cagcactttg | gttctggtgg | ggcggaatcg 24840 |
| gtgccatagg | gcagagctag | aaaccgcgga | ctgaatgttc | ccagtggcac | tggacccagg 24900 |
| gcagagcctc | catccacgag | tggggctcta | tggaagaagt | gagtctctgg | ctctcagtag 24960 |
| ctctcgtcca | gcactgaacc | tcagcatcat | gtgctgtgtg | cagggtcaga | gggccaacgt 25020 |
| actgcccct | gggaaagcgt | tcctctggt | gggagttggt | agaaggtgtc | ctgtcttctt 25080 |
| ggctgcatct | gtccgcagtg | gagtttacat | catgctgagc | tgggatgtgg | aaggaaggaa 25140 |
| gagcatctta | gatcaaatat | gatgactggc | cttactgagt | tttctagatt | ttcctgaata 25200 |
| aatgtttctt | cactcactgt | gtgctgttag | agtctttcca | aacctgtaat | ttcccaaaat 25260 |
| aattttcact | ggtctcatga | gggcatggat | tcattgagcc | cctcatgctg | tcaaagaaa 25320 |
| atagaactgt | ttttttttt | cacttcatag | cgaacatcca | tgggttatca | aataatgggc 25380 |
| tggcttttct | tccaacactt | tacagacacc | atcaattttc | ttcttgctta | taaggtttta 25440 |
| accagaagaa | tgctgtcatg | gtctttctg | ttcttttgga | aggaatgccc | cctctactca 25500 |
| cctccacttg | tctgcctgta | tttctatttg | tctttggttt | tcaacaattt | taataagatt 25560 |
| tacctaaatg | tgtgtggggg | gagcatgggg | tgttattctg | ctgttctgtg | ttctctgaga 25620 |
| tgcatggatt | caccatttac | tctgtctcca | tttttgtgaa | aacaattaga | aaaaagtca 25680 |
| gtatgagccc | agaaacaagc | ctccctgaag | tgggcacagg | accacctggg | ggcgctcagg 25740 |
| acccactgaa | cacaagagcc | agccccaggg | caggtcaga | tgcgggttaa | gttctggttt 25800 |
| cctgtcaacc | ctgtggcttc | ctctccataa | aacagtttcc | tttgtggcat | atctctggat 25860 |
| tccttatcct | gttcttcctg | tgaagtctct | gaagaagaaa | catttgtcgt | aacaagagaa 25920 |
| aaactttctc | acatgcacca | aaggcagagt | cacctacagt | cacttactcc | tgtttctcaa 25980 |
| tgtcaataag | ttaccaatgc | ttctgaagtt | aatcagctaa | atctataaaa | ggtgcggtgt 26040 |
| ttaactcagc | attacagccc | agctcaacag | aactccaaag | gtcagccagc | agcagccagg 26100 |
| aaaaagtgca | tgctgggcat | tggggcagag | ggagttacca | tccagtgcaa | gagaagaaag 26160 |
| cccccgtggt | ggtcattgtc | aggactccaa | tcccacagtt | ccaattgtag | gtgatgccag 26220 |
| gcaaaggaag | agagacccca | ccaatggtta | gtgtggatgt | cgagtttgat | gtttccacac 26280 |
| tcacactcca | ggtgaatatg | aaaagattta | ttagctctat | ttctgaggtg | tctgctgaga 26340 |
| gcagcacagt | cctctcaaga | aattacagat | tggaatttcc | tcagtagagc | aggaaaggag 26400 |
| gctggctcag | ggctttataa | tgatttggtg | gtggggtcgg | cgggggggg | ggggcgtttc 26460 |
| tactcaggag | aaggagcttg | tgtgatttaa | acctcacact | gacatcacat | gagggagctt 26520 |
| ccatgatttc | ttactagatt | tcccatgtgt | ggggacaag | gatgagggag | aataaacctt 26580 |
| aattcatcag | catcaaggca | ccaaaaatag | gacctgacac | tttattctcc | ctagcagctt 26640 |
| aagaaaatga | gtgaaaaaga | gagataagag | tccacccatg | tgctgaaaag | catagctctt 26700 |
| ggtaaagacg | agaaaaaggc | actcctacga | agaaggggtt | gggcagaagc | tttatgctga 26760 |
| agggtttggc | taaagagaca | taatcaacag | gttacaggag | gggctactga | tgttcatgga 26820 |

```
ggtggtcctc acacatgcat actgaacaaa catgtctgta acgtatgacc cctgttcact   26880
taccagtgga gacttagcat ttaaattcat tccagtcagg ccctatgtgc aaacagcaga   26940
agcagagaca caaaggtact cagggtgcag cctctgtgaa cggccagagc caggccatgg   27000
tcagcggtct cggattagga gaaagttcct gatatcactg tagtgttcaa tcaaagctgg   27060
ggttatggtt tgtggaacag gggtcagttc atcaggggt gggctgcaat tgtcttcata   27120
gtgcttgtct cagtgccggt gcttactgag ccactagaga aaaaggttta attgagcttc   27180
tttaaaatca acattttgaa ttatttatca gacgtttcaa atatgtcatg ttgtttagat   27240
tctattgctg gagagttaag gtgatatttg gggttttgta actctgtttt ttcatacttc   27300
ctgaattgct tatctgtttg cttttcatta gctaaactat cgcttcttct tattttttaa   27360
ttcattctga ttttgatgaa tatttaattc cctttagaat gtgaatataa tgtacattgt   27420
gtgggtattt tgattttggt tcttggttta cttagtggca aagactctgt aagagttcct   27480
tgtctataga tagccattat ttagtggctt tctgaaatgg tggttttagt accaaagtac   27540
tggacttgtg agtaggctca ctgcccctg caggtcctag atagtggagg cctcaggaac   27600
tgtttctcat ttggaatgcc tttgtttcag cagattttgt gttgggttgt taagttcacc   27660
ctccacatta gtagatgtcc ttacagatta gagctgactc tggtagaagc agttgagtgc   27720
atgcttgata tctgtgcaca gggagaagct ctctgttgcc tcaggcgatg gactggtcta   27780
tgaaatgcac agtgacctga gttccctgct cagcccctga gaggtggacc aagctggaca   27840
cacatgagcc accgagcctg gcaagcaaaa gcgccagcct tgatggaaat ggcgagctga   27900
gcggcatcta ctcagtgtgg tttcttttgt tattaagagc tttagtgtgg tggctgtttc   27960
aaattcccgt tgtagtagta atatactggg tatgtgagca ggcccgtggt cttttgcggg   28020
gttggaatca ccgaagtaat gagaagctaa tctcattttc aactgctgta cactggtggt   28080
attgagtttg tatgaggtca tgcagtttga acgtcaggcc agtaggtggt gctcgcaggt   28140
aagagccggc tatggtggca gcagaagggt ttatgcttta ctggtgatta aagtgggaaa   28200
cttggcgtgt tccagatctt agagaaaaga tttttagtta tttctcattc aacctgatac   28260
tacctgaaag tctctcgaat gtaacttta ttttgtcgag atgggttctt tctatacccca   28320 tttttatgt ttttttttgtg aaaggatgtt gtttcatcaa atgcgttttc agcatcaatt   28380
gaaaaaagtt atatgtggat taaagatcaa atgtaaaac ctaacactat aaaacctctg   28440
gataataaca taggaaacag aatttaggag gtaagaactg acaaaggttt tataatgaaa   28500
atgctagaag tagttgcaac aaaattgaaa attgacaaat gggacctaag taaattaaag   28560
aacttctgta cagcaaaaga cactatcgac agagtaaaca ggcaacctac agaatgggaa   28620
ataaaatatt tgcagcctat acatctgaca aaggtccgac acttagtata tacatggaaa   28680
tttaacaaac atacaagaaa taaaagtga ccaaaggaca tgaaaagaca cttcaaaaaa   28740
gacctacatg tggccaacaa gcataggaaa aaatgctgaa tatcactatc attagagaaa   28800
tacatatcaa aacctcaatg aggtaccgtc tcacatcagt caggatggct aatcttaaaa   28860
aaaaaataac agattttaa ggttacagaa aaaggggaa atttatacac ttttggcggg   28920
aatataaatg agttcaacca ttgtggaaag cagtgtggtg atccctccaa taacctaaaa   28980
cagaagtttc atttgaccca acaatcctac aactggacat atacctaaag gaatataaac   29040
atgtaggttc actgcagcac tatccacaat agcatagaca tggaatttac ctaaatcccc   29100
atcactggca gaatgataga gaaaaatgtg gtacatacaa ccatggaata ctatgcagct   29160
```

```
aaggaaagaa tgaaactatg tcctttgtag gaacatgatg gaactggcag tcaatactct   29220
tagaaaacta attcaggaac agaaaaccag atattatata ttctcccta tttgttggag    29280 ataaataaaa gcaaatattc ttccagggcc tgagtcttcc ttattcaaca agtcattcta   29340
aattaagtgt tcagcaagtt gctgatactc atctaaatat tctatttcat ctgggccact   29400
tacatcactc aaaaagcaat gagagctata tttctaaggg gggttctagg ataataaata   29460
cctgaatagt gagaatatga aggatatgga aactgggcca cttatatcac tcaaaaagga   29520
atgagagcta tatttataag gggggttcta ggataataaa tacctgaata gtgagaatat   29580
gaaggatatg gaaactgggc cacttatatc actcaaaaag caatgaaagc tatatttaca   29640
aggggggttc taggataata aatatctgaa tagtgagaat atgaaggata tggatggttt   29700 tttttttaact caatgggcac ataactgtgg gagatactat attcctatga agaaggtatt   29760
cagacttcag agataagtaa tgtttcctac attgtgcttg tgacttggaa gcagtggatt   29820
gaagagtgtg ataagtgccc agaccaagca gaacagaaat cagcatgtaa agatgatgat   29880
ctatggatat gatctaaaac catgtaaata cttcaaataa ttctatttaa tgcagtttga   29940
aataaaacac aaacttattc aaaatacaaa ttacttggta attattttgg gagctatgag   30000
ttcaccaaga aactcaaatt cctatttcta tttcaacccc tgattcctac tgtcaatggg   30060
agggaagtct cagaaccaat cacacatcag acggcaaatc tgtcaaccaa gagtctttcc   30120
actgaaggac ctgggaggtc aggaccctca ggaaagtgct ggggaccctg tcttgggagt   30180
gcccagcaga tctcagaact ctccatgggt cctgctggac actcatgtag ggtaacgagt   30240
ggccaccttt tcagtgttac cagtgagctc tgagtgttcc taatgggacc aggatgggtc   30300
taggtgcctg ctcaatgtca gagacagcaa tggtcccaca aaaacccag gtaatcttta    30360 ggccaataaa atgtgggttc acagtgagga gtgcatcctg gggttggggt ttgttctgca   30420
gcgggaagag cgctgtgcac agaaagctta gaaatggggc aagagatgct tttcctcagg   30480
caggatttag ggcttggtct ctcagcatcc cacacttgta cagctgatgt ggcatctgtg   30540
ttttctttct catcctagat caggctttga gctgtgaaat accctgcctc atgcatatgc   30600
aaataacctg aggtcttctg agataaatat agatatattg gtgccctgag agcatcacat   30660
aacaaccaca ttcctcctct gaagaagccc ctgggagcac agctcatcac catggactgg   30720
acctggaggt tcctctttgt ggtggcagca gctacaggta aggggcttcc tagtcctaag   30780
gctgaggaag ggatcctggt ttagttaaag aggattttat tcacccctgt gtcctctcca   30840
caggtgtcca gtcccaggtg cagctggtgc agtctgggc tgaggtgaag aagcctgggt    30900
cctcggtgaa ggtctcctgc aaggcttctg gaggcaccct cagcagctat gctatcagct   30960
gggtgcgaca ggcccctgga caagggcttg agtggatggg agggatcatc cctatctttg   31020
gtacagcaaa ctacgcacag aagttccagg gcagagtcac gattaccgcg gacaaatcca   31080
cgagcacagc ctacatggag ctgagcagcc tgagatctga ggacacggcc gtgtattact   31140
gtgcgagaga cacagtgtga aaacccacat cctgagagtg acaaaaaccc tgagggagaa   31200
ggcagctgtg ccgggctgag gagatgacag gggttattag gtttaaggct gtttacaaaa   31260
tgggttatat atttgagaaa aaaagaacag tagaaacaag tacatactct aattttaaga   31320
taaatattcc attcaagagt cgtaatataa gccaaattca cagagtggaa aaggcgcgat   31380
cgcggagcag gggatcctta gatattggtt ggggttatct caccttaggt ctgaatatgg   31440
ggttgtctta gactgttttg tgctgttaga atagaatacc caagactggg aaatttatac   31500
tgaacggaaa tttatttctc acagttctag aggctgtgaa gtccaagagc acaggtgcca   31560
```

```
gagcaagtcc aagagcaagg gaaagtccaa agcaagtcca ggagcatctg gcgaggacct   31620
tcttgctgtg tcatcacatg gcggaaggca agaaagagag caagaggggg ccgaactcac   31680 cctttatiaa cagcaccaat cccacccatg aggtggggac cttatgacct aatcactctt   31740
catactgtta caatggcaat gaaatttcaa catgagtttt ggaggagaga agcattcaaa   31800
ccacagcaag ggtgctccta cctcctctct cagggcatct gcagaaagag ctgcaactgc   31860
acgtccttcc tccgtccatc ctccatccct tcccaatgtc cgtgcatatc ctgtgaccca   31920
ggaggtctgg catagggggt gctcctgcct taggtctgag gccctgtctg aagaggggta   31980
ggtgaggagg ccatctgatg gtctgggcca agacagtcac aggacgcatc atttatcatc   32040
aaggaggctg agggttgagt ctccaggtcc agggaactcc ccacaaagtg ggaaccctgc   32100
ccagctccac acagcctctg ctgggggacc ctgctctggt gcagagcctg gggacaggtc   32160
ttgagctcag ccagagtctg cctccctgtc atttaggaac taaaccaagc ggcaggatgc   32220
tggagcccag cccccatctg accttacagg gccaaggctg gggccctggg ttcccctcaa   32280
ggcgcagcag gactggagcc ccaggcagtg caggagtggc caaagctggg gcttcctcca   32340
gagcccccaa gcatcacggc accaagaagg gtaggaccct ggcctgagga attggcacca   32400
aagcccagaa aactaccctg gacaccatgg agagaggcct ggaggggaag caccaggcac   32460
tgcctcccct tctgatccca cctgaggtgg ctgccaagcc cagagagccg ctctgatgtc   32520
ccccagccct gcagcccagg gatacctgta ctgtgcccct gggggacccc tggccagtct   32580
gtgcaaagaa gtcaccaccc tacactcaga gacagtgggg gtcctcgtcc cacatcctca   32640
gagcatggcc cggctgctgc agggatggtc tcctggtcct cagagcatgg cccggctgct   32700
gcagggatgg tctcctggtc tcagagcat ggcccagctg ctgcagggat ggtctcctgg   32760
aggcccccca gtgctctatt gtcagggctc cctccacccc ccgcaccaa gagagagcca   32820 gaccccagca aggcttccag tggcttcagg tcacacccct aggctgaccc cagccccatt   32880
aacacctgcc tgagaaagct ccacgcacca gaactgaccg tctgctccaa ctcttgacct   32940
cccgttctca gggcgtctgc tgaaaaggct gcaactgcac atccttcctc cgtccgttcc   33000
cgatgtccgt gtgtctcctg tggccaggaa ggtcttctc gggacctgag agccgctccc   33060
tgaagtgtcc ccattgggaa ggatggggcc tgtgtctcca ggctctggga ggacagaatc   33120
ctgacctcaa cagtggccgg cacgacaca actggcccca tcccggggac gctgaccagc   33180
gctgggcaac ttttcccttc cccgacgact gagccccgag caccctccct gctcccctac   33240 cacctcccctt tacaaggctg tggcctctgc acagatgata atggagcttg gctcattccc   33300
ctagagtcgg tagggagtta aggacaaaac tcagtttcct ccacctgaac tcaagtctgc   33360
ctatgtttac ctaatcacac ctggtggaca gtttggacaa acttgcacac tcagagacac   33420
agacacttct agaaatcatt atctccctgc cccggggacc ccactccagc agaagtctgc   33480
taggcactgg cctgggccct cctgctgtcc taggaggctg ctgacctcct gcctggctcc   33540
tgtccccagg tccagagtca gagcagactc cagggacgct gcaggctagg aagccgcccc   33600
ctccaggcca gggtctagtg caggtgccca ggacaagaaa gattgtgaat gcaggaatga   33660
ctgggccaca cccctcccgt gcacgccccc tcttgccctg cacccacag cccagccccc    33720 cgtgctggat gcccccccac agcagaggtg ctgttctgtg atccctggg aaagacgccc    33780 tcaacctcca cccgtcccca cggcccaagg aagacaagac acaggccctc tcctcacagt   33840
ctccccacct ggctcctgct gggaccctca aggtgtgaac agggaggatg gttgtctggg   33900
```

```
tggcccctag gagcccagat cttcactcta cagaccccaa cccaagcacc cccttctgca    33960
gggcccagct catcccccte ctcctccctc tgctctcctc tcgtcgcctc tacgggaaat    34020
ccgggactca gcagtaaccc tcaggaagca gggcccaggc gccgtttaat aggaggcttc    34080
ctcacaatga aacttttaga aagccttgac tacaatgatg accttggtgt ggctgtgaac    34140
actgtcagct cccacagctg ctgcagcaaa aaatgtccat agacagggtg ggggcccggg    34200
gtcgtctgct gtcctgctca gcccacagca cgcatggagg atctgaggtg ccacacctga    34260
cgcccaggcc agaacatgcc tccctccagg gtgacctgcc atgtcctgca ttgctggagg    34320
gacaggggca gcctatgagg atctgggggcc aggagatgaa tcctattaac ccagaggaaa    34380
actaacagga cccaagcacc ctccccgttg aagctgacct gcccagaggg gcctgggccc    34440
accccacaca ccggggcgga atgtgtacag gccccggtct ctgtgggtgt tccgctaact    34500
ggggctccca gtgctcaccc cacaactaaa gcgagcccca gcctcagag cccccgaagg    34560 agatgccgcc cacaagccca gccccatcc aggaggcccc agagctcagg gcgccggggc    34620
agattctgaa cagccccgag tcacggtggg tacaactgga acgaccaccg tgagaaaaac    34680
tgtgtccaaa actgtctcct ggccctgct ggaggccgcg ccagagggg gagcagccgc    34740 cccgaaccta ggtcctgctc agctcacacg accccagca cccagagcac aacgagtcc    34800 ccattgaatg gtgaggacgg ggaccagggc tccagggggt catggaaggg gctggacccc    34860
atcctactgc tatggtccca gtgctcctgg ccagaactga ccctaccacc gacaagagtc    34920
cctcagggaa acgggggtca ctggcacctc ccagcatcaa ccccaggcag cacaggcata    34980
aaccccacat ccagagccga ctccaggagc agagacaccc cagtaccctg ggggacaccg    35040
accctgatga ctccccactg gaatccaccc cagagtccac caggaccaaa gaccccgccc    35100
ctgtctctgt ccctcactca ggacctgctg cggggcgggc catgagacca gactcgggct    35160
tagggaacac cactgtggcc ccaacctcga ccaggccaca ggcccttcct tcctgccctg    35220
cggcagcaca gactttgggg tctgtgcaga gaggaatcac agaggcccca ggctgaggtg    35280 gtggggggtgg aagaccccca ggaggtggcc cacttccctt cctcccagct ggaacccacc    35340
atgaccttct taagatatggg gtgtcatccg aggcaggtcc tccatggagc tcccttcagg    35400
ctcctccccg gtcctcacta ggcctcagtc ccggctgcgg gaatgcagcc accacaggca    35460
caccaggcag cccagaccca gccagcctgc agtgccaag cccacattct ggagcagagc    35520
aggctgtgtc tgggagagtc tgggctcccc accgcccccc cgcacacccc acccacccct    35580
gtccaggccc tatgcaggag ggtcagagcc cccatggggg tatggactta gggtctcact    35640
cacgtggctc ccctcctggg tgaagggtc tcatgcccag atccccacag cagagctggt    35700
caaaggtgga ggcagtggcc ccaggccac cctgacctgg accctcaggc tcctctagcc    35760
ctggctgccc tgctgtccct gggaggcctg gactccacca gaccacaggt ccagggcacc    35820
gcccataggt gctgcccaca ctcagttcac aggaagaaga taagctccag acccccaaga    35880
ctgggacctg ccttcctgcc accgcttgta gctccagacc tccgtgcctc ccccgaccac    35940
ttacacacgg gccagggagc tgttccacaa agatcaaccc caaaccggga ccgcctggca    36000
ctcgggccgc tgccacttcc ctctccattt gttcccagca cctctgtgct ccctccctcc    36060
tccctccttc aggggaacag cctgtgcagc ccctccctgc accccacacc ctggggaggc    36120
ccaaccctgc ctccagccct ttctcccccg ctgctcttcc tgcccatcca gacaaccctg    36180
gggtcccatc cctgcagcct acaccctggt ctccacccag accctgtctc ctccctccag    36240 acaccctcc caggccaacc ctgcacatgc aggccctccc cttttctgct gccagagcct    36300
```

```
cagtttctac cctctgtgcc taccccctgc ctcctcctgc ccacaactcg agctcttcct    36360
ctcctggggc ccctgagcca tggcactgac cgtgcactcc cacccccaca ctgcccatgc    36420
cctcaccttc ctcctggaca ctctgacccc gctcccctct tggacccagc cctggtattt    36480
ccaggacaaa ggctcaccca agtcttcccc atgcaggccc ttgccctcac tgcccggtta    36540
cacggcagcc tcctgtgcac agaagcaggg agctcagccc ttccacaggc agaaggcact    36600
gaaagaaatc ggcctccagc accctgatgc acgtccgcct gtgtctctca ctgcccgcac    36660
ctgcagggag gctcggcact ccctgtaaag acgagggatc caggcagcaa catcatggga    36720
gaatgcaggg ctcccagaca gcccagccct tcgcaggcc tctcctggga agagacctgc    36780
agccaccact gaacagccac ggagcccgct ggatagtaac tgagtcagtg accgacctgg    36840
agggcagggg agcagtgaac cggagcccag accatagga cagagaccag ccgctgacat    36900
cccgagcccc tcactggcgg ccccagaaca ccgcgtggaa acagaacaga cccacattcc    36960
cacctggaac agggcagaca ctgctgagcc cccagcacca gccctgagaa acaccaggca    37020
acggcatcag aggggctcc tgagaaagaa aggaggggag gtctccttca ccagcaagta    37080
cttcccttga ccaaaaacag ggtccacgca actcccccag gacaaaggag gagccccctg    37140
tacagcactg ggctcagagt cctctcccac acaccctgag tttcagacaa aaaccccctg    37200
gaaatcatag tatcagcagg agaactagcc agagacagca gaggggact cagtgactcc    37260 cgcggggaca ggaggatttt gtgggggctc gtgtcactgt gaggatattg tagtagtacc    37320
agctgctata cccacagtga cacagcccca ttcccaaagc cctgctgtaa acgcttccac    37380
ttctggagct gagggctgg ggggagcgtc tgggaagtag ggcctagggg tggccatcaa    37440
tgcccaaaac gcaccagact cccccccaga catcaccca ctggccagtg agcagagtaa    37500
acagaaaatg agaagcagct gggaagcttg cacaggcccc aaggaaagag ctttggcggg    37560
tgtgcaagag gggatgcggg cagagcctga gcagggcctt ttgctgtttc tgctttcctg    37620
tgcagatagt tccataaact ggtgttcaag atcgatggct gggagtgagc ccaggaggac    37680
agtgtgggaa gggcacaggg aaggagaagc agccgctatc ctacactgtc atctttcaag    37740
agtttgccct gtgcccacaa tgctgcatca tgggatgctt aacagctgat gtagacacag    37800
ctaaagagag aatcagtgaa atggatttgc agcacagatc tgaataaatt ctccagaatg    37860
tggagccaca cagaagcaag cacaaggaaa gtgcctgatg caagggcaaa gtacagtgtg    37920
taccttcagg ctgggcacag acactctgaa aagccttggc aggaactccc tgcaacaaag    37980
cagagccctg caggcaatgc cagctccaga gccctccctg agagcctcat gggcaaagat    38040
gtgcacaaca ggtgtttctc atagccccaa actgagaatg aagcaaacag ccatctgaag    38100
gaaaacaggc aaataaacga tggcaggttc atgaaatgca aacccagaca gccagaagga    38160
caacagtgag ggttacaggt gactctgtgg ttgagttcat gacaatgctg agtaattgga    38220
gtaacaaagg aaagtccaaa aaatactttc aatgtgattt cttctaaata aaatttacag    38280
ccggcaaaat gaactatctt cttaagggat aaactttcca ctaggaaaac tataaggaaa    38340
atcaagaaaa ggatgatcac ataaacacag tggtcgttac ttctactggg aaggaagag    38400 ggtatgaact gagacacaca gggttggcaa gtctcctaac aagaacagaa caaatacatt    38460
acagtacctt gaaaacagca gttaaaattc taaattgcaa gaagaggaaa atgcacacag    38520
ctgtgtttag aaaattctca gtccagcact gttcataata gcaaagacat taacccaggt    38580
tggataaata aacgatgaca caggcaattg cacaatgata cagacataca ttcagtatat    38640
```

| | |
|---|---|
| gagacattga tgatgtatcc ccaaagaaat gactttaaag agaaaaggcc tgatatgtgg | 38700 |
| tggcactcac ctccctgggc atccccggac aggctgcagg cacactgtgt ggcagggcag | 38760 |
| gctggtacct gctggcagct cctggggcct gatgtggagc aggcacagag ccgtatcccc | 38820 |
| ccgaggacat ataccccaa ggacggcaca gttggtacat tccggagaca agcaactcag | 38880 |
| ccacactccc aggccagagc ccgagaggga cgcccatgca cagggaggca gagcccagct | 38940 |
| cctccacagc cagcagcacc cgtgcagggg ccgccatctg gcaggcacag agcatgggct | 39000 |
| gggaggaggg gcagggacac caggcagggt tggcaccaac tgaaaattac agaagtctca | 39060 |
| tacatctacc tcagccttgc ctgacctggg cctcacctga cctggacctc acctggcctg | 39120 |
| gacctcacct ggcctagacc tcacctctgg gcttcacctg agctcggcct cacctgactt | 39180 |
| ggaccttgcc tgtcctgagc tcacatgatc tgggcctcac ctgacctggg tttcacctga | 39240 |
| cctgggcttc acctgacctg gcctcatct gacctgggcc tcactggcct ggacctcacc | 39300 |
| tggcctgggc ttcacctggc tcaggcctc atctgcacct gctccaggtc ttgctggaac | 39360 |
| ctcagtagca ctgaggctgc aggggctcat ccagggttgc agaatgactc tagaacctcc | 39420 |
| cacatctcag cttctgtggt ggaggcacct ggtggcccag ggaatataaa agcctgaat | 39480 |
| gatgcctgcg tgatttgggg gcaatttata aacccaaaag acatggcca tgcagcgggt | 39540 |
| agggacaata cagacagata tcagcctgaa atggagcctc agggcacagg tgggcacgga | 39600 |
| cactgtccac ctaagccagg ggcagacccg agtgtccccg cagtagacct gagagcgctg | 39660 |
| ggcccacagc ctcccctcgg tgccctgcta cctcctcagg tcagccctgg acatcccggg | 39720 |
| tttccccagg cctggcggta ggtttggggt gaggtctgtg tcactgtggt attacgattt | 39780 |
| ttggagtggt tattataccc acagtgtcac agagtccatc aaaaacccat ccctgggaac | 39840 |
| cttctgccac agccctccct gtggggcacc gccgcgtgcc atgttaggat tttgactgag | 39900 |
| gacacagcac catgggtatg gtggctaccg cagcagtgca gcccgtgacc caaacacaca | 39960 |
| gggcagcagg cacaacagac aagcccacaa gtgaccaccc tgagctcctg cctgccagcc | 40020 |
| ctggagacca tgaaacagat ggccaggatt atcccatagg tcagccagac ctcagtccaa | 40080 |
| caggtctgca tcgctgctgc cctccaatac cagtccggat ggggacaggg ctggcccaca | 40140 |
| ttaccatttg ctgccatccg gccaacagtc ccagaagccc ctccctcaag gctgggccac | 40200 |
| atgtgtggac cctgagagcc ccccatgtct gagtaggggc accaggaagg tggggctggc | 40260 |
| cctgtgcact gtccctgccc ctgtggtccc tggcctgcct ggccctgaca cctgggcctc | 40320 |
| tcctgggtca tttccaagac agaagacatt cccaggacag ctggagctgg gagtccatca | 40380 |
| tcctgcctgg ccgtcctgag tcctgcgcct ttccaaacct caccgggaa gccaacagag | 40440 |
| gaatcacctc ccacaggcag agacaaagac cttccagaaa tctctgtctc tctccccagt | 40500 |
| gggcaccctc ttccagggca gtcctcagtg atatcacagt gggaacccac atctggatcg | 40560 |
| ggactgcccc cagaacacaa gatggcccac agggacagcc ccacagccca gcccttccca | 40620 |
| gacccctaaa aggcgtccca cccctgcat ctgcccagg gctcaaactc caggaggact | 40680 |
| gactcctgca caccctcctg ccagacatca cctcagcccc tcctggaagg gacaggagcg | 40740 |
| cgcaagggtg agtcagaccc tcctgccctc gatggcaggc ggagaagatt cagaaaggtc | 40800 |
| tgagatcccc aggacgcagc accactgtca atggggggccc cagacgcctg gaccagggcc | 40860 |
| tgcgtgggaa aggcctctgg gcacactcag gggcttttg tgaagggtcc tcctactgtg | 40920 |
| tgactacagt aactaccaca gtgatgaacc cagcagcaaa aactgaccgg actcccaagg | 40980 |
| tttatgcaca cttctccgct cagagctctc caggatcaga agagccgggc ccaagggttt | 41040 |

```
ctgcccagac cctcggcctc tagggacatc ttggccatga cagcccatgg gctggtgccc    41100
cacacatcgt ctgccttcaa acaagggctt cagagggctc tgaggtgacc tcactgatga    41160
ccacaggtgc cctggcccct tccccaccag ctgcaccaga ccccgtcatg acagatgccc    41220
cgattccaac agccaattcc tggggccagg aatcgctgta gacaccagcc tccttccaac    41280
acctcctgcc aattgcctgg attcccatcc cggttggaat caagaggaca gcatccccca    41340
ggctcccaac aggcaggact cccacaccct cctctgagag gccgctgtgt tccgtagggc    41400
caggctgcag acagtccccc tcacctgcca ctagacaaat gcctgctgta gatgtcccca    41460
cctggaaaat accactcatg gagccccag ccccaggtac agctgtagag agagtctctg    41520
aggcccctaa gaagtagcca tgcccagttc tgccgggacc ctcggccagg ctgacaggag    41580
tggacgctgg agctgggccc atactgggcc acataggagc tcaccagtga gggcaggaga    41640
gcacatgccg gggagcaccc agcctcctgc tgaccagagg cccgtcccag agcccaggag    41700
gctgcagagg cctctccagg gggacactgt gcatgtctgg tccctgagca gcccccacg    41760 tccccagtcc tggggccccc tggcacagct gtctggaccc tctctattcc ctgggaagct    41820
cctcctgaca gccccgcctc cagttccagg tgtggttatt gtcaggggt gtcagactgt    41880 ggtggataca gctatggtta ccacagtggt gctgcccata gcagcaacca ggccaagtag    41940
acaggcccct gctgtgcagc cccaggcctc cagctcacct gcttctcctg gggctctcaa    42000
ggctgctgtt ttctgcactc tcccctctgt ggggagggtt ccctcagtgg gagatctgtt    42060
ctcaacatcc cacggcctca ttcctgcaag gaaggccaat ggatgggcaa cctcacatgc    42120
cgcggctaag atagggtggg cagcctggcg ggacaggac atcctgctgg ggtatctgtc    42180
actgtgccta gtggggcact ggctcccaaa caacgcagtc cttgccaaaa tccccacggc    42240
ctcccccgct aggggctggc ctgatctcct gcagtcctag gaggctgctg acctccagaa    42300
tggctccgtc cccagttcca gggcgagagc agatcccagg ccggctgcag actgggaggc    42360 cacccctcc ttcccagggt tcactgcagg tgaccagggc aggaaatggc ctgaacacag    42420
ggataaccgg gccatccccc aacagagtcc accccctcct gctctgtacc ccgcaccccc    42480
caggccagcc catgacatcc gacaacccca caccagagtc actgcccggt gctgccctag    42540
ggaggacccc tcagccccca ccctgtctag aggactgggg aggacaggac acgccctctc    42600
cttatggttc ccccacctgg ctctggctgg gaccctggg gtgtgacag aaaggacgct    42660 tgcctgattg gccccagga gcccagaact tctctccagg gaccccagcc cgagcacccc    42720
cttacccagg acccagccct gccctcctc ccctctgctc tcctctcatc accccatggg    42780
aatccagaat ccccaggaag ccatcaggaa gggctgaggg aggaagtggg gccactgcac    42840
caccaggcag gaggctctgt ctttgtgaac ccagggaggt gccagcctcc tagagggtat    42900
ggtccaccct gcctatggct cccacagtgg caggctgcag ggaaggacca gggacggtgt    42960
gggggagggc tcaggccccc gcgggtgctc atcttggat gagcctatct ctctcaccca    43020
cggactcgcc cacctcctct tcaccctggc cacacgtcgt ccacaccatc ctaagtccca    43080
cctacaccag agccggcaca gccagtgcag acagaggctg gggtgcaggg gggccgactg    43140
ggcagcttcg ggagggagg aatggaggaa ggggagttca gtgaagaggc ccccctcccc    43200
tgggtccagg atcctcctct gggacccccg gatcccatcc cctccaggct ctgggaggag    43260
aagcaggatg ggagaatctg tgcgggaccc tctcacagtg gaatacctcc acagcggctc    43320
aggccagata caaaagcccc tcagtgagcc ctccactgca gtgctgggcc tgggggcagc    43380
```

| | |
|---|---|
| cgctcccaca caggatgaac ccagcacccc gaggatgtcc tgccaggggg agctcagagc | 43440 |
| catgaaggag caggatatgg gaccccccgat acaggcacag acctcagctc cattcaggac | 43500 |
| tgccacgtcc tgccctggga ggaacccctt tctctagtcc ctgcaggcca ggaggcagct | 43560 |
| gactcctgac ttggacgcct attccagaca ccagacagag gggcaggccc cccagaacca | 43620 |
| gggatgagga cgccccgtca aggccagaaa agaccaagtt gcgctgagcc cagcaaggga | 43680 |
| aggtccccaa acaaaccagg aagtttctga aggtgtctgt gtcacagtgg agtatagcag | 43740 |
| ctcgtcccac agtgacactc gccaggccag aaaccccatc ccaagtcagc ggaatgcaga | 43800 |
| gagagcaggg aggacatgtt taggatctga ggccgcacct gacacccagg ccagcagacg | 43860 |
| tctcctgtcc acggcaccct gccatgtcct gcatttctgg aagaacaagg gcaggctgaa | 43920 |
| gggggtccag gaccaggaga tgggtccgct ctacccagag aaggagccag gcaggacaca | 43980 |
| agcccctcc ccattgaggc tgacctgccc agagggtcct gggcccaccc aacacaccgg | 44040 |
| ggcggaatgt gtgcaggcct cggtctctgt gggtgttccg ctagctgggg ctcacagtgc | 44100 |
| tcaccccaca cctaaaacga gccacagcct ccggagcccc tgaaggagac cccgcccaca | 44160 |
| agcccagccc ccacccagga ggccccagag cacagggcgc cccgtcggat tctgaacagc | 44220 |
| cccgagtcac agtgggtata actggaacta ccactgtgag aaaagcttcg tccaaaacgg | 44280 |
| tctcctggcc acagtcggag gccccgccag agagggagc agccacccca aacccatgtt | 44340 |
| ctgccggctc ccatgacccc gtgcacctgg agccccacgg tgtccccact ggatgggagg | 44400 |
| acaagggccg ggggctccgg cgggtcgggg caggggcttg atggcttcct tctgccgtgg | 44460 |
| ccccattgcc cctggctgga gttgacccctt ctgacaagtg tcctcagaga gtcagggatc | 44520 |
| agtggcacct cccaacatca accccacgca gcccaggcac aaaccccaca tccagggcca | 44580 |
| actccaggaa cagagacacc ccaatacccct gggggacccc gaccctgatg actcccgtcc | 44640 |
| catctctgtc cctcacttgg ggcctgctgc ggggcgagca cttgggagca aactcaggct | 44700 |
| taggggacac cactgtgggc ctgacctcga gcaggccaca gacccttccc tcctgccctg | 44760 |
| gtgcagcaca gactttgggg tctgggcagg gaggaacttc tggcaggtca ccaagcacag | 44820 |
| agcccccagg ctgaggtggc cccaggggga accccagcag gtggcccact acccttcctc | 44880 |
| ccagctggac cccatgtctt ccccaagata ggggtgccat ccaaggcagg tcctccatgg | 44940 |
| agccccttc aggctcctct ccagacccca ctgggcctca gtccccactc taggaatgca | 45000 |
| gccaccacgg gcacaccagg cagcccaggc ccagccaccc tgcagtgccc aagcccacac | 45060 |
| cctggaggag agcagggtgc gtctgggagg ggctgggctc cccaccccca cccccacctg | 45120 |
| cacacccac ccaccctttgc ccgggccccc tgcaggaggg tcagagcccc catgggatat | 45180 |
| ggacttaggg tctcactcac gcacctcccc tcctgggaga aggggtctca tgcccagatc | 45240 |
| ccccccagcag cgctggtcac aggtagaggc agtggcccca gggccaccct gacctggccc | 45300 |
| ctcaggctcc tctagccctg gctgccctgc tgtccctggg aggcctgggc tccaccagac | 45360 |
| cacaggtcta gggcaccgcc cacactgggg ccgcccacac acagctcaca ggaagaagat | 45420 |
| aagctccaga cccccaggcc cgggacctgc cttgctgcta cgacttcctg ccccagacct | 45480 |
| cgttgccctc ccccgtccac ttacacacag gccaggaagc tgttcccaca cagaccaacc | 45540 |
| ccagacgggg accacctggc actcaggtca ctgccatttc cttctccatt cacttccaat | 45600 |
| gcctctgtgc ttcctcccctc ctccttcctt cgggggagca ccctgtgcag ctcctccctg | 45660 |
| cagtccacac cctggggaga cccgaccctg cagcccacac cctggggaga cctgaccctc | 45720 |
| ctccagccct ttctcccccg ctgctcttgc cacccaccaa gacagccctg ggtcctgtc | 45780 |

```
cctacagccc ccacccagtt ctctacctag acccgtcttc ctccctctaa acacctctcc    45840
caggccaacc ctacacctgc aggccctccc ctccactgcc aaagaccctc agtttctcct    45900
gcctgtgccc accccgtgc tcctcctgcc cacagctcga gctcttcctc tcctagggcc    45960
cctgagggat ggcattgacc gtgccctcgc acccacacac tgcccatgcc ctcacattcc    46020
tcctggccac tccagcccca ctcccctctc aggcctggct ctggtatttc tgggacaaag    46080
ccttacccaa gtctttccca tgcaggcctg ggcccttacc ctcactgccc ggttacaggg    46140
cagcctcctg tgcacagaag cagggagctc agcccttcca caggcagaag cactgaaag    46200 aaatcggcct ccagcgcctt gacacacgtc tgcctgtgtc tctcactgcc cgcacctgca    46260
gggaggctcg gcactccctc taaagacgag ggatccaggc agcagcatca caggagaatg    46320
cagggctacc agacatccca gtcctctcac aggcctctcc tgggaagaga cctgaagacg    46380
cccagtcaac ggagtctaac accaaacctc cctggaggcc gatgggtagt aacggagtca    46440
ttgccagacc tggaggcagg ggagcagtga gcccgagccc acaccatagg gccagaggac    46500
agccactgac atcccaagcc actcactggt ggtcccacaa caccccatgg aaagaggaca    46560
gacccacagt cccacctgga ccagggcaga gactgctgag acccagcacc agaaccaacc    46620
aagaaacacc aggcaacagc atcagagggg gctctggcag aacagaggag gggaggtctc    46680
cttcaccagc aggcgcttcc cttgaccgaa gacaggatcc atgcaactcc cccaggacaa    46740
aggaggagcc ccttgttcag cactgggctc agagtcctct ccaagacacc cagagtttca    46800
gacaaaaacc ccctggaatg cacagtctca gcaggagagc cagccagagc cagcaagatg    46860
gggctcagtg acacccgcag ggacaggagg attttgtggg ggctcgtgtc actgtgagga    46920
tattgtacta atggtgtatg ctatacccac agtgacacag ccccattccc aaagccctac    46980
tgcaaacgca ttccacttct ggggctgagg ggctgggga gcgtctggga aatagggctc    47040
aggggtgtcc atcaatgccc aaaacgcacc agactccct ccatacatca cacccaccag    47100
ccagcgagca gagtaaacag aaaatgagaa gcaagctggg gaagcttgca caggcccaa    47160 ggaaagagct ttggcgggtg tgtaagaggg gatgcgggca gagcctgagc agggcctttt    47220
gctgtttctg ctttcctgtg cagagagttc cataaactgg tgttcgagat caatggctgg    47280
gagtgagccc aggaggacag cgtgggaaga gcacagggaa ggaggagcag ccgctatcct    47340
acactgtcat ctttcgaaag tttgccttgt gcccacactg ctgcatcatg ggatgcttaa    47400
cagctgatgt agacacagct aaagagagaa tcagtgagat ggatttgcag cacagatctg    47460
aataaattct ccagaatgtg gagcagcaca gaagcaagca cacagaaagt gcctgatgca    47520
aggacaaagt tcagtgggca ccttcaggca ttgctgctgg gcacagacac tctgaaaagc    47580
cctggcagga actccctgtg acaaagcaga accctcaggc aatgccagcc ccagagccct    47640
ccctgagagc ctcatgggca aagatgtgca caacaggtgt ttctcatagc cccaaactga    47700
gagcaaagca aacgtccatc tgaaggagaa caggcaaata aacgatggca ggttcatgaa    47760
atgcaaaccc agacagccac aagcacaaaa gtacagggtt ataagcgact ctggttgagt    47820
tcatgacaat gctgagtaat tggagtaaca aagtaaactc caaaaaatac tttcaatgtg    47880
atttcttcta aataaaattt acaccctgca aaatgaactg tcttcttaag ggatacattt    47940
cccagttaga aaaccataaa gaaaaccaag aaaaggatga tcacataaac acagtggtgg    48000
ttacttctgc tggggaagga agagggtatg aactgagata cacagggtgg gcaagtctcc    48060
taacaagaac agaacgaata cattacagta ccttgaaaac agcagttaaa cttctaaatt    48120
```

| | |
|---|---|
| gcaagaagag gaaaatgcac acagttgtgt ttagaaaatt ctcagtccag cactgttcat | 48180 |
| aatagcaaag acattaaccc aggtcggata aataagcgat gacacaggca attgcacaat | 48240 |
| gatacagaca tatatttagt atatgagaca tcgatgatgt atccccaaat aaacgacttt | 48300 |
| aaagagataa agggctgatg tgtggtggca ttcacctccc tgggatcccc ggacaggttg | 48360 |
| caggctcact gtgcagcagg gcaggcgggt acctgctggc agttcctggg gcctgatgtg | 48420 |
| gagcaagcgc agggccatat atcccggagg acggcacagt cagtgaattc cagagagaag | 48480 |
| caactcagcc acactcccca ggcagagccc gagagggacg cccacgcaca gggaggcaga | 48540 |
| gcccagcacc tccgcagcca gcaccacctg cgcacgggcc accaccttgc aggcacagag | 48600 |
| tgggtgctga gaggaggggc agggacacca ggcagggtga gcacccagag aaaactgcag | 48660 |
| acgcctcaca catccacctc agcctcccct gacctggacc tcactggcct gggcctcact | 48720 |
| taacctgggc ttcacctgac cttggcctca cctgacttgg acctcgcctg tcccaagctt | 48780 |
| tacctgacct gggcctcaac tcacctgaac gtctcctgac ctgggtttaa cctgtcctgg | 48840 |
| aactcacctg gccttggctt cccctgacct ggacctcatc tggcctgggc ttcacctggc | 48900 |
| ctgggcctca cctgacctgg acctcatctg gcctggacct cacctggcct ggacttcacc | 48960 |
| tggcctgggc ttcacctgac ctggacctca cctggcctcg gcctcacct gcacctgctc | 49020 |
| caggtcttgc tggagcctga gtagcactga gggtgcagaa gctcatccag ggttggggaa | 49080 |
| tgactctaga agtctcccac atctgacctt tctgggtgga ggcagctggt ggccctggga | 49140 |
| atataaaaat ctccagaatg atgactctgt gatttgtggg caacttatga acccgaaagg | 49200 |
| acatggccat ggggtgggta gggacatagg gacagatgcc agcctgaggt ggagcctcag | 49260 |
| gacacaggtg ggcacggaca ctatccacat aagcgaggga tagacccgag tgtccccaca | 49320 |
| gcagacctga gagcgctggg cccacagcct cccctcagag ccctgctgcc tcctccggtc | 49380 |
| agccctggac atcccaggtt tccccaggcc tggcggtagg tttagaatga ggtctgtgtc | 49440 |
| actgtggtat tacgatattt tgactggtta ttataaccac agtgtcacag agtccatcaa | 49500 |
| aaacccatgc ctggaagctt cccgccacag ccctccccat ggggccctgc tgcctcctca | 49560 |
| ggtcagcccc ggacatcccg ggtttcccca ggctgggcgg taggtttggg gtgaggtctg | 49620 |
| tgtcactgtg gtattactat ggttcgggga gttattataa ccacagtgtc acagagtcca | 49680 |
| tcaaaaaccc atccctggga gcctcccgcc acagccctcc ctgcagggga ccggtacgtg | 49740 |
| ccatgttagg attttgatcg aggagacagc accatgggta tggtggctac cacagcagtg | 49800 |
| cagcctgtga cccaaacccg cagggcagca ggcacgatgg acaggcccgt gactgaccac | 49860 |
| gctgggctcc agcctgccag ccctggagat catgaaacag atggccaagg tcaccctaca | 49920 |
| ggtcatccag atctggctcc gaggggtctg catcgctgct gccctcccaa cgccagtcca | 49980 |
| aatgggacag ggacggcctc acagcaccat ctgctgccat caggccagcg atcccagaag | 50040 |
| cccctccctc aaggctgggc acatgtgtgg acactgagag ccctcatatc tgagtagggg | 50100 |
| caccaggagg gagggctggg ccctgtgcac tgtccctgcc cctgtggtcc ctggcctgcc | 50160 |
| tggccctgac acctgagcct ctcctgggtc atttccaaga cagaagacat tcctggggac | 50220 |
| agccggagct gggcgtcgct catcctgccc ggccgtcctg agtcctgctc atttccagac | 50280 |
| ctcaccgggg aagccaacag aggactcgcc tcccacattc agagacaaag aaccttccag | 50340 |
| aaatccctgc ctctctcccc agtggacacc ctcttccagg acagtcctca gtggcatcac | 50400 |
| agcggcctga gatccccagg acgcagcacc gctgtcaata ggggcccaa atgcctggac | 50460 |
| cagggcctgc gtgggaaagg cctctggcca cactcgggct ttttgtgaag ggccctcctg | 50520 |

```
ctgtgtgact acagtaacta ccatagtgat gaacccagtg gcaaaaactg gctggaaacc    50580
caggggctgt gtgcacgcct cagcttggag ctctccagga gcacaagagc cgggcccaag    50640
gatttgtgcc cagaccctca gcctctaggg acacctgggt catctcagcc tgggctggtg    50700
ccctgcacac catcttcctc caaatagggg cttcagaggg ctctgaggtg acctcactca    50760
tgaccacagg tgacctggcc cttccctgcc agctatacca gaccctgtct tgacagatgc    50820
cccgattcca acagccaatt cctgggaccc tgaatagctg tagacaccag cctcattcca    50880
gtacctcctg ccaattgcct ggattcccat cctggctgga atcaagaagg cagcatccgc    50940
caggctccca acaggcagga ctcccgcaca ccctcctctg agaggccgct gtgttccgca    51000
gggccaggcc ctggacagtt cccctcacct gccactagag aaacacctgc cattgtcgtc    51060
cccacctgga aaagaccact cgtggagccc ccagccccag gtacagctgt agagacagtc    51120
ctcgaggccc ctaagaagga gccatgccca gttctgccgg gaccctcggc caggccgaca    51180
ggagtggacg ctggagctgg gcccacactg ggcacatag gagctcacca gtgagggcag    51240
gagagcacat gccggggagc acccagcctc ctgctgacca gaggcccgtc ccagagccca    51300
ggaggctgca gaggcctctc cagggagaca ctgtgcatgt ctggtaccta agcagccccc    51360
cacgtcccca gtcctggggg cccctggctc agctgtctgg gccctccctg ctccctggga    51420
agctcctcct gacagcccg cctccagttc caggtgtggt tattgtcagg cgatgtcaga    51480
ctgtggtgga tatagtggct acgattacca cagtggtgcc gcccatagca gcaaccaggc    51540
caagtagaca ggcccctgct gcgcagcccc aggcatccac ttcacctgct tctcctgggg    51600
ctctcaaggc tgctgtctgt cctctggccc tctgtgggga gggttccctc agtgggaggt    51660
ctgtgctcca gggcagggat gattgagata gaaatcaaag gctggcaggg aaaggcagct    51720
tcccgccctg agaggtgcag gcagcaccac ggagccacga agtcacagag ccacggagcc    51780
cccattgtgg gcatttgaga gtgctgtgcc cccggcaggc ccagccctga tggggaagcc    51840
tgtcccatcc cacagcccgg gtcccacggg cagcgggcac agaagctgcc aggttgtcct    51900
ctatgatcct catccctcca gcagcatccc ctccacagtg gggaaactga ggcttggagc    51960
accacccggc cccctggaaa tgaggctgtg agccagaca gtgggcccag agcactgtga    52020 gtacccccggc agtacctggc tgcagggatc agccagagat gccaaaccct gagtgaccag    52080
cctacaggag gatccggccc cacccaggcc actcgattaa tgctcaaccc cctgccctgg    52140
agacctcttc cagtaccacc agcagctcag cttctcaggg cctcatccct gcaaggaagg    52200
tcaagggctg ggcctgccag aaacacagca ccctccctag ccctggctaa gacagggtgg    52260
gcagacggct gtggacggga catattgctg gggcatttct cactgtcact tctgggtggt    52320
agctctgaca aaaacgcaga ccctgccaaa atccccactg cctcccgcta ggggctggcc    52380
tggaatcctg ctgtcctagg aggctgctga cctccaggat ggctccgtcc ccagttccag    52440
ggcgagagca gatcccaggc aggctgtagg ctggaggcc accctgccc ttgccggggt    52500 tgaatgcagg tgcccaaggc aggaaatggc atgagcacag ggatgaccgg gacatgcccc    52560
accagagtgc gcccctttcct gctctgcacc ctgcaccccc caggccagcc cacgacgtcc    52620
aacaactggg cctgggtggc agccccaccc agacaggaca gacccagcac cctgaggagg    52680
tcctgccagg gggagctaag agccatgaag gagcaagata tggggccccc gatacaggca    52740
cagatgtcag ctccatccag gaccacccag cccacaccct gagaggaacg tctgtctcca    52800
gcctctgcag gtcgggaggc agctgacccc tgacttggac ccctattcca gacaccagac    52860
```

```
agaggcgcag gccccccaga accagggttg agggacgccc cgtcaaagcc agacaaaacc    52920
aaggggtgtt gagcccagca agggaaggcc cccaaacaga ccaggaggtt tctgaaggtg    52980
tctgtgtcac agtggggtat agcagcagct ggtaccacag tgacactcac ccagccagaa    53040
accccattcc aagtcagcgg aagcagagag agcaggagg acacgtttag gatctgagac     53100
tgcacctgac acccaggcca gcagacgtct cccctccagg gcaccccacc ctgtcctgca    53160
tttctgcaag atcaggggcg gcctgagggg gggtctaggg tgaggagatg ggtcccctgt    53220
acaccaagga ggagttaggc aggtcccgag cactctcccc attgaggctg acctgcccag    53280
agagtcctgg gcccacccca cacaccgggg cggaatgtgt gcaggcctcg gtctctgtgg    53340
gtgttccgct agctggggct cacagtgctc accccacacc taaaatgagc cacagcctcc    53400
ggagcccccg caggagaccc cgcccacaag cccagccccc acccaggagg ccccagagct    53460
cagggcgccc cgtcggattc cgaacagccc cgagtcacag cgggtataac cggaaccacc    53520
actgtcagaa tagctacgtc aaaaactgtc cagtggccac tgccggaggc cccgccagag    53580
agggcagcag ccactctgat cccatgtcct gccggctccc atgaccccca gcacgcggag    53640
ccccacagtg tccccactgg atgggaggac aagagctggg gattccggcg ggtcggggca    53700
ggggcttgat cgcatccttc tgccgtggct ccagtgcccc tggctggagt tgacccttct    53760
gacaagtgtc ctcagagaga caggcatcac cggcgcctcc caacatcaac cccaggcagc    53820
acaggcacaa accccacatc cagagccaac tccaggagca gagacacccc aatacccctgg   53880 gggaccccga ccctgatgac ttcccactgg aattcgccgt agagtccacc aggaccaaag    53940
accctgcctc tgcctctgtc cctcactcag gacctgctgc cgggcgaggc cttgggagca    54000
gacttgggct taggggacac cagtgtgacc ccgaccttga ccaggacgca gacctttcct    54060
tcctttcctg gggcagcaca gactttgggg tctgggccag gaggaacttc tggcaggtcg    54120
ccaagcacag aggccacagg ctgaggtggc cctggaaaga cctccaggag gtggccactc    54180
cccttcctcc cagctggacc ccatgtcctc cccaagataa gggtgccatc caaggcaggt    54240
gctccttgga gcccattca gactcctccc tggaccccac tgggcctcag tcccagctct     54300
ggggatgaag ccaccacaag cacaccaggc agcccaggcc cagccaccct gcagtgccca    54360
agcacacact ctggagcaga gcagggtgcc tctgggaggg gctgagctcc ccaccccacc    54420
cccacctgca caccccaccc acccctgccc agcggctctg caggagggtc agagcccac    54480 atggggtatg gacttagggt ctcactcacg tggctcccat catgagtgaa ggggcctcaa    54540
gcccaggttc ccacagcagc gcctgtcgca agtggaggca gaggcccgag gccacccctg    54600
acctggtccc tgaggttcct gcagcccagg ctgccctgct gtccctggga ggcctgggct    54660
ccaccagacc acaggtccag ggcaccgggt gcaggagcca cccacacaca gctcacagga    54720
agaagataag ctccagaccc ccagggccag aacctgcctt cctgctactg cttcctgccc    54780
cagacctggg cgccctcccc cgtccactta cacacaggcc aggaagctgt tcccacacag    54840
aacaacccca aaccaggacc gcctggcact caggtggctg ccatttcctt ctccatttgc    54900
tcccagcgcc tctgtcctcc ctggttcctc cttcggggga acagcctgtg cagccagtcc    54960
ctgcagccca cacctgggg agacccaacc ctgcctgggg cccttccaac cctgctgctc     55020
ttactgccca cccagaaaac tctggggtcc tgtccctgca gtccctaccc tggtctccac    55080
ccagacccct gtgtatcact ccagacaccc ctcccaggca aacctgcac ctgcaggccc     55140 tgtcctcttc tgtcgctaga gcctcagttt ctcccccctg tgcccacacc ctacctcctc    55200
ctgcccacaa ctctaactct tcttctcctg gagcccctga gccatggcat tgaccctgcc    55260
```

```
ctcccaccac ccacagccca tgccctcacc ttcctcctgg ccactccgac cccgcccct   55320
ctcaggccaa gccctggtat ttccaggaca aaggctcacc caagtctttc ccaggcaggc   55380
ctgggctctt gccctcactt cccggttaca cgggagcctc ctgtgcacag aagcagggag   55440
ctcagcccett ccacaggcag aaggcactga agaaatcgg cctccagcac cttgacacac   55500
gtccgcccgt gtctctcact gcccgcacct gcagggaggc tccgcactcc ctctaaagac   55560
aagggatcca ggcagcagca tcacgggaga atgcagggct cccagacatc ccagtcctct   55620
cacaggcctc tcctgggaag agacctgcag ccaccaccaa acagccacag aggctgctgg   55680
atagtaactg agtcaatgac cgacctggag ggcaggggag cagtgagccg agcccatac   55740
catagggaca gagaccagcc gctgacatcc cgagctcctc aatggtggcc ccataacaca   55800
cctaggaaac ataacacacc cacagcccca cctggaacag gcagagact gctgagcccc   55860
cagcaccagc cccaagaaac accaggcaac agtatcagag ggggctcccg agaaagagag   55920
gaggggagat ctccttcacc atcaaatgct tcccttgacc aaaaacaggg tccacgcaac   55980
tcccccagga caaaggagga gcccctata cagcactggg ctcagagtcc tctctgagac   56040
accctgagtt tcagacaaca acccgctgga atgcacagtc tcagcaggag aacagaccaa   56100
agccagcaaa agggacctcg gtgacaccag tagggacagg aggattttgt gggggctcgt   56160
gtcactgtga ggatattgta gtggtggtag ctgctactcc cacagtgaca cagacccatt   56220
cccaaagccc tactgcaaac acaccactc ctggggctga ggggctgggg gagcgtctgg   56280
gaagtagggt ccaggggtgt ctatcaatgt ccaaaatgca ccagactccc cgccaaacac   56340
cacccccacca gccagcgagc agggtaaaca gaaaatgaga ggctctggga agcttgcaca   56400
ggccccaagg aaaagctttt ggcgggtgtg caagagggga tgcaggcaga gcctgagcag   56460
ggccttttgc tgtttctgct ttcctgtgca gagagttcca taaactggtg ttcaagatca   56520
gtggctggga atgagcccag gagggcagtc tgtgggaaga gcacagggaa ggaggagcag   56580
ccgctatcct acactgtcat ctttcaaaag tttgccttgt gaccacacta ttgcatcatg   56640
ggatgcttaa gagctgatgt agacacagct aaagagagaa tcagtgagat gaatttgcag   56700
catagatctg aataaactct ccagaatgtg gagcagtaca gaagcaaaca cacagaaagt   56760
gcctgatgca aggacaaagt tcagtgggca ccttcaggca ttgctgctgg gcacagacac   56820
tctgaaaagc cttggcagga tctccctgcg acaaagcaga accctcaggc aatgccagcc   56880
ccagagccct ccctgagagc gtcatgggga agatgtgca gaacagctga ttatcataga   56940
ctcaaactga gaacagagca aacgtccatc tgaagaacag tcaaataagc aatggtaggt   57000
tcatgcaatg caaacccaga cagccagggg acaacagtag agggctacag gcggctttgc   57060
ggttgagttc atgacaatgc tgagtaattg gagtaacaga ggaaagccca aaaaatactt   57120
ttaatgtgat ttcttctaaa taaaatttac accaggcaaa atgaactgtc ttcttaaggg   57180
ataaactttc ccctggaaaa actacaagga aaattaagaa aacgatgatc acataaacac   57240
agttgtggtt acttctactg gggaaggaag agggtatgag ctgagacaca cagagtcggc   57300
aagtctccaa gcaagcacag aacgaataca ttacagtacc ttgaatacag cagttaaact   57360
tctaaatcgc aagaacagga aaatgcacac agctgtgttt agaaaattct cagtccagca   57420
ctattcataa tagcaaagac attaacccag gttggataaa taaatgatga cacaggcaat   57480
tgcacaatga tacagacata catttagtac atgagcatc gatgatgtat ccccaaagaa   57540
atgactttaa agagaaaagg cctgatgtgt ggtggcactc acctccctgg gatccccgga   57600
```

```
caggttgcag gcacactgtg tggcagggca ggctggtaca tgctggcagc tcctggggcc    57660
tgatgtggag caagcgcagg gctgtatacc cccaaggatg gcacagtcag tgaattccag    57720
agagaagcag ctcagccaca ctgcccaggc agagcccgag agggacgccc acgtacaggg    57780
aggcagagcc cagctcctcc acagccacca ccacctgtgc acgggccacc accttgcagg    57840
cacagagtgg gtgctgagag gaggggcagg gacaccaggc agggtgagca cccagagaaa    57900
actgcagaag cctcacacat ccacctcagc ctcccctgac ctggacctca cctggtctgg    57960
acctcacctg gcctgggcct cacctgacct ggacctcacc tggcctgggc ttcacctgac    58020
ctggacctca cctggcctcc ggcctcacct gcacctgctc caggtcttgc tggaacctga    58080
gtagcactga ggctgcagaa gctcatccag ggttggggaa tgactctgga actctcccac    58140
atctgacctt tctgggtgga ggcatctggt ggccctggga atataaaaag ccccagaatg    58200
gtgcctgcgt gatttggggg caatttatga acccgaaagg acatggccat ggggtgggta    58260
gggacatagg gacagatgcc agcctgaggt ggagcctcag gacacagttg gacgcggaca    58320
ctatccacat aagcgaggga cagacccgag tgttcctgca gtagacctga gagcgctggg    58380
cccacagcct cccctcggtg ccctgctgcc tcctcaggtc agccctggac atcccgggtt    58440
tccccaggcc agatggtagg tttgaagtga ggtctgtgtc actgtggtat tatgattacg    58500
tttgggggag ttatcgttat acccacagca tcacacggtc catcagaaac ccatgccaca    58560
gccctccccg caggggaccg ccgcgtgcca tgttacgatt ttgatcgagg acacagcgcc    58620
atgggtatgg tggctaccac agcagtgcag cccatgaccc aaacacacag ggcagcaggc    58680
acaatggaca ggcctgtgag tgaccatgct gggctccagc ccgccagccc cggagaccat    58740
gaaacagatg gccaaggtca ccccacagtt cagccagaca tggctccgtg gggtctgcat    58800
cgctgctgcc ctctaacacc agcccagatg gggacaaggc caaccccaca ttaccatctc    58860
ctgctgtcca cccagtggtc ccagaagccc ctccctcatg gctgagccac atgtgtgaac    58920
cctgagagca ccccatgtca gagtaggggc agcagaaggg cggggctggc cctgtgcact    58980
gtccctgcac ccatggtccc tcgcctgcct ggccctgaca cctgagcctc ttctgagtca    59040
tttctaagat agaagacatt cccggggaca gccggagctg ggcgtcgctc atcccgcccg    59100
gccgtcctga gtcctgcttg tttccagacc tcaccaggga agccaacaga ggactcacct    59160
cacacagtca gagacaaaga accttccaga aatccctgtc tcactcccca gtgggcacct    59220
tcttccagga cattcctcgg tcgcatcaca gcaggcaccc acatctggat caggacggcc    59280
cccagaacac aagatggccc atggggacag ccccacaacc caggccttcc cagacccta    59340 aaaggcgtcc cacccctgc acctgcccca gggctaaaaa tccaggaggc ttgactcccg    59400
cataccctcc agccagacat cacctcagcc cctcctgga ggggacagga gcccgggagg    59460
gtgagtcaga cccacctgcc ctcgatggca ggcggggaag attcagaaag gcctgagatc    59520
cccaggacgc agcaccactg tcaatggggg cccagacgc ctggaccagg gcctgcgtgg    59580
gaaaggccgc tgggcacact caggggcttt ttgtgaaggc ccctcctact gtgtgactac    59640
ggtgactacc acagtgatga aactagcagc aaaaactggc cggacaccca gggaccatgc    59700
acacttctca gcttggagct ctccaggacc agaagagtca ggtctgaggg tttgtagcca    59760
gaccctcggc ctctagggac accctggcca tcacagcgga tgggctggtg ccccacatgc    59820
catctgctcc aaacaggggc ttcagagggc tctgaggtga cttcactcat gaccacaggt    59880
gccctggccc cttcccgcc agctacaccg aaccctgtcc caacagctgc cccagttcca    59940
acagccaatt cctggggccc agaattgctg tagacaccag cctcgttcca gcacctcctg    60000
```

| | | | | | |
|---|---|---|---|---|---|
| ccaattgcct | ggattcacat | cctggctgga | atcaagaggg | cagcatccgc | caggctccca | 60060 |
| acaggcagga | ctcccgcaca | ccctcctctg | agaggccgct | gtgttccgca | gggccaggc | 60120 |
| ctggacagtt | cccctcacct | gccactagag | aaacacctgc | cattgtcgtc | cccacctgga | 60180 |
| aaagaccact | cgtggagccc | ccagcccag | gtacagctgt | agagagactc | cccgagggat | 60240 |
| ctaagaagga | gccatgcgca | gttctgccgg | gaccctcggc | caggccgaca | ggagtggaca | 60300 |
| ctggagctgg | gcccacactg | ggccacatag | gagctcacca | gtgagggcag | gagagcacat | 60360 |
| gccggggagc | acccagcctc | ctgctgacca | gaggcccgtc | ccagagccca | ggaggctgca | 60420 |
| gaggcctctc | caggggggaca | ctgtgcatgt | ctggtccctg | agcagccccc | cacgtcccca | 60480 |
| gtcctggggg | ccctggcac | agctgtctgg | accctccctg | ttccctggga | agctcctcct | 60540 |
| gacagcccg | cctccagttc | caggtgtggt | tattgtcagg | gggtgtcaga | ctgtggtgga | 60600 |
| tacagctatg | gttaccacag | tggtgctgcc | catagcagca | accaggccaa | gtagacaggc | 60660 |
| ccctgctgtg | cagccccagg | cctccacttc | acctgcttct | cctggggctc | tcaaggtcac | 60720 |
| tgttgtctgt | actctgccct | ctgtggggag | ggttccctca | gtgggaggtc | tgttctcaac | 60780 |
| atcccaggg | ctcatgtctg | cacggaaggc | caatggatgg | gcaacctcac | atgccgcggc | 60840 |
| taagatagg | tgggcagcct | ggcggggac | agtacatact | gctgggtgt | ctgtcactgt | 60900 |
| gcctagtggg | gcactggctc | ccaaacaacg | cagtcctcgc | caaaatcccc | acagcctccc | 60960 |
| ctgctagggg | ctggcctgat | ctcctgcagt | cctaggaggc | tgctgacctc | cagaatgtct | 61020 |
| ccgtccccag | ttccagggcg | agagcagatc | ccaggccggc | tgcagactgg | gaggccaccc | 61080 |
| cctccttccc | agggttcact | ggaggtgacc | aaggtaggaa | atggccttaa | cacagggatg | 61140 |
| actgcgccat | cccccaacag | agtcagcccc | ctcctgctct | gtaccccgca | ccccccaggc | 61200 |
| cagtccacga | aaaccagggc | cccacatcag | agtcactgcc | tggcccggcc | ctggggcgga | 61260 |
| cccctcagcc | cccaccctgt | ctagaggact | tgggggaca | ggacacaggc | cctctcctta | 61320 |
| tggttccccc | acctgcctcc | ggccgggacc | cttgggtgt | ggacagaaag | gacacctgcc | 61380 |
| taattggccc | ccaggaaccc | agaacttctc | tccaggacc | ccagcccgag | cacccccctta | 61440 |
| cccaggaccc | agccctgccc | ctcctcccct | ctgctctcct | ctcatcaccc | catgggaatc | 61500 |
| cggtatcccc | aggaagccat | caggaagggc | tgaaggagga | agcggggccg | tgcaccaccg | 61560 |
| ggcaggaggc | tccgtcttcg | tgaacccagg | gaagtgccag | cctcctagag | ggtatggtcc | 61620 |
| accctgcctg | ggctcccac | cgtggcaggc | tgcggggaag | gaccagggac | ggtgtggggg | 61680 |
| agggctcagg | gccctgcggg | tgctcctcca | tcttcggtga | gcctcccct | tcacccaccg | 61740 |
| tcccgcccac | ctcctctcca | ccctggctgc | acgtcttcca | caccatcctg | agtcctacct | 61800 |
| acaccagagc | cagcaaagcc | agtgcagaca | aaggctgggg | tgcagggggg | ctgccagggc | 61860 |
| agcttcgggg | agggaaggat | ggagggaggg | gaggtcagtg | aagaggcccc | cttcccctgg | 61920 |
| gtccaggatc | ctcctctggg | accccggat | cccatcccct | cctggctctg | ggaggagaag | 61980 |
| caggatggga | gaatctgtgc | gggaccctct | cacagtggaa | tatcccaca | gcggctcagg | 62040 |
| ccagacccaa | aagcccctca | gtgagccctc | cactgcagtc | ctgggcctgg | gtagcagccc | 62100 |
| ctcccacaga | ggacagaccc | agcaccccga | agaagtcctg | ccaggggag | ctcagagcca | 62160 |
| tgaaagagca | ggatatgggg | tcccgatac | aggcacagac | ctcagctcca | tccaggccca | 62220 |
| ccggaccca | ccatgggagg | aacacctgtc | tccgggttgt | gaggtagctg | gcctctgtct | 62280 |
| cggacccac | tccagacacc | agacagaggg | gcaggccccc | caaaaccagg | gttgagggat | 62340 |

```
gatccgtcaa ggcagacaag accaagggc actgacccca gcaagggaag gctcccaaac    62400
agacgaggag gtttctgaag ctgtctgtat cacagtgggg tatagcagtg gctggtacca    62460
cagtgacact cgccaggcca gaaacccgt cccaagtcag cggaagcaga gagagcaggg    62520
aggacacgtt taggatctga ggccgcacct gacaccagg gcagcagacg tctcccctcc    62580
agggcaccct ccaccgtcct gcgtttcttc aagaataggg gcggcctgag ggggtccagg    62640
gccaggcgat aggtcccctc taccccaagg aggagccagg caggacccga gcaccgtccc    62700
cattgaggct gacctgccca gacgggcctg ggcccacccc acacaccggg gcggaatgtg    62760
tgcaggcccc agtctctgtg ggtgttccgc tagctggggc cccagtgct caccccacac    62820 ctaaagcgag cccagcctc cagagccccc taagcattcc ccgcccagca gcccagcccc    62880 tgccccacc caggaggccc cagagctcag ggcgcctggt cggattctga acagccccga    62940
gtcacagtgg gtataactgg aacgaccacc gtgagaaaaa ctgtgtccaa aactgactcc    63000
tggcagcagt cggaggcccc gccagagagg ggagcagccg gcctgaaccc atgtcctgcc    63060
ggttcccatg accccagca cccagagccc cacggtgtcc ccgttggata atgaggacaa    63120
gggctggggg ctccggtggt ttgcggcagg gacttgatca catccttctg ctgtggcccc    63180
attgcctctg gctggagttg acccttctga caagtgtcct cagaaagaca gggatcaccg    63240
gcacctccca atatcaaccc caggcagcac agacacaaac cccacatcca gagccaactc    63300
caggagcaga gacaccccaa cactctgggg gaccccaacc gtgataactc cccactggaa    63360
tccgccccag agtctaccag gaccaaaggc cctgccctgt ctctgtccct cactcagggc    63420
ctcctgcagg gcgagcgctt gggagcagac tcggtcttag gggacaccac tgtgggcccc    63480
aactttgatg aggccactga ccctccttc ctttcctggg gcagcacaga ctttggggtc    63540
tgggcaggga agaactactg gctggtggcc aatcacagag ccccaggcc gaggtggccc    63600 caagaaggcc ctcaggaggt ggccactcca cttcctccca gctggacccc aggtcctccc    63660
caagataggg gtgccatcca aggcaggtcc tccatggagc ccccttcaga ctcctcccgg    63720
gaccccactg gacctcagtc cctgctctgg gaatgcagcc accacaagca caccaggaag    63780
cccaggccca gccaccctgc agtgggcaag cccacactct ggagcagagc agggtgcgtc    63840
tgggaggggc taacctcccc accccccacc ccccatctgc acacagccac ctaccactgc    63900
ccagaccctc tgcaggaggg ccaagccacc atggggtatg gacttagggt ctcactcacg    63960
tgcctcccct cctgggagaa ggggcctcat gcccagatcc ctgcagcact agacacagct    64020
ggaggcagtg gccccagggc caccctgacc tggcatctaa ggctgctcca gcccagcag    64080 cactgccgtt cctgggaagc ctgggctcca ccagaccaca ggtccagggc acagcccaca    64140
ggagccaccc acacacagct cacaggaaga agataagctc cagacccag ggcgggacct    64200 gccttcctgc caccacttac acacaggcca gggagctgtt cccacacaga tcaaccccaa    64260
accgggactg cctggcacta gggtcactgc catttccctc tccattccct cccagtgcct    64320
ctgtgctccc tccttctggg gaacaccctg tgcagcccct ccctgcagcc cacacgctgg    64380
ggagacccca ccctgcctcg ggccttttct acctgctgca cttgccgccc acccaaacaa    64440
ccctgggtac gtgaccctgc agtcctcacc ctgatctgca accagacccc tgtccctccc    64500
tctaaacacc cctcccaggc caactctgca cctgcaggcc ctccgctctt ctgccacaag    64560
agcctcaggt tttcctacct gtgcccaccc cctaaccct cctgcccaca acttgagttc    64620
ttcctctcct ggagccctg agccatggca ctgaccctac actcccaccc acacactgcc    64680
catgccatca ccttcctcct ggacactctg accccgctcc cctccctctc agacccggcc    64740
```

```
ctggtatttc caggacaaag gctcacccaa gtcttcccca tgcaggccct tgccctcact   64800
gcctggttac acgggagcct cctgtgcgca gaagcaggga gctcagctct tccacaggca   64860
gaaggcactg aaagaaatca gcctccagtg ccttgacaca cgtccgcctg tgtctctcac   64920
tgcctgcacc tgcagggagg ctccgcactc cctctaaaga tgagggatcc aggcagcaac   64980
atcacgggag aatgcagggc tcccagacag cccagccctc tcgcaggcct ctcctgggaa   65040
gagacctgca gccaccactg aacagccacg gaggtcgctg gatagtaacc gagtcagtga   65100
ccgacctgga gggcagggga gcagtgaacc ggagcccata ccatagggac agagaccagc   65160
cgctaacatc ccgagcccct cactggcggc cccagaacac cccgtggaaa gagaacagac   65220
ccacagtccc acctggaaca gggcagacac tgctgagccc ccagcaccag ccccaagaaa   65280
cactaggcaa cagcatcaga gggggctcct gagaaagaga ggaggggagg tctccttcac   65340
catcaaatgc ttcccttgac caaaaacagg gtccacgcaa ctcccccagg acaaaggagg   65400 agcccctgt acagcactgg gctcagagtc ctctctgaga caggctcagt ttcagacaac   65460
aacccgctgg aatgcacagt ctcagcagga gagccaggcc agagccagca agaggagact   65520
cggtgacacc agtctcctgt agggacagga ggattttgtg ggggttcgtg tcactgtgag   65580
catattgtgg tggtgactgc tattcccaca gtgacacaac cccattccta aagccctact   65640
gcaaacgcac ccactcctgg gactgagggg ctggggagc gtctgggaag tatgccctag   65700
gggtgtccat caatgcccaa aatgcaccag actctcccca agacatcacc ccaccagcca   65760
gtgagcagag taaacagaaa atgagaagca gctgggaagc ttgcacaggc cccaaggaaa   65820
gagctttggc aggtgtgcaa gaggggatgt gggcagagcc tcagcagggc cttttgctgt   65880
ttctgctttc ctgtgcagag agttccataa actggtattc aagatcaatg ctgggagtg    65940 agcccaggag gacagtgtgg gaagagcaca gggaaggagg agcagccgct atcctacact   66000
gtcatctttt gaaagtttgc cctgtgccca caatgctgca tcatgggatg cttaacagct   66060
gatgtagaca cagctaaaga gagaatcagt gaaatgcatt tgcagcacag atctgaataa   66120
atcctccaga atgtggagca gcacagaagc aagcacacag aaagtgcctg atgccaaggc   66180
aaagttcagt gggcaccttc aggcattgct gctgggcaca gacactctga aaagcactgg   66240
caggaactgc ctgtgacaaa gcagaaccct caggcaatgc cagccctaga gcccttcctg   66300
agaacctcat gggcaaagat gtgcagaaca gctgtttgtc atagcccaa actatggggc    66360 tggacaaagc aaacgtccat ctgaaggaga acagacaaat aaacgatggc aggttcatga   66420
aatgcaaact aggacagcca gaggacaaca gtagagagct acaggcggct ttgcggttga   66480
gttcatgaca atgctgagta attggagtaa cagaggaaag cccaaaaaat acttttaatg   66540
tgatttcttc taaataaaat ttacacccgg caaaatgaac tatcttctta agggataaac   66600
tttcccctgg aaaaactata aggaaaatca agaaaacgat gatcacataa acacagtggt   66660
ggttacttct actggggaag gaagagggta tgagctgaga cacacagagt cggcaagtct   66720
cctaacaaga acagaacaaa tacattacag taccttgaaa acagcagtta aacttctaaa   66780
tcgcaagaag aggaaaatgc acacacctgt gtttagaaaa ttctcagtcc agcactgttc   66840
ataatagcaa agacattaac ccaggttgga taaataagcg atgacacagg caattgcaca   66900
atgatacaga catacattca gtatatgaga catcgatgat gtatccccaa agaaatgact   66960
ttaaagagaa aaggcctgat gtgtggtggc aatcacctcc ctgggcatcc ccggacaggc   67020
tgcaggctca ctgtgtggca gggcaggcag gcacctgctg gcagctcctg gggcctgatg   67080
```

```
tggagcaggc acagagctgt atatcccaa ggaaggtaca gtcagtgcat tccagagaga    67140
agcaactcag ccacactccc tggccagaac ccaagatgca cacccatgca cagggaggca    67200
gagcccagca cctccgcagc caccaccacc tgcgcacggg ccaccacctt gcaggcacag    67260
agtgggtgct gagaggaggg gcagggacac caggcagggt gagcacccag agaaaactgc    67320
agaagcctca cacatccacc tcagcctccc ctgacctgga cctcacctgg cctgggcctc    67380
acctgacctg gacctcacct ggcctgggct tcacctggcc tgggcttcac ctgacctgga    67440
cctcacctgg cctcgggcct cacctggcct gggcttcacc tggcctgggc ttcacctgac    67500
ctggacctca cctggcctgg gcctcacctg acctggacct cacctggcct gggcttcacc    67560
tggcctgggc ttcacctggc ctgggcttca cctgacctgg acctcacctg gcctgggctt    67620
cacctgacct ggacctcacc tggcctcggg cctcacctgc acctgctcca ggtcttgctg    67680
gagcctgagt agcactgagg ctgtaggac tcatccaggg ttggggaatg actctgcaac    67740
tctcccacat ctgaccttc tgggtggagg cacctggtgg cccagggaat ataaaaagcc    67800
ccagaatgat gcctgtgtga tttgggggca atttatgaac ccgaaaggac atggccatgg    67860
ggtgggtagg gacagtaggg acagatgtca gcctgaggtg aagcctcagg acacaggtgg    67920
gcatggacag tgtccaccta agcgaggggac agacccgagt gtccctgcag tagacctgag    67980
agcgctgggc ccacagcctc ccctcggggc cctgctgcct cctcaggtca gccctggaca    68040
tcccgggttt cccagggct ggcggtaggt ttgaagtgag gtctgtgtca ctgtggtatt    68100
actatgatag tagtggttat tactaccaca gtgtcacaga gtccatcaaa aactcatgcc    68160
tgggagcctc ccaccacagc cctccctgcg ggggaccgct gcatgccgtg ttaggatttt    68220
gatcgaggac acggcgccat gggtatggtg gctaccacag cagtgcagcc catgacccaa    68280
acacacgggg cagcagaaac aatggacagg cccacaagtg accatgatgg gctccagccc    68340
accagcccca gagaccatga aacagatggc caaggtcacc ctacaggtca tccagatctg    68400
gctccaaggg gtctgcatcg ctgctgccct cccaacgcca aaccagatgg agacagggcc    68460
ggccccatag caccatctgc tgccgtccac ccagcagtcc cggaagcccc tccctgaacg    68520
ctgggccacg tgtgtgaacc ctgcgagccc cccatgtcag agtaggggca gcaggagggc    68580
ggggctggcc ctgtgcactg tcactgcccc tgtggtccct ggcctgcctg gccctgacac    68640
ctgagcctct cctgggtcat ttccaagaca ttcccaggga cagccggagc tgggagtcgc    68700
tcatcctgcc tggctgtcct gagtcctgct catttccaga cctcaccagg gaagccaaca    68760
gaggactcac ctcacacagt cagagacaac gaaccttcca gaaatccctg tttctctccc    68820
cagtgagaga aaccctcttc cagggttct cttctctccc accctcttcc aggacagtcc    68880
tcagcagcat cacagcggga acgcacatct ggatcaggac ggcccccaga acacgcgatg    68940
gcccatgggg acagcccagc ccttcccaga cccctaaaag gtatcccac cttgcacctg    69000 ccccagggct caaactccag gaggcctgac tcctgcacac cctcctgcca gatatcacct    69060
cagccccctc ctgaggggga caggagcccg ggagggtgag tcagacccac ctgccctcaa    69120
tggcaggcgg ggaagattca gaaaggcctg agatcccag gacgcagcac cactgtcaat    69180
gggggcccca gacgcctgga ccagggcctg tgtgggaaag gcctctggcc acactcaggg    69240 gcttttttgtg aagggccctc ctgctgtgtg actacggtgg taactcccac agtgatgaaa    69300
ccagcagcaa aaactgaccg gactcgcagg gtttatgcac acttctcggc tcggagctct    69360
ccaggagcac aagagccagg cccgaggggtt tgtgcccaga ccctcggcct ctaggacacc    69420
ccgggccatc ttagccgatg ggctgatgcc ctgcacaccg tgtgctgcca aacagggggct    69480
```

```
tcagagggct ctgaggtgac ttcactcatg accacaggtg ccctggtccc ttcactgcca    69540
gctgcaccag accctgttcc gagagatgcc ccagttccaa aagccaattc ctggggccgg    69600
gaattactgt agacaccagc ctcattccag tacctcctgc caattgcctg gattcccatc    69660
ctggctggaa tcaagagggc agcatccgcc aggctcccaa caggcaggac tcccacacac    69720
cctcctctga gaggccgctg tgttccgcag ggccaggccg cagacagttc ccctcacctg    69780
cccatgtaga aacacctgcc attgtcgtcc ccacctggca aagaccactt gtggagcccc    69840
cagccccagg tacagctgta gagagagtcc tcgaggcccc taagaaggag ccatgcccag    69900
ttctgccggg accctcggcc aggccgacag gagtggacgc tggagctggg cccacactgg    69960
gccacatagg agctcaccag tgagggcagg agagcacatg ccggggagca cccagcctcc    70020
tgctgaccag agaccgtcc cagagcccag gaggctgcag aggcctctcc aggggacac     70080 agtgcatgtc tggtccctga gcagccccca ggctctctag cactgggggc ccctggcaca    70140
gctgtctgga ccctcctgt tccctgggaa gctcctcctg acagcccgc ctccagttcc     70200 aggtgtggtt attgtcaggg ggtgccaggc cgtggtagag atggctacaa ttaccacagt    70260
ggtgccgccc atagcagcaa ccaggccaag tagacagacc cctgccacgc agccccaggc    70320
ctccagctca cctgcttctc ctggggctct caaggctgct gtctgccctc tggccctctg    70380
tggggagggt tccctcagtg ggaggtctgt gctccagggc agggatgact gagatagaaa    70440
tcaaaggctg cagggaaag gcagcttccc gccctgagag gtgcaggcag caccacagag     70500
ccatggagtc acagagccac ggagccccca gtgtgggcgt gtgagggtgc tgggctcccg    70560
gcaggcccag ccctgatggg gaagcctgcc ccgtcccaca gcccaggtcc ccaggggcag    70620
caggcacaga agctgccaag ctgtgctcta cgatcctcat ccctccagca gcatccactc    70680
cacagtgggg aaactgagcc ttggagaacc acccagcccc ctggaaacaa ggcggggagc    70740
ccagacagtg ggcccagagc actgtgtgta tcctggcact aggtgcaggg accacccgga    70800
gatccccatc actgagtggc cagcctgcag aaggacccaa ccccaaccag gccgcttgat    70860
taagctccat cccctgtcc tgggaacctc ttcccagcgc caccaacagc tcggcttccc    70920
aggccctcat ccctccaagg aaggccaaag gctgggcctg ccaggggcac agtaccctcc    70980
cttgccctgg ctaagacagg gtgggcagac ggctgcagat aggacatatt gctggggcat    71040
cttgctctgt gactactggg tactggctct caacgcagac cctaccaaaa tccccactgc    71100
ctcccctgct aggggctggc ctggtctcct cctgctgtcc taggaggctg ctgacctcca    71160
ggatggcttc tgtccccagt tctagggcca gagcagatcc caggcaggct gtaggctggg    71220
aggccacccc tgtccttgcc gaggttcagt gcaggcaccc aggacaggaa atggcctgaa    71280
cacagggatg actgtgccat gccctaccta agtccgcccc tttctactct gcaaccccca    71340
ctccccaggt cagcccatga cgaccaacaa cccaacacca gagtcactgc ctggccctgc    71400
cctggggagg acccctcagc ccccaccctg tctagaggag ttgggggggac aggacacagg    71460 ctctctcctt atggttcccc cacctggctc ctgccgggac ccttggggtg tggacagaaa    71520
ggacgcctgc ctaattggcc cccaggaacc cagaacttct ctccagggac cccagcccga    71580 gcacccccctt acccaggacc cagccctgcc cctcctcccc tctgctctcc tctcatcact    71640
ccatgggaat ccagaatccc caggaagcca tcaggaaggg ctgaaggagg aagcggggcc    71700
gctgcaccac cggcaggag gctccgtctt cgtgaaccca gggaagtgcc agcctcctag     71760
agggtatggt ccaccctgcc tggggctccc accgtggcag gctgcgggga aggaccaggg    71820
```

```
acggtgtggg ggagggctca gggccctgca ggtgctccat cttggatgag cccatccctc    71880
tcacccaccg acccgcccac ctcctctcca ccctggccac acgtcgtcca caccatcctg    71940
agtcccacct acaccagagc cagcagagcc agtgcagaca gaggctgggg tgcagggggg    72000
ccgccagggc agctttgggg agggaggaat ggaggaaggg gaggtcagtg aagaggcccc    72060
cctcccctgg gtctaggatc cacctttggg accccggat cccatccct ccaggctctg     72120 ggaggagaag caggatggga gattctgtgc aggaccctct cacagtggaa tacctccaca    72180
gcggctcagg ccagatacaa agcccctca gtgagccctc cactgcagtg cagggcctgg    72240
gggcagcccc tcccacagag gacagaccca gcaccccgaa gaagtcctgc caggggggagc   72300 tcagagccat gaaggagcaa gatatgggga ccccaatact ggcacagacc tcagctccat    72360
ccaggcccac caggacccac catgggtgga acacctgtct ccggcccctg ctggctgtga    72420
ggcagctggc ctctgtctcg gaccccatt ccagacacca gacagaggga caggccccc      72480 agaaccagtg ttgagggaca cccctgtcca gggcagccaa gtccaagagg cgcgctgagc    72540
ccagcaaggg aaggccccca acaaaccag gaggtttctg aagctgtctg tgtcacagtc     72600
gggtatagca gcggctacca caatgacact gggcaggaca gaaacccat cccaagtcag     72660 ccgaaggcag agagagcagg caggacacat ttaggatctg aggccacacc tgacactcaa    72720
gccaacagat gtctcccctc cagggcgccc tgccctgttc agtgttcctg agaaaacagg    72780
ggcagcctga ggggatccag ggccaggaga tgggtccct ctaccccgag gaggagccag     72840
gcgggaatcc cagccccctc cccattgagg ccatcctgcc cagaggggcc cggacccacc    72900
ccacacaccc aggcagaatg tgtgcaggcc tcaggctctg tgggtgccgc tagctggggc    72960
tgccagtcct cacccacac ctaaggtgag ccacagccgc cagagcctcc acaggagacc     73020
ccacccagca gcccagcccc tacccaggag gccccagagc tcagggcgcc tgggtggatt    73080
ctgaacagcc ccgagtcacg gtgggtatag tgggagctac taccactgtg agaaaagcta    73140
tgtccaaaac tgtctcccgg ccactgctgg aggcccagcc agagaaggga ccagccgccc    73200
gaacatacga ccttcccaga cctcatgacc cccagcactt ggagctccac agtgtcccca    73260
ttggatggtg aggatgggggg ccggggccat ctgcacctcc caacatcacc cccaggcagc   73320
acaggcacaa accccaaatc cagagccgac accaggaaca cagacacccc aatacctggg   73380
gggaccctgg ccctggtgac ttcccactgg gatccacccc cgtgtccacc tggatcaaag    73440
accccaccgc tgtctctgtc cctcactcag ggcctgctga ggggcgggtg ctttggagca    73500
gactcaggtt tagggccac cattgtgggg cccaacctcg accaggacac agatttttct     73560
ttcctgccct ggggcaacac agactttggg gtctgtgcag ggaggaccttt ctggaaagtc   73620 accaagcaca gagccctgac tgaggtggtc tcaggaagac ccccaggagg gggcttgtgc    73680
cccttcctct catgtggacc ccatgccccc caagataggg gcatcatgca gggcaggtcc    73740
tccatgcagc caccactagg caactccctg gcgccggtcc ccactgcgcc tccatcccgg    73800
ctctggggat gcagccacca tggccacacc aggcagcccg gtccagcaa ccctgcagtg     73860 cccaagccct tggcaggatt cccagaggct ggagcccacc cctcctcatc cccccacacc    73920
tgcacacaca cacctacccc ctgcccagtc ccctccagg agggttggag ccgcccatag     73980
ggtgggggct ccaggtctca ctcactcgct tcccttcctg ggcaaaggag cctcgtgccc    74040
cggtcccccc tgacggcgct gggcacaggt gtgggtactg gccccagggg ctcctccagc    74100
cccagctgcc ctgctctccc tgggaggcct gggcaccacc agaccaccag tccagggcac    74160
agccccaggg agccgcccac tgccagctca caggaagaag ataagcttca gaccctcagg    74220
```

```
gccgggagct gccttcctgc cacccctctc tgccccagac ctccatgccc tcccccaacc   74280
acttacacac aagccaggga gctgtttcca cacagttcaa ccccaaacca ggacggcctg   74340
gcactcgggt cactgccatt tctgtctgca ttcgctccca gcgcccctgt gttccctccc   74400 tcctcccctcc ttcctttctt cctgcattgg gttcatgccg cagagtgcca ggtgcaggtc   74460
agccctgagc ttggggtcac ctcctcactg aaggcagcct cagggtgccc aggggcaggc   74520
agggtggggg tgaggcttcc agctccaacc gctccactag ccgagactaa ggaagtgaga   74580
ggcagccaga aatccagacc attccatagc aaatggattt cattaaagtt accagacttc   74640
agtgtaagta acatgagccc catgcacaac aatcccttat gaaggggaag tcagtgtcgc   74700
ctcggatttc ttgaaaaaca caaaaactta tcaatgcctg taaaagtctg ttggaaagaa   74760
aatatgattc aagaatgtta tgcccaacaa agctggcata ttttctaccc ggacacactc   74820
agggaatgtg gtcccttgag tgcttctctc actgcgtaaa tcctacgtgg tgtttaagca   74880
tattcataaa tgtgtatgtc tattttatg tgtaagatgg ttcattttta ttttatttat   74940
tcaatatgta caataaagaa tattgacaaa taggctggac atggtggctc ccacctgtaa   75000
tcccagccct ttgggaggcc gaggcgggca gatcacctga ggtctggagt tcgagaccag   75060
cctggccaac atgatgaaaa cccatctcta ctaaaaatac aaagattagc caggcatggt   75120
ggtgcatgcc tgtaatccca gccactcagg aggctgagac aggagaaatg cgtgaacccg   75180
gaaggcggag gttgcagtga gccgagatca caccactgca ctccagcctg cgacagagc    75240 aagattccat ctcaaaaaaa aaaaaagaca agaaatttg ttttttgaa taaagacaaa     75300 tttcatcaca cgaagataaa gatgcaaagc tccagacagg aaggcacgga cagcacagtg   75360
aagcccggag cgggcgctgg ggggccaggg gcatggcggg ggtgccagcg tctctcggtt   75420
cctaccatgg ccactccagc ctgtgttctc acgaggatgg ctgtgcaatg ctaggagcgt   75480
gttcgaagct ctagggcaac cactggaagt gaggctgagg agcagagccc agaggcccgt   75540
ggagctgatg aaaagaaagc tggagaaagt gtttgctgcc tcccaacatg gtaagaaaag   75600
atagaaagag agagcacacg gcaaagggag cttgctgagg gactctttac aatggcttgc   75660
acagagctca gggggtctgg gaggctaggg ccctgcgcag ggcagtcacc ccagcctgct   75720
gaccaaggtt tgctgcaggc agctctgggg gtggttgagg cgcggtccct ggagccaccc   75780
ctcaagggaa cgaggcagca gagtgggcca aggcccaggt cggctgcaag gctgcccagg   75840
acttggggtc cttacatcag cagccactga tgcagctggc ccagagagag gcgccgagca   75900
ggttgcctcc aggggacaaa ccaggtcgga gaggtgagg cagtggatgg agccacaaca    75960
accccgggca cgggtgacac gcacgttcat gcacatctga cccttcctcc ctcaccaaac   76020 aggtcccct gccttcccca tggttgcgaa aaagcaaaat gtagacgttt ttctttttt     76080 aattcatgtt ttaattgaca aatgaagccg tatatattta ttgtgtacaa catgatgctt   76140
taaaatatgt atacatcgtg aacagcaac gttgagctaa tttaacacgc attacttcac    76200
atacttgtca tcttttgtgg cgagaatgct taaaatccac tctcttagta tttttaaga    76260 atgcaataca ttgttgtcaa ctgtggtcac cgtcatgcat agccaagctc ccgacctcac   76320
cctcctgcca gctcaggctg tgcatccttt caccagcatc ccccaccccg gcccctggcc   76380
ctggtaacta ccactctata ctctacgtat gagttcagct ttttaagatt ccacagatga   76440
atgagatcat acagtatttg ctttctatgc ctggcttatt ttagttaaca cactgtcctc   76500
cagatccatc cgttgttgca aatgacaggg tttcattctt tttaaagtct aaagagtatt   76560
```

```
ccattgtgtc aatggacctc atttgcttta tccatgcatc aactatggac atttaggttg    76620
attccatttc ttagctgttg tggatggtgc tgcagtaaac atggggctgc agatgtctct    76680
tcaacatact gacatcatgt cctttggata aatacccagt agtgggatcg ctggatcaca    76740
atgtacagtt ttttttttaa tggaaacttt cattttttgg tgaaattagg aaaacagata    76800
aaacccacag aatccaaaat atatgtgaag atgccaaaaa cagttgacat tgggcagagg    76860
tcacatggaa ggaagtgaat acatgacggg gtgtgagggc ccagaggcag ctgaaatacg    76920
cttctaaac acaaggacct cttctgagag ggcagaagtt ttatcctgca catgcaatga     76980
ccagcacagc taaaatacac tttctaaaca tgaggacctc ttctgagagg gcagctttat    77040
cctgcaaatg caatgaccag cacaggaccc agaataaaga gagttgccag cggacgcctg    77100
gtgtccatgt gtccaggtga gttcgagatg cggacggcgc tggccagcca gtcacaccct    77160
aagtcaatct gctgcatgca tttgtccttg ccacagcaga aaacgagaaa gcctttgggc    77220
tgcaaagctt cacaggctcc tcttctcccg actccatgga aacagctaca aagagcaggc    77280
ccagtagagc ttaattcatg aaaatgagta ataaacttga actggaacag tatcgactt     77340
ttagaaacgg cagcaaagtg tataaaaaat attcaccaga acaatatttc caaacgatga    77400
gatgagaatt tcagccaagt aatcctccat ggatagaaaa taatgaaggg attggattta    77460
tgaaggaaaa tcatggagct caaatacaag aaaagagaat caaaaatgaa caggaggaga    77520
taaaatatgg tttggccaaa gttacaaaat aaatttttta aaaaccctc atcatgcaa      77580
gtagaaagag cgagaggaaa aacagatccc gtggaagaca caaataggac atggggagaa    77640
aaatgaatga gatgaaacag agcagaaata aaattttacg gaactaaaga caagtgatct    77700
gaacctgcct ggggcctggg ggacctcgcc accctgaagg gaaagaacat gcctggctgg    77760
cttttgccacc tgctcattgc agagcccac agcttgcaac aaacataggc ggtagccagg     77820
gagtggttac agcaggcctt gagcaagacc cagtgttgtg ctgacttcag gtctgaccca    77880
gcactgtcat agtggtggtg tccatagtgg tagtgggggt gcttgtgtca ctccaccccc    77940
atctccagga ggctcagaac agacagagag agactccatt tgtttgggag aaagtaaggg    78000
atgagaacaa gagtctctgc ctggtaatcc agagaattat tctagatctt ggccaagatt    78060
atcaaagcag tacctctatg agtcttttgg gcttggagtc ccctaaagc agatatagct     78120
aagatcacaa cacccaagtc cttttgaata tgtgggaaga cttcccaagg acaggagcaa    78180
acaaacaagc ccagactgca aaaaaacaag ccgagactgc aataaacacc tcactcttca    78240
atgcccaggc actgaagaac atctcctagc agcaacacca tccaggaaaa catggcctca    78300
accagtgaac taaataaggc accagggacc agtctcggag aaatagaggt atgttatctt    78360
tcagagaatt caaagtagct ttgttgagga aactcaaaga aattcaagat aacacagtga    78420
aggaattcag aatcctatcc gataaattta acagagattg aagcaattaa aaagaattaa    78480
gcagaaatta tggagctgaa aaatgcaatt ggcatactga aaaatgcatc agagtatttt    78540
catagcctca tatatcaagt agaagaaaga attagtgagc ttgaaaacag gctatttgga    78600
aaagcacgat aaaaggagac aaaagagaaa agaataaata acaatgaagc atatctacag    78660
gatctagaaa atagcctcaa aaggccaaat ctaagaatta ttagccttaa agaggaggta    78720
gagaagagg gatggagagt ttattcaaag ggataataac agaaaacttc ccaaacctag     78780
agaaagatat caatatccaa atgcaagaag gatgtagtac accaaggaga tttaatgcaa    78840
agaagactac ctcaaggcat tcaatactca aactcccata tgacaaggac tttaaaaga     78900
tcctaaaagc agcaaaagaa aagaaatgaa taaaatacta tggagctcca atatgtctgg    78960
```

```
cagcagactt ttcagtgaag actttatatg ccaggagaga gtgtcataat ggatttaaag    79020
tgctgaagga aaaaactttt accctcgaac agtatagctg gtgaaattat ccttcaaaca    79080
tgaaggagaa ataatttgtt tccagacaaa tgttgaggga tttcatgaac accagacctg    79140
tcttttaaga aatgctaaag ggagtacttc aatcagaaag aaacacgtta gtgaacaata    79200
agaaatcatc tgaaggcaca aaactcaccg gtaatagtaa gtacacagaa aaacacagaa    79260
tattataaca ctgtaactgt ggtgtgtaaa ctccttttgt ttgtttgttt gtttgtttgt    79320 ttgttttttgt ttttagacgg agttttgctc cagcccaggc tggagtgcaa tggcacaatc    79380
tcagctcact gcaacttcca cctcccgggt tcaagcaatt ctcctgcctc agcctcccaa    79440
gtagctggga ttacaggcat gtgctaccat gtccagctaa ttttgtattt tagtagagac    79500
ggtgtttcac catgttggtc aggctagcct tatcttgagt agaaaaacta atgatgaag    79560 caatgaaaaa taataactac aacttttcaa gacatagtac aataagatat aaatcataac    79620
aaaaagttaa aaggtggagg gatgaagtta aggcatagag tctttattag ttttcttttt    79680
acttgtctgt ttatgcaaac agtgttaagt tgtcatcagt ttaaaataat gggtcataag    79740
atactatttg caagcctcat ggtaacgtca aaccaaaagc aatacaacag atacacaaaa    79800
aacaaaaagc aagaagctaa attacgtcat cagagaaaat caccttcact aaaaggaaga    79860
cggagaaaag aatgaagaga gagaagacca aaagcaaata gcaatatggc aggagtaagt    79920
ccttacttat caataatacc attgaatgta aatggactaa actctccaat caaaagacat    79980
agagtggctg aatcaattaa agaaaaaaca agacccattg atctgttgtc cacaagaaac    80040
acactttatc tataaagaca cacatagact gaaaacaaag ggatggaaaa agatactcca    80100
cgccaatgga aaccaagaa agagcaggag tagctacact tatatcaggc aaaatagatt    80160
tcaagacaaa aactataaga agagacaagg tcactaatga taaacaggtc aattcagcaa    80220
gaggatataa caattgtaaa tatatatgca cccaatgctg gagcacccag atatataaag    80280
caagtattta ctagagctaa agagagaaat agactccaat gcaataatag ctggagattt    80340
caacatccca ctttcaacat tgaacagatc ctccagatag aaaatcaaca agaaatatt    80400 ggacttaatc tgcactatcg accaaatgga tctaacagat atttacagaa catttcatcc    80460
aacagctgca gaacacacat tcttttcctc agcacataga tcattctcaa ggatagacca    80520
tatgttgggt cacaaaacaa gttttaaaat attcaaatac attgaaataa tatcaagcat    80580
cttctgtgac cacaatggac taaaactaga aatcaataac aagaggaatt ttggaaacta    80640
tataaatata tggaaattaa tgaatgctga gtgggtcaat gaagcaatta agaaggaaac    80700
tgaaattttt cttggaacga atgatcatgg aaacagaaaa taccaaaacc tatgggatac    80760
agcaaaagca gtactaagag ggaagtttac agctacaaat gcttacatta aaaagaaga    80820 aaaacttcaa taaaaaaacc taacaatgca tcttaaagaa ctagaaaagc aagaggaaat    80880
caaatccaaa attagtagaa gaaaacagta aaggtcagag cagaaataag taaaattgaa    80940
atgaagaaaa caatacaaaa gatcaataaa acaacaggtt gttttcttga aaagttaaac    81000
aaaattgaca aacctttagc cagactaaga aaaaagaca gaagatccaa ataaataaaa    81060
tcagagatga aaaaggtgac attacaactt acaccacaga aattcaaagg atcattagtg    81120
gctactataa gcaactatat gccaataaat tggaaaatct agaagaaatg cagaaattcc    81180
tagacacata caacctccca agattaaacc aagaagaaat tcaaaacctg aacagactga    81240
taacaagtaa tgagatcaaa gccgtaataa aaagcctccc agtaaagaga agcccaggac    81300
```

```
ccgacggctt cactgctgaa ttctaccaaa catttaaagt agaactaata ccaatcctac   81360
tcaaactatt ccaaaaaata gaggtggaag gaatacttca aaactcatta tacgaggcca   81420
gtattaacct gacaccaaaa ctagacaaag acacatgaaa aaagaaaac tacaggccaa    81480
tatgtctgat gaatattgac acaaaaatcc tcaacaaaat actagcaaac caaattcaac   81540
tacacattag aaagttcact catcatgacc aagtggaatt tatctaactt gggatgcaaa   81600
gatggttcaa catatgcaaa tcaatcaatg tgatacatca tatcaacaga atgaacaaca   81660
aaaccatttt gatcatttaa ttgatactga aaaagcattt gataaaattc aacattcctt   81720
cataataaaa attctcttct atactaggta caaaagaaac ttacctcaac ataataaagc   81780
catatatgac agtcccacag tatgatacta aatgaggaaa aactgagagc ctttcctcta   81840
cgatctggaa catgacaaag atgcccactt tcatcactgt tattcaacat agtactggaa   81900
gtcctagctg gagcgatcag acaagagaaa gatataaaag acatccaaat tggaaaggaa   81960
taagtcaaat tatcctcatt tgcatatggt atgatcttct atttagagct aactaaagac   82020
tccaccaaaa aaagttatta gaactgacga acaaattcag taaagctgca ggatacaaaa   82080
tcaacataca aaaatcagta gcatttctat atgccaacaa tgaccaatgt gaaaagaaa    82140
ttaaaaagta accctattta caataaccac aaataaacac ctaggaatta ccaaagagg    82200
taaaagattt ctgtaatgaa aactataaaa cactgatgaa agaaattgaa gagtacacca   82260
aaaaatggaa agcaattgca tgttcatgga ttagaagaat cagtgttgtt ataatgtcca   82320
tactatccaa agcaatctac agattcaatg caatccttat caaaatacca atgacatcat   82380
tcacagaaat agaaaaaaaa aatcctaaaa tttacgtgga accacaaaga cccagaatag   82440
ccaaagctct cctaagcaaa agaacgaaa ctgtaggaat gacattgcct gtcttcaaat    82500
tctactacag agctatagat agtaaccaaa acagcgtggt actggcataa aaacagacac   82560
agagacaaac agaacaaaat ttaaaaaccc agaaataaat ccacacacct acagcaaatt   82620
cattttttgac aaagttgcca agaacatact ctggggaata gataatgata tctcttcaat   82680
aaatagtgtg gggaaaactg gatatccata tacataacag tgaaactaga cccctctctc   82740
tctcactata tacaaaaatc aaatcaaaat tgtttaagga cttaaatcta agacctcata   82800
ctatgaaacc actgcaagac aaccttggcg gaaactctcc aagacatcag tccaggcaaa   82860
gatttcttga gtaatatccc acaagcacag acaaccaaag caaaaatgga caaatgggat   82920
cacatcaagt taaaaagctt ctgcacagta agggaaacaa ccaacaaaat gaagagacaa   82980
cccacagaat gggagaaaat atttgaaaaa tacccatctg gcaagggatt aaaaaccaga   83040
atatatgcag aatatataag gagctcaaac agtgctatag aaaaaaaaat ctaataatct   83100
gatttaaaaa tgggaaaaat gttagaatag acatttctta aaataagaca tacagatggc   83160
aaaccgacat ggaacggtgc tcaacatcat ggattatcac agaaacacaa tcaatcaaaa   83220
ctaaaactaa aatgtgctat catctcaccc cagttaaaat ggctgatatc cagaagacag   83280
gcaataacaa atgctggcaa ggatgtgggg aaaagggagc ccccatacac tgttgctggg   83340
attgtaaatt agtacaacca ctgtggagag cagcatgaaa gttcctcaaa aaactgaaag   83400
aaagctacca taggatccag caatcccact gctgtgtata tactacaaaa gaaaggaagt   83460
cagtatatga agaggtatct gcactcccat gtttgttgca gccctgttca caacagccaa   83520
gatttggaag caacctaagt gtccatcagc agttgaatgt ataagaaaa tgtggtgcat    83580
atacacaatg gagtattatt caataataaa aaggaatgag attgagtcat ttgcaacaac   83640
atggatggaa ctggagatca ttatgtgaag tgaaataagc caggcacaga aagacaaaca   83700
```

```
ttacaatgtt cttacttatt aatgagatct aaaaatcaaa acaattgcac ccatgttcat   83760
aaagagtaaa aggatggtta ccagatgctg agaacggtgg tggggggata gggaaaggtg   83820
gcagtggtta acgggtacaa aaaaatagaa agaatgaata agacttgcta cttgatagca   83880
cagcaaggtg gctatagtca gtaatttagt tgtatatttt taataatgaa aggtgtataa   83940
ttggattgtt tctaacacaa aggataatgc ttaagaggat ggatacccca ttttccatga   84000
tgtgattatt tcacattgca cgcctagatc aaaacatcca atgtacccca taaatatata   84060
catcttctat gtacccataa aaattctgta aaataaaata tataaaaaga ggtgacagat   84120
atggaagaca ggcaaagaag agacgacatc cacataatcc gagtacctaa gaagaatgg    84180 agtccagtgc atctcaggag ccaccattct aagccaattt tctctggttc tctcagtcac   84240
cctaccaata cgtgggcaat cttgttttat ttcaggatag agttttgaa attatagatt    84300 taagtatgct ttctgttcta ttacttttgg taattaattt tagaaagaac taatttgggc   84360
acaaatttga aaaaattcta aatccaaaaa aaaaagaaa aaaacacaca cacaatcatc    84420 tataagggg atgatgacca gtcctagatt tctcaccagc cacattcaag atcagtaaat    84480
ggtaggacaa aacctgtagg gtccttaagg gggaaagaag tagtggatag tccagagtct   84540
atatacagcc aactgttctt gaagaaaaaa ggctgctgaa aaggagttcc aaacattcta   84600
taatccataa tctcatgatg aaactactag aggaagacca ccagccatca aaaggtgctt   84660
ggagaaccca gggccaagaa ccaaaagtaa atattaagtg tccttaactg cgagactaag   84720
atagaaatga ctgtgggga ccatgtggcc tcaacagagg tgaaatggtg tctgcctgac    84780
aaagtggaca ttttacaatg atcaaaacac agaatatgag atagagagca cttctgaatt   84840
actgcctcac tccaaataac tctcagccaa aggacttcag taaaaccaaa ttgggcatat   84900
tagacagtac aaacaaattc taagaaaata atattactga ttacaatcac atgatgctag   84960
agatggaggg gaaaaggaag aggaaaccag gtaatttcat actcgtatat agtaaagaac   85020
taaagtacat tgtccaaaga agaacaaaga atattttgga aagttataaa ggtagccact   85080
acacatagaa gatagcaaag aacaagaaaa cttaagatgg aaaacttttt ggaagcataa   85140
gaatagaaaa tataaactac taagataaga ttgaagccaa acagatctat gaaaacaaca   85200
aacatcaatg gccttaactt gcctattaaa aggaagagac tttcaaattg gaccacaaga   85260
taaaacccaa ctctatatag catatgagta ttacacacaa aatgggaaaa gctgaaaaaa   85320
cttgggcaaa attcaccccca agcaaattcc actgtttcct ttgggacaaa atgccaagct   85380
ccatgccagg gaagatgatt ctcctcagac cttctcctca ctctcccagt cctcttaggg   85440
aaggaattgg gtgttagagg agggagactc tgtcgattat cagctgaagc agtggtgtgc   85500
tcctgcgttg cttctgacct gggaaatgaa gcagcaagac tctttctgct gtgtctttgc   85560
ccagaagggc catcccccca gagcagagta cccaggccgg caggagcagt ggtggaagcg   85620
tggaaaccac gtctcctaca gcagagacca tcagaagcgg agcctcgggt ataagggaaa   85680
caacgcgttc tccctaacct gggagtgaca gacagcgtca ttcctcacag tgatacccctg   85740 tgttctagcc atctggccca tgacagagcc agcccagagc cagccagag ccagcccctc     85800 accatcctgg agcctggcca gctcgccaag ctgcaccata ggcctggaag gcgtggagac   85860
ctgcggcagt gccctgtcct cccgtgaggc ctgccatccc tgccaggggt cgcctctggc   85920
ttctccttct ccaggaccgc acggtccaga ggctcagtgc ctggagtagg tgttgcctcc   85980
ctgcttctag gcccagaccc tcccttgttc ctgaccccgg gcctttccct ctggcttgga   86040
```

```
catccagggc cctgtctcag ctggggagct gctcctgctc aaggactgtc ttccgcggga   86100
tcgaaaggcc gcgtcctgaa caatgcgtgg gccacgtaag cggagcaggc tctaaaggcc   86160
gcgtcctaaa cagtgcgtgg gccacgtgag cggagcaggc tctaaaggcc gcgtcctaaa   86220
cagtgcgtgg gccacgtgag cggagcaggc tctaaaggcc gcgtcctaaa cagtgcgtgg   86280
gccacgtgag cggagcaggc tctaaaggcc gcgtcctaaa cagtgcgtgg gccacgtgag   86340
cggagcaggc tctaaaggcc gcgtcctaaa cagtgcgtgg gccacgtgag cggagcaggc   86400
tctaaaggcc gcgtcctaaa cagtgcgtgg gccacgtgag cggagcaggc tctaaaggcc   86460
gcgtcctaaa cagtgcgtgg gccacgtgag cggagcaggc tctaaaggcc gcgtcctaaa   86520
cagtgcgtgg gccacgtgag cggagcaggc tctaaaggcc gcgtcctaaa cagtgcgtgg   86580
gccacgggag cggagcagac tctaaaggcc gcgtcctaaa cagtgtgtgg gccacgtgag   86640
cggagcgccc tctccactgc cctcggggcc gcagctccca gctcagctcc cagccctgct   86700
cagggcagcc aggccaggag gtaccatcca ggctaagtga ccctcagggg ggacaggtgc   86760
cccaggagat gccagctgtt gggagaggct gggggaccaa ctcgacctgg cctgtgggcc   86820
ctgccctggc cacccattgt aggatccagc cgccacgcct gtgacactcg tgtgctttcc   86880
ctggtgtgtg cttgtggcag gtgggggcag agggtcctca ggccagagag ccactccccc   86940
agcgccagac caccctcttc ctcactcccc cacctcaccc cctcacaggt gcctcccagg   87000
ccatcagggc ccaaccaccc ctaaacaaat gggttctcgg cccctcgtgg ctggaggtgg   87060
gttctctcac cattcccagc ctaagactcc atccccatgc tggcagctgt caaccatgt    87120 ctagagagat ccactgtccc agacagcacc tcagggtccc ccgtcctgcc tggaaccctg   87180
taggaaactc cacaaaccgc cgccattctg tccacacccc tacaggagcc caaccctct    87240 ccccacatcc aggcttccct cccagacccc tcatccctgc ccgcacggtg cctgaggggg   87300
ccttcttggg cagcgcctaa gcaagccccc agcacccttc ggccccttca aggcacacag   87360 gcccccttc cacccagcct caggaaacca cctgtgtcct ccaacgacag gtcccagcct   87420
cccagccttt gccttgcctg ttcctctccc tggaactctg ccccgacaca gaccctcccc   87480
agcaagcccg caggggcacc tcccctgccc ccagacaccc tgtgcccgtc agttcatccc   87540
cagcagaggc cctcaccagg cacaccccca tgctcacacc tggccccagg cctcagcctc   87600
cctgagggcc ccacccagcc cgcgtctggc cagtggtgcg tgcaaagccc ctcacccaga   87660
ctcggcggaa ggcagccagt gcaggcctgg ggaggggctc tccttagacc accttgcacc   87720
ttccctggca ccaccatgg gaagagctga gactcactga ggaccagctg aggctcagag    87780
aagggaccca gcactggtgg acacgcaggg agcccacgcc agggcgccgt ggtgagtgag   87840
gcccagtgcc acccactgag gcctcccgtt cagtgggacg acggtgaaca ggtgaaccca   87900
accaggcaac cccgccggg ccccacagac gggatcagag caggaaaggc ttcctgcccc    87960
tgcaggccag cgaggagccc tggcgggggc cgtggccctc caggcgagga ggctcccctg   88020
gccaccgcca cccgggcctc tctgctgctg ggaaaacaag tcagaaagca agtggatgag   88080
aggtggcgtg acagacccag cttcagatct gctctaattt acaaaagaaa aggaaaaaca   88140
cacttggcag ccttcagcac tctaatgatt cttaacagca gcaaattatt ggcacaagac   88200
tccagagtga ctggcagggt tgagggctgg ggtctccac gtgttttggg gctaacagcg    88260
gaagggagag cactgcaaa ggtgctgggg gcccctggac ccgacccgcc ctggagaccg    88320
cagccacatc agccccagc cccacaggcc cctaccagc gcagggttt tggctgagct      88380 gagaaccact gtgctaactg gggacacagt gattggcagc tctacaaaaa ccatgctccc   88440
```

```
ccgggacccc gggctgtggg tttctgtagc ccctggctca gggctgactc accgtggctg   88500
aatacttcca gcactggggc cagggcaccc tggtcaccgt ctcctcaggt gagtctgctg   88560
tctggggata gcggggagcc aggtgtactg ggccaggcaa gggctttggc ttcagacttg   88620
gggacaggtg ctcagcaaag gaggtcggca gagggcggcgg gggtgtgttt ttgtatggga   88680
gaagcaggag ggcagaggct gtgctactgg tacttcgatc tctggggccg tggcaccctg   88740
gtcactgtct cctcaggtga gtcccactgc agcccctcc cagtcttctc tgtccaggca   88800
ccaggccagg tatctggggt ctgcagccgg cctgggtctg gcctgaggcc acaccagctg   88860
ccatccctgg ggtctccgcc atgggctgca tgccagagcc ctgctgtcac ttagccctgg   88920
ggccagctgg agcccccaag acaggcagg gaccccgctg ggcttcagcc ccgtcaggga   88980
ccctccacag gtagcaagca ggccgagggc agggacggga aggagaagtt gtgggcagag   89040
cctgggctgg ggctgggcgc tggctgttca tgtgccgggg accaggcctg cgctttagtg   89100
tggctacaag tgcttggagc actggggcca ggcagcccg gccaccgtct ccctgggaac   89160
gtcacccctc cctgcctggg tctcagcccg ggggtctgtg tggctgggga cagggacgcc   89220
ggctgcctct gctctgtgct tgggccatgt gacccattcg agtgtcctgc acgggcacag   89280
gtttgtgtct gggcaggaac agggactgtg tccctgtgtg atgcttttga tatctggggc   89340
caagggacaa tggtcaccgt ctcttcaggt aagatggctt tccttctgcc tcctttctct   89400
gggcccagcg tcctctgtcc tggagctggg agataatgtc cggggctcc ttggtctgcg   89460 ctgggccatg tggggccctc cggggctcct tctccggctg tttgggacca cgttcagcag   89520 aaggccttc tttgggaact gggactctgc tgctggggca aagggtgggc agagtcatgc   89580
ttgtgctggg gacaaaatga ccttgggaca cggggctggc tgccacggcc ggcccgggac   89640
agtcggagag tcaggttttt gtgcacccct taatgggggcc tcccacaatg tgactacttt   89700
gactactggg gccagggaac cctggtcacc gtctcctcag gtgagtcctc acaacctctc   89760
tcctgcttta actctgaagg gttttgctgc attttggg ggaaataagg gtgctgggtc   89820
tcctgccaag agagccccgg agcagcctgg ggggctcagg aggatgccct gaggcaacag   89880
cggccacaca gacgaggggc aagggctcca gatgctcctt cctcctgagc ccagcagcac   89940
gggtctctct gtggccaggg ccaccctagg cctctgggt ccaatgccca acaaccccg   90000 ggccctcccc gggctcagtc tgagagggtc cagggacgt agcggggcgc cagttcttgc   90060
ctggggtcct ggcattgttg tcacaatgtg acaactggtt cgaccccctgg ggccagggaa   90120 ccctggtcac cgtctcctca ggtgagtcct caccaccccc tctctgagtc cacttaggga   90180
gactcagctt gccagggtct cagggtcaga gtcttggagg cattttggag gtcaggaaag   90240
aaagccgggg agagggaccc ttcgaatggg aacccagcct gtcctcccca gtccggcca   90300 cagatgtcgg cagctgggg gctccttcgg ctggtctggg gtgacctctc tccgcttcac   90360
ctggagcatt ctcagggct gtcgtgatga ttgcgtggtg ggactctgtc ccgctccaag   90420
gcacccgctc tctgggacgg gtgccccccg gggttttttgg actcctgggg gtgacttagc   90480
agccgtctgc ttgcagttgg acttcccagg ccgacagtgg tctggcttct gaggggtcag   90540
gccagaatgt ggggtacgtg ggaggccagc agagggttcc atgagaaggg caggacaggg   90600
ccacggacag tcagcttcca tgtgacgccc ggagacagaa ggtctctggg tggctgggtt   90660
tttgtggggt gaggatggac attctgccat tgtgattact actactacta cggtatggac   90720
gtctggggcc aagggaccac ggtcaccgtc tcctcaggta agaatggcca ctctagggcc   90780
```

```
tttgttttct gctactgcct gtggggtttc ctgagcattg caggttggtc ctcggggcat    90840
gttccgaggg gacctgggcg gactggccag gaggggacgg gcactggggt gccttgagga    90900
tctgggagcc tctgtggatt ttccgatgcc tttggaaaat gggactcagg ttgggtgcgt    90960
ctgatggagt aactgagcct ctagactgag cattgcagac taatcttgga tatttgtccc    91020
tgagggagcc ggctgagaga agttgggaaa taaactgtct agggatctca gagcctttag    91080
gacagattat ctccacatct ttgaaaaact aagaatctgt gtgatggtgt tggtggagtc    91140
cctggatgat gggataggga cttggaggc tcatttgagg gagatgctaa aacaatccta    91200
tggctggagg gatagttggg gctgtagttg gagattttca gttttagaa taaaagtatt    91260 agctgcggaa tatacttcag gaccacctct gtgacagcat ttatacagta tccgatgcat    91320
agggacaaag agtggagtgg ggcactttct ttagatttgt gaggaatgtt ccacactaga    91380
ttgtttaaaa cttcatttgt tggaaggaga gctgtcttag tgattgagtc aagggagaaa    91440
ggcatctagc ctcggtctca aaagggtagt tgctgtctag agaggtctgg tggagcctgc    91500
aaaagtccag ctttcaaagg aacacagaag tatgtgtatg gaatattaga agatgttgct    91560
tttactctta agttggttcc taggaaaaat agttaaatac tgtgactttta aaatgtgaga    91620 gggttttcaa gtactcattt ttttaaatgt ccaaaattct tgtcaatcag tttgaggtct    91680
tgtttgtgta gaactgatat tacttaaagt ttaaccgagg aatgggagtg aggctctctc    91740
ataacctatt cagaactgac ttttaacaat aataaattaa gtttcaaata tttttaaatg    91800
aattgagcaa tgttgagttg gagtcaagat ggccgatcag aaccagaaca cctgcagcag    91860
ctggcaggaa gcaggtcatg tggcaaggct atttggggaa gggaaaataa aaccactagg    91920
taaacttgta gctgtggttt aagaagtgg ttttgaaaca ctctgtccag ccccaccaaa    91980
ccgaaagtcc aggctgagca aaacaccacc tgggtaattt gcatttctaa aataagttga    92040
ggattcagcc gaaactggag aggtcctctt taacttatt gagttcaacc ttttaatttt    92100
agcttgagta gttctagttt ccccaaaact aagtttatcg acttctaaaa tgtatttaga    92160
attcattttc aaaattaggt tatgtaagaa attgaaggac tttagtgtct ttaatttcta    92220
atatatttag aaaacttctt aaaattactc tattattctt ccctctgatt attggtctcc    92280
attcaattct tttccaatac ccgaagcatt tacagtgact ttgttcatga tctttttag    92340 ttgtttgttt tgccttacta ttaagacttt gacattctgg tcaaaacggc ttcacaaatc    92400
tttttcaaga ccactttctg agtattcatt ttaggagaaa gactttttt ttaaatgaat    92460 gcaattatct agacttattt cagttgaaca tgctggttgg tggttgagag gacactcagt    92520
cagtcagtga cgtgaagggc ttctaagcca gtccacatgc tctgtgtgaa ctccctctgg    92580
ccctgcttat tgttgaatgg gccaaaggtc tgagaccagg ctgctgctgg gtaggcctgg    92640
actttgggtc tcccacccag acctgggaat gtatggttgt ggcttctgcc acccatccac    92700
ctggctgctc atggaccagc cagcctcggt ggctttgaag gaacaattcc acacaaagac    92760
tctggacctc tccgaaacca ggcaccgcaa atggtaagcc agaggcagcc acagctgtgg    92820
ctgctgctct taaagcttgt aaactgtttc tgcttaagag ggactgagtc ttcagtcatt    92880 gcttlagggg gagaaagaga catttgtgtg tcttttgagt accgttgtct gggtcactca    92940
catttaactt tccttgaaaa actagtaaaa gaaaatgtt gcctgttaac caataatcat    93000
agagctcatg gtactttgag gaaatcttag aaagcgtgta tacaattgtc tggaattatt    93060
tcagttaagt gtattagttg aggtactgat gctgtctcta cttcagttat acatgtgggt    93120
ttgaattttg aatctattct ggctcttctt aagcagaaaa tttagataaa atggatacct    93180
```

```
cagtggtttt taatggtggg tttaatatag aaggaattta aattggaagc taatttagaa    93240
tcagtaagga gggacccagg ctaagaaggc aatcctggga ttctggaaga aaagatgttt    93300
ttagttttta tagaaaacac tactacattc ttgatctaca actcaatgtg gtttaatgaa    93360
tttgaagttg ccagtaaatg tacttcctgg ttgttaaaga atggtatcaa aggacagtgc    93420
ttagatccga ggtgagtgtg agaggacagg ggctgggta tggatacgca gaaggaaggc    93480
cacagctgta cagaattgag aaagaataga gacctgcagt tgaggccagc aggtcggctg    93540
gactaactct ccagccacag taatgaccca gacagagaaa gccagactca taaagcttgc    93600
tgagcaaaat taagggaaca aggttgagag ccctagtaag cgaggctcta aaaagcacag    93660
ctgagctgag atgggtgggc ttctctgagt gcttctaaaa tgcgctaaac tgaggtgatt    93720
actctgaggt aagcaaagct gggcttgagc caaaatgaag tagactgtaa tgaactggaa    93780
tgagctgggc cgctaagcta aactaggctg gcttaaccga gatgagccaa actggaatga    93840
acttcattaa tctaggttga atagagctaa actctactgc ctacactgga ctgttctgag    93900
ctgagatgag ctggggtgag ctcagctatg ctacgctgtg ttggggtgag ctgatctgaa    93960
atgagatact ctggagtagc tgagatgggg tgagatgggg tgagctgagc tgggctgagc    94020
tagactgagc tgagctaggg tgagctgagc tgggtgagct gagctaagct ggggtgagct    94080
gagctgagct tggctgagct agggtgagct gggctgagct ggggtgagct gagctgagct    94140
ggggtaagct gggatgagct ggggtgagct gagctgagct ggagtgagct gagctgggct    94200
gagctggggt gagctgggct gagctgggct gagctgggct gagctggggt gagctgagct    94260
ggggtgagct gagctgagct ggggtgagct gagctgagct ggggtgagct ggggtgagct    94320
gagctggggt gagctgagct gagctggggt gagctgagct ggggtgagct gagctgagct    94380
ggggtgagct gagctgagct gagctgagct gagctggggt gagctgagct gagctgagct    94440
ggggtgagct ggggtgagct gagctgagct ggagtgagct gagctgggct gagctggggt    94500
gagctgggct gagctggggt gagctgagct gagctgagct gagctggggt gagctgagct    94560
gagctggggt gagctgagct ggggtgagct gggctgagct gagctgagct gagctgagct    94620
gagctgagct gagctgagct gagctgagct gagctgagct gagctgagct gagctgagct    94680
ggggtgagct gagctgagct ggggtgagct ggggtgagct gggctgagct gggctgagct    94740
gggctgagct ggggtgagct gagctggggt gagctgagct gagctgggct gagctgagct    94800
gagctggggt gagctgagct gagctggggt gagctgagct gagctgagct ggggtgagct    94860
gagctgagct gggctgagca gggctgagct ggggtgagct gagctgagct ggggtgagct    94920
gggctgagct gggctgagct gagctgagct gggctgagct gggctgagct gggctgagct    94980
gggctgagct gggctgagct ggggtgagct gagctggggt gagctggggt gagctgagct    95040
ggggtgagct gagctggggt gagctgagct gagctggggt gagctgagct ggggtgagct    95100
gagctgagct ggggtgagct gagctgagct ggggtgagct gagctagggt gaactgggct    95160
gggtgagctg gagtgagctg agctgaggtg aactggggtg agccgggatg tttgagttg     95220 agctggggta agatgagctg aactgggta aactgggatg agctgtggtg agcggagctg     95280
gattgaactg agctgtgtga gctgagctgg ggtcagctga gcaagagtga gtagagctgg    95340
ctggccagaa ccagaatcaa ttaggctaag tgagccagat tgtgctggga tcagctgtac    95400
tcagatgagc tgggatgagg taggctggga tgagctgggc tagctgacat ggattatgtg    95460
aggctgagct agcatgggct ggcctagctg atgagctaag cttgaatgag cggggctgag    95520
```

```
ctggactcag atgtgctaga ctgagctgta ctggatgatc tggtgtaggg tgatctggac   95580
tcaactgggc tggctgatgg gatgcgccag gttgaactag gctcagataa gttaggctga   95640
gtagggcctg gttgagatgg ttcgggatga gctgggaaaa gatggactcg gaccatgaac   95700
tgggctgagc tgggttggga gaccatgaat tgagctgaac tgagtgcagc tgggataaac   95760
tgggttgagc taagaataga ctacctgaat tgtgccaaac tcggctggga tcaattggaa   95820
attatcagga tttagatgag ccggactaaa ctatgctgag ctggactggt tggatgtgtt   95880
gaactggcct gctgctgggc tggcatagct gagttgaact taaatgagga aggctgagca   95940
aggctagcct gcttgcatag agctgaactt tagcctagcc tgagctggac cagcctgagc   96000
tgagtaggtc taaactgagt taaaaatcaa cagggataat ttaacagcta atttaacaag   96060
cctgaggtct gagattgaat gagcagagct gggatgaact gaatgagttt caccaggcct   96120
ggaccagtta ggctaggacc tcgttctata gaggcagact gtgtgctaca gtggagtttc   96180
aagatgattc catgagtcct ccccgccccc aacataaccc accttcctcc taccctacac   96240
gcctgtctgg tgtgtaaatc ccagcttgt gtgctgatac agaagcctga gcccctcccc   96300
cacctccacc tacctattac tttgggatga gaatagttct cccagccagt gtctcagagg   96360
gaagccaagc aggacaggcc caaggctact tgagaagcca ggatctaggc ctctccctga   96420
gaacgggtgt tcatgcccct agagttggct gaagggccag atccacctac tctagaggca   96480
tctctccctg tctgtgaagg cttccaaagt cacgttcctg tggctagaag gcagctccat   96540
agccctgctg cagtttcgtc ctgtatacca ggttcaccta ctaccatatc tagccctgcc   96600
tgccttaaga gtagcaacaa ggaaatagca gggtgtagag ggatcctctg tctgacagga   96660
ggcaagaaga cagattctta ccctccatt tctcttttat ccctctctgg tcctcagaga   96720
gtcagtcctt cccaaatgtc ttccccctcg tctcctgcga gagccccctg tctgataaga   96780
atctggtggc catgggctgc ctggcccggg acttcctgcc cagcaccatt tccttcacct   96840
ggaactacca gaacaacact gaagtcatcc agggtatcag aaccttccca acactgagga   96900 caggggcaa gtacctagcc acctcgcagg tgttgctgtc tcccaagagc atccttgaag   96960
gttcagatga atacctggta tgcaaaatcc actacggagg caaaaacaaa gatctgcatg   97020
tgcccattcc aggtaagaac caaaccctcc cagcaggggt gcccaggccc aggcatggcc   97080
cagagggagc agcggggtgg ggcttaggcc aagctgagct cacaccttga cctttcattc   97140
cagctgtcgc agagatgaac cccaatgtaa atgtgttcgt cccaccacgg gatggcttct   97200
ctggccctgc accacgcaag tctaaactca tctgcgaggc cacgaacttc actccaaaac   97260
cgatcacagt atcctggcta aaggatggga agctcgtgga atctggcttc accacagatc   97320
cggtgaccat cgagaacaaa ggatccacac cccaaaccta caaggtcata agcacactta   97380
ccatctctga aatcgactgg ctgaacctga atgtgtacac ctgccgtgtg atcacaggg   97440 gtctcacctt cttgaagaac gtgtcctcca catgtgctgc cagtgagtgg cctgggctaa   97500
gcccaatgcc tagccctccc agattaggga agtcctccta caattatggc caatgccacc   97560
cagacatggt catttgctcc ttgaactttg gctccccaga gtggccaagg acaagaatga   97620
gcaataggca gtagagggt gagaatcagc tggaaggacc agcatcttcc cttaagtagg   97680
tttgggggat ggagactaag cttttttcca acttcacaac tagatatgtc ataacctgac   97740
acagtgttct cttgactgca ggtccctcca cagacatcct aaccttcacc atccccccct   97800
cctttgccga catcttcctc agcaagtccg ctaacctgac ctgtctggtc tcaaacctgg   97860
caacctatga aaccctgaat atctcctggg cttctcaaag tggtgaacca ctggaaacca   97920
```

```
aaattaaaat catggaaagc cctcccaatg gcaccttcag tgctaagggt gtggctagtg    97980
tttgtgtgga agactggaat aacaggaagg aatttgtgcg tactgtgact cacagggatc    98040
tgccttcacc acagaagaaa ttcatctcaa aacccaatgg taggtatccc cccttcccctt   98100 cccctccaat tgcaggaccc ttcctgtacc tcatagggag gcaggtcct cttccaccct     98160 atcctcacta ctgtcttcat ttacagaggt gcacaaacat ccacctgctg tgtacctgct    98220
gccaccagct cgtgagcaac tgaacctgag ggagtcagcc acagtcacct gcctggtgaa    98280
gggcttctct cctgcagaca tcagtgtgca gtggcttcag agagggcaac tcttgcccca    98340
agagaagtat gtgaccagtg ccccgatgcc agagcctggg gccccaggct tctactttac    98400
ccacagcatc ctgactgtga cagaggagga atggaactcc ggagagacct atcctgtgt     98460 tgtaggccac gaggccctgc cacacctggt gaccgagagg accgtggaca agtccactgg    98520
taaacccaca ctgtacaatg tctccctgat catgtctgac acaggcggca cctgctattg    98580
accatgctag cgctcaacca ggcaggcct gggtgtccag ttgctctgtg tatgcaaact     98640
aaccatgtca gagtgagatg ttgcatttta taaaaattag aaataaaaaa aatccattca    98700
aacgtcactg gttttgatta tacaatgctc atgcctgctg agacagttgt gttttgcttg    98760
ctctgcacac accctgcata cttgcctcca ccctggccct tcctctacct tgccagtttc    98820
ctccttgtgt gtgaactcag tcaggcttac aacagacaga gtatgaacat gcgattcctc    98880
cagctacttc tagatatatg gctgaaagct tgcatgcctg caggtcgact ctagaggatc    98940
cccgggtacc gagctcgaat tcgccctata gtgagtcgta ttacaattca ctggccgtcg    99000
ttttacaacg tcgtgactgg gaaaaccctg gcgttaccca acttaatcgc cttgcagcac    99060 atccccccttt cgccagctgg cgtaatagcg aagaggcccg caccgatcgc ccttcccaac    99120
agttgcgcag cctgaatggc gaatggcgcc tgatgcggta ttttctcctt acgcatctgt    99180
gcggtatttc acaccgcata tggtgcactc tcagtacaat ctgctctgat gccgcatagt    99240
taagccagcc ccgacacccg ccaacacccg ctgacgcgaa ccccttgcgg ccgc          99294
```

<210> SEQ ID NO 4
<211> LENGTH: 17
<212> TYPE: DNA
<213> ORGANISM: Artificial Sequence
<220> FEATURE:
<223> OTHER INFORMATION: synthetic

<400> SEQUENCE: 4
tgcggccgat cttagcc                                                   17

<210> SEQ ID NO 5
<211> LENGTH: 18
<212> TYPE: DNA
<213> ORGANISM: Artificial Sequence
<220> FEATURE:
<223> OTHER INFORMATION: synthetic

<400> SEQUENCE: 5
ttgaccgatt ccttgcgg                                                  18

<210> SEQ ID NO 6
<211> LENGTH: 21
<212> TYPE: DNA
<213> ORGANISM: Artificial Sequence
<220> FEATURE:
<223> OTHER INFORMATION: synthetic

```
<400> SEQUENCE: 6
acgagcgggt cggcccatt c                                          21

<210> SEQ ID NO 7
<211> LENGTH: 19
<212> TYPE: DNA
<213> ORGANISM: Artificial Sequence
<220> FEATURE:
<223> OTHER INFORMATION: synthetic

<400> SEQUENCE: 7
ggtggagagg ctattcggc                                            19

<210> SEQ ID NO 8
<211> LENGTH: 17
<212> TYPE: DNA
<213> ORGANISM: Artificial Sequence
<220> FEATURE:
<223> OTHER INFORMATION: synthetic

<400> SEQUENCE: 8
gaacacggcg gcatcag                                              17

<210> SEQ ID NO 9
<211> LENGTH: 23
<212> TYPE: DNA
<213> ORGANISM: Artificial Sequence
<220> FEATURE:
<223> OTHER INFORMATION: synthetic

<400> SEQUENCE: 9
tgggcacaac agacaatcgg ctg                                       23

<210> SEQ ID NO 10
<211> LENGTH: 19
<212> TYPE: DNA
<213> ORGANISM: Artificial Sequence
<220> FEATURE:
<223> OTHER INFORMATION: synthetic

<400> SEQUENCE: 10
tcctccaacg acaggtccc                                            19

<210> SEQ ID NO 11
<211> LENGTH: 20
<212> TYPE: DNA
<213> ORGANISM: Artificial Sequence
<220> FEATURE:
<223> OTHER INFORMATION: synthetic

<400> SEQUENCE: 11
gatgaactga cgggcacagg                                           20

<210> SEQ ID NO 12
<211> LENGTH: 24
<212> TYPE: DNA
<213> ORGANISM: Artificial Sequence
<220> FEATURE:
<223> OTHER INFORMATION: synthetic

<400> SEQUENCE: 12
tccctggaac tctgccccga caca                                      24

<210> SEQ ID NO 13
<211> LENGTH: 25
```

```
<212> TYPE: DNA
<213> ORGANISM: Artificial Sequence
<220> FEATURE:
<223> OTHER INFORMATION: synthetic

<400> SEQUENCE: 13
ctctgtggaa aatggtatgg agatt                                          25

<210> SEQ ID NO 14
<211> LENGTH: 26
<212> TYPE: DNA
<213> ORGANISM: Artificial Sequence
<220> FEATURE:
<223> OTHER INFORMATION: synthetic

<400> SEQUENCE: 14
ggtaagcata gaaggtgggt atcttt                                         26

<210> SEQ ID NO 15
<211> LENGTH: 30
<212> TYPE: DNA
<213> ORGANISM: Artificial Sequence
<220> FEATURE:
<223> OTHER INFORMATION: synthetic

<400> SEQUENCE: 15
atagaactgt catttggtcc agcaatccca                                     30

<210> SEQ ID NO 16
<211> LENGTH: 20
<212> TYPE: DNA
<213> ORGANISM: Artificial Sequence
<220> FEATURE:
<223> OTHER INFORMATION: synthetic

<400> SEQUENCE: 16
tggtcacctc caggagcctc                                                20

<210> SEQ ID NO 17
<211> LENGTH: 21
<212> TYPE: DNA
<213> ORGANISM: Artificial Sequence
<220> FEATURE:
<223> OTHER INFORMATION: synthetic

<400> SEQUENCE: 17
gctgcagggt gtatcaggtg c                                              21

<210> SEQ ID NO 18
<211> LENGTH: 30
<212> TYPE: DNA
<213> ORGANISM: Artificial Sequence
<220> FEATURE:
<223> OTHER INFORMATION: synthetic

<400> SEQUENCE: 18
agtctctgct tcccccttgt ggctatgagc                                     30

<210> SEQ ID NO 19
<211> LENGTH: 28
<212> TYPE: DNA
<213> ORGANISM: Artificial Sequence
<220> FEATURE:
<223> OTHER INFORMATION: synthetic

<400> SEQUENCE: 19
```

```
gatgggaaga gactggtaac atttgtac                                          28

<210> SEQ ID NO 20
<211> LENGTH: 26
<212> TYPE: DNA
<213> ORGANISM: Artificial Sequence
<220> FEATURE:
<223> OTHER INFORMATION: synthetic

<400> SEQUENCE: 20
ttcctctatt tcactctttg aggctc                                            26

<210> SEQ ID NO 21
<211> LENGTH: 27
<212> TYPE: DNA
<213> ORGANISM: Artificial Sequence
<220> FEATURE:
<223> OTHER INFORMATION: synthetic

<400> SEQUENCE: 21
cctccactgt gttaatggct gccacaa                                           27

<210> SEQ ID NO 22
<211> LENGTH: 23
<212> TYPE: DNA
<213> ORGANISM: Artificial Sequence
<220> FEATURE:
<223> OTHER INFORMATION: synthetic

<400> SEQUENCE: 22
ggtgtgcgat gtaccctctg aac                                               23

<210> SEQ ID NO 23
<211> LENGTH: 25
<212> TYPE: DNA
<213> ORGANISM: Artificial Sequence
<220> FEATURE:
<223> OTHER INFORMATION: synthetic

<400> SEQUENCE: 23
tgtggcagtt taatccagct ttatc                                             25

<210> SEQ ID NO 24
<211> LENGTH: 32
<212> TYPE: DNA
<213> ORGANISM: Artificial Sequence
<220> FEATURE:
<223> OTHER INFORMATION: synthetic

<400> SEQUENCE: 24
ctaaaaatgc tacacctggg gcaaaacacc tg                                     32

<210> SEQ ID NO 25
<211> LENGTH: 17
<212> TYPE: DNA
<213> ORGANISM: Artificial Sequence
<220> FEATURE:
<223> OTHER INFORMATION: synthetic

<400> SEQUENCE: 25
gccatgcaag gccaagc                                                      17

<210> SEQ ID NO 26
<211> LENGTH: 24
<212> TYPE: DNA
<213> ORGANISM: Artificial Sequence
```

<220> FEATURE:
<223> OTHER INFORMATION: synthetic

<400> SEQUENCE: 26
agttcttgag ccttagggtg ctag                                              24

<210> SEQ ID NO 27
<211> LENGTH: 24
<212> TYPE: DNA
<213> ORGANISM: Artificial Sequence
<220> FEATURE:
<223> OTHER INFORMATION: synthetic

<400> SEQUENCE: 27
ccaggaaaat gctgccagag cctg                                              24

<210> SEQ ID NO 28
<211> LENGTH: 22
<212> TYPE: DNA
<213> ORGANISM: Artificial Sequence
<220> FEATURE:
<223> OTHER INFORMATION: synthetic

<400> SEQUENCE: 28
aactacgcac agaagttcca gg                                                22

<210> SEQ ID NO 29
<211> LENGTH: 18
<212> TYPE: DNA
<213> ORGANISM: Artificial Sequence
<220> FEATURE:
<223> OTHER INFORMATION: synthetic

<400> SEQUENCE: 29
gctcgtggat ttgtccgc                                                     18

<210> SEQ ID NO 30
<211> LENGTH: 16
<212> TYPE: DNA
<213> ORGANISM: Artificial Sequence
<220> FEATURE:
<223> OTHER INFORMATION: synthetic

<400> SEQUENCE: 30
cagagtcacg attacc                                                       16

<210> SEQ ID NO 31
<211> LENGTH: 19
<212> TYPE: DNA
<213> ORGANISM: Artificial Sequence
<220> FEATURE:
<223> OTHER INFORMATION: synthetic

<400> SEQUENCE: 31
tgagcagcac cctcacgtt                                                    19

<210> SEQ ID NO 32
<211> LENGTH: 23
<212> TYPE: DNA
<213> ORGANISM: Artificial Sequence
<220> FEATURE:
<223> OTHER INFORMATION: synthetic

<400> SEQUENCE: 32
gtggcctcac aggtatagct gtt                                               23

-continued

<210> SEQ ID NO 33
<211> LENGTH: 18
<212> TYPE: DNA
<213> ORGANISM: Artificial Sequence
<220> FEATURE:
<223> OTHER INFORMATION: synthetic

<400> SEQUENCE: 33
accaaggacg agtatgaa                                                 18

<210> SEQ ID NO 34
<211> LENGTH: 296
<212> TYPE: DNA
<213> ORGANISM: Homo sapiens
<220> FEATURE:
<223> OTHER INFORMATION: synthetic

<400> SEQUENCE: 34
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag ggcttgagtg gatgggaggg atcatcccta tctttggtac agcaaactac   180
gcacagaagt tccagggcag agtcacgatt accgcggacg aatccacgag cacagcctac   240
atggagctga gcagcctgag atctgaggac acggccgtgt attactgtgc gagaga        296

<210> SEQ ID NO 35
<211> LENGTH: 98
<212> TYPE: PRT
<213> ORGANISM: Homo sapiens
<220> FEATURE:
<223> OTHER INFORMATION: synthetic

<400> SEQUENCE: 35

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg

<210> SEQ ID NO 36
<211> LENGTH: 294
<212> TYPE: DNA
<213> ORGANISM: Homo sapiens
<220> FEATURE:
<223> OTHER INFORMATION: synthetic

<400> SEQUENCE: 36
caggtccagc tggtgcaatc tggggctgag gtgaagaagc ctgggtcctc ggtgaaggtc    60
tcctgcaagg cttctggagg caccttcagc agctatacta tcagctgggt gcgacaggcc   120
cctggacaag ggcttgagtg gatgggaagg atcatcccta tccttggtat agcaaactac   180
gcacagaagt tccagggcag agtcacgatt accgcggaca aatccacgag cacagcctac   240

```
atggagctga gcagcctgag atctgaggac acggccgtgt attactgtgc gaga    294
```

<210> SEQ ID NO 37
<211> LENGTH: 98
<212> TYPE: PRT
<213> ORGANISM: Homo sapiens
<220> FEATURE:
<223> OTHER INFORMATION: synthetic

<400> SEQUENCE: 37

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Thr Ile Ser Trp Val Arg Gln Ala Pro Gly Gln Gly Leu Glu Trp Met
         35                  40                  45

Gly Arg Ile Ile Pro Ile Leu Gly Ile Ala Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg
```

<210> SEQ ID NO 38
<211> LENGTH: 275
<212> TYPE: DNA
<213> ORGANISM: Homo sapiens
<220> FEATURE:
<223> OTHER INFORMATION: synthetic

<400> SEQUENCE: 38

```
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaggg atcatcccta tctttggtac agcaaactac   180
gcacagaagt tccagggcag agtcacgatt accgcggacg aatccacgag cacagcctac   240
atggagctga gcagcctgag atctgatgac acggc                             275
```

<210> SEQ ID NO 39
<211> LENGTH: 91
<212> TYPE: PRT
<213> ORGANISM: Homo sapiens
<220> FEATURE:
<223> OTHER INFORMATION: synthetic

<400> SEQUENCE: 39

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Asp Asp Thr
                 85                  90
```

<210> SEQ ID NO 40
<211> LENGTH: 296
<212> TYPE: DNA
<213> ORGANISM: Homo sapiens
<220> FEATURE:
<223> OTHER INFORMATION: synthetic

<400> SEQUENCE: 40

```
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaagg atcatccctc tccttggtat agcaaactac     180
gcacagaagt tccagggcag agtcacgatt accgcggaca atccacgag cacagcctac      240
atggagctga gcagcctgag atctgaggac acggccgtgt attactgtgc gagaga        296
```

<210> SEQ ID NO 41
<211> LENGTH: 98
<212> TYPE: PRT
<213> ORGANISM: Homo sapiens
<220> FEATURE:
<223> OTHER INFORMATION: synthetic

<400> SEQUENCE: 41

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Arg Ile Ile Pro Ile Leu Gly Ile Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg

<210> SEQ ID NO 42
<211> LENGTH: 294
<212> TYPE: DNA
<213> ORGANISM: Homo sapiens
<220> FEATURE:
<223> OTHER INFORMATION: synthetic

<400> SEQUENCE: 42

```
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accacggacg aatccacgag cacagcctac      240
atggagctga gcagcctgag atctgaggac acggccgtgt attactgtgc gaga           294
```

<210> SEQ ID NO 43
<211> LENGTH: 98
<212> TYPE: PRT
<213> ORGANISM: Homo sapiens
<220> FEATURE:
<223> OTHER INFORMATION: synthetic

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 44
<211> LENGTH: 296
<212> TYPE: DNA
<213> ORGANISM: Homo sapiens
<220> FEATURE:
<223> OTHER INFORMATION: synthetic

<400> SEQUENCE: 44
caggtgcagc tggtgcagtc tgggctgag gtgaagaagc ctgggtcctc ggtgaaggtc      60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggaca atccacgag cacagcctac    240 atggagctga gcagcctgag atctgaggac acggccgtgt attactgtgc gagaga        296

<210> SEQ ID NO 45
<211> LENGTH: 98
<212> TYPE: PRT
<213> ORGANISM: Homo sapiens
<220> FEATURE:
<223> OTHER INFORMATION: synthetic

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 46
<211> LENGTH: 233
<212> TYPE: DNA
<213> ORGANISM: Homo sapiens
<220> FEATURE:

<223> OTHER INFORMATION: synthetic

<400> SEQUENCE: 46

```
agaagcctgg gtcctcggtg aaggtctcct gcaaggcttc tggaggcacc ttcagcagct    60
atgctatcag ctgggtgcga caggcccctg gacaagggct tgagtggatg ggaaggatca   120
tccctatctt tggtacagca aactacgcac agaagttcca gggcagagtc acgattaccg   180
cggacgaatc cacgagcaca gcctacatgg agctgagcag cctgagatct gag          233
```

<210> SEQ ID NO 47
<211> LENGTH: 77
<212> TYPE: PRT
<213> ORGANISM: Homo sapiens
<220> FEATURE:
<223> OTHER INFORMATION: synthetic

<400> SEQUENCE: 47

```
Lys Pro Gly Ser Ser Val Lys Val Ser Cys Lys Ala Ser Gly Gly Thr
1               5                   10                  15
Phe Ser Ser Tyr Ala Ile Ser Trp Val Arg Gln Ala Pro Gly Gln Gly
            20                  25                  30
Leu Glu Trp Met Gly Arg Ile Ile Pro Ile Phe Gly Thr Ala Asn Tyr
        35                  40                  45
Ala Gln Lys Phe Gln Gly Arg Val Thr Ile Thr Ala Asp Glu Ser Thr
    50                  55                  60
Ser Thr Ala Tyr Met Glu Leu Ser Ser Leu Arg Ser Glu
65                  70                  75
```

<210> SEQ ID NO 48
<211> LENGTH: 296
<212> TYPE: DNA
<213> ORGANISM: Homo sapiens
<220> FEATURE:
<223> OTHER INFORMATION: synthetic

<400> SEQUENCE: 48

```
caggtccagc tggtgcaatc tggggctgag gtgaagaagc ctgggtcctc ggtgaaggtc    60
tcctgcaagg cttctggagg caccttcagc agctatacta tcagctgggt gcgacaggcc   120
cctggacaag gcttgagtg gatgggaagg atcatcccta tccttggtac agcaaactac   180
gcacagaagt tccagggcag agtcacgatt accgcggaca aatccacgag cacagcctac   240
atggagctga gcagcctgag atctgaggac acggccgtgt attactgtgc gagaga        296
```

<210> SEQ ID NO 49
<211> LENGTH: 98
<212> TYPE: PRT
<213> ORGANISM: Homo sapiens
<220> FEATURE:
<223> OTHER INFORMATION: synthetic

<400> SEQUENCE: 49

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Thr Ile Ser Trp Val Arg Gln Ala Pro Gly Gln Gly Leu Glu Trp Met
        35                  40                  45
Gly Arg Ile Ile Pro Ile Leu Gly Thr Ala Asn Tyr Ala Gln Lys Phe
    50                  55                  60
```

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 50
<211> LENGTH: 296
<212> TYPE: DNA
<213> ORGANISM: Homo sapiens
<220> FEATURE:
<223> OTHER INFORMATION: synthetic

<400> SEQUENCE: 50
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag ggcttgagtg gatgggaagg atcatcccta tccttggtat agcaaactac   180
gcacagaagt tccagggcag agtcacgatt accgcgaca aatccacgag cacagcctac    240
atggagctga gcagcctgag atctgaggac acggccgtgt attactgtgc gagaga       296

<210> SEQ ID NO 51
<211> LENGTH: 98
<212> TYPE: PRT
<213> ORGANISM: Homo sapiens
<220> FEATURE:
<223> OTHER INFORMATION: synthetic

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 52
<211> LENGTH: 296
<212> TYPE: DNA
<213> ORGANISM: Homo sapiens
<220> FEATURE:
<223> OTHER INFORMATION: synthetic

<400> SEQUENCE: 52
caggtccagc tggtgcagtc tggggctgag gtgaagaagc ctgggtcctc agtgaaggtc    60
tcctgcaagg cttctggagg caccttcagc agctatgcta tcagctgggt gcgacaggcc   120
cctggacaag ggcttgagtg gatgggaggg atcatcccta tccttggtat agcaaactac   180
gcacagaagt tccagggcag agtcacgatt accgcggaca aatccacgag cacagcctac   240
atggagctga gcagcctgag atctgaggac acggccgtgt attactgtgc gagaga       296

<210> SEQ ID NO 53
<211> LENGTH: 98
<212> TYPE: PRT
<213> ORGANISM: Homo sapiens
<220> FEATURE:
<223> OTHER INFORMATION: synthetic

<400> SEQUENCE: 53

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Leu Gly Ile Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg
```

<210> SEQ ID NO 54
<211> LENGTH: 296
<212> TYPE: DNA
<213> ORGANISM: Homo sapiens
<220> FEATURE:
<223> OTHER INFORMATION: synthetic

<400> SEQUENCE: 54

```
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaagg atcatcccta tccttggtac agcaaactac     180
gcacagaagt tccagggcag agtcacgatt accgcggacg aatccacgag cacagcctac     240
atggagctga gcagcctgag atctgaggac acggccgtgt attactgtgc gagaga        296
```

<210> SEQ ID NO 55
<211> LENGTH: 98
<212> TYPE: PRT
<213> ORGANISM: Homo sapiens
<220> FEATURE:
<223> OTHER INFORMATION: synthetic

<400> SEQUENCE: 55

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Arg Ile Ile Pro Ile Leu Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg
```

<210> SEQ ID NO 56
<211> LENGTH: 296
<212> TYPE: DNA
<213> ORGANISM: Homo sapiens
<220> FEATURE:
<223> OTHER INFORMATION: synthetic

<400> SEQUENCE: 56

```
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaga        296
```

<210> SEQ ID NO 57
<211> LENGTH: 98
<212> TYPE: PRT
<213> ORGANISM: Homo sapiens
<220> FEATURE:
<223> OTHER INFORMATION: synthetic

<400> SEQUENCE: 57

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg
```

<210> SEQ ID NO 58
<211> LENGTH: 296
<212> TYPE: DNA
<213> ORGANISM: Homo sapiens
<220> FEATURE:
<223> OTHER INFORMATION: synthetic

<400> SEQUENCE: 58

```
caggtccagc tggtgcagtc tggggctgag gtgaagaagc ctgggtcctc agtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaga        296
```

<210> SEQ ID NO 59
<211> LENGTH: 98
<212> TYPE: PRT
<213> ORGANISM: Homo sapiens
<220> FEATURE:
<223> OTHER INFORMATION: synthetic

<400> SEQUENCE: 59

-continued

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg
```

<210> SEQ ID NO 60
<211> LENGTH: 305
<212> TYPE: DNA
<213> ORGANISM: Homo sapiens
<220> FEATURE:
<223> OTHER INFORMATION: synthetic

<400> SEQUENCE: 60

```
gagcccactc ccaggtgcag ctggtgcagt ctggggctga ggtgaagaag cctggggcct    60
cagtgaaggt ctcctgcaag gcttctggat acaccttcac cggctactat atgcactggg   120
tgcgacaggc ccctggacaa gggcttgagt ggatgggacg gatcaaccct aacagtggtg   180
gcacaaacta tgcacagaag tttcagggca gggtcaccag taccagggac acgtccatca   240
gcacagccta catggagctg agcaggctga gatctgacga cacggtcgtg tattactgtg   300
cgaga                                                               305
```

<210> SEQ ID NO 61
<211> LENGTH: 98
<212> TYPE: PRT
<213> ORGANISM: Homo sapiens
<220> FEATURE:
<223> OTHER INFORMATION: synthetic

<400> SEQUENCE: 61

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Arg Ile Asn Pro Asn Ser Gly Gly Thr Asn Tyr Ala Gln Lys Phe
 50                  55                  60

Gln Gly Arg Val Thr Ser Thr Arg Asp Thr Ser Ile Ser Thr Ala Tyr
 65                  70                  75                  80

Met Glu Leu Ser Arg Leu Arg Ser Asp Asp Thr Val Val Tyr Tyr Cys
             85                  90                  95

Ala Arg
```

<210> SEQ ID NO 62
<211> LENGTH: 307
<212> TYPE: DNA
<213> ORGANISM: Homo sapiens
<220> FEATURE:

<223> OTHER INFORMATION: synthetic

<400> SEQUENCE: 62

```
gagcccactc ccaggtgcag ctggtgcagt ctggggctga ggtgaagaag cctggggcct    60
cagtgaaggt ctcctgcaag gcttctggat acaccttcac cggctactat atgcactggg   120
tgcgacaggc ccctggacaa gggcttgagt ggatgggatg gatcaaccct aacagtggtg   180
gcacaaacta tgcacagaag tttcagggca gggtcaccat gaccagggac acgtccatca   240
gcacagccta catggagctg agcaggctga gatctgacga cacggccgtg tattactgtg   300
cgagaga                                                             307
```

<210> SEQ ID NO 63
<211> LENGTH: 98
<212> TYPE: PRT
<213> ORGANISM: Homo sapiens
<220> FEATURE:
<223> OTHER INFORMATION: synthetic

<400> SEQUENCE: 63

```
Gln Val Gln Leu Val Gln Ser Gly Ala Glu Val Lys Lys Pro Gly Ala
  1               5                  10                  15
Ser Val Lys Val Ser Cys Lys Ala Ser Gly Tyr Thr Phe Thr Gly Tyr
                 20                  25                  30
Tyr Met His Trp Val Arg Gln Ala Pro Gly Gln Gly Leu Glu Trp Met
             35                  40                  45
Gly Trp Ile Asn Pro Asn Ser Gly Gly Thr Asn Tyr Ala Gln Lys Phe
         50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg
```

<210> SEQ ID NO 64
<211> LENGTH: 307
<212> TYPE: DNA
<213> ORGANISM: Homo sapiens
<220> FEATURE:
<221> NAME/KEY: variation
<222> LOCATION: (124)...(124)
<223> OTHER INFORMATION: n=a, g, t, or c

<400> SEQUENCE: 64

```
gagcccactc ccaggtgcag ctggtgcagt ctggggctga ggtgaagaag cttggggcct    60
cagtgaaggt ctcctgcaag gcttctggat acaccttcac cggctactat atgcactggg   120
tgcnacaggc ccctggacaa gggcttgagt ggatgggatg gatcaaccct aacagtggtg   180
gcacaaacta tgcacagaag tttcagggca gggtcaccat gaccagggac acgtccatca   240
gcacagccta catggagctg agcaggctga gatctgacga cacggccgtg tattactgtg   300
cgagaga                                                             307
```

<210> SEQ ID NO 65
<211> LENGTH: 98
<212> TYPE: PRT
<213> ORGANISM: Homo sapiens
<220> FEATURE:
<221> NAME/KEY: VARIANT
<222> LOCATION: (38)...(38)
<223> OTHER INFORMATION: Xaa=any amino acid

<400> SEQUENCE: 65

Gln Val Gln Leu Val Gln Ser Gly Ala Glu Val Lys Lys Leu Gly Ala
1               5                   10                  15

Ser Val Lys Val Ser Cys Lys Ala Ser Gly Tyr Thr Phe Thr Gly Tyr
            20                  25                  30

Tyr Met His Trp Val Xaa Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 66
<211> LENGTH: 294
<212> TYPE: DNA
<213> ORGANISM: Homo sapiens
<220> FEATURE:
<223> OTHER INFORMATION: synthetic

<400> SEQUENCE: 66
caggtgcagc tggtgcagtc tggggctgag gtgaagaagc tggggcctc agtgaaggtc      60 tcctgcaagg cttctggata caccttcacc ggctactata tgcactgggt gcgacaggcc    120
cctggacaag ggcttgagtg gatgggatgg atcaaccta acagtggtgg cacaaactat    180
gcacagaagt tcagggctg gtcaccatg accaggaca cgtccatcag cacagcctac      240
atggagctga gcaggctgag atctgacgac acggccgtgt attactgtgc gaga          294

<210> SEQ ID NO 67
<211> LENGTH: 98
<212> TYPE: PRT
<213> ORGANISM: Homo sapiens
<220> FEATURE:
<223> OTHER INFORMATION: synthetic

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 68
<211> LENGTH: 346
<212> TYPE: DNA
<213> ORGANISM: Homo sapiens
<220> FEATURE:

<223> OTHER INFORMATION: synthetic

<400> SEQUENCE: 68

```
aggatgtggg ttttcacact gtgtctctcg cacagtaata cacgaccgtg tcgtcagatc    60
tcagcctgct cagctccatg taggctgtgc tgatggacgt gtccctggtc atggtgaccc   120
tgccctgaaa cttctgtgca tagtttgtgc caccactgtt agggttgatc cgtcccatcc   180
actcaagccc ttgtccaggg gcctgtcgca cccagtgcat atagtagccg gtgaaggtgt   240
atccagaagc cttgcaggag accttcactg aggccccagg cttcttcacc tcagccccag   300
actgcaccag ctgcacctgg gagtggacac ctgtggagac tcgcga               346
```

<210> SEQ ID NO 69
<211> LENGTH: 98
<212> TYPE: PRT
<213> ORGANISM: Homo sapiens
<220> FEATURE:
<223> OTHER INFORMATION: synthetic

<400> SEQUENCE: 69

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg
```

<210> SEQ ID NO 70
<211> LENGTH: 150288
<212> TYPE: DNA
<213> ORGANISM: Artificial Sequence
<220> FEATURE:
<223> OTHER INFORMATION: synthetic

<400> SEQUENCE: 70

```
gcgcgccctg gcatggagga aatgacaaag attattagat tgaagacttt ctcagaaaat    60
gatattaagt cattaaggaa aaggaacaat ataaacgtgt atttgagaaa ttttaattat   120
ttgagagatt tttcatacaa tatttattct gcaagcaaat ttcagggatt gaattaataa   180
aactgataca gaacttcctc tgtaggtatc tgtgtaaaca tcaatttctg aatcagtgtt   240
gtaaatattt tggaacacac acacaaatca cattttatct ctactttat ctctatttt    300
aaaaatgcca aaaaaactca ttttgtgcat gtagcatttt gaattcccac catcaatgca   360
tgatagttct tggttttcca cattcatatt gccatttatc attatgagaa ttgtgtgttt   420
taaccattct aataggtgag taatggtatc taatttttag ttaaatgcac atttccctaa   480
taaaaattca catttaacaa ttttcatata attttttgcca agatgcctct tctcatattt   540
ggttcatttt taactgcatt gttttctttt gattagttgt aagtttactt gcatattgat   600
tataaaatca tttaacaaat taaagaatt catttaacaa atatgtgact tggaagtatt   660
ttctccaagt ctgcggctgt cttttactcc cttatcagta tgtattgcag aaaagtgtgt   720
```

```
gtgtgtgtgt gtgtgtgtgt ttatacaaat ttagatttaa aaaatgtaaa atgttattca    780
tccacagatc atgtctttgg tattatatct gaaatctcat tataaaatac agtaatagca    840
attactttt  ccacgtctct aatctcaggc tacaatcaac tcatgagtgt ttaagcttca    900
cctacttgat tagaggacta tcaacctaac atatttggaa tacttctgta aaaagatgtg    960
ttcctcttcc tattatttct ttatttgatc acttattaat atgtgtattg gtttatggat   1020
gtctatttca tactctgaag aagatccatg ctacattatt cattttatt  ttcaaaccac   1080
cacggcttta ttatgtgctg ggagctcatt gagtttggat cctgcatcct tacagctcac   1140
ctcatgcttt tgtttttgaa cacttccctg tttcctgcta ttataataaa ttctaaactc   1200
attttctata ttatctttt  catacataga atcagccatt tttctaaaga ttgcttgctt   1260
ctgatgttaa agaatagtat ttaaaaaatt gtaatactgg gtatgtgcat tgttaatgtg   1320
gtataagtac ttgcaggacc tctcaaccaa ctggcctagt aaactatgta tctaaccttc   1380
tgtaatgtga ttcattaaa  aatgagaaca cactggtctc tctacccaat tatgctacca   1440
catggatctt tctagccttc cttccttgac tgtctataac ctctcactgc aaaatgagga   1500
accccatcca accatatgcc attttattac ttagctgcac aatttcagga cacatgcata   1560
gcagtatcag aaatgtaaag ctgtaccctt gtaggaaaca tgtttatcta ctagaataga   1620
gtgcttatgt tcagtttctt tacactttaa acttacagag tttcctcatt ttcaaagttc   1680
cttaggtcag caacttcatt ttccacttc  ttcagtgagg tcatttcaat gacactgtat   1740
aatttgattt atttgaaatt ctataaaagc caaaactgta gtcaagtgaa caacaacata   1800
tagaggatat tcgaggagtt tagagactgg tataaaataa gttaaaaaga cactgtttaa   1860
gaagattaaa attatttta  gtgatatgca atggttcaga tatgcacaa  ttaatttgtc   1920
taagcacata gttttgtgat ggaaaatata aacctaaata tatacaatta aaaaaaaatt   1980
tagcagttca ttaacccaag gatcaaatgc agattgtata aaattatctc attacttatt   2040
ttgtgagggt ggagatttca tgagatgtat gcaacaaaga atgaggtaat tttcctgatt   2100
tgcatataag atgttgccat tcactaaaga cctttaattt tttaaattgt ttttttttta   2160
aatcaatttt ctatgtgacc caggttttt  tctcttgaca agcaaataac ccacaggatt   2220
atttctttc  cttggttgag aaatatttcc ccaaacttca gctcagttca ggcatacact   2280
gtccctgaat gggcatttac cctcagatgg gtacacacac ctgtcaacat gtggactctt   2340
ctgtcagaca aacgcacctt tactcacgtg gattcttctc tcagacaaac acacatgtcc   2400
ccacgtggac tctttcctca gactaccaca tatgttctta catttactct ttcctcagaa   2460
aacagacatt tcctcatgtg gactcttgtc tcagacaagc aaacatgtct ccatgtgaac   2520
tcttcactca cataagtaca catatgtcca cattgactgt ttccttacac aagtacatat   2580
atccaatgtc gaattgttct gtggcaaaat gatctcaaga taatgataat cataaacccc   2640
ctccctgaca aggcatagat ctgtattttt ttcattgcaa cctaactttg ccttattgtc   2700
aagaacagta gtttgcagct ctaaatatac caattagaga caggtgtcca ttttctctgg   2760
aaacgtattt ttatgttctt actggacata tttgttgata atgtttgcta ttatgaagat   2820
accccaacag tgtccacatt agagaataaa aaatagtaat gggcagatta actctgtgca   2880
tccagaccca gaaatccttt gaccttgact tccctgaaat gtagacacag aggatggatg   2940
agcaatgctg agcagtgcac ccatgaccac aaaaagaaag acgtggaaat gtgtcccctc   3000
cacttctcat gaaaggcagc tcatcccctg ttccctcagg ccctggcgag gagccacccc   3060
```

```
atgtctgtgc ccttcctcag tgtccacacc gtggggtctg cattgatctg gattctcttc    3120
tcatccccgt caatattagt gtccttcgta aatcaggtcc agctgtggct tctcctcacg    3180
gggctgttct cagtctgttt gctgtgttca cggaagtcct gtgtgaagtt tactgatgga    3240
gtcagagggg gaaaaaattt acagcccagt ggtgagactc tcctgcaaag cctctggttt    3300
cacctttact ggttacagca tgagcttggt ccagcacgct tcacaacagg gataggtgtg    3360
ggtgccaaca gtgagtgatc aagtatgaat tctcagggtt actttccatg agtacaaata    3420
aattaacaat ctcaagcaac ccctttttaa gtgcagtctg ccttacaatg accaatctga    3480
aagccaagga caaggtcatg tattactgtg agtgacacag tgagggaaac cctgtgtgag    3540
cccagacaca aagctcaccg caggagacag ggaggggact atgtggtaga tgctgctcag    3600
aaccaccagg gggcatcagg accatcaggg agggtgcaca gaaccaccag gagggctca    3660
ggacaccagg gggcgctcag aaccaccagg gggccctcag gacaccagag ggtgctcaga    3720
accaccagga ggcgctcagg acaccagggg gcgctcagaa cactaggagg tgctatgaat    3780
cactaggggg cgctcaggac acaagggagc actcagaacc accagggata gctcaggata    3840
ccagggggca ctcggaaccg caggggggcg ctcaggacac tagggggcgc tcagaaccac    3900
cagggggcac tcaggaccat cagggagggt gcacagaacc accaggaggg gctcaggaca    3960
ccagggggcg ctcaggacca aaggggggcc ctcaggacac caggggcac tcggaaccac    4020
cagggggcac tcagaaccat cagggagggt gcacagaacc accaggaggg gctcaggacc    4080
accaggaggt gctcaggaca ccagggggcg ctcagaacac taggaggtgc tatgaatcac    4140
taggggggcgc tcaggacaca agggagcact cagaaccacc agggatagct caggacacca    4200
gggggcactc ggaaccgcca ggggggcgctc aggacactag ggggcgctca gaaccaccag    4260
gaggcactca ggaccatcag ggagggtgca cagaaccacc aggaggtgct caggacacca    4320
gggggcgctc agaacactag gaggtgctat gaatcactag ggggcgctca ggacacaagg    4380
gagcactcag aaccaccagg gatagctcag gataccaggg ggcactcgga accgccaggg    4440
ggcgctcagg acactagggg gcgctcagaa ccaccagggg gcactcagga ccatcaggga    4500
gggtgcacag aaccaccagg aggggctcag gacaccaggg ggcgctcagg accacaaggg    4560
ggccctcagg acaccagggg gcactcggaa ccaccagggg gcactcagaa ccatcaggga    4620
gggtgcacag aaccaccagg aggggctcag gaccaccagg aggtgctcag gacaccaggg    4680
ggcgctcaga acactaggag gtgctatgaa tcactagggg gcgctcagga cacaagggag    4740
cactcagaac caccagggat agctcaggac accaggggc actcggaacc gccagggggc    4800
actcaggaca ctaggggggca ctcagaaccg ccaagggggcg ctcagaagaa caggggggtg    4860
ctcagaacac cagagggtgc tcagaagcac caggggggcgc tcaggacacc aaagggcact    4920
catgagactg tggcaagggg gtgctgagaa ccacaggatg tgaccaagac caagggggc    4980
actcagaact gccaggggggt gctcaggaca ccagaggatt ctcagaacca ccaggggatg    5040
ctcaggaaac tagcgggtgc tcagaaccac cggaggacac tcagaaaacc agggatgct    5100
caggaaccac cagggggcgc ccacgacacc agagggcagt cagaaccacc ggggcatgct    5160
cagaaccacc agggggcgct caggacacca ggggatgctc aggacactag gggcgctcag    5220
gaaccaccag gggacgctca ggacactagt agggtctcag aaccaccagg ggatgctcag    5280
gacactaggg ggcgctcagg aaccaccagg ggtcacccag gacaccaggg gtcgctcagg    5340
aaaccagagg gtgcccagga aaccagggga ggttcaggaa ccaccagggg gcactgagga    5400
caccaagggg tgctcagaac caccagggggg cgctcaggaa ccaccagggg gcgctcagga    5460
```

```
cactagtagg cactgaggaa ccaccagggg gcgctcagga cactagtagg cactgaggaa    5520
ccaccagggg gggctcagga cactagtagg cactgaggaa ccaccagggg gcgctcagga    5580
cactagtagg cactgaggaa ccaccagggg gggctcagga caccagaggt cgctcagaaa    5640 accaggggt gctcagaacc accaggggc actcaggaac caccagtggg tgttcaggac      5700
agcaagaatg gctcaggaca ccagggagca ctcaggacct ccaaggggct ctttggaggc    5760
agctccatat caggtacctg ggaggatgaa ggtttccttt tccaccttgg tgattcctga    5820
cctggtcaag caaaagtctt ccccaggatc tcttacgatg tcttccttgt aactcatggt    5880
ttctttcacc tataaaacat taacttagaa caggggttca attcaacttt taactctgcc    5940
tattttcaga gttatactag caatgatata tctcagtata tttttttaa ttgtgtatat     6000 tcaatccaaa gtctggctct atgcacaatt tttttgtttt ctgtgctgtc agacacacta    6060
ttgtaaatgc ttttctaaca actcagcata tgcatggggt ccagtttctt ttcctttcat    6120
cggctgtttg tgcagatgaa acaccacttt aagggctcct gtcctccact ttggcccctg    6180
gtgttctgct tctcaaactt tctccatctt ctcttttct gtcaaaatat tttatcttcc     6240
tcagtctcca tgcaggaaac aggaagtcct tttacttcct gtcctccatg tctggtaaat    6300
cagttcactt cttttcatga tcactgaagc caaccaagtt taggagagta acagttctcc    6360
ttagaataca ctctacctgc agaccctctg ccctcatcac acttttctag ggtcctgcag    6420 acataaccc cacccattcc tctttttccc taagtaccac agactaggct ctgcaactta    6480
tgctaccctc tgtgtgctca gcccaggggc tcagtagtgc tttcatgaag tccaaatccc    6540
taatgtgttt gcccactctc agaccaccct ccagcaagct gccattgtga ttgaatcctg    6600
caaagcatgg gctgctttca gtttcctatt gctggatgtt cttattata aaggcatatt     6660 ggcaaataac gactagagtt tgtattgaaa attaacgcca aaagttttt taaaagttt      6720 ttcaaataga aaagttctat cctgcctagt ttaaaaaaat acaatgttac tttaatcaat    6780
gatttaataa aaatttaagt gatgtttgtc ttattagtta ttcaatttat taataactga    6840
ctgatattta aaaagtaaat actggctggg cgcagtggct cacgcctgta atctcagcac    6900
tttgggaggg tgaggtgggt ggatcacctg aggtcgggaa ttcgagacca gcctgaccaa    6960
catggagaaa cccctctct actaaaaata caaaattagc tgggcgtggc ggggaagctg    7020
aggcaggaga atcgcttgaa cctgggaggc ggaggttgcg gtgagccgag aacacgccat    7080
tgcactccag cctgggcgac aagaccaaaa ctctgtctca aaaaaaaaa aaagtaaata    7140 ccattgtaca cttaagtaat atatttggca agaatggcat ttacattcat tcaaaaatga    7200
aactgcaaat acgagttaca ttcaattaaa taattaaaat aatatagaaa aaaatgggtg    7260
tgttgttttg gtgtttaata tacattcatt tttgcatgga cgggtatatg tgtcattgct    7320
gggctgttgt gtatgtgtgc gtgtgtgtgt gtgtctgtgt gtacaactat gaagtttaaa    7380
atatattatt aaattacgta gttatattaa tccaaattta tcatgttaaa atattaggaa    7440
aaaaacacca gtagagaaat tacagagaac atcagcaatg cctacagcat ttacaagagt    7500
cacattaata acaaacaaac tagttcaaat gtttagatat gacacatgca gtagaaaacg    7560
ttcacatggt attaacacaa aaatggtgca caactgagga aattataata cgttcatgat    7620
attggctaca taaatgctta tgatagtaat gcttttcatc catcaaatgc ttatgataat    7680
gcttttcatc catcatatta tagatgataa aacaactcta taaacacttc catcactagc    7740
gtttaatatg agatgcctca catctttttc tgaaataaat aaacatctgt ccaccacttc    7800
```

```
gatgatcatt tcaggattat cctctgaaat aattatccat aataatttta gtaacaatat      7860
tattttcaga agcctatttt ataaggtctt tgaactatta tttttatgat tgttacttta      7920
tattttacac acttttttatt tggaataatt ataggttatc agaacaattg taaggaaaat     7980
acagtgtgtt cacatccatc tccaagtttt cactaaagtt aatatgtcaa aaaaaacatg     8040
ggacatggga ctaatatatt tacattgata agtttctgtt tattcagctc tgggatttat     8100
ttgaattttg ccaattttta acagtttcct tttttccttt ttcttttctt tttgagataa     8160
ggtgtcactt tcctattgct ttttgtttgt ttctttgttc aacccacgta accacatcaa     8220
attcagtcac catgttcctc tcatatcttc tggttaatca cagtttgggt tcctgctgtc     8280
ttcccattga atattctata aatgaaacta gtcaaataag ttgattctgg tcacttatat     8340
atttacctat tttatcacgt ttgttttgtc aatcacagta agtgtcgaat tcgctatctg     8400
ttatagatgt tagcctattt tctatcccag atccattggt taaatctttg gtgatgcctt     8460
ttagaaaact gatcccttta ccctatgtaa tatgcccctt gattcctgaa agtcttatgt     8520
ctaccttgtc tgaatttaac atagctaagc acgctttctt ttcgttcata ttttcatggt     8580
ccatgttttc ctgtatttaa cttttctatg tagagcaaat ttctgtacag agctagtagt     8640
tgggtcttgc tttttaaatc aactataata attctatttt aaaactggta ttactatttt     8700
tctgttaatt tctgttttaa tttggcattt tatgatcatg tttatttctc tattaactta     8760
ttgtttagtt catcttttat gaatattgta ttggccctaa gatatacaat aagaattgtg     8820
tataatcaga ttctaattca aataacgtaa aacctcttca taggttgtag agctattata     8880
acttattctt ctaaacactc tttctcatcc gttgtcttag tttattctca gtttgcactt     8940
atatgtgcta taaaatataa tatgtgcatt tttatcatta catagacata tattagaaca     9000
attaaaaata taaaaactac atttcaactt cattttttca ttcttgacca catgtttat      9060 ttggatagat tcatgtttcg gatgtatatc atatggctac tcaccctggc agaaaatttg     9120
ccaaagcacc tactgaagga tgaatgcact agcaataaat tttctcagaa tcgatttgtc     9180
ttacagggta ttcatttgac tttcgcttta aatgaaattt ttaatatata tagaattcca     9240
gtttgacttt aatttgtaat ttattttctt gtactcatgt attcattatt ttcttcctga     9300
agatggtcac acattccatt ctgctgggcc ttcattatag atatttgtgt gtatctattc     9360
agggctatat ttgcaatttta tggatgccac aattatcaga gttgaagtca gcttctgctg     9420
tccacagaga tttcaagttc ctcccatgat acttgctttt gtgtccctgt tgatcctgg      9480 gtctttatat ttagttttcc ccagggaggc tgtctgtttc agctgtggaa agtgcaccct     9540
actgacagtt taaattgatg actgtgtggt gaaggaggtt ggacaaagcg ggacttcctc     9600
caaccttctg actgagtctc cttcttatgc aggagtagta agcatagttc tggggagtgg     9660
ccttccacat tgtcctgtcc ttaactcttt ccccagggct ggaacgtctt tcccagaca      9720 caactgtttt tcaccagtgt ccccagcttt ttacccacta tccttaccct aaagagtaag     9780
gatttctttc ctgaggaagg agatgggagg tgtttctgga tcaagtttcc ttggtgtcgt     9840
ctgtttcctt ttgtttctgt tgacttcacc acagctcata tgacacatgc tttggtggat     9900
ttcccctgga ggtagtggag gtgcattcag gcattccaca ggagctgctg ttcttttccc     9960
cagtcaacac cacaagacac cagatgagga agttgtccgt ggatttttca agttctctag    10020
gaaaagcttg caagcactag gccaatctaa caccattagt acatgcatac taaaaaaaaa    10080
aaagtcatta agtatttcta ggttagtctg tttctatctc aaatgccatc cagtggcacc    10140
tgccctacgt acactagcag gtaggtcctg gttctctctg caggctccta tcttctcaga    10200
```

```
tttcagtttt cttgtttgct tggtgaaatc aactcagata tgttgaatgt tttttctctc    10260
ttttatttgt agctgttcag cttcgttgtt aatgaggtca gaataaaatc acagttttct    10320 cattttttc acattccac actgaatagc tgctttccgt ataaaagcca gaaactgaga      10380
gaacacattg aatatccatt acaggtgaat gttaaacaat ttgagatatg tttgtgtact    10440
ggaataaaat gctgcattac aatcaagtca tcactcattc acataaaaca tggccacatt    10500
ctcaaataat gtagggacct gagtgcccct ccatctactg gcctctcctg gggccctagc    10560
ctggccacac cttcttgcag ggcagtcttg gacgccctgg gatcccgcac caaaatttct    10620
gccctggcag aacatgcctg actggtggag agctccaatc gggcagccct catgtgcaca    10680
caccagctta cacacttcct ccgaatactg taggttcacc caggcccacg taacttccca    10740
catcactttg cagtcacatg tctgtatagg tgggttttgc ttttcttgtc ccaccattgc    10800
gtggagtgca gtcccctccc cccaccccaa ccaccatggc agaggaagct ttggtgggga    10860
aaaagccagg gccgctcctg tcagcgtccc gcacttgcgc taattctgca cagagaatag    10920
cagatcatct cacacattca gaaatcactc ctgcttgtgg ggcatgaata cggcacccgg    10980
gcctgtgccc acaagtgtcc catccctgag ccaacacctc ctccagtgtg accttgaaca    11040
cagtcaccaa cagggcccca cagacgcaat gcctctgcca ctgtggcgaa cacctgcagg    11100
gaggcaggca cccagacacc cactagcact ctgccacagc tgccacacct caacagccc     11160 aggacagtgg attcctaacc ttaaggagcc ggagaaccaa gtcagggact agtataactt    11220
cccccagagt cagagcacac agtctaggtg ttgggagctg agcactggcc acctaaattt    11280
ttccagaaat gaagccagtt ggctgaatcc accttatacc acaatcaaac cctcaaggtc    11340
atccaatagg gtaaaagaaa ataaaaatgt atccaaaggt cagcaacttc aaagattgaa    11400
ggtggataag cccacaaaga tgagaaagaa ccagtgcaaa agtcctgaaa acaaaaaggg    11460
cgccctcttt cctccaaaca accacagcac ctcttcaaca gcagttctga atggggctga    11520
gatggctgaa atgacagaaa cagaactcag aatatggaga gtgaaaatgt agatgaatac    11580
agctatttat ggagaatact ataaatgttc ctcaaaaaat aaagaaacaa aatctactgt    11640
agaatccagc agtctcactg ctggctatgt atccaaagga aatgaaatca acatgtcaaa    11700
gagatatctg cactccatgt tcacgttcat tgcagcatta tttaaaatag taaagatatg    11760
gaaacatcct aaattcccat gaatggatga atgaataaag aaaatgcata cagacacaac    11820
agagtaatgt tcatccttaa ataagaagga aaccctgcct ctgtgacagc atgcatgaat    11880
ctagaggacc ttatgccaag tgaaacaagc caggaacaga ggaagagtca ttcatgattt    11940
cactgtatat attaaagcag tagacttgca gaggtagagt agaatgttgg ttaccagggc    12000
ctagaggggt ggactgggaa agggagatgt gggttaaagt gcacaacgtt ccagttagac    12060
cggaggtata agttatgcct ttctaatgca cagcatgtca actatagctg ataaggtagt    12120
atatatttca aaattactaa aaaaataaac attagaattt ccccactaag aaatgataaa    12180
tttgtgaggt gatgaatata agcggcttga gttacccagt tcataatgta tacatgtatc    12240
ataactaaac aacatatgtc ataaatatat gcaaaaatta tttgtaattt ataataaaat    12300
aagtttcata tttaaataat tacattaaga aaatgaacag aaactttcag atttcaagaa    12360
tattttatat atatatatat atatcttaaa acaaacttgc aacagaatat agaaataagt    12420
tttacgactc aatggaaaag aacagaattc aataaaaact ggctaaaaga aacaacagct    12480
gcatcattat agaaaattct ggaataatca gccatataaa gattctcact ctcttagaac    12540
```

```
tagaattccg taggacttgt aattcctcct gacctgggtg ggaggcaaaa ggaagaacag     12600
ctaatggtga ttcagtgagt tttatacctg tgtgtacttc tgtgctcact cagcagaaag     12660
aaaagaagaa aagaaagaaa gagagaaaga aagaaacaga agaaagaaa gaaagaagaa      12720 agaaagaaag aaagaaagaa agaagaaag aaagaaagaa agaaagagaa agaaagaaga      12780
aggaagaagg aaggaaagaa aagaaagaaa gaaagagaga gagggagaga gggaaggaag     12840
ggacagcaga agtcattgtg gtgtgtgtga aagcacaatc cttgggctcc cccacatcca     12900
tctctactcc agtcccatca atgtccagca aatacatttt ctaagatgaa gtattttaaa     12960
ctttctaaat cctgctagaa aacccctcag ctctttcagt tttgctctat cacttgaatt     13020
attgaattaa atctagttttt tgtgggccta tcaataccat aagccaaaat aacacatgaa     13080
gaaattgcac tgagacacat gaaaaccttc tgaaagctcc ataatttcag atctgcattc     13140
ttatttcccc gaacctaaat cactgaatag agactcagaa cgagttgatc ttgttcctga     13200
acgtgcacag agccaaggac atcctgtctg tctggaacag ctcaggtttg ttcctgtttc     13260
tcctagagga tataaaatct tgagttaggg aaaaacagcc agggacaccc tgggctttgt     13320
tcttctctcc cctggaggca ggatgtcctt cagagctttg tcccagtggg taacacagct     13380
gctgaggtgt acaacccacg tggcctcgtt ttggtcactt ttgcatggtg agcctgcttt     13440
gcaccatggc ctacaatatg cgtgtgtaac taatctgtct ccatcttcaa aatgacatta    13500
ttccacatca aatctagtgc aggtgcctca cacagaacat tctcaattac ctccatcatt     13560
cataaaattg atgccattaa tttcaagtat acatacatca gactcattta acgtattgtt     13620
attctcattg tttgaaacat aacttttaga tcaaataatt aacaataata aaaatataaa     13680
ttttgaagtc aggtaatgtg atttctctag ttgtgttctc tttgctcaga atggcttggg    13740
ctgttctgca tcttttgttt ttccacatat attttaggat tttttaaaaa tttctgtgaa    13800
gaatatcatt gttgttttca tagggattgt actgagtctg tagattgctt taagtattat    13860 ggacattta acaatattga atctttgaat tcataaacat ggaatattgt tccatcttgt    13920
gtcctcttta tttcctcaat gttttataga tttattgtag ttttttttta ctttgttcat    13980
tacacattgt atgcctgtac caaaacatca catatacccca acaaatagaa atatatatac    14040
tattatgtgc ttataacaat taaaaattat gtatgtatat tgaatctatt caaaatcaga    14100
aactatttct ttttactgtt tgtaaggtct tgtctctagg ctataaaaag aatttgtaaa    14160
actcaacaga aagcataata taaacagaat tctaaaatga gtgaaaatct gaacaaacac    14220
ctcaccaaga aaaatgttta tctgaaaata agaatatata aaattgttca gtatcaattg    14280
tcataaactg atactcatat ttaccaaata caaaagtaaa catgatgtat ttcaacagaa    14340
ttgattctca aatatttgta tactcataca gtggaatact atcagtcata aaaactatgg    14400
gttattaatt cagaagacaa cattttaaca ttttttctaa gtgaaggaag atggacaaaa    14460
gagactaagt attgtacaat tccattcatg agacctgcta aatacagtaa aattaaaagg    14520
atttaaaaaa caggtttgtg ataggcaggg cttttgggga aagacaagag actgacttgg    14580
caaagctcag gggatatttt tagggtaaaa caaactgtgt gccattgtga tatgcctaat    14640
ttcttattat atttgttcag agttaatagt gtacgtttca accaactcgg tgatttata    14700 ttttctattt gctgatagag acatgttcat ttttgtcaat cactttgcta aatgtggctg    14760
agaggctgtt gaaatgaacg ctgagcaaat gtattcacca aatctacaag agcaaattat    14820
ttgccaattg ctgattgagt ggggtctata atgtatttga gattgggtgt ggggatgtta    14880
ttgtgtgaga tcatgatgtt tagaccatga cactctctgg tgagggatca ctcattcatt    14940
```

```
gcacatttaa tgaaaggcag gtaggaggag cagaagggga tgagtcacac tcctgaccac  15000
agccacaggt tattgaaggc agaactgatg taatcccta aggtagacca ctgcccctcc  15060
aaggtgacct tatcctagag ttgacacaca tcctgggaca ccagagacaa ctccttctct  15120
cccctttctc tgcacttcag ctggaagcaa ctgtctcacc gagcaccttg tgttaaggaa  15180
tgagagttcc tgttccaggt gtgagggccc aggtgcatcc acttgatcca gcacaagagc  15240
aagaacagcc ttccagaaaa tgacatcgcc tgaggtataa ccagctctca cctgctgcag  15300
cttcctctga ataaaaagga aactgttgaa acttcctcat aagtgtcctg ctgtgccatt  15360
ccctttgtcc ccacatgttc agttgtgtct gtccagatgt cacttttgtg tagggagatt  15420
agggttctgc ttccagtacc agaacacaca tgacctctta ggggacttca gggttttgct  15480
gacatatgtg atgatcttaa aagtcattag ctccatttct acatcaaaaa acatctgaac  15540
caaaggagca cataggctca ggcctgtaat cccagcactt tgggaagcca aggcagagga  15600
atcacttgag gtcaggaatt tgagaccagc ctggtgaaca tggtgaaacc ccgtctctac  15660 taaaaatat atacaaaaat tagccaggcg tggtggcact agcctgtaat cccagctact  15720
tgaaaggctg aggcaggaga attgcttgaa cccaggaggt ggagattgaa gtgagctgag  15780
atcgcaccac ttcactccag cctgggcgac agagtgagcc tccatctaaa aaaaaaaaa  15840 atttatatat atatatatat atatatatat ataataaata tatattatat atcatatata  15900
tattttatat aatatatatg tatattttta tatattatac atacatatca atatatgata  15960
tataatatgt atatataata tataatatgt atattcatat attatataat atgtatattg  16020
atatatatta cacatatata ttttgatata tatatatctc caaaccatct aaatatcaag  16080
tattttttaa tccatctaag agctgaaatt gctgaaaaaa ctactccctc caaaagctgt  16140
agagacaggc acatccacag tcacagcaga gacttgctga cttggaagag aagctcctgg  16200
agacacattg gtgagaacat ttacctggtg attatgctga atgtctggag gacaaatgtg  16260
gactaggggg agggtgagca ctcctagagg ctgtacaccc cacacttgtg tggacttgcc  16320
ctccagggcc ttcaggttct cgtggaagca attaaaatag attccctata gccatgaact  16380
ggggaggagt aatcacggag aaaagatgca caaaaagact tttctagaaa gctcatccaa  16440
gggaaggtat tctccaaaat cttagtttat gtggggaag gaaatacttc caaattacag  16500 accccctcctc ctcagccttc ctctatcacg caaatgataa aattagccaa gaggagtcag  16560
attcaaggcg gtagccctgg gtgcagcatc tgcagaaggg aggaaagaga gaaaatcagc  16620
tgtatcactg gagattcctt gtgaaggtca ctgctcagga gaagagggca ccaaaccag  16680 ggagagtcaa ctgtaagaac ataccatgct cccctgcccc acacattacc tcctcaacag  16740
catcattaat atggattaaa gagggcagtg tgattgcttt agatctgttt gagaaagaaa  16800
gtcacatact gaggcctagg gtcagggtcg gcggcacttc ccgtgagtaa gatactacga  16860
agaaggaaaa attagggtc cataactgtg aaaatcagcc acagtgtgtg tgagaatgtt  16920
tgtgtttgtg tttctgtgtg tttgagtagg agttattgga acagcggacg tggagtgagc  16980
tttaatccac atccatctgc agcttcaggt attctcagat gcagtattca tctgcaagag  17040
ccgaaatgag aaaagagcca cctccaaccc ccccagagtt ttagcctccc tttgtttcca  17100
gtgatccagt gcatctagac ctccaggaag tggactccct ggtgatttta gcgattcttc  17160
tcttggagcc accctgaaga ggacattggg tttccaaagg cccattcact atttcaagaa  17220
gtggtgccat cagctcatgt tgtcactgaa ggagcattct gagccagggc acagtcactt  17280
```

```
cctagtgagc tacagaggct gagagaaaaa tgctctgtga gacccaatgg gaagctccct  17340
gcagtgcaag gtctgggtgg cagggagcgc tagggcctcg cccagcacag gctgcagccc  17400
tggagcaggt gcaagggagg ctggggaggg gttcctccca gggtctgatg tcttccttt   17460 ctcggacaaa catgctttaa taagttaaac aagactttag taaagactat tgatgtgtct  17520
ttgtgtcttt cagtatacag ttctatttgt aggatttatc taacctaaca agtcaatgag  17580
aatcacatgt aaaaggagaa atttctagga ttttcagata tcttaatagg taggagatgg  17640
agaaaaggga tggttttatt aattcagtgc ttgccaatct taacagagac agtagtaaga  17700
catgcagaaa gcaaagccca gaaaagtatg aaggtgtcaa agtgccattt aagtatgggt  17760
tcacttggag gaccatgttc tgcgggaact tgttttcagc agacaatcta ttttagcaga  17820
gttctgggca tacaagggga cacacatcat taaacaagga ttgggacagg gacttcagcg  17880
tcccactgtt gcatggccca taaattatgt gtgttctctt tctcatcttg gatcaagtct  17940
agagctatga aatagtatcc ctcatgaata tgcaaataac ctgagattta ctgaagtaaa  18000
tacagatctg tcctgtgccc tgagagcatc acccagcaac cacatctgtc ctctagaaa   18060 tccectgaga gctccgttcc tcaccatgga ctggacctgg aggatcctct tcttggtggc  18120
agcagccaca ggtaagaggc tccctagtcc cagtgatgag aaagagattg agtccagtcc  18180
agggagatct catccacttc tgtgttctct ccacaggagc ccactcccag gtgcagctgg  18240
tgcagtctgg ggctgaggtg aagaagcctg ggcctcagt gaaggtctcc tgcaaggctt   18300
ctggatacac cttcaccggc tactatatgc actgggtgcg acaggcccct ggacaagggc  18360
ttgagtggat gggatggatc aaccctaaca gtggtggcac aaactatgca cagaagtttc  18420
agggcagggt caccatgacc agggacacgt ccatcagcac agcctacatg gagctgagca  18480
ggctgagatc tgacgacacg gccgtgtatt actgtgcgag agacacagtg tgaaaaccca  18540
catcctgagg gtgtcagaaa cccaagggag gaggcagctg tgctggggct gagaaatgaa  18600
agggattatt attttttaatg ttgtttacag tatgtcatta ataaattgaa aaaagtaac   18660 aatagaagta tatactctaa ttatatggga actttgttt ttcagttttt tcatttttt    18720 tttttttttt ggtttgtttg tgacagagtc tcactctgcc acccaggctg gagtgtaacg  18780
gcacaatctc agctcactac aacctccacc tcccaggttc aagcaattct cctgcctcgg  18840
cctccagagt agttgggatt acaggcaccc gccaccatgc ccggtgaatt tttgtatttt  18900
tagtagagac gggggtttcac catgttagct aggctggtct caaactgctg atctcaggtg  18960
atctaccctc ctcagcctcc caaagtcctg ggattacagg cgtgagccac tgcgcctggc  19020
ccaattatat gggaattgtt tatataatta tcaccctata agcaaaattc atggaggagg  19080
aaaagctcta ctgaagaaag ctgataccgg cattcccatg aaagtatctg tgtagaagta  19140
agtattaaaa tcagttgaat aggcaaggca tggtggctca cgcctataat cccagcactt  19200
tgggagaccg aggcaggtgg atcacaaggt aaggagttca agatcagcct gcccaagatg  19260
gtgaaacccc ttctctacta aaaatacaaa gaattagctg ggcgtggtgg tgggtgcctg  19320
taatcgcagc tattcgggag gctgaggcag agaattgctt gaacctggga ggtgaaggtt  19380
gcagtgagcc gagatcacgc cactgcactc cagcctgggc gacagagtga actccatct   19440 caaaacaaaa caaaacaaaa caaaacaaaa aaacagttga ataaagtacc ttagagtcat  19500
ctgttcaatt aacatgttta actccaaaga aatactgaaa atattttcca aaaaggaagt  19560 gccatttac gttcctacca acagtgaata agattttctt ttctggagcc ttgtcagtat    19620
tcactaatgc tttgctgtgc agccgttgta atattatagt aaatgagtag cagtatttaa  19680
```

```
tggttgtttt aaatatacat attcttaata caaagtcttg atgaacactt ttttatacat    19740
tgttttatga ggtgtgtgtt cagatctatg tatgccagaa atgcctggca gcgttaattt    19800
aagcacactg tgagaatgac cctatagttt atgaagaatg tatgttcaga gctctgagct    19860
aagaaatcca ggagctgtca acccagaagt ttattccttg tctgtgaagg acatctgaat    19920
ccctggccta tcccttggaa cacaggatgt ccaggtgatt gatgctcttt gttaaatctg    19980
gaggttgcta ggtagagggt gctaagtgaa aatcataata taaactacac gtgttttaca    20040
aatggtagtg gttttcctgt ccaacacact tttcctgggc acattgtat gcaagtcctc     20100 aatacaccct aggtcttgtt catgggctcc aggtctcctc ttcagccttt tggacatggt    20160
gccatgccta ttacagtcaa tagggtcta gcatgacaac tggtaggccc agaacaaggt     20220
caaagaaaat cctgcaagct cttagacaac agtgtcaagg aagggagac ctgtggggaa     20280 atcccaggca ggccatgcac atctctgtgg gcccaacagc tgcaatcctt gatggatggg    20340
gcccgctgca tgtgtacggg gatgcctcca aaatgccaaa agttctggag gacctgttgc    20400
ctgaggtgga tgtgacaatg tgacaaagtg acagtcagat tcctgagctg tggcagctgt    20460
tggccactcc tgactgcact ctgagcaacc actgaggcag agctcattgc acaggctagg    20520
gtgtgtcagc cacgagaaca gttgtaacta taatgagatg ccgcctgtag ggataggata    20580
gcaaattgga gaccattgtt tatttggtag gccatttaaa gtgttgctga ctgccacacc    20640
aatgcattag gactactatg actacgtcat cctgggagcc taagtcctgg cgtccgatgt    20700
agagctccag tgggaaggag atgaaggtta ggatgagtcc ataaaggttc ttgctctgca    20760 gccccctgctt tgctgtctca cttggtgaac agagaatggg aggtcaatgc ggacaaagtc    20820
cagggtccag gcttatcagt caaatacttg gtgtcatctg gttacataag actatagtta    20880
ttccatattt catcatagat aagataagat gcaggtctac tcatgtccca ccacaccaaa    20940
gcagttggaa acctcccaag gcctcctggg acattggcga tcctttattc cccatttcgg    21000
caaacccctt gggcccccat ggcacttaga caagaaggtg ccccactgcg actgttccaa    21060
aagggaggat gagggctctg aagaagctga agtcacagtg aaatgaatac aaaccttggg    21120
agttctagtg cagggacagc cctgtgaatt ggatgtagtc agttaccctg aggggtttag    21180
gtggggactg tgttaaaggc aaggacataa gtgtgtgtcc ctaagaccct ggtctcaaag    21240
acagaaggaa gctgaagtga gatatactgt ttaggagtag caactgcact acatgtcatg    21300
ccttacgagt gtaggatgtg acaaagaggg ccactccaca tccggaacaa cctttagcag    21360
gctggctaaa ggatgccttc cagacacaaa agccttggaa tgccaggaca cagtctgtag    21420
ccaaatggta cttgtggtgg tcaccaccaa cataaaagtg ggccaactgt gccagcagaa    21480
gttagcccca cagaactttc ccccacctaa gagaaggcag tgcaccacaa tgcggaattc    21540
caccactgtg gaattggggg agcttagaat tggattcaga cacaagggga gagagtggat    21600
cacagggtgg cttctctatg ggataggggg tggagagtat tatactctct ggactcaaga    21660
tgagtaaaat gacacccatc acaaaccatc cagccctatg atggcacctt tatggtaagt    21720
ggttgcaggc tccaaggggg ccgggtccaa tgaggaagat gccccacag ctcgttctca     21780 atggcagact atagaagagt tgcaggatat cttctgggag tcgagatgag gcatgctaat    21840
tatgctgaga attattgaag tcccaacaat gaattgttta ctgcaaaata aaagctacag    21900
ttatgtattc agtgcctacc caatggcatg gtgcactgat ttccacgtta agcccctgg     21960 gagggcagcc aacatttcat gtgccccagg tagttgctga cttaggagaa aagaagaaac    22020
```

```
tgagtaagca agggatgcac cctactgtga tgaagaacaa tggcaccaaa ggaagagaga    22080
cagccaagga gccagtcagg gtggccagac aacgaatgtg ctctaactgg caacacctac    22140
cagttctctg ggcccatagc ggcaataggt ggttatggaa gggccacgga agtcagaccg    22200
gttgaactag tgatacgacc tgggggactg ccacccagac cctgtgtagt atacacagct    22260
tccatcctag aacacatgag aatggatatc ttcttaggcg tgaccctcca aacaacggcc    22320
agggaattcc aacggagagt tagagtggtg atatgtgtga ccaagcagaa ggcaaactgg    22380
atgccagtag agctgccaac ccatggggag tcccacagct ggagcaacac cacccgccct    22440
gggaggggaa gatgatccaa tcatgaagat tgttaaggag ctagcccagg taggcattag    22500
gaggccactg catggttcct acaacagacc tgcatggccc atgcagaggc cagttgagac    22560
atggagaatg acagtagatt actgggagtt aaataaggtg gtctcccgag tgaatgcagc    22620
tgttcctaat atctcctcca gtctgacgag aataggagag gtgttagcca cgtagcattt    22680
ccttatcagt ttagtcaata ccttcttcag catttctgtt gccccagagt caagatcaat    22740
ttgcattaac ctaaaagaa caatggactt ttactgtctt gttccaggga tatttacaca    22800
gcccaaatct cacagcctag tgacctccaa cctcagtcga tgggctgacc caaggggat    22860 acatgttttc cactacattg gtgttatcat gataacctct gagtcttttt tcagcttata    22920
aattacagcc cctgtcttgc tgtctcactt gctgaataga ggatgggagg ttaatacaga    22980
caaaatccag ggtccaggct tatcagtcaa atagttggtg tcatctggtt gggtaaaact    23040
aaagtcattc catctgccat catagataag gtgcaggcct acccacgtcc caccacaaca    23100
aagcagctgc aaactctcaa ggccttctgg agcatcagtg tccttttatt ccttttattt    23160
gacatccctg aaggaggctg ctaggggaga ctgtgtccct cctaaattca tgtgctgaag    23220
tcccaaccct tggtccttca gaatgaaatc atacttggat tagtgtcctt taaagaggtg    23280
aataagttaa agtgagattc ctggagtggg ccctaatgc aatctgactg ttgttataag    23340
aagaggaagc aggagggagg gtgcacaggc cccgagggac ggccatgtta ccacagaaca    23400
gtgagaaggc gccatctgca tgccagggag cgagacctca gaggaaaccc acccagctgg    23460
cagcttgatc ttaggctttc atcctccata agtgtgagga aattggtttt gtattgtaag    23520
ccatccgatc tgtggtattt cgttataaaa gccctataaa atgaatacag taggtaatag    23580
gagagcttct atacattgaa aaagtcggat ggccagaaaa acctagacac tcctgttcag    23640
acctgagcag ggtgatggac ctgctttggg acaggagagg ggaagagatg aacccagcac    23700
ccagacccag ctgagcccat tcctcagcag gccgtccctg ggccggagct tgcacaggtg    23760
tgaaagagcc tgtcttggtc ttcaggggct catggagttg gacggagaat ggtgtagact    23820
caagaacacg tcatcggtgt gcccgtgttt atctgaatgg gatgtgtttc tagggtgtgc    23880
tcatccccaa agaagaatta atcaggtctc ttgggctaaa aagaggttgt ggcatttgtg    23940
tgtattaata actgtggtcg gacagtaaat tatgttaaac tgcttatggg aaggcacaat    24000
ggaaagaaac actttgttac agaaggaaaa aaaaggtgat tatttaaatg aggtgccttt    24060
gaaggtcacc atgccaagag gagcccatca catgatagtg ctggctttca tgttcaggag    24120
atcaggaggg tccgtccgct ggcttttatg acaccctaga cagagctgag agtgtaatgt    24180
atgaatggag gggaagtgga gagagggag gccaaatgtt tggtgggaat ggagggtcac    24240
tattggagcc attaggaaat acacaagcat gaattatgct ggaggacaga acagtgttcc    24300
tggggaatat tgtgttgctt tgggagctgc tgaaacataca ggagtttcac tgttcctagt    24360
tctcaaattc tctagactct ctggacaacc cagttttaaa tattgggaat ataggtaaga    24420
```

```
cacattcgtt attaaaaatt attaagagaa gatgtaggaa gaaatttaaa gtaatccatt    24480
tggttatgaa aatttagtta cagcgaactg tgatgtccgt ttcttacttg gaataatgga    24540
atgtaagtca ttagtcatct caacggttca tttttccata accatcaatt acaaaactgc    24600
tgagtaattt cctgaattgc ccaccataga aactgacctc acatttcctc aatgagaaac    24660
tgccagtccc gttgatccag cctcgttctt cccatcaggg attttgtatc tctgtggacg    24720
tgtggcacag tgctgcatat ccatcggcat atggcctcag gaaaggcgcc agcctatcca    24780
tgcatgatga agcttactta ggggatgaag cccgcatgct gggtgagcca gtgccaacag    24840
ctgaaagaat caactgcctg gtgtatgatg cttttatgaa aacaagccca gggcctcttg    24900
cattcttctg tattagattc tctggtgaag attttttattc atttctgcct gaaattgcca    24960
catataatta cctggaagca ttacaataaa ctgatttgga agttaactga cttcctggtg    25020
aggttaaaat gagtgtcagg tgcatagtga cagaccgg agacatggat gcatagcaaa    25080
cttgtgctca ccatggtttc tatcttagtt agggaaactt ctgtaccttc cttagatgtt    25140
caggcactcc attgaggacc ctggcataac attatttatt gacagaccat agctcaaagt    25200
atagaactgg atactaccaa ggaggatata ctattactat tttatcttta tcttaaaata    25260
tactcttcca tctgaggtga aaattaatcc agatggtaga acttattgca gttactacag    25320
cattttagca aatcaaaagc cgcagaacaa acatatggac agatggcagg tatgttttcg    25380
gaatcgtaaa caagttcgtg atgactgtaa aaccaagggg tgtctcacga gggctggaaa    25440
cctctcacaa tgaaacaaca caatgaggat ctttgaaaag tactctgacc tcctggtgag    25500
ctggctgata tggaggctga gctccatgta gaaagccaaa ggaatttctg caggacgtca    25560
tcatgccaag cacagccgta acctgggtcc cagcccttt cacacgctca atggttagat    25620
cttgggaggg aatcaaagaa gccatagtaa aatatcaaaa tttaaacccc gattttgaat    25680
ttaaaaagtg ttaaaatatg gttgtggcct acactcagaa aatctgtgtc cttcagatgg    25740
tttctcagtg gcaccagatg gtttcaagtg gctattcatt aagtttctca gtgaaattac    25800
cagacataga ataaataaat tgtcactgtc ttaaatcaac ccatgggaaa ggaaaactgt    25860
gtaaatacag cagagaggaa acattgctca agggaaaaac aatctccaga aagtattgtt    25920
aaagaaacag aggccctctt tccagccagc gccgagcgat gggcacctct cgggacaact    25980
ggcacaaggg ccgcaaagct gggggcaaga gaaggccctg ccacaagaag cggaagtatg    26040
agttggggcg cccagctgcc aacagcaaga ctgacccgtg ccgcatccac acagtccgtg    26100
tgcgaggagg taacaagaaa tactgtgccc cgaggctgga cgtggggaat ttctcctggg    26160
gctcagaatg ctgcgctggt gaaacaaggg tcatcgatgt tgtctacaat gcatccaata    26220
acgagctggt tcgtaccaag accgtggtga agaattgcat cgtgcccatc gacagcacgc    26280
cctaccgaca gtggtacgag tcccactgtg cactgcccct gggccgcaag aagggagcca    26340
agctgactcc tgaggaagaa gagattttaa acaaaaaacg atctaaaaaa attcagaaga    26400
aatatgatga aaggaagaag aatgccaaaa tgagcagtct cctgggggag cagttccagc    26460
agggcaagct tcttgcgtgc atggcttcaa ggccgggaca gtgtggccga gcagatggct    26520
atgtgctaga gggcaaagag ttggagttct atcttaggaa aatcaaggcc cagaaaggca    26580
aataaatcct tgttttgtct tcacccatgt aataaaggtg tttattgttt tgttcccaaa    26640
aaaaaaaaag aaagaaaaag aaacagaggc atcacactta ctagaaaaac atattctatt    26700
tcatatatta tggggatatg acgtgatgtt ttgacatatg cgggcattgt gaaattatta    26760
```

```
aatcaagtaa ataaacatgt ccatcacctc acatacttat tttttatggt gtaaacgtgt   26820
aaaatctact ctcttatcag ttttcaagta tatagtacat tagtatcatg gaagtcacca   26880
tgctgtgcaa tagatcttca aacgaattcc ttctatctaa ccaaaactct gtacccttc    26940 accaacgtct cagcttttca catgcccctga cgccagcccc tggtaggcac cattctactc   27000
tctactctga gttcaacatt tttagattgc atgtgtaagt gagatcatgg agtaatttt    27060 tatacctggc ttatttcact caacataaag agtcaaatgc tcaacatcac taatcatcag   27120
ggaaatgcaa attaaaacca cgataagata tcacctcaca catgttacaa tggcttagtc   27180
tcagtctgtc ttttttgttac tataaccgaa taccagagac tgggcaattt ctaaagaaaa  27240
ggaatttatg ctttatggtg cttgagtcag agaagtctaa tatcaaggca ctggcatctc   27300
acaagggcct tctcactgcc tcatctcaca gcagaggtgg gtgagcaaga gaccatttgt   27360
ccacgagaga aaagagacca tcttttatta gaaattcact cctataataa ctaacccact   27420
ccattgatag tgacagtaat ccattcatga ggacagagcc ttcatgactt gatcacataa   27480
taaaggtccc acctctcaac actgttgcat taaagattat ttccagatcc taaactttgg   27540
gagacacatt taaaccatag cattccattc ctaatatcaa aatttatgtc cttatcacaa   27600
tgcaaattac attcattcca tcccaattgt ctccaaagtc ttatccagca tcagtgcaaa   27660
agtctgaagt ccaaagtctc atctaaatca gatatgagtg tgactcgagg cacaatttag   27720
cctgatataa attgtttcca tctgcgagcc tataaagtca aaacaagtta tctactttca   27780
aatacagtga acaatggggc aggtatggga tagaaattcc cattccaaag ctcagagaga   27840
ggcaaggaga aagcggtgcc tagttcaaaa cccaacaggg aaaaaaacat taagtcttat   27900
agctggaaaa tcatcctctt taacggcatc ttgtgcacac tggggagggg gatgggcccc   27960
caaggcctcc ggcagtcttg cctctatata ttttctgggt tcagtccact cagccgctct   28020
cacaggtggg actctcaggc ctctagctct cctaggctga ctggaaactc tttgtggtac   28080
ctccaaaccc acatttctgc ttggcattgt gctaagggcc cagtgtggtg actctgtctc   28140
tgcaacaagt cactgcccga gaccttaggc tgtccttagg ctgcccgaga ccttaggccg   28200
tccacagcat tctttgaaat ctaggtggag aaagccatgc cctcgtggtt cttgtattct   28260
gcacacctgc agaattaaca acacatggat gccatggaag ttgatgactt gtaccattaa   28320
agtgatggct tgagccacac ctaggtcctc ctgagccaca gcatgggcag ccaaggagtg   28380
ctgtgcctgg acaccgggaa cagagtccta aagtgcctgc tagaagtcag gccatagatt   28440
tccttcaaat ttctcccacc atataacctc gttcatggct ctgaacttcc accttacaga   28500
aggacctagg gatgaacaca attcagccac gttctttgcc actttatggc aaggatggcc   28560
tttgctccat tttccgatga gctattcttc tttttctcct gagacctcat cagaacggcc   28620
tttattgtcc acggttctac tgacattcta atggtcatca cctaaataat ctctaagaag   28680
tttcagaatt tcctcacagc tctcttcttc tgagtcctca aaagaatcac ctctagtgtt   28740
ctattcaggg caatccagac ttttttatagt ctgatcctcc aaattattcc agtctttgtg   28800
cattactaca tccacttcta catttttgggg tatttgttat cgcaacagcc ccacctcttg   28860
atactgattt ttcgtcttag tccactttgt ggtgcaatga gtgaatacca cacactggct   28920
aaagtataag gaaaagaaat ttattttctc gcagctctag aggctgggaa gtcaatatca   28980
aggtgttagc atctggcaag agccttcttg ctgtgatgtc catgtggaag gcaggagagc   29040
aggtgcgaag gatggaaagg ggtttaaact catttttaa tgaggaaccc aggcctgtag   29100
taactaatct gctaccacaa tgagtaacct actctgacga taatggcatt cattgcttca   29160
```

```
tgagggcaga gccctcatga cctaatcatt tcttaacatt cccacctctg gacactatgg   29220
aatttgggat taagtttcca atacacatcc tttctaaaca gcaggggctt tttaataggt   29280
tgaccaccca aggctgcagg aggctctgaa gcagtggcct gaggttggct gtcctttgtg   29340
agaatggaga gaagtgaact gactcatgga gacacaagta gatgaggtaa aggcattcat   29400
tgcttcatta catggatggt gaggtcgatt gaaggcatta acggattaaa gatggtggca   29460
aaaccgtctg aggtggagac cacggggagt ccatcagaaa tggaggacac gtcccaataa   29520
atggtgcttc atttccctgc aaagcagaag aaagcaaaga acaaaacaca acatcatagt   29580
gtacactgag cagtggattg agagaagagt ttcctaaggc ataactgaca gagtggagaa   29640
gacacacaaa tctttgcatg atgctaacat ttggactgtg gcttcattat ttcttattaa   29700
tattttactg aaatatcgct agaaggagac tgaaaatgaa gtgtgaaaag ttaaatggga   29760
tttctgctct atgtcctttt cagatgagag gaactaggga attccaggga agaaacaata   29820
atagctgctg agcaaggctt ttgcagggca ggacaaggaa tccccaaaga gaaaacggaa   29880
acctcagctt cactttgcat ctgctcctga gccaggtcct gagcgacccc tgtaggtcct   29940
gagtgcccct ccgtaggttc tgagcatccc ttggttgctg ggcgccctct ggtggtgtct   30000
gagcccctct ggtggtttct gagccccccg ccttatgtct gatcctccct ggtggtgtcc   30060
gagtgcccct gctagtgtct gagcccccctg gtggtgtctg agtcccctcc ttagtgtctg   30120
agccacccta ttagtgtctg aggaccctg atggtgtctg agccccccagt tagtgtctga   30180 gccaccctat tagtgtctga gcccccctgg tggtgtctga gcacaggaga gctcctctga   30240
aggaagggtc tacatgggga caggcgtgct tgtctcaggg aagggtccat gtggggacag   30300
gtgtgcttgt ctgaaggaag gttccacatg gagacaggtg tgcttgtctc agggaagggt   30360
ccacatgggg acaggtgagc ctgtctgagg ggacagaagt gcttgtctca aggaagggtc   30420
ctcatgtgga caggtgagct cttttgaggg aagggttgac ctgggacag gcatgcttgt    30480 ctgaggtaag ggtcctcctg gggacaggtg tgcttctctc agggaagggt ccacgtgggg   30540
acagaggtgc ttgtctaagg caagaatcca agtagggaca ggtgagctcg tctcagggaa   30600
gggtccaggt ggggacagtt gtgctcatct gagagaagcg ttgaagtggg gacaggtgtg   30660
cttgtctcaa ggaagggtcc atgtggggac aggtgtgcta gtatcaagaa agggtccaca   30720
tagggacagg tgtgcttctc tcagggaagg gtgcatgtgg ggacaggtgt gcacatcgga   30780
gagaatggtc cacctgggga caggtgttct tgcctcaggg aagagtccac cttctcaggg   30840
aagaagtgtg ctcctctgag ggaagggtgc acatggggac aggtgtgctt gtctcaggga   30900
agggtccatg tgggaacagg tgagctcatc tgagggaaga gtccacgtgg ggacaggtga   30960
gctcatctga gggaagggtc cacatgggga caagtgacct cgtctgaggg aagggtccac   31020
gtggggacag gtgagctcgt ctgaaggaag gtccacttgg ggaccggtg tgctcctctg    31080 agggaagggt ccacgtgggg acaggtgtgc tcctctggag ggaagggtcc acgtggggac   31140
aggtgagttc atctgaagga agggtccaca tggggacagt tatgctcctc tgagggaagg   31200
gtccatgtgg ggacaggtgt gcttgtctca gggaaaggtc cacgtgggga caggtgtgct   31260
caccttgggg aagaggacag atgagctcat ctcaggaag gggccatgtg gggacaggac    31320
caagggttgg gacttcagca caagaattta ggaggaacac agtcttccct agcagcctcc   31380
ttcagggatg tcaaatattt tccttctgtt ccctgtgaaa gccttaaagg ggtagggaaa   31440
gggcgttcaa cctgcacact cgtagagggg aaaccagctt cattagtaat cgttcatctg   31500
```

```
tggtaaaaag gcaggatttg aagcgatgga agatgggagt acggggcgtt ggaagacaaa    31560
gtgccacaca gcgcagcctt cgaaacacac cacggtcacg ttaagtttaa atggagtgac    31620
cacattcgcc aggaaaggga aatatttaca cttttgaaga aacagtaatt tgtgtttctg    31680
attatgatct ggccttggat tttccctccc ctcataagca atgacagaat tggcagaaat    31740
atgtgaaacg ttagttctca gacatgagac acccacagag ggcccctgt gcccttccct     31800 gagagctgat cagctcctgc atctgaagaa atgaccaaag accaggagag aaccacacag    31860
aagcatcgga gggacagcac ctggggctct gatggggtca ggaatagcat ctgttcccaa    31920
tagatggact aagtaaaaag tatcataatt cacaagagtt ttacatagca cagaagaaaa    31980
agttacccta tatcaactgt tgatcttgtg aatccaggaa ctctggattc aaggtggtcg    32040
ggcacatctt gatttacgca tttcaggac acatgagaca tcagtcaata taagtaagaa      32100
ggacattagt tccatccaga aaggctgaga caactcaaag caagtcctcc ccacttaggg    32160
cttccaggtc acaggtaggt gagagacaga tggttgcatt cttttgagtt tctgataagt    32220
gtttgcaaag gaggccatga ggatatgcac ctgtctctgt gagcagaggg acaactttaa    32280
atagactggg aggcagattt gtcctgagtg gtttccagct tgacggggcc caagatattt    32340
tcctttcaca atctggtaac ttcaaacaaa acttcaaagc cacaacaaaa caacacaaca    32400
acaaaaagaa taagacatgg gtacttatta agagtagaaa aacattcagt ccccaaggaa    32460
aatattggca gtgtctacct ccacatgaca aaggagtaag cagtgtgagc cacagaaagg    32520
agcactatta acccacagag caaccgagaa taacacgggt gatgcgaggg cattggacgc    32580
acatcattgc attttgtaga ttcagaaaga aacggaaaag attgacggtg gtaaaagaga    32640
cagccctgct tccctctccc ttttccctcc ccgatgaggc ctcacagcca tgaccctcag    32700
cctcatcccg cagtgcagca gctgccgtcc tgtccaggcc caccccctgc cccgccctgg    32760
gactgttacc tcattccctc ccggagtcca ggtgccccc ggggtgtggt gcgggagcct      32820
ggggaggccc tttgttctct gtcagggtct ccctgggagg gacgcagcca ccgcagctgg    32880
ttggggcctg gcttcgccca ggacagtcct ttccttccc attgtctttg gatgactatc      32940
gctgggctgg gacatgaggc gggcagaggc gcgggtcacc cttaggaccc ccctcttgct    33000
gctggggctc tgggcgctcc tggctccggt ccggtgttct caaggccgtc ccttgtggca    33060
ctatgcctcc tccgaggtgg tgattcccag gaaggagaca caccatagca aaggccttca    33120
gtttcccggc tggctgtcct acagcctgtg ttttggggtc aaagacacgt cattcacatg    33180
cggaggaaac accttctttg gcctagacat ctgctggtga caactcagga tgaccaagga    33240
gtcttgcaga tgggtgaccc ctacatccct ccagactgct agtacctcgg ctacctggag    33300
gaggtgcctc tgtccatggt caccgtcgac acgtgctatg gggacctcag aggcatcatg    33360
aggctggacg accttgcgta cgaaatcaaa ccccctccagg attcccgcag gtttgaacat    33420 gttgttttc agatagtggc cgagcccaac gcaacagggc ccacatttag agatgatgac    33480
aatgagacag acccctgtt ctctgaagca aatgacagca tgaatcccag gatatctaat     33540
tcgctgtata gttctcatag aggcaatata aaaggccacg ttcaatgttc caattcatat    33600
tatcgcatat atggcaatat tacaacttgt tccaaagagg tggtccagat gttcagtctc    33660
attgacagca ttgctcaaaa tattgatctg cggtactata tttatctttt gaccatatat     33720
aataatcgtg acccagcccc tgtgaatgaa tatcgaattc agagtgcaat gtttacctat    33780
tttaaaacaa cttttttga tactttcat gttcattcat ccacactact tattaaatac        33840
gtgccacatg aatctaacta tgaacctgaa aggtataact tctgttcccg tatagccctg    33900
```

```
ttacacattg gtactccagg cagacattat ttattggtag ccgtcataat aacccagaca   33960
cagatgagaa gtattggtct ggagtatgat gataactact gcacatgtca gagaagggcc   34020
tcctgcatta tgcagcgatt tcctgggatg acagatgcgt tcagtaactg ttcttatgga   34080
catgcacaaa attgttttat acattcaggc cggtgtgttt ttgaaacact tgctcctgtg   34140
tataacgaaa ccatgacaac ggttcgctgt ggaaacctca tagtggaggg gagggaggaa   34200
tgtgactgtg gctccttcaa gcagtgttat gccagttatt gctgccaaag tgactgtcac   34260
ttaacaccgg ggagcatctg ccatatagga gagtgctgta caaactgcag cttctcccca   34320
ccagggactc tctgcagacc tatccaaaat atatgtgacc ttccagagta ctgtcacggg   34380
accaccgtga catgtcccgc aaacgtttat atgcaagatg aaccccgtg cactgaagaa    34440 ggctactgct atcgtgggaa ctgcactgat cgcaatgtgc tctgcaaggc gatctttggt   34500
gtcagtgctg aggatgctcc cgaggtctgc tatgacataa atcttgaaag ctaccgattt   34560
ggacattgta ttagacaaca acatatctc agctaccagg cttgtgcagg aatagataag    34620
ttttgtggaa gactgcagtg taccaatgtg acccatcttc cccggctgca ggaacgtgtt   34680
tcattccatc actcagtgag aggagggttt cagtgttttg gactggatga acaccatgca   34740
acagacacga ctgatgttgg gcgtgtgata gatggcactc cttgtgttca tggaaacttc   34800
tgtaataaca cccagtgcaa tgtgactatc acttcactgg gctacaactg ccaccctcag   34860
aagtgcggtc atagaggagt ctgcaacaac agaaggaact gccattgcca tataggctgg   34920
gatcctccac tgtgcctaag aagaggtgct ggtgggagtg tcaacagcgg gccacctcca   34980
aaaagaacac gttccgtcaa acaaagccag caatcagtga tgtatctgag agtggtcttt   35040
ggtcgtattt acgccttcat aattgcactg ctctttggga cagccaaaaa tgtgcgaact   35100
atcaggacca ccaccgttaa ggaagggaca gttactaacc ctgaataaca ctaattcagc   35160
ctcccgatcc ctgtaaagat acagagaata taacagcaaa atctatgaaa caggatcagg   35220
ggaagggatg gcaaagctca agtccacatt tcttgaagtc cacaggaagc acagggtcct   35280
gtttcacatc acagggaaac gggaggcatt ggcttctgtc ccaggttctt gtaggtcgct   35340
gatgctcact ctgaaataaa tcttcaaaaa cacacattgg tgccttccac attttcttag   35400
actcctctgg gagcccaaac ttggccagaa cctcttgcct ggagagacat gaatgagcat   35460
ctggctcttg tcctgaggtc tctggtccca gaattaacgg aagttgccac cagctcctta   35520
cagggaacat tcatgacatt tctccagaag agagctccag agcaatgagc ttcctcattc   35580
cccaggtaat ctgtccttct ctaaacccga agtcagttta gggtgatcca gggctactcc   35640
ctgttccctg tctgttcctc acggggtgc tgtgggcttt gcagtgagag ggacttgggt    35700
tcaaatcccc caccaagcaa atcccctac ctggggccga gcttcccgta tgtgggaaaa    35760
tgaatccctg aggtcgattg ctgcatgcaa tgaaattcaa ctagaaaaat aggtagacgt   35820
gaggggcaag ctgtctgtca tttagtgtga gctctgtgag tggcagctgc cccctttctt   35880
cctgccccca catttccttg aactgaaaca ggaagggaag ctgagtaagt cgtgatgagg   35940
aagagaaacc aggcttgtag cagcacaggc tggtccgggt ggaaaacagg gctaggtgta   36000
tcactgagtt attgtaaagg aaaatggaag ttaaatgtat aaataactga atgagataac   36060
attttatttt aacttaaaat tcacactaat attgactttt aaaatgcagt gtagatatgt   36120
cagagagaat ttcaaaggca aagcccaccg acggaagaaa tcacccttcc cataccatcc   36180
acagaaaact gttggtattc tagggtagta ctgagatcta gcattttct gaatacatct    36240
```

```
gtggttctag atgtcctgct tccatagata ttgtttagaa ttcccacccc tttctccaaa    36300
cacagcttga tatcctttct ctgaacctgt tagaaatttc ctccattcag ctgtcataaa    36360
gatgcgagca atccattcct gtgcctctgt cagtgtgttc tattattttg tggctgaacg    36420
ctaatggaca gttaagtgtg aggtcagtga atacagtgcc ctccctctat gtgtccttcg    36480
ggtgtgaggg gttttgctga tagagcagca ggccccatcc caccctttat gcatctccgc    36540
cccccacctc acgctccagc tgacctctcc cctgtggcct ggggcgttcc caggggggaa    36600
tgacctctcc tctctccagg gcccacccac tcagtgcccg tgcaagacca ccacgcttgg    36660
cacggcccca cctcgtgtca gggcctgtgt cccctgcccc accccctaaa cagatgggaa    36720
ccactgggac tctgctcagg cagggggcg gaggtatgtg tgaaaggaag gcaaatgtgc     36780
actctgttgg agaaatatta taggtagttt gagcaaaaaa tctaatgcca tgggaacttt    36840
tagaatgata cgtattttaa caaagaacat gaccaataga gtttgtattg aagccaggaa    36900
aacactattt agagcaacag caatatcaaa aacacaagcc aacagttcac caagaaaaac    36960
caccattaac cccatggaaa tggtcttcca agagcatcgg cacttaaatc ctggaaatct    37020
gcctgcctca gcacctgttg tcctgacctg ccctcctgtg tgtcctaatc actcccaaac    37080
acggggcctg cactgtggga gattcacact gtgccaggtg gagggagcag acaactgct     37140 aacaggttgt tggtgtggat gccgaggcca cccaagcagg tgtaaactcc cacctgtggg    37200
gcagggaaga gtgcacggga gacatgtccc gggcataggg tgaggagag ctgtgggggc     37260 tctgggttct gaagtgggtt ctgaagaggg ttctggcctg gcagggataa gaccaaccag    37320
catgtgaggc caggctggag tctggacctc tgaagctgca agggtcatgg gctgcttggc    37380 cccagggct gtcctggttc tctatggagt actttcaaac attctttctt cttccaatcc     37440
ccctccttct ctcccaaagc ctgcatctcc caaatcctct ttgtcggatc ctcggcttca    37500
ctctgcatcc gtcctgagca tcgatcttcc aattccatcc tcttctcttc tgctatgtct    37560
aagctgctgt gaagccacct gctgtaattt actgctttat atttaatatt gtaccgtaca    37620
tctgttctgt ttccctcatc ataaatgctt catttcatgc tcagcatctg agaacacaag    37680
gccttgtcag ctgtcacctc cttccgttct ctgtttcctt cctcctatcc ccatattgct    37740
catcatgtcc agtctcctgc catcctgaat gcttctgatg gaaggtctga gatgtctcat    37800
gagcactgtg aagattcttt gtaatgtgag cttgttccag gcaggaattc ccttcaccc     37860 agccctggaa gccaagtata ggcagatggc catgctcaat caaagactga gctaacttaa    37920
cagtggcttt ggttttaagg tttctccaat ccccagggca caggatttca gggaattcag    37980
gtgagagtct gggtgttacc cttcaggagg ctgtaaactc catttcacct agtctacacc    38040
acagactatg gaaactatat atatatatag ttctgtccct ctagagaaac ctaatatgta    38100
tatatacaat atataatacg tattatatat tatatataat acgtattata tattatatat    38160
attatatata tattagagtt tattgaggag tattaaactc acaatcacaa ggtcccacag    38220
taggccatct gcaagctgag gagcaaggaa gccagtccga gtcccaaagc tgaagaattt    38280
gaagtctgat gttcgacggc aggaagcatc cagcacagga gaaagatgta ggctgggagg    38340
ctaagccagt ctagtctttt cacgttttc tgcctgcttt atatcctggc cacactggca    38400
gctgattaga tggtgcccac ctagattaag ggtgggtctg cctttcccag tttactggct    38460
caaatgttaa tctcctttgg caacaccctc acagacacac ccaggatcaa tactttgcat    38520
gcttcaatcc aatcaagttg acactcagta tcaaccatca caagtccacc ccttgtcaac    38580
ttgaacccat acaaatctcc tgagatcata cataatcttc aaataaagac aataataagg    38640
```

```
tcataattac acctaatgta atacaactat cttttgtaca accagaaatg caccaatccc   38700
caacccaaat gctattatgt aaagttaaga acacttaaat gctgatatga agtcaataaa   38760
ttttatgtca catgataaag gaaaaagaa atgaaggaat tttcttagta caagtgtgta    38820
catgcacaaa catgttttta acaaaagaag aaggaaatac tgatgacaat tacagtcctc   38880
atttctgcaa ctgatcacgt ggttgtagct ggtattgatg actaccttct tctactaccc   38940
attctgtatt ccctttgcct tcagcaagca tcacagcagg tagagttttt tctcctagtg   39000
gagtgatgca aaccttcatt cctgaagggt ctgggccatt tgtagtcctg cctggattgg   39060
gctgttgtag tttcccgttg accttaatga cagggcatgg taatgttaag agacgcccta   39120
atggatctcc tgtattccat acatattctt ccttacctcc attgtggagt aatagactga   39180
ttgcatcttg atagtccagg tcaatcagcc cagccaacac tgtaactccc ctcttagcct   39240
gtggacttaa aggtaggagg ggcccaaagt ggccaggtgg aaatctttac ttccagttta   39300
atggaattgt tgttgtttct cctgatggca gcattattcc cactggaact aagacctcta   39360
ggccaacaga atgtaatgtc atgggaccag aagcaaaaa ttttgctagt ggatcactag    39420
gggtgatggt gaatggtgcc atttccactt ccacccttg attcctggat ccatgaatta    39480
tggctatggg agaaagagta ccatatattg gatgctgatt tggagcatac atggcctttt   39540
ggagagcttt gccccagccc tgcaaagtat tggagcctag ttgacattgt aattgtgact   39600
ttgaaaggcc attccattct tctatcaatc cagctgcttc aggatgatgg ggaaaatggt   39660
aagacaagtg aatcccatga gcatgagccc actgccacac ttctttagcc gtaaagggag   39720
tgccttggtc agaggcaatg ctatgtggaa tactgtgaca gtggataagg cattccatga   39780
ctccacagat ggtagtcttg gcagaagcat tgcatgcata tctgcagtaa gtgtctattt   39840
cagtgaggac aaacctctgc cctttccagg atggaagagg tccaatataa tccaacctgc   39900
catcaggtag ctcactgatc accctgagga atggtgtcat ttgggtagag acccagagcc   39960
aaaccagatc acgccaccca accctcca aatctcatgt cctctttgca tttcaaaacc     40020
aatcatgcct tcccaacagt cccccaacat cttaactcat ttcagtatta actcaaaagt   40080
ccaaatccaa agtcacattg gagacaaggc aagtccctt catctatgaa cctgtaaaat    40140
gaaaaacaag tcagttactt ccaagacaaa atgggggtac aggcattaga tacatgctcc   40200
catttcagtt gggagaaatg agccagaata aaggggcttc aggtcacatg caagcccaaa   40260
ctccagtggg gcagtcatta aatcttaaag cttcaaaata atctcctttg actccattcc   40320
tcacattcag ggcatgctta tgcaaagtgg gggctcctac aaccttggga agctctcacc   40380
ctgtggcttt gcagctctga ccccatggct gctctcatgg gctttgcaga gttcagccct   40440
cctggctgct ctcattgagt gcatgcagct tttccaggtg cacagtgcaa gccgttaatg   40500
gatctaccat tctggggtct gaaagatggt ggccctcttc tcacagcccc attagtcact   40560
gtctccagtg gggactctgt gtgggggctc caaccccaca tttcccttct gcactgccct   40620
agcagaggct ctccatgaag gctttgcccc tggcgcagac ttctggctgg acatccagtc   40680
atttctataa atcctctgag atctgggtgg aggatcacaa agctgaactc ttctcttccg   40740
cacatcccta ggcccaacat catgtagaag ccaccaatga ttggggcttt ctgaagcaat   40800
ggcctgagct gtacattgga cttttttagc cacagctaga cctggagcag ctgggacaca   40860
gggcaccaag tccaaggct ccaaagagaa gctgggccct ggaccagcc catgaaaaca     40920 tttttccctg ataggcctcc aggcctgtga ttggaagggc tgctgcaaag atctccgaca   40980
```

```
tgccctggaa acattttccc cattgtcttg attattaata ttcatctctt cattacttat   41040
gcaaatttct gcagccaact tgaatttctc cctagcaaat gtgtttttct ttactaccac   41100
atggccaggc tgcaaatttt ccaaactttt atgctctgtt tcccttttaa aaataagttc   41160
ctatttcaga tcatctctct caagggcaaa gttccacaga tttctagggc agggacaaaa   41220
ttccatcaag cttggtttta tacattttag agaggcatga gacatcaatc aaatacattt   41280
aagagacaca ttggtttggt ccagaaaggt ggaacaactc aaagctaggg cttccaggct   41340
ataggtgaat ttaaatattt tctggttgac aattggttga gtttgtctaa agacctggga   41400
tagatagaaa ggtaatgttc aggttaagat aaagattgta gagtccaaag ttcttttgaa   41460
gtcttatagt ggctgccctt agagataata ggtgacaaat gtttcctatt caaatcttag   41520
ttgaactctt taggattggg aggttctaga agaaaaagat ctagctatgt taatagagat   41580
tctttacaga tgcaaatttt cccccacaaa gaacagcttt gcagggccct ttctttcttt   41640 cttttctttct ttctttctttt ctttctttct ttctttctttt ctttctttct tttttagatg   41700
gagttttgct cttgttgccc aggctagagt ataatggcac gatcttgtct caccacaacc   41760
tccacctcct gggttcaagt aattctcctg cctcagtctc cgagtagct atgattacag   41820 gcatgcacca ccacacccgg ctaattctgt attttagta gacacagggt ttctccatgt   41880
tggtgaggct ggtctcgaac tcccaacctc aggtgatccg cccacctcag cctcccaaag   41940
tgctgggatt acaggcatga gccaccatgc ccggcctgca gggccatctc agagtatggc   42000
aaagaaacat gttttggggt aaaatatttt gattttctta tttgtctcat aatgttatgc   42060
cagagtcagt ttgaaaagta aatcatgata tataggttta aataaaaccc atctgatgag   42120
aatttatgat ttgtagagca tgcctcccca gactctttag ataggaattt gggcaagatg   42180
aaaaaaaaat cagagtttag tcctcactac ctaagaccag ctcagcttgg acttcactgt   42240
tcatgtcact atcagcattt tagtcaaaac cactcaataa gtctctagga agttccaaac   42300
tttcccacat cttcccttct cctttcaagt tctccaaact gttccaaccg ctgccaggag   42360
gtacccagtt ccaaagttgc ttccagattt tgagttatct ttatagcagt tccccactcc   42420
tggtaccaat ttactatatt agtctgtttc cacagtgcta taaagaactg cccgaaagtg   42480
gttaatttgt aaagaaaaga ggtttaattg actcacagtg ctgtgtggtt agggtcggag   42540
gctcaggaaa cttgcaatca tggtggaagt ggaagcaggc atgtgacaca tggcagcagg   42600
tgagagagag aaagagagag agagggaatg aaggaggaac caccatacat ggataaaacc   42660
atcagatctc atgagaactc actcactatc aggagaacat gaggacagca tgggggaaac   42720 caccccctatg acccagtcac ctcccaccag gtccacccct tgacacataa ggattactat   42780
ttgagatgag atttgtttaa tgacacagag ccaaaccaca tcagcatgtg acaaaggtct   42840
aatatcaaga atctatgagg gggcagttcc aaaatggctg aataggaaca gctccagtct   42900
acagctccca gcatgagcta cacagaagac aggtgatttc tgcatttcca actgaggtac   42960
tgggttcatc tcacgggggc ttgttggaca gtggggcag acagtgggt gcagcccacc   43020 aagagtgagc tgaagcaggg cgaggcattg cctaacccag gaagtgcaag gggtcaggga   43080
attcccgttc ctagccaagg gaagcggtga tggacggcac ctggaaaatc cggtcactcc   43140
caccctaata ctgcactttt ccaacggtct tagcaaatgg cacaccagga gattatatcc   43200
tatgcctggc ttggaggttc ccatgcccac ggaacctcgc ttattgctag cacagcagtc   43260
tgagatcaaa ctgcaaggtg gcagtgaggc tgggggaggg gtgcccacaa ttgctgaggc   43320
ttgagtaagt aaacaaagtg gctgggaagc tcaaactggg tggagtccac tgcagctcaa   43380
```

```
ggagacctgt ctgcctctgt agactccacc tctgggggca gggcatagct gaacaaaagg   43440
cagcagaaac ctctgcagac ttaaatgtcc ctgtctgaca gctttgaaga gagtagtgtt   43500
tctcccacat ggactttgag atctgagaat ggacagactg cctcctcaag tgggtccctg   43560
acccccgagt agcctaactg ggaggcaccc tccagtaggg gcagactgac accttacacg   43620
gctgggtgcc cctctgagat gaagcttcca gaggaattat caggcagcaa catttgctgt   43680
tcagcaatat tcgctgttct gcagcctctg ctgctgatac ccaggaaaat agggtctgca   43740
gtagacctcc agcaaactcc aacagacctg cagctgaggg tcctgactgt cagaaggaaa   43800
actaacaaac agaaaggaca tccacatgaa aaccccatct gtacatcacc attatcaaag   43860
acaaaaggta gataaaacca caaagatggg gaaaaacag ggcagaaaag ctgaaaattc    43920
taaaaatcaa agtgcctctc cccctccaaa ggaatgcagc tcctcgccag caatggaaca   43980
aagctggatg gagaatgact ttgatgagtt gagagaaggt ttcagatgat caaacttctc   44040
cgagctaaag gaggaagttg gaacccattg caaagaagct aaaaaccttg aaaaaagatc   44100
agatgagtag ctaactagaa taatcagtgt agagaagtcc ttaaatgacc tgatggagct   44160
gaaaaccatg gtatgagaac tacgtgatga atgcacaagc ttcagtagcc gattcgatca   44220
actggaagaa agggtatcag tgattgaaga tcaaatgaaa gaatgaagg gagaagagaa    44280 gtttagagga aaaaaagta aaagaaaga aacaaaccct ccaagaaata tcagactatg     44340
tgaaaagacc aaatctatgt ctgattggtg cacctgaaag tgacagggag aatggaacca   44400
agttggaaaa cacctgcag tatattatcc agcagaactt ccccaaccta gcaagacagg    44460
ccaacattca aattcaggaa atacagagaa ccccacaaag atactcctcg agaagagcaa   44520
ctccaagaca cataattgtt agattcacca aagttgaaat gaaggaaaaa atattaaggg   44580
cagccagaga gaaaggtcgg gttaccctca aagggaagcc catcagacta acagctgatc   44640
tctcagcaga aactctacaa gccagaagag agtgggggcc aatattcaac attcttaaag   44700
aaaagaaatt tcaacccaga atttcatatc catccaaact aagcttcata agtgaaggag   44760
aaataaaatc ctttacagac aaacaaatgc tgatagattt tgtcatcacc aggcctgccc   44820
tacaggagct cctgaaggaa gcactaaaca tggaaaggaa caactggtac cagccactgc   44880
aaaaacatgc caaatcataa agaccaccaa agcgaggaag aaactgcatc aactaacgag   44940
ccaaataacc agctaacatc ataatgacag gatcaaattc acacataaca atattaacct   45000
ttaatgtaaa tgggctaaat gctccaatta aaagacacag actggcaaat tggataaaga   45060
gtcaagaccc atcagtgtgc tgtattcagg agacccatct cacatgcaga gacacacata   45120
ggctcaaaat aaaggcatgg aggaagatct accaagcaac tggaaaacaa aaaaaggcag   45180
gagttgcaat cctagtctct gataaaagag actttaaacc aacaaagatc aaaagagacg   45240
aagaagacca ttacataatg gtaaagggat caattcaaca agaagagcta actatcctaa   45300
atatatatgc atccaataca ggagcaccca gattcataaa gcaagtcctt ggagacctac   45360
aaagagactt agattcccac acaataataa tgggagactt taacacccca ctgtcaacat   45420
tagacagatc aacgagacag aaagttaata aggatatcca gcaactgaac tcggctctgc   45480
accaagcaga cctaatagac atctacagaa ctctccaccc caaatcaaca gaatatacat   45540
tcttttcagc accaccacc acctattcca aaattgacca catagatgga agtaaagcac   45600
tcctcagcaa atgtaaaaga acagaaatta aacaaactg tctctcagag cacagtgcaa   45660
tcaaactaga actcaggatt aagaaactca ctcaaaacca ctcaactaca tggaaactga   45720
```

```
acaacctgct cctgaatgac tactgggtac ataatgaaac gaaggcagaa ataaagatgt    45780
tctttgaaac cagtgagaac aaagacacaa cataccagaa tctctgggac acattcaaag    45840
cagagtgtag agggaaattt atagcactaa atgcccacaa gagaaagcag gaaaaatcta    45900
aaattgacac cctaacatca caattaaaag agctagagaa gcaagtgcaa acacattcaa    45960
aagccagcag aaggcaagac ataactaaga tcagagcaga actgaaggaa acagagacac    46020
aaaaaaaccc ttcaaaaaat caatgaatcc aggagctggt tttttgaaaa gatcaacaaa    46080
attgatagac cactagcaag actaataaag aagaaaagag agaagaatca aatagatgca    46140
ataaaaaatg ataaagggga tatcaccacc gatcccacag aaatacaaac taccatcaga    46200
gaatactata aacacctcta cggaaataaa ctagaaaatc tagaagaaat ggataaattt    46260
ctcgacacat acaccatccc aagactaaac caggaagaag ttgaatctct gaatagacca    46320
ataacaggct ctgaaattga ggcaataatt aatagcttaa caaccaaaaa aagtccagga    46380
acagatggat tcacagccga attctaccag agctacaagg aggagctggt accattcctt    46440
ctgaaactat tccaatctat agaaaagag ggaatcctcc ctaactcatt ttatgaggcc    46500
agcatcatcc taataccaaa gcctggcaga gacacaacaa aaaaaagag aatttttaggc    46560 caataaccct gatgaacatc aatgcaaaaa tcctcaataa aatactggca aaccgaatcc    46620
agcagcacat caaaaagctt atccaccatg atcaagtggg cttcatccct gggatgcaag    46680
tctggttcaa catacgcaaa tcaataaacg taatccagca tataaacaga accaacgaca    46740 aaaacacat gattatctca atagatgcag aaaaggcctt tgacaaaatt caacaacact    46800
tcatgctaaa aactctcaat aaattagata ttgatgggac gtatctcaaa ataataagag    46860
ctatctatga caaacccaca gccaatatca tactgaatgg gcaaaaacta caagcattcc    46920 cttttgaaagc tggcacaaga cagagacacc ctctctcacc actcctattc aacatagtgt    46980
tggaagttct ggccagggca atcaggcagg agaaggaaat aaagggtatt caattaggaa    47040
aagaggaagt caaattgtcg ctgtttgcag atgacatgat tgtatatcta gaaaccccca    47100
tcgtctcagc ccaaaatctc cttaagctga taagcaactt cagcaaagtc tcaagataca    47160
aaatcaatgt gcaaaaatca cacgcatttc tataacccaa taacagacaa acagagagcc    47220
aaatcatgag tgaactccca ttcacaattg cttcaaagag aataaaatac cttggaatcc    47280
aacttacaag ggacgtgaag gacctcttca aggagaacta caaaccactg ctcaatgaaa    47340
taaaagagga tacaaacaaa tggaaaaaca ttccatgctc atgggtagga aggatcaata    47400
tcctgaaaat ggccatactg cccaaggtaa tttatagatt caatgacatc cccatcaagc    47460
taccaatgac tttcttcaca gaattgggaa aaactgcttt aaagttcata tggaaccaaa    47520
aaagagcctg caatgtcaag tcaatcctaa gccaaaagaa caaagctgga ggcatcacgc    47580
tacctgactt caaactatac tacgaggtta cagtaaccaa acagcatgg tactggtacc    47640 aaaacagaga tacagaccaa tggaacagaa cagagccctc agaaataatg ccgcatatct    47700
acaactatct gattttggc aaacctgaca aaaacaagaa atgggaaaac gattccctat    47760
ttaataaatg gtgctgggaa aactggctag ccatatgtag aaagctgaaa ctggatccct    47820
tccttacaca ttatacaaaa attaattcaa gaggattaaa gacttaaatg ttagacctaa    47880
aaccataaaa accctagaag aaaacctagg caataccatt caggacatag gcatgggcaa    47940
ggacttcatg tctaaaacac caaaagcaat gacaacaaaa gccaaaattg acaaatggga    48000
tctaattaaa ctaaagagct tctgcacagc aaaagaaact accatcagag taaacaggca    48060
acctacagaa tgggagaaaa ttttgcaat ctacttatct gacaaagggc taatatccag    48120
```

| | | | | | |
|---|---|---|---|---|---|
| aatctacaat | gaactcaaac | aaatttacaa | gaaaaacaaa | caaccccatc | aaaaagtggg | 48180 |
| caaaggatat | gaatagacac | ttctcaaaag | aagacattta | tggagccaaa | agacacatga | 48240 |
| aaaaatgctc | atcatcacta | gccatcagag | aaatgcaaat | caaaaccaca | atgagatacc | 48300 |
| atctcacacc | agttagaacg | gcgatcatta | aaaagtcagg | aaacaacagg | tgctggagag | 48360 |
| gatgtggaga | aataggaaca | cttttacact | gttggtggga | ctgtaaacta | gttcaaccat | 48420 |
| tgtgaagtc | agtgtggcga | ttcctcaggg | atctagaact | agaaatacca | tttgacccag | 48480 |
| ccatcccatt | actgggtata | tacccaaagg | attataaaac | atgctgctat | aaagacacat | 48540 |
| gcacacgtat | gtttattgcg | gcactattca | caatagcaaa | gacttggaac | caacccatat | 48600 |
| gtccaacaat | gatagactgg | attaagaaaa | tgtggcacat | atacaccatg | gaatactctg | 48660 |
| cagccataaa | aaaggatgag | ttcatgtcct | ttgtagggac | atggatgaag | ctggaaacca | 48720 |
| tcattctcag | caaactatca | caaggacaaa | aagacaaaca | ctgcatgttc | tcattcatag | 48780 |
| gtgggaattg | aacaatgaga | acacttggac | acaggaaggg | gaacatcaca | caccagggcc | 48840 |
| tgttgtgggg | tgggggagt | ggggagggat | agcattagga | gatataccta | atgttaattg | 48900 |
| atgagtttat | gggtgcagca | caccaacatg | gcacatatat | acatatgtaa | caaacctgca | 48960 |
| cgttgtgcac | atgtacccta | aaacttaaag | tataataaaa | aaattttaa | aaaagaaac | 49020 |
| acctgctttt | ttctgttttc | catttgctta | gtagattttt | ctccatcctt | ttactttgag | 49080 |
| cctggggatg | tcattgcatg | tgagatgggt | ctcttgaaga | cagcatacat | ttgggtcttg | 49140 |
| cttctttctc | caacttggca | attctctgcc | ctttaattgg | ggcatttagc | ccatttacat | 49200 |
| tcaaggttaa | tattgatatg | tgcatatttc | atcctgttat | catgttgtta | gctgctcaat | 49260 |
| atgcagattt | gattgtatag | ttgatttata | gtggcaatcg | ttatgtactt | aagtgtgttt | 49320 |
| ttgtggtggc | cagtaacgtt | cttccattat | catatttagc | aatcccttaa | gggcctcttg | 49380 |
| taaggcaatc | tagtggtgat | gaatacccct | agcatttgct | tgtctgaaaa | ggatcttatt | 49440 |
| tctccttcac | ttgtgaagct | tcatttggct | agatatgaaa | ttcttgcttg | gaatttcttt | 49500 |
| tctttaagaa | tgctgaatat | aggccccccaa | tctcttctgg | attgtacagt | ttctgctgaa | 49560 |
| acctccattg | ttagcctcat | tgggttccct | ttgtatgtga | cctgaacctt | cttcctagct | 49620 |
| gcctctaata | ttttttttcc | tttcaacctt | taagagtctg | atgtctgatg | gctatatgtc | 49680 |
| ttagggatgg | ttgtcatgta | taatatcatg | cagaggttat | ttgcatttct | tgaatttgaa | 49740 |
| tgttggcctc | tctggtgagg | ttggagaaat | tttcatggag | gatagcctga | aatgtttttc | 49800 |
| aagtttcttt | ttttctcttt | ctcttcttaa | gggataccaa | tgtgtcatag | atctggtctt | 49860 |
| tttacataat | tgcacatttc | tctgaggttt | tatgccttct | tttttattct | ttgttctta | 49920 |
| ttttttgtctg | actgagttaa | ttcagagaat | cagtttttaa | gctctgtgat | tctttcctca | 49980 |
| gcttggtcta | ttctgctgtt | aatacttgta | attgtattct | gaaattcttg | aagtgagttt | 50040 |
| tttagctcta | tcaaatcagt | ttggttcttt | cttaaaatgg | ccattcatc | tttcagcttc | 50100 |
| tgtatcattt | tactttattt | cttagctccc | ttggattggg | tttcaacatt | ctcctgaatc | 50160 |
| tcagtgatct | tctttcctgt | gcatattctg | aattctatgt | ctgtcatttc | agccatttca | 50220 |
| gtcaggttaa | gaaccattgc | tgggaaacca | gtgtgattat | ttggaggtaa | gaagacactc | 50280 |
| tggattttag | agttgcagag | tttcttgcat | taattctttc | tcatctttgt | gggctgtttc | 50340 |
| tttaatcttt | gaagtggctg | tccttttggat | gttttttgtct | tttttgttgt | tttttggtgt | 50400 |
| gtgttttttgt | ttgtttgttc | atttgtttgt | ttttttgctct | tatcttcttt | gatactcttg | 50460 |

```
caggtttgat tgtggtataa agtggattca gttagctgtg tttcttgaaa atcttagagg    50520
gtccaggctc acctcagcac tcttgtggtg tgttctctgc tctgggactg ggcccctggc    50580
tttattctct ggccccttga gtttagaaac ttgctgcatt ggaggggctg aggtgttccc    50640
agtccattgg ccacaacact atagtagggg gtgccggcca aagcacttca ttagagtggt    50700
ggcagtggga tccattctta ctcatgggtg ccagcagttg tggagtcatg gcagggtgca    50760
catgcatctg ctggggtggg ggtactggca ggagcagagt ggcagcatcc ctacataggt    50820
tcctgctggc agtcacagcg cagtgaggtg cccgtgtgtt ggcagggaca gggtggtggg    50880
gcacacatgc acatgcttgc tggtggtaga gggagttgtg atctgctgtg cactcatgcc    50940
agcaaagcag ttgggaggta ctatgggtgg actggtgcac atcagcagag gctggcctgc    51000
tggaggtctc caatggttag gcatggtctg ctggcaaagg agctatgatg agggccccca    51060
ggaaacaccc tggttgggct tccaaggctg tactgcaagc aggcacagcc agcctggggc    51120
cccaggagag gccagaaggc aaggaaattc tcatttcaga tgggccctgt cccatggaca    51180
agaccaccct gctttattca ggtcccatag tcactctaag gttaaaatct cctagaggag    51240
gttggtgagc cttgggggat gggtgtcccc tggctgtgct ccactacagc cattctcatg    51300
tcaaacactc tgggctttac acagactgga gtcctgcccc tggcatctct ctaagcagct    51360
gtcccttcca gcacaagtgt ccatgggggt catgggtct cctgctgcta ggattctgga    51420
ggcccatggc aacagcaggc cactcctcac ctgttcaact caacctttcc ccaggagttg    51480
ctgggagcca ggaatgagtc ctggtgcttg gcatccccat gcagggttcc catcttcctc    51540
cacctcagc tcagcatctg tgtcctcccc cgtctactct caatccactc tcaatgcctc    51600
cccttcaaag atctgcttgg aaagcacccg tcttcctgat gtctcactcc ctccatggca    51660
gatattcctc ctggctgcat ctagtcagcc atcttgactc gcctccaaag tcttttaat    51720
taccacttcg gttaaattag taactatcat tttacaatgg cctgtgattc tgttttgatc    51780
aaatattttg agccttttag catctataac aaatgttctc aaaaatcaaa atcctaaatc    51840
aagtctctgc cttagtctta tttctggggc ttattaaggc tataaaaatt aatcaccata    51900
aggttgtaca agcttttttac agcttccagt caggctatga actccagtat caccacctcc    51960
agcctgataa ttacatatat tggaagaaaa tcagttaaag gactccctct agacccttga    52020
aagggtgtga gagacaacat ggtttcgcct gccttcatgt gtcccagtcc atccctgtgg    52080
ctgcctctgt ccacctcagc ttgcccactg tctttccttc ccaactgtct gccctgctga    52140
cttctggcct cagtgacaga tgcaaagaca aggcgacagc cccacataga ccgtttaacc    52200
agtcccacat ttgcataagc taaatggtca tgtcacagtc tgttgcccag gctggtctca    52260
aactcctggg ctcaagtgat ccacccacct tgacccccaa ggtgctggga ttacaggctt    52320
gagccacagt gcccagccaa gaacccgttt ttgagtgggc accttggcac acacctgtaa    52380
acgcaacact ttgggaggcc aaggtgggag tgtggcttga ggccaggagg ttgaggttgc    52440
agtgagctat gatggcacca cctcactcca gcgtgggtgg cagagtgaga tcctttagaa    52500
aaaaaaaaa aaaaaacttg ttttctctgc agccgggctc cgtgaccaaa cacaaacaca    52560
aacttcccct ccagagggtc caggaggggc tgggctgcag gaggtgctta gggcctctta    52620
gggaatggta agtgaccacc caacgcaggc actcagcccc aggggcatat gcagagagag    52680
ggtccaggag gagctgggct gcaggaggtg cttagggcct cttagggaat ggtaagtgac    52740
cacccaacgc aggcactcag ccccaggggc atatgcagag agagggtcca ggaggagctg    52800
ggctgcagga ggtgattagg gcctcttagg gaatggtaag tgaccatcca acgcaggcac    52860
```

```
tcagccccag gggcatatgc agagagaggc tgggaggaca ctttcagtga ctggggttac    52920
aaaccccaac cataagacat tgctggctct gtgagccgcc acctccagaa atctcccact    52980
tagttcttag cacttatcca ctcttccctt ttcctactct caattcctgg aggatgccct    53040
cctttctcag gctcagacca acctaccagc tccactctag acctgaacac atgactcctc    53100
cctctgtctc cacctggaaa tctcatcagt gcctcacatt tacactcctg aaaatcaggt    53160
cctgcctacc caccctcttg ctccacctga ttcctgccct gtttcagcca gagaccttgc    53220
agtctccttt aactctcaaa cccacccatg tcgtgtgagc atactgactg tgttctatgc    53280
aagaaagagc agtttcttgg tggtcctgcg gttttattag tccagaggca aagcgttggc    53340
agagctggtt tcttctgaac cctgggaggg agattctgtt ttcatgcctt ttccagattc    53400
tagaacccat attccttgct ctgtgtcccc ttcttccatc ttcaaaggcc atcctctcat    53460
ctctgtgtcc atcatcacat cacccttccc ctgactctgg ttctcctgct tccacttata    53520
agcacccttg tgattacatc atacccaccc agacaatgca gggccatatt ctcccctctc    53580
gagattaatt taatcacatc tacaaagttc ctcgtgccat atgaggtcac taaaccacat    53640
gttctggggg tttgaatgta aacatttggg ggatgcatta ttcagccacc cacaagcact    53700
gctccccact ggccacacac tatgcacagc cgagatcatg caagtgaggc acgttcatca    53760
acagcagctt cagcaggaaa ctatatgctc cactttcctg ccatttgtat ctggattttt    53820
ttttcgctat cattgtagaa agagtggtat tgtaaaatta aagatggatt attttctttc    53880
tagaacactt tggcaatcta tccaacatta tttatcccct tctgagtgtc aagtgtgagg    53940
tcattctttc attgagagct caatgcctac aattatgata atgcatattg ggtactttca    54000
cacatcagaa agttcttctt tcttaaaatc tgttcttgaa ttattcattc ttctctagct    54060
ttttgttgat ctattttata attttagaaa aatcagaaag taacttgaag tatctgtcat    54120
ctctacaggt ttacctccct ctttgtggcc ttcagaatgt catgcacgc ttttcccttg    54180
ctcatcacat ggtttctatg tatgagacct catcacagga gctgtggtcc cccgggagca    54240
ggcatctgtg gatggtgcct tgctcctggc tgctgggacc tgtgtgctgc cagtggcact    54300
ccacgacagt gatttcccag ctcagttttg cagctccaga tggtgggtga gacactagga    54360
ccactttgtg aacagcgagg gcttggggtt tgcttttcta ccatgtccag ggctgctgtt    54420
catgagggaa tgtttctaac ctgacatcat ggctgaagcc aacttagaac ctctctagcc    54480
gtatggggag taggtgagtg atacagatgt taattagctc agtggagcca ctcccctatg    54540
tagacatgtt acaaaacatt atgctgtaca gaataaatat aggtcatttt tatgtgtcaa    54600
tcaaaagaga aactaattat ttaaaaaaaa aaaaaaacc tctctactca agccgaaacc    54660
tcagctccag tccacaagt cacacaaggc tgctcccgtc ctgtgtatgt taaacctacc    54720
tcagaaatgc aaggggcat tcaggtttca ttctcaattc aaatgcccctt tttaattttg    54780
tctattccta gcacctggca acttccagct ctttttttcg gggctcattc attatttaaa    54840
gcacgtataa ttttttcaccc acattctaac acatgtagta ctgtagagaa tccttcccta    54900
ggaggatcta cagcattaga aaagaattaa gaactccaat atttacaaga aggaaaaagc    54960
aaaagagat caaaaaatgg gcaacttcta gaaatagaaa accctcatga gtatgatgat    55020
aaatcgctgg cacacatgtg aatagttact tgatgcttat agtgatgtct gggaaaataa    55080
catgaaatac ttataatctg tttctcacac atgtaattca aaagaataga gagaagatga    55140
tttgaaatat tcttaagttt gtaggaaaaa agctacttcc atatgcataa ttgcatgtat    55200
```

```
tttgatactg ccattattaa gaactatcta agagggtcca ttaaaaataa aatttcttgg    55260
ctgggcacag tggctcatgc ctgtatccca gcactttgga aggccgaggc aggtggctca    55320
cctgaggtca gaagttcaaa accagcctgg ccaacatggt gaaacgctgt atctaccaaa    55380
aatacaaaaa ttagctgggc atggtggcat gcacctgtag tctgagctac ttggggggct    55440
gaggcaggat aatcgtttga acccaagagg tgtaggttgc agtgagctaa gatcatacca    55500
ccgcactcca gcctgacaga caaagcaaga ctctgtctca aaatattaa aataaaattt     55560 ctcattccta ttacagagta atttaattca ttaatgccct gccctgttac aaaactcatt    55620
tgtaaaatac taattgtaat tgtgaaaaaa tggcaattga tactaatttt aaattctaaa    55680
aacagggcac ccatattaaa gattattctg cagtaagaga attagctata acattttgta    55740
ataaggtgga gaaacattc tccaacttac aatggttggt gagaagaaag tttccagcac     55800
ggtagatgga ccctaagagc ccttgttgaa ataataagac aaaagatat acagagagat     55860 gagccagatg aagggagaca gagagagaga gagagagaga gagagaggca cagaaatgag    55920
agatacaaag tgaaagaggg caacctgtgg ggtcatcaga tatttgtttt ctgttttgtt    55980
tattctaaca taaaggcagt ggtgggtcat cgatgtattt agagtttgca caatcactgt    56040
ggaacacaga cagacacagg ggaagaggag aaacacaggg cggtggcttg cccttggact    56100
gttcttagtt cctcaaaacg taacagcttt gcccaaccta agggaacttt cagcagctgc    56160
tcttctgcca taggcctctt tcctgccttg ttttcatgtg gctgactgtt tctgttcctg    56220
caggtcttag ctcatcagac aggcatttat tacctctgtg tcaacagtgg gagcttccat    56280
tactctctag catgacactc cccttcctct tttaggaaat ttaacatgga agtgagtttg    56340
ccatcggcct tctccccaca gtgttaacag tggtgaggaa gccagcctgt tccaccttgc    56400
ccctcccatg attccaacac tgagttcaga cttgtcacat ggaacttatc tttgcatgtt    56460
tgtggcacag acagatggac ccaaccatgg attagtggat ggatggatgg atggatggat    56520
ggatggatgg atggatggat ggatagatgg atggatggat ggctgagtag gtgtgtggat    56580
ggaagagtga aaagatagat ggatgcatgt atgggtggat gggtaggttg atggatgcat    56640
ggatgggtgg atggatgggt gagtggatga atgggtgggt aggtgggtgg ctacatgcat    56700
ggatgagtac ttggatagat aagtgagtgg atggatggat ggatggatga atgggtatgt    56760
gaagggatga tgtattaga gtgggtagtt aggcaggcat gagctgatag tcaagtgatt    56820
gttaaactgc ctctctaaaa taataattgg tctcggctgg acgcggtggc tcatgtctgt    56880
aatcccaaca ctttgggagg ctgaggtggg cggatcacaa ggtcaagaga ttgagaccat    56940
cctgaccaac atggtgaaac cctgtcttta ctaaaaatac aaaaattagc tgggcgtggt    57000
ggcgtgcatc tatagttcca gctactcggg aggctgaggc aggagaattg cttgaacctg    57060
ggaggaagag gctgcagtga gctgagattg tgccactgca ctccagcctg gtgacagagc    57120
aaagctctgt ctcaaataat aataataata ataataata attgatctca gccagcgcca    57180
agaaaaggca gtctcccaat agatagaaaa cacccgaaac tggtcatcag cagcttcctg    57240
ataagatctc aggcattggg tgagtgggct caagcatatg cactaagagg caaagtggca    57300
gagtttaact ggcacataat cttcctctag gaacactcta atagtaagag aaggacacct    57360
caaatgagca tgtgcacatt tcattaaacc cactgtgtat gcagcccctc ccaagtgctg    57420
gcaggccact gtacatgtgg gcagcccact ccaaggaag aatcaaggga gaagaaatac     57480
aaatcccaga accatgtcaa tgtataaaac cccaagtcaa gggccggaca gagcacttag    57540
atctctcaag tcgcccactt agccctcttc caagtgtact ttacttcctt tagttcccac    57600
```

```
tttaaaactt taataaacat ttactcctgc tctaaaactt gcttgggtct ctcactcttc    57660
tgtatgcccc ttggccaaat tctttcctcc aaggaggcga gaatcaagtt gctgcagacc    57720
tgtatggatt cgctcctgct aacagatagc tggatgggtg gacagatgca tgaattagtg    57780
gatgacgtt  tggatgtgtg ggtgggtggg tggattgtgg gatggctgga tgaatgcatg    57840
gctggatggg tggacagatg catgaattag tggatggatg tttggatgtg tgagtgggtg    57900
ggtggattgt gggatggctg gatgaatgca tggctggatg ggtggacaga tgcatgaatt    57960
cgtggatgga cgtttggatg tgtgggtggg tgggtggatt gtgggatggc tggatgaatg    58020
catggctgga tgggtggaca gatgcatgaa ttcgtggatg gacgtttgga tgtgtgggtg    58080
ggtgggtgga ttgtgggatg gctggatgaa tgcatggctg gatgggtgga cagatgcatg    58140
aattcgtgga tggacgtttg gatgtgtggg tgggtgggtg gattgtggga tggctggatg    58200
aatgcatggc tgggtgggtg gatggatgca tggataagtg gtggacggat ggacgggtga    58260
gtggatgggt ggatgtgtgt gtggatgggt ggataggaaa gccctctaat tgattacagg    58320
gctcagtgtg tgcttcaaca tcatgatggc atcatcacat tggtccctgt atgaagcagt    58380
gggggaggag agtgtaccag gggagcagga atgacttttc tccagaatcg acctctccca    58440
ccctgcagcc tgggctgtgc aggccacatt ggagaaggtg cggtcgacta ctcctaaatg    58500
ttgttgtgtc caatggcttg ttgacgttga tgtaggaatg agcctacatc tccaccatag    58560
atggaactgt ttgggtcccc aaagcagaaa gcctcttctg ttgcaggtgc tgaagtttcc    58620
atcttcttct gcttatacgg aagctcacgc atcccttgga tggcaggcgt caggttcctg    58680
tgcgcactga gttccccct  tacatgcttt ggacagaagt gtgagacaca caagattgct    58740
gcaggaagtc cacctgtggg gatgctgcga cttctccagc aagaacacga gtctgctcat    58800
tgaccatcac cacacataac aaattaagtg tcccttttt  gataacacgt cattgtttca    58860
cagagtattc ttttaaagtg tataagttga ctgcagttat tatttttac  ttctgttact    58920
aatttactca taattaggca caatttacac ttaagaaatt tcttaatagt ttttcctcc    58980
ttaaggtgaa ctacagtcag ataacatact tatcaattgt ctctagctct tgtcagaaaa    59040
acatatagat gtgtgtgtgc gtgtgtcttg gcctttccaa tgatgaatta agatgtgcat    59100
tgagaaggca ttcactttat ttgacgttaa ggaagtacca agaagacgct ctccacagac    59160
cctgggaaag ccagcagctg cacccgagg  ctgtgccagg cagggaacaa ggaggcagca    59220
ccacctgctg ggcagggaaa atgtcctccc agtccctgcc gcttctctgc agaggcacaa    59280
agagctgccc cttctcctgg gccttctcct gggctgatga gattgctccc cgatatgcca    59340
aatcagggtt gtgcatctga ggctctgtct agactctcag ctccttccta ctcctgcaaa    59400
gtgaagaaaa caatgccaag gggtcctgga ggcgtctcta cccctggaga gttttgactc    59460
tcttcaatag tctccactac cctgccctca ctccatgtcc tccgtttctc cctaaagcgg    59520
tgcccagtct gattgcactg tggcagggat aacgagggc  caggacatca ggggagaaa    59580
gtttctacct gagtcacagc agcggctgcc ctgcagactc ctgaagacac aagacacatt    59640
tccatcccag agacccagcg aaatgcaacc tcaggctaga gacagccagt tattttttct    59700
tgttctgtcc tggagaggcc actgagaaag tcgagcccct tgttgaggaa aacatgagat    59760
ctctgtgtgt cgtcctctgc ctgatggctg tacctccatg tgagtgtctc agagatttca    59820
gaacgggggc tgtgggctgt ggtgtccgct tgtgactcat ctctttgctt cttgtccctg    59880
agtgtcctgc atcagatgca gctactggag tcatgcccag ggctggtgag gtcctcacag    59940
```

```
acctctgggc ctggacccag cagccctctg ggaaggcgct ggggcacctc agctccaggg    60000
gcagcacaca cttcagccca gcctttctgg gccaactctc catctgtaga gacacatcca    60060
aggcccagtt atccctgcag ctgagctccg tgatggccaa gggcagggcc gcacattccc    60120
gtgggagaca gaatggggac ctcagcgtga gcccagacac aaacctccct gcagggaagc    60180
acaagaccac caggcggcgc tccagaccac acagcggccc cagaagcagg ttttaggggg    60240
cggggcagac gtgtccgcgt tgagtcaggt cattggtttt actttccctg agcaaacggc    60300
ctctgccaag gactcactgc acctctcacc ttcacagttg ttttttttt tttttaatc    60360 accctgtaga gttttgctag ctaatttaga tattgaggag tgcttcatac ttccttgggc    60420
ctctgcttgc agaaacatag caattgtaag gaggcacgtg ggaaagcccc ggctcggtga    60480 cccggggggat gctgctgtgg ccctggcaag agggcgtcgg gccgcagtaa caaaggtgca    60540
gacggctctc agcctgcgcc cgcggagtac aacacataag ggctgtaacc taacgaaaaa    60600
agaatcgcag tgcaactgtc ctgcatttga gttttgtgatc agttttgccc tttgtcttta    60660
acaggttcta acataaaatt ttgaatgttg gttcaagccc tgtgggtaaa atgcacttac    60720
ccacattcct taaacaaata gaacactgag gtggaaatgt tttgaaaaag tagttttcag    60780
acatttggaa acaagcatca caggatcata accctgaga aaagaaaaac aaatgaacga    60840
atcctgctat tgcctgaaag cagctgccag gacacacgga aaggcttagt gagctgagcg    60900
gacagagagc agagttcaag gcagcagcag cccgagggga ggagcaccgg ggagcaggct    60960
gctgtgcagc caggatgggc cggggtgggg cgggggggaga acagctggag acttgccgca    61020
gggaggggga tccctcaggt ttggggctga gaactgactt atgcctgact tatgcctgca    61080
tgaaaagaaa ctactcgata tcagggggaa atcaccagaa acctgtggac ccaaaactac    61140
acagagccta cacaaggaaa gcattgtttg tgttctccca gccagggtgg aaagaccttg    61200
agatatgtaa agcttcaagc aatcttccga agtaatctcg tgagtagtgg tgccacatta    61260
attcaggact aaaggctgct ctgaactgaa cctaagaaat gcttcaagtg tagcctggag    61320
cccgggtgca gtggctcaca cctgtaatcc cagcactgtg ggaggccgag gcaggcggat    61380
cacttgaggt caggactttg agaccagcct ggccaacatg gcaaaacctg tctctactaa    61440
aaacacaaaa attagctggg cgtggtggca gatgcctgta atcacctccc acctggaccc    61500
ttccttgata catcagaatt acaactagag atgagattgg ggtggggaca cagagccaaa    61560
ccgtatcaca taggaaccta aaaggataat aaagtaggaa aacttcccac atcagtaacc    61620
ctttatccga tagtaatccc aatctgcaaa gtaaaactgt gtgatttac taagataacg    61680 gaatcttctc tacagaagga cttttccagtg caaaagctcc ccaccctcac catgaaatgc    61740
acgtgaccat ttccaatttg tgtaaagtcc tcagttagta ctgagacttc ggaaggttag    61800
aaatcccttt gctcatgctg catggtccgg atgagatgta agaatcatta gctaatagac    61860
atgcaacagc ttttgtgtga aagatgttat gagacattta aggtatttgc ttgtgattac    61920
taagcattca ttgtatcatt ggagcacatg tgctttttata ccctggagaa attccagtaa    61980
ttgaattgct gggttgaatg ggattttgat ttggattaaa tttaaactat agattttatt    62040
tagggaaaac tggcatctta attatgttat tggggggccc ttgctcccag agctcccaag    62100
atggtggcag gccgcttcca aaatgaccgc aggccacttc caagatggtg gcaagcctca    62160
tgttctctga cctgggggttc ttggcctcac ggattccaag gaatggaagc ttgggccatg    62220
cagtgagtgt tatagctcta ttagaagccg tgggtcacgg aagagaaccg tggaacccag    62280
tgactagtgt tcagctcgat taggacgaac ccaggcactt agccgtgcag gaacaatggc    62340
```

```
gagcatttgg cccgatcgag agtggcaatg ggcgcctcgc tggatcagga gcacagcgga    62400
taccctgatg gatccggagg gatggaagcc agcggtgggt ctcccacggg ggcaaacagc    62460
agtggtggac ggtgagcgaa agcgaagctc gagccgtaac aaacatggac cagaagagtg    62520
cagttgcaag atttagtaga gtgaagacag agctcccata caaagggagg ggacccaaag    62580
agggtagctg ttaccggctc gaatgcctgg gtttatatcc cgatcattgt ccctcccgct    62640
gtgctctcag gtgatagatg attggctatt tctttacctc ctgcttttgc ctaattagca    62700
ttttagtgag ctctctttac tatctgattg gtcgggtgtg agctgagttg caagcccgt    62760 gtttaaaggt ggaagtggtc accttcccag ctgggcttag ggattcttag tcggcctagg    62820
aaatccagct agtcctgtct ctcaattaca ctgagttttc caatccatgc atccaatatg    62880
tggtgtatct cttcatatgt tcatagcctc tgagcaatgt tttacaattt tctgtgtaaa    62940
gaactccaca tcgttttatg tttcttctaa ggtatatcct gattgctttt tatgtcttca    63000 caagttttt cctttcaaaa ttaattttcc aattgtttgg tgctaatatg ctcaaatgtc    63060
cttgattttc ttagtttgaa cagtccgttt ttgttttggg gatttatttt tttttcagat    63120
tctttaagat tttctatgtc tataaccata taatctctga acagagacag ttttgctttt    63180
tcctttcaac ttgaggtagg ttttctgggt agttcaggac gcgcaggcac tgggtgggtg    63240
gtgttagcag ctgcacgatg ccttggagag gacactctcg ggggactgtg gccgctgctc    63300
agctgtgacc gttcttatag caccagcagc tgcggccacc attcttatcc aatttccaaa    63360
gccacaccac aggccctctc aagaacgagg cgtggaggct atgccctctc ctggacacat    63420
catcattccc aagcccacg atgtgggccc catgggacgc acacctttgt ctgtccagac    63480
ctcagcccca cctcctcatc ctgcaccaga actcttcaga gcccagtgca tgaaatgggc    63540
taccaaggaa atgagggtag gttcctgaga ggaaactggc cctgcatttg ggagctagga    63600
gtctgctaat tcgcctggca gccctgtgca gccctccgtg gctacagtcc accccgtgcc    63660
catcagtgcc tccttcctgt gcaagcctgg acctcgccct gggctcagga tgggctgtag    63720
accgagaatg caggcgggaa agtctttgtc tatcggggcc atagtcaggt tctacagtga    63780
gtcagggaaa gacctgtgga ggtgtggatg aggacaatgg gtccaccatc aacaggagga    63840
cacgggttcg accccttgca gaggcacagt cccacatcac tgggaggcag ccacactcac    63900
tgcctcgccc tctcctcaca cagtgcagtt ccacgttca cagccccagc cagtcaccag    63960
gaatgccctg ggggcggcct ttccccagtg cactccgagc cctcccttgg ctgtgcggtg    64020
agctccatgc ccaggagata tccacccata gtcctccgga aagcagctga cctgccatgc    64080
cctggaacca caaatcccca cagatcagcc agcctgcagt gggccttgga tgtggtgagg    64140
agtggtggca ccccgttcc caccccacag atgcaacgcc tgtgggtgac gcatgtgagt    64200
actgaggagt agagggtaga actgtaggcc ccgagaacca cagaaactcg ggtgttacac    64260
tctggggcca tgtaaggaga aagtgtcact ggacagaaac aggcccctcc tagacactgt    64320
gtgcgccata gtcacctgtc attagctctc actcttgcag attcatgatt gaggtggtta    64380
aaaaaaaaaa agctcctact cacccatcca accccatcct ggggtgtttc caccacccctt    64440 ggggtttggg atgagctgcc cttgcccact gtgctctgtg gacctccctt tagaagctca    64500
cagctccctg cactcggctc catcctgccc caccacacag aagcaaaacc cctctccttt    64560
ccactgcagg cttttcctgg accagaatgc tgacctgctg cccttcactc ccgaagtggt    64620
gggactgcct ggggtggtgt gggtgttgag ccttcttact ctagggacct ggcacctggc    64680
```

```
cccagggca  cagggatggt  gcatctgcct  agggatgcct  cctcatgcca  ggggtgggg   64740 gttagtacca  tcggccctca  ggatttgttg  catgaatgag  tgaatgggtg  aataaatgaa  64800
ggggatctga  tctatgaata  agggtatata  gactttggtt  gatgtaggac  gccaaatgct  64860
ggaatttcag  agtcatcaca  cccaggggcc  ctgcctctga  gctcctcttt  gcatccaatc  64920
tgctgaagaa  catggctcta  gggaaaccca  gttgtagacc  tgagggcccc  ggctcttcaa  64980
tgagccatct  ccgtcccggg  gccttatatc  agcaagtgac  gcacacaggc  aaatgccagg  65040
gtgtggtttc  ctgtttaaat  gtagcctccc  ccgctgcaga  actgcagagc  ctgctgaatt  65100
ctggctgacc  agggcagtca  ccagactcga  gtgccatttc  attacctctt  tctccgcacc  65160
cgacatagat  tctcactcac  ctgtgccatc  tccggggaca  gtgtctctag  caacagtgct  65220
gcttggaact  ggatcaggca  gtccccatcg  agaggccttg  agtggctggg  aaggacatac  65280
tacaggtcca  agtggtataa  tgattatgca  gtatctgtga  aaagtcgaat  aaccatcaac  65340
ccagacacat  ccaagaacca  gttctccctg  cagctgaact  ctgtgactcc  cgaggacacg  65400
gctgtgtatt  actgtgcaag  agacacagtg  agggaagtc   agtgtgagcc  cagacacaaa  65460
cctccctgca  gggatgctca  ggaccccaga  aggcacccag  cactaccagc  gcagggccca  65520
gaccaggagc  aggtgtggag  ttaagcaaaa  atggaacttc  ttgctgtgtc  ttaaactgtt  65580
gttgtttttt  tttttttttt  ggctcagcaa  cagagatcat  agaaaaccct  ttttcatatt  65640
tttgaaatct  gttcttagtc  taatggagat  tctctaatat  gtgacaatgt  ttttctcttg  65700 ctgttttttgg  aattctttgt  ctttgacttt  tgacaacttg  acttttgaca  gtgtgcctca  65760
aagaagttct  attttgggtt  ctgtgaacct  cctggatctg  ggaagttttc  agctatgatt  65820
tcattaaacg  tgttttctac  accatttccc  tactcttttg  gaatacccat  aatgcaaata  65880
tttgttcact  taattgtgtc  ccataaatgc  tggggatttt  cttcattcct  ttttactctt  65940
tttttctttt  tattcatctg  cctgaattat  ttcaaaagat  ctgtcttcaa  cttcagaaac  66000
tcttttgctt  ggcctagtct  aatcttgaag  gtctcaattg  tactttaat  ttcattcatt  66060 gaattcttca  actctggaat  ttctgttggt  tcttttttat  gatacttatc  tctttgttga  66120
attcctcatt  caaatgataa  attgttttcc  tgatttcact  gaattttcta  tctgtacact  66180
attgtatctc  cctgagtttc  ttagagatta  tccttttgaa  ttatttttct  gacattctgt  66240
atatttcctt  atgattgggg  tctgctactg  gagaatgact  gttgtctttt  tcaggtgtcg  66300
tgtttcctgg  ccttttcatg  ttttatgtgt  tcctacgttg  atttctacac  atctggcgga  66360
ccagtcatcc  cttgcaattt  aatggagtag  gttttgcagg  aaaagacttc  ctagtacaga  66420
cgggtctcag  ggtgtcagtg  tggcggggcg  tgctggcttt  agttctaggt  tgacgcagta  66480
gcgtagtctc  catgtcgttt  cttcagctgc  cgtccacatt  ggtgacgttt  gcgagtgtct  66540
cagtggcctg  ggctgagagg  tttgtggcag  tggaagtgca  acgttgctag  aggtggactc  66600
accaggctgt  ttctgaggtc  gaggcacatg  catgcacatg  gtggattgac  caacttggtg  66660
ccaggctcac  tagggttggg  gacatggggc  tgtttctcag  gcccaggatg  caaacacaag  66720 tctcttttggc  tggcctgggg  gtgtggcttc  tgagggcaat  ccacagggct  gtttctcagg  66780
ttcaggacac  aagtgcatgg  ccgctcaact  ggcctgggca  tgtgtctccc  agggccaccc  66840
catgggctct  ttctcagacc  caggacatgg  ccacatggct  tcctcagctg  gcctgggtgt  66900
gtgtctgctg  gggggctgca  ggggcacagg  gttattctc   aggccggggt  catgggcgca  66960
cagctgcttg  ctggcttata  ggagtgcctg  ccaggggtgg  cccatgatgc  tgtttctcag  67020
gcctaatttc  aggtgcagag  ccttgggca   ggtcaacggc  atacctgtgg  aaattggagt  67080
```

```
ggatgccaca gggctatttc tcaggtgcct gagtgtgggc acatatccac tctgccagcc    67140
tggagttagt atcaggtgct cggtggctca ggggcctctc ctgctcaggg gagggccctc    67200
agcagcttgg ccaaatcaat ggtggattca ccctgggcag gcctggcagg ctcttcctcc    67260
agctggatgt gcagcagcag gggttgggtt ttttgctgtg cagggccaga gtcacggcca    67320
atcctcagcc taggctctgc acagccaggg ttgtggcatt cagccaccca gatatgggca    67380
tcctgaagat ggagccccaa tgctagaaag gggcagtggc taccagcctc agggcaggat    67440
gcactccaga ggcggctccg gtctcaaggt ggcgctgggc tgcagcagct aggctcacag    67500
tggatgaatg ggggcaggga gtacacacct tgtgctccta atctgggatc attcctggca    67560
gctcccaaac ttggctgagg gcttgcaaaa cctgtggaat tctcctgttg caagggctgt    67620
agatgtttgc agtggcagtg ggtgctggcg ggaaatctgc ttacctttc cctacatggg     67680
aagtccctcc tgtgtccaga ccaatccgat ctgggtgggg aagacaaggc tgcaaaggcc    67740
aggtgcctcc atgctgccct ccgatcacca cgggtgcgtt tccacacctc cactgcactc    67800
cgtcagtctc ccttcaacac tccagtcaaa ccttagctgt ttcttctttg ccttattcct    67860
tcctcatggg gagggtgtgg gtgaacacca ggcttctcta agttcttcat ccatcttgct    67920
gatgtcattc tccatccagg catgggtttt taagaagtag tgaatactga aatttcagca    67980
gaggacacct ctataaaaat tctgcaactg gaaaacctcc ttaaattggc tgattgtcat    68040
tacaattgga ggaaaactgc caataatttc aaatttagaa ggctgagact ctataaacaa    68100
agactaacaa tatgttttct gatatttttc cccaaaataa tacttttcca agacgaaaat    68160
ttttccaggg tatataagca catgtgctcc aatgatacaa caaatactta ctaatcataa    68220
gcaaatacct taaatgtctt ataacatctt tcacacaaaa gctgttgcat gtctattagc    68280
taaaaattct tatgtctcgt ccagatcatg cagcatgagc aaagggattt ttgaccttca    68340
aaagtctcag tactaactga ggactttaca caaattggaa atggtcacct gcatttcatg    68400
gtggtggtgg ggagcttttg cactggaaaa tccttctgta gagaagattc cattatcttg    68460
gtaaaattac atagtttat tttgcagatt gggattacca actgataaag ggttactgat     68520
gtggaagttt tcctacttta ttctcctatt aggttcctat gtgatatggt ttggctctgt    68580
gtccccaccc caatctcatc tccaattgta attcccatgt gtccaggag gtccaggtg      68640
ggagtgatta gatcaagggt ggttttccc aggctgtttt catgataggg tgttatcatg     68700
agatatgatg gtttaaaagt ggcaggttcc cctgctctct ctctcgcctg ctgccacata    68760
agacgtgcct tgctttccct tcaccttctg ccatgattgt aagtttcctg aggcctcccc    68820
agccatgcgg aactatgagt caattaaacc tcctctcttt ataaattacc cagtctcagg    68880
tagtatcttt atagcggtgt gaaaatggac taatacacta tggctttgaa ttaataattt    68940
aaaatttgtc agcttggcaa taaaacatcc tgttgacatt tattttttag gtaatatttt    69000
aaattggcag tttcattcat gttttttacaa attcttattt tcagggtgtt taaggccttt    69060
gctttgaact tggtggttcc ttacactcca tgctgttagt gaagagggac caggttggga    69120
ggcattggtt tgggtggtgg tcaggaaggg cagagtgatt tgagtagggt ctgagtggat    69180
aatagctcat cagtttggaa tttataaatg accaggggatg atttaaggag attcctgcca   69240
gacacctatg ccatggccat gccctatctg gatctccagc cgtgagatga gaacccagcc    69300
atgcggggga gtctgttcgt tctgctcaat gttgtaagtg gcacatgcta ttggataatg    69360
tagaattgaa tggatatcat tttattatta taatttacaa acttcctaca ataaacttat    69420
```

```
cacctttata catagaaaca aatataagta cattttccct cccctatgtc attttgagcc    69480
ctctctccaa accatcctcc cactctgcga ctcactgtcc tgcatttggc tatgctctgg    69540
caagtcctgc ttagacaagc actcaccaga ccacctactc agcctccctt cagcgcccac    69600
ctggcccacc tgctcaaata catgttgagt ggtcacacac atggactgaa ccatcatctat   69660
tccatgcact gccccagtga ccgcactgag cagcaagaga gaaatgatcg cattagctat    69720
caattatgcc aattcaaatg ctggagtctt tctcagatac ttttcaatgt tcaagaattg    69780
ttgattgtga attctatacc caatgaaact atccttcaga aatgagcaga aaatggatac    69840
cttctcaaat aaacaaaaac taaaagaatt cttgctacaa gatgtactct aaagactgg    69900
ctaaaggaag ttcttcaaac agcaaggaaa ttgaattgat cttatgtcct gcacacttgc    69960
taaatttcct ctcaattta gcagcactgt ttagattcca taggattttc catacaaaca    70020
gtcatgtggt ctatatatag agacagattt tcctcttttc cagtggggat aaatttatgt    70080
cttttctttt ctgtgttaca gcaggtagga cctccagtac aatgttaaac agaagtggtg    70140
aaaacagaca ttcttgcctg tttcctaacg ttggagtttg gtcttttact atggtgtcag    70200
atgttagctg tagggttttt ataaatgccc ttcatcacat tgaggaagtt tgctcctatg    70260
cctaattttc tgagagtctt ttaatgtgac actcatgcta gaatttatta aatgctttct    70320
gtctactaag atgattatgc agttcttata ttaacatgaa taattacatt tatttattct    70380
ttaatatcaa ggcaattttg cattcctgag acaaacccca tttagtcatc atgtgttgtt    70440
attgttacat attgttggat tcaatttcct caaaatttgt taagaattgt tacatctatg    70500
tttacaagga agattagtct gtagggtatt ttttcttata ataactttgc ctagttttgc    70560
aatcagggta atgctggact cacagaatga gttgggaagc tatttcctcc tcttcatttt    70620
tctgaaagaa tttgtataaa attggaatta tatcttcctt aaaggtttgc aagatttcat    70680
aatgaagtca ttggcctaga gttttctttg tgggaaagtc tttgtttgtt tgttttgtgg    70740
tttgggtttt tttttaagag acacagtctc actctgttgc ccaggctgga atgcagtggt    70800
gtaatcatag ctcacagcag cctcaacctc ctgggctcaa gcaatcctcc tacctcagcc    70860
ttcagagtag ctgggactac gggcatgtac caccacaccc agctgtttgt ttgtttgttt    70920
atcgctttgt cttgttttg aggtcttatt atgttgccca ggctggtctt gaactcctgg    70980
cctcaagtaa tcctcatgcc tcagcctccc acagtgctgg aattacaggc atgagccact    71040
gcacacagac tgtgggaaag ttttttaacta aaaattcaat tttctcttcc ttttccagtg    71100
agctttccag tgtctttcaa ttaatgtatc tatttttatct aagttgttga atttattgtc    71160
aaaatttttt taaacaatat tcctctctta gaggttgaac atctgtagaa tctgtagtga    71220
tggcacctct taaatccctg atcttgctca tctgtgtcgt ctctctttct ctaatcagta    71280
tgcctaaagt ttaatttcat tgattttctt aaaaaactgg ttttggtttt attgattttt    71340
ttccctagtt ttttgtgtta catttcattg acttctgctc tgatatttac tatttccttt    71400
ctactgccta cagtaagttt aatttgctat tttcttagtt tcctaaagtg gaagctaagt    71460
ttattgactt gaggcctttc ctctgtctgg atgcggatat tgctgctaa acatttccct    71520
ccaacaccat gctgtgagtt ttagttacag cgggcttgga gttggcctga gaaattctac    71580
ttaaacagct gcacctatca tgtaagtgat aaatgatgta cctgcctggc cctcacccct    71640
ggtcaaagaa tgggatgtac taatgagcaa tgttgctgcg tagctgtgga tttcaaggta    71700
ttttctgtgt ggttttatca tcagcattgt ttgttgatga ctgcaagact gatgatttgc    71760
acctggcctc ggtgagatcc ccgaaagacc ctgcagatgg gctggttact tagcagaaaa    71820
```

| | | | | | |
|---|---|---|---|---|---|
| tatgacaacg | tggccagcag | gaaacaggaa | ggtacaatcg | gctgcaggtg | agctgttgga | 71880 |
| agtaagttcc | aattttccta | ttttgtattt | gcattttaat | agtgagactg | cgcttatgtt | 71940 |
| atttgtgtga | aacagcttta | ttcatagcac | tgtaatttaa | agagaaaacc | cattcatggg | 72000 |
| aacaacaaac | gacctagaca | ccaaggtagc | tcatgccatc | caaggctata | ctgtgcagtg | 72060 |
| attgggaaaa | tgggcactgg | tcccagaagt | ctgatcgaca | ctctgccact | ggctagtccc | 72120 |
| gtgctggggg | gcgaggatcc | acactctgcc | actggttagt | cccatgctgg | ggacaagtat | 72180 |
| ccacactctg | ccactggcta | gtcccgtgct | gggggcgag | gatccacact | ctgccactgg | 72240 |
| ttagtcccat | gctggggaca | agtatccaca | ctctgccact | ggctagtccc | gtgctggggg | 72300 |
| gcaaggatcc | acactctgcc | actgattagt | gttgtgaaga | tttaaataaa | gaacccacac | 72360 |
| catattcttt | gacttgtgct | ttccgtatac | tgagagatag | taagagtaca | ttattattat | 72420 |
| ttataaagta | aactagaaag | cacatgggaa | gacaagaaga | aaacctgaat | aaacatgaat | 72480 |
| taccccattt | tcctcaggag | aaaactttca | cactctgaag | gtacacaaat | tagcctacaa | 72540 |
| atttaatgta | aagcaaatag | actgttgtag | gtaccaattc | tcaatgtcac | agtgttacat | 72600 |
| ggaaagtaaa | atacacaaga | acagcccaaa | agatggaaac | aatggacgtg | gtcaaatgac | 72660 |
| atcagtacaa | catccatatg | gtcctaagta | gccatcttta | aaatgggtta | gaaatgcctt | 72720 |
| caatcattca | cacagacaca | tgcattgaac | aaactctaag | aagtgttctt | acacgggaaa | 72780 |
| agcaagttac | agatgcatgg | gcatgatatg | gatgtagatg | tgtgtatgtg | catcccactc | 72840 |
| atacacaaaa | tacccagcat | cgcccacatg | cctgctgtgt | gcgtaagtgt | gagcgagtgc | 72900 |
| acagacaaca | gcgtgcagaa | attcaaacca | agctgtgggt | acttgttacc | actgggaagg | 72960 |
| gagtcggtca | cagagggaaa | gagaaacagg | acatcagcct | ttgacttcag | aactgttcct | 73020 |
| gcctttcac | atcctgtgct | gttttcagca | tcatcggagc | ccttaacaca | catcacggga | 73080 |
| gtaagagtgt | gttagaggga | gcattcggtg | ggacagatat | tgccatggct | tgtggataga | 73140 |
| gttcacagtc | cttaataatc | cccgagatgg | cagccaagag | ctacgttctc | aatcacgcag | 73200 |
| cttcacccca | gaaactgaca | gaaacccaac | aaccaaaagg | tgtccattct | gacagcctca | 73260 |
| gcctgtgctg | gctcagatga | gcaaaaatgt | acagatatta | ataatgatgt | tgatttgaag | 73320 |
| agcacagagg | ggggtatgca | tgataagggt | ccaaattttt | accttaaaaa | agaatacatt | 73380 |
| tacttctcaa | tcacctacat | aacgatcatt | ttttaaaaaa | ctgatcaaat | ttggtgttac | 73440 |
| aagggcacgt | tgcaaattct | tctggctact | tttctctgac | tattctaatt | acgttaccgt | 73500 |
| gttttctcct | gtatgtgccc | gttcatgtga | atgtcatttc | tggctacttt | tctctgacta | 73560 |
| ttctaattac | gttaccgtgt | tttctcctgt | atgtgcccgt | tcatgtgaat | gtcatttctg | 73620 |
| gctacttttc | tctgactatt | ctaattacat | taccgtgttt | tcctgtatgt | gcccgttcat | 73680 |
| gtgaatgtca | tttctggcta | cttttctctg | actattctaa | ttacgttacc | atggtttctc | 73740 |
| ctatatgtgc | ccgttcatgt | gaatgtcatt | tctggctact | tttctctgac | tattctaatt | 73800 |
| acgttaccgt | gttttctcct | gtatgtgccc | gttcatgtga | atgtcatttc | tggctacttt | 73860 |
| tctctgacta | ttctaattac | attaccgtgt | tttcctgtat | gtgcccgttc | atgtgaatgt | 73920 |
| catccaggca | gatttcccaa | atccggcttc | ctgtaaccaa | gggctgaaag | agggaacggt | 73980 |
| ttcctgggaa | tcctttttgc | agtttatttt | acccggaggc | agaagcccac | ggttccgtga | 74040 |
| agagtctatt | gctctcccct | ctctcctttt | gtgtctctat | ttttaattga | caaaaaagca | 74100 |
| aatgtgaaga | ttcctggggt | acaatgcaaa | gtgacaatgc | ctgtctatat | tgtgggatga | 74160 |

```
ttaaaacaag gtaagtggca tatccatcac ctcacacact tatcattttg tggtgagaac    74220
atttaaaatc tcatctttta gcaattttga aatagtcatt attgttaact atagtcacca    74280
tgctgtgcaa cagatcaaaa gaactgactc ctcccatcag cagaaacttc atgcccttg     74340 accagcatct ctcctttccc cgtccacgac taaccccag cccaagagaa cagccaacac     74400
ccacctcgct gctgccacac gacatgtcgg gctttgatgg gatggaggtg agggtgggga    74460
agacaattcc aaagctggag cactggcctc acagctcaga cactcttcta cttatcctga    74520
gagaatgatg tgctgagacc aactaaacct ccctgctct tcccacatgg cagaaaagag     74580
gcaacccagg gaagccattg ccaggacatc atggtcaccc aaccttgtg cagaaaggaa     74640 gcacctgccc aggatgccat agcacccaac cctcatcccc aaggaaacac agcccagggc    74700
accatggaca cccaaccgtc atccccaggg gaggacacag cccagggcac catggacacc    74760
caaccctcat ccccagggga ggacacagcc cagggtatct tggacaccca gccctcattc    74820 ctagggagt acacagccca gggcatcttg gacatccaac cctcatcccc agggaaggac     74880
acagcccagg gcatcttgga cacccaaccc tcattcccat aagagcacac agcccagggc    74940
atcgtggagg cccgaccctc atccctaggg gaggacacag cccagggcac catggacacc    75000
caaccctcat ccccagggga agacacaacc caggccacca ttaacaccca atcatgtgca    75060
gggagggtgt ccttggagcc tgggactctt gccagtgaag cggtggacaa gaaactgagg    75120
atgcgatcag cacacagaaa tctcaggcag cctaggatac atgaggcctc tcaccctgg    75180 gaacactgag cagccaccag gagcccacac cttgaggtac agcaggagcc atgcgctctt    75240
gctcttgctc actcacactc ctgcacacag ccactgacac acgccctcgt gcacgttgca    75300
gattaactcc actggccttg cacttgcaac gctggaggct gagaggtatc cccaggttct    75360
tttctcgtga gagggcagg ctgactttca ctctcctcca tgtgctagag gcagctccac     75420
caacactggc tgccctgagt ggatgcacct ggctctggaa ttcctgtcat ttgctttgga    75480
tccaggagcc cctgcctcat gtagctactt aacagaaagg aggaatccac ccaggacatg    75540
cccagacggg agcctcacag gatggacagt ggtgtctggg gtcacgggca ccctgaccc     75600 agcagcgcca gcaccagcac acccagtggg gaaggcgggg aggcccaaac gccacccaca    75660
gtttgttact ccactgggtg ggacccggca cccctgcctt cctgacaccc tggagtccct    75720
gcctcctcct agagccccca agcccatctg cctcagagca tccagagaca gacctgggga    75780
gccatttcct caggccctgg acaaggaaac agggaattcc aggttatggg tgcctggggc    75840
aggtctcagg caggtgctgg gaaccagaga gagggtcac cgcgaggcct caggcctggc     75900
accagcactt tgagcctcag tttaccagcc cacgaggtgc tgagtctgga ctggatgacc    75960
ttcccacccc cagtgacctc tgccctttcc cgagcatgtc agctctgctc cagcatcctg    76020
gtgtgagcgc aatgccactt tttttctcaa caaatacgaa aggaggaagg tgccccagg    76080 gccctgtgcc ctgaggatgc ctgtgtggag gggtccattt catcactggt gtcactcaca    76140
ggaagggacg aagccacctg ccttgacgga gcttactcca cctccgccga aggccgggga    76200
ggtccctcac agagaacctg aggcccagca ggctgcagag gtgctggcat ggaatgactg    76260
ctcagacgcc cgggccggc agagaggacg gatgtgggg aggtgcacac tgaggagcct     76320
ctccttggag gtggagacac gtgcaccaca tggaccagga cacagtccac gaagcctcgc    76380
atccccctga gctgcagctc aagggcctct ctctgagccc agagtccacc cctgggagg     76440 cagctgcccc agctctgagg gaggagggca tccaccaggc cctccatctc ctgggggcac    76500
cagcccagcc cagaggctct gcaggactct gcacctccaa ttcatggcca ggactttctg    76560
```

| | | | | | |
|---|---|---|---|---|---|
| gatgtatctt | aaggactgag | gactccacat | cagggaccac | acaagaccgg | ggtcccggac | 76620 |
| acggggttg | ggggtgagca | tgtcaccggg | atgggctgtg | gcgtcactct | ggtacttcat | 76680 |
| ccggacagcc | agggaccaaa | gccacgccct | cagccccacc | ccaccctgc | ctcacatggc | 76740 |
| aacgcagggt | ctgcagatgc | aggagagtga | aagcatggt | agccaggcag | actagaggac | 76800 |
| ccgagctggg | gttgagcacc | tccctgtcta | cccagggcat | ggcctgtgag | actgcaggtg | 76860 |
| gcctagtgtg | tgctgcaggc | tcaaggtcct | gccccaggga | gcatgacatt | caggcccaga | 76920 |
| aattgcatcg | tgctgcacac | agtccaaggg | gataaccctg | tgaagttcag | gtcaccagca | 76980 |
| ggcttgggt | caagaccgag | ctgcagagga | caggtttctg | gaaggcacag | catcatgggt | 77040 |
| ggagggactt | ggagcaaggt | ccttagcccc | gggaccagtg | aatgtgtgcc | cttataggga | 77100 |
| aaggggtct | gtgcagaagc | aagttagctg | aaaatcatga | agtggagagg | ctcccctgga | 77160 |
| ttaaaggggt | gagccctaat | gtaatcacaa | gtgtccttct | aggaggttgg | cagagggaga | 77220 |
| ctgacataga | cagaagccag | gtgaggtggg | aagcggaggc | agaggccgag | agagcagacg | 77280 |
| ctacgccctg | gccctgaaga | cggaggagga | gccgagagct | cagggatgga | gagactggag | 77340 |
| gaggcaggga | agttctcccc | gcaagcctgg | agggagcatg | gcctccagca | ccccagacc | 77400 |
| ttggccctgc | aggattcatc | tggacctgtg | gtataaatgg | tgtttaagcc | actgggctgt | 77460 |
| gcaaattgtc | atagcagcca | tggcgcattc | ctagagggag | ccctggtggg | gacccagcag | 77520 |
| gcagcgacgg | ggccctcaca | agcctgtgag | ccactcagag | ccgcgagagt | ggctaggctt | 77580 |
| ggtgaggtgc | aggccacgcg | cacctccact | aaggcagcct | tagggcccac | acttcctctc | 77640 |
| tctctctctc | tctctctatc | tctctccctc | cctccttccc | tccctcccgc | tctcttggtt | 77700 |
| ggacagctct | ccatcatccc | cctggacatg | accacctccc | aaggccgagc | tggggcgctt | 77760 |
| tgctcgaggt | gagcactgac | atcctggggg | tgtgagggc | acctgcccag | cggccccgtg | 77820 |
| tgcaggatgg | gcggtgggcc | ctagctggca | ctgggcatat | ggcccggctg | gtgcctgcag | 77880 |
| gctgcagctt | ttctggggtg | gctgggatca | gtgaaggcct | ccagagtctg | ggcctgggat | 77940 |
| ccctgcagtg | ctggctgagg | acaggcgggg | ctgggcagtg | agggcactgg | gtcactatca | 78000 |
| ccacccacgg | tttattactt | cactaggtgg | gacctggcac | ccctgccttc | ctgacaccct | 78060 |
| ggaatccctg | cctcctccta | cagccccaa | gcccatctcc | ctcagagcct | ccagagacag | 78120 |
| acctggggag | gcatttcttc | tgcccccagc | agaagcccgg | gaggccggga | aggcacagtg | 78180 |
| ggtctaaagg | agaggatccc | aggactgcct | gaggggtgac | tccgacgagg | caagcataga | 78240 |
| gcccactgag | aagcggggtg | ggagcccac | cagggatggg | ctagttcctc | atgaaggacc | 78300 |
| aggacccagg | aaggacaagg | gggcctgctg | gggcagggtc | tgctatgccg | gagtccctgt | 78360 |
| gagcctggcc | cagacctgcc | tctctcttt | ctcattggtc | cccacaggtc | cgtggtggtt | 78420 |
| gccgtatcgg | gaggcccat | ggtggcaggg | gtgggacacc | tggtatacgt | cgccaggtgt | 78480 |
| gtccaatagg | ctcatgctca | caccttctcc | tggcacctgg | gcaaagcctg | agcacccagg | 78540 |
| cactgaagtg | agggcaaggc | ctcggggccc | cacaggatgg | ccgaggagac | agctgcaggg | 78600 |
| cgcctgggac | ccctgggctc | aggaggtaga | aggatacagc | ctgaaaaccc | acaccacaag | 78660 |
| ctcaccggcc | agtgcaggcc | cacagagctc | gaggaggcag | ccctgagcct | cccagggaga | 78720 |
| gatgctctgt | gcacgccggc | acaggccctg | ggttacaaac | cctaggcaca | gcccaggaga | 78780 |
| ggcccaggcc | ccagtccagc | aagggggttgc | aggaagcaag | aggtccccgg | ccacagcatg | 78840 |
| agataagccc | atcaagccag | ggccaggtgg | gcaatgggag | gcaggcaggg | cttgggggtg | 78900 |

```
agtccctgct gcagcgccgt ccactgtcga ccggaggagt ttcttccctg tgcggagtcc   78960
acgggcctcc tgtgagtgtg tgcatgggca caagtgtgtg tgtggctctg ctgtgtgtct   79020
gtacacacat atgttttggg ttttttttgtg tctcagacca cagagtctgc ccctcccacc   79080
aaagcccagg cagaaggatg aacccacgcc cctggggccc aggcctcagc agcctctgcg   79140
ggatcattgt tcccagttgt cacttgcctt tgccacagcc ctatttctcc acaattcctt   79200
aaagtcctca acatgcattt aaggcacaaa ggtgaaactg cccagaaaca tctgactccg   79260
ccgtggaacc caggagcaag ctgggttagc taaggagcgg ggccgttggc agaggctggg   79320
gatccaggct gaactttgga ggaggcatgt cccagcatgg gctcctgact atgtcctcct   79380
gggacaaacc caaacccgct ctttgaatat gggagggact ttgctggccc cggccctgac   79440
cgcagcactt ggaaactgag gagtggtcgc ctcctccgtg tcacagctgc ccgttcacca   79500
tcatagaagc aactctgtca cctccatggg cccctctgtg gctgctgcct gggtccaagc   79560
tgagcccagc tgcccaggcc cagaaggaaa gccaggcca ggtgcccagc acagaggcag   79620
tcacataccc cggggagagc cacagcaagc agccaatatt gcccaggaga ggagtagctg   79680
acaaggcaga acgtgagctg ccatcggctc gagaggcttt gctggtcctc ctggggctct   79740
ggacatgacc aggaggagcg agggaagaag tcgcatggtg gtcccatcct gggtggggcc   79800
tgatggcagc tggccacccg tcccagagtg gcagccagat gccagcgcca ttcccacagt   79860
cacatcattg gtcacagaat gcaggacata gagtgtcttc tttccatcac agtgctgtcc   79920
agacccatag cctagggtag acctggaaga ttcaatgtcc acaccggggg ctggagcgta   79980
gccatgagcc acgccccctg cccgtgcatg gaaagccagc ccaagctctg ctccatccct   80040
agccaaagtc agtgtccttt cccttctcc caagtgagct ctagccacct gcctaccctg   80100
ccatctgagg atgacagcct tcattccatt ggaacctggc tctgccacca gcaggcttgc   80160
agtcctgggc agactccgtc acctctctat gcctcagcct ttccatctgc acaggaggaa   80220
gatgatgatg gtggtgatga tgatggcgat ggtttccttt tgcatctgag gcaaggacta   80280
attgagatga tacacatcag gcactgggta tggtgctggt ccttcctgag cactcaatct   80340
atgtgagctg tccttgtgaa atgggtgtca ccacatttcc ccacgcagaa catcctttgt   80400
ctgccatact tgaaacgtct gccccaatac taacagctcc tcatggaaga tgtgcacacc   80460
cacccaccct catactccca aaggtgcccg tgctttatca agccaaagtc cagccaggaa   80520
ctttacagca gcatcccttt ccctctccaa gcaccaagga gcaaggcaaa gcactacatc   80580
ttccatctgg aggcaatgcc accctcttct cccattttca ctgccatccc taagaggcag   80640
tgcttcccca aaaggttcca tagcagcctg cctacagcaa ctctgttcac acgagtttca   80700
gcatccttgc agtggctccc ctgccatgct gtggctcttc attcaccctc ttctcctgct   80760
ccccgtgaca ggcatagatt ctgagtgatc tggatacatt gctttgttta ataacattac   80820
agcttctgtg ctgaaaaaga tacagcagat agagaaggca attgttgaac acaaaatagt   80880
gacagcagag atgacggcaa gttggcattt ttctttttcta gcaataaaac ttaaagctga   80940
ctcaaggaga aatggaaatc ataattggaa cagtaatcct caagaaagca ttaagattat   81000
taaataattg ccctcacaga tgacttcagg ccaagatggc tttatgggtg aagtttagac   81060
tttcacaaaa ctaatcagtt cccataagaa ctgctccagg atttggagga acatgggaaa   81120
gtctattaaa gggatcacaa ttcacagtcc ccagagtaaa acatgggcta acttgcattt   81180
tggcaaagag ccaaatgtta taatgacat cctagaaggc caaattctgt ccatctcgtt   81240
gaacaaggac ttacaccagg aatttagaac tatttatagc tcatcccacc actcaggcca   81300
```

```
atgatgaccc atgatcatct caccagaaat ggaaagactc agatgattaa tagagtctca   81360
atttctctga gacatctaag agcccagccc aagcccagac ccaggagggc acccaggcct   81420
ggacagagaa cactgatatc acaccagccc tccagaggga agcagagact ccttcaagct   81480
ctggaaacac aggcccagac agctgcccaa agttgggcag gcttcactgc aaacccaaat   81540
catgaagcta ggtaacacct ttacagattc tttacattta aaaatcatca aaacaagagt   81600
aaataataaa ctcaaataat attaatctaa tatgtaaagg tcttgtacca ttattatgca   81660
aacaacatac ataagctaat aagaaaaaga acaaatccct taagaaatcg gcaaaaagga   81720
tataacacaa tttctaaaag aaaacaaatg gctagcacac ataaggaaaa cactttgtga   81780
acagacattc ttcagaacat tatttataat tataaaatag ttgaaagcaa gatagtgcct   81840
gaagaaatta tggtgcatac attagtggga ctattctgca aacattccca attatacttg   81900
tcacatatct gtgataacgt gacagccagc attcatgggg tgacctcatt tggtaaaagg   81960
gtgcaaagct caacacgcat tgtgagatga ctgtggtgta aaattagtgg gattattccg   82020
caaacattcc caattatact taccgcatat ctgtgataac atgacagcat tcatggggtg   82080
acctcatttg gtaaagggt gcaaagctca acacgcattg tgagatgact ggtgtaaata   82140
caaagaccaa actgtgaaaa ggagtccatc aattaatcga tgcttacctt cagttttggg   82200
ctaattttta aagtatgcta taagcatatg ctcctgttat aacagaatgg agggattatg   82260
agagatgatg caggtgtgtc ctgggcctcc cctggcccac tgggccctag agatgccttc   82320
ccaggcatcg ctgtcagggc ttccctcaga gggagtcctg tattgacctc accaccaagg   82380
tctggagcag gggatcctta gatattggtt ggggttatct caccttaggt ctgaatatgg   82440
ggttgtctta gactgttttg tgctgttaga atagaatacc caagactggg aaatttatac   82500
tgaacggaaa tttatttctc acagttctag aggctgtgaa gtccaagagc acaggtgcca   82560
gagcaagtcc aagagcaagg gaaagtccaa agcaagtcca ggagcatctg gcgaggacct   82620
tcttgctgtg tcatcacatg gcggaaggca agaaagagag caagaggggg ccgaactcac   82680 cctttttataa cagcaccaat cccacccatg aggtggggac cttatgacct aatcactctt   82740
catactgtta caatggcaat gaaatttcaa catgagtttt ggaggagaga agcattcaaa   82800
ccacagcaag ggtgctccta cctcctctct cagggcatct gcagaaagag ctgcaactgc   82860
acgtccttcc tccgtccatc ctccatccct tcccaatgtc cgtgcatatc ctgtgaccca   82920
ggaggtctgg cataggggggt gctcctgcct taggtctgag gccctgtctg aagaggggta   82980
ggtgaggagg ccatctgatg gtctgggcca agacagtcac aggacgcatc atttatcatc   83040
aaggaggctg agggttgagt ctccaggtcc agggaactcc ccacaaagtg gaaccctgc   83100 ccagctccac acagcctctg ctgggggacc ctgctctggt gcagagcctg gggacaggtc   83160
ttgagctcag ccagagtctg cctccctgtc atttaggaac taaaccaagc ggcaggatgc   83220
tggagcccag ccccccatctg accttacagg gccaaggctg gggccctggg ttcccctcaa   83280
ggcgcagcag gactggagcc ccaggcagtg caggagtggc caaagctggg gcttcctcca   83340
gagcccccaa gcatcacggc accaagaagg gtaggaccct ggcctgagga attggcacca   83400 aagcccaga aactaccctg gacaccatgg agagaggcct ggaggggaag caccaggcac   83460
tgcctcccct tctgatccca cctgaggtgg ctgccaagcc cagagagccg ctctgatgtc   83520
ccccagccct gcagcccagg gatacctgta ctgtgcccct gggggacccc tggccagtct   83580
gtgcaaagaa gtcaccaccc tacactcaga gacagtgggg gtcctcgtcc cacatcctca   83640
```

```
gagcatggcc cggctgctgc agggatggtc tcctggtcct cagagcatgg cccggctgct   83700
gcagggatgg tctcctggtc ctcagagcat ggcccagctg ctgcaggat  ggtctcctgg   83760 aggcccccca gtgctctatt gtcagggctc cctccacccc ccgcaccaa  gagagagcca   83820 gaccccagca aggcttccag tggcttcagg tcacacccct aggctgaccc cagccccatt   83880
aacacctgcc tgagaaagct ccacgcacca gaactgaccg tctgctccaa ctcttgacct   83940
cccgttctca gggcgtctgc tgaaaaggct gcaactgcac atccttcctc cgtccgttcc   84000
cgatgtccgt gtgtctcctg tggccaggaa ggtctttctc gggacctgag agccgctccc   84060
tgaagtgtcc ccattgggaa ggatggggcc tgtgtctcca ggctctggga ggacagaatc   84120
ctgacctcaa cagtggccgg cacggacaca actggcccca tcccggggac gctgaccagc   84180
gctgggcaac ttttcccttc cccgacgact gagccccgag cacctcccct gctcccctac   84240
cacctccctt tacaaggctg tggcctctgc acagatgata atggagcttg gctcattccc   84300
ctagagtcgg tagggagtta aggacaaaac tcagtttcct ccacctgaac tcaagtctgc   84360
ctatgtttac ctaatcacac ctggtggaca gtttggacaa acttgcacac tcagagacac   84420
agacacttct agaaatcatt atctcccctgc cccggggacc ccactccagc agaagtctgc   84480
taggcactgg cctgggccct cctgctgtcc taggaggctg ctgacctcct gcctggctcc   84540
tgtccccagg tccagagtca gagcagactc cagggacgct gcaggctagg aagccgcccc   84600
ctccaggcca gggtctagtg caggtgccca ggacaagaaa gattgtgaat gcaggaatga   84660
ctgggccaca cccctcccgt gcacgccccc tcttgccctg caccccacag cccagccccc   84720
cgtgctggat gcccccccac agcagaggtg ctgttctgtg atcccctggg aaagacgccc   84780
tcaacctcca ccctgtccca cggcccaagg aagacaagac acaggccctc tcctcacagt   84840
ctccccacct ggctcctgct gggacccctca aggtgtgaac agggaggatg gttgtctggg   84900
tggcccctag gagcccagat cttcactcta cagaccccaa cccaagcacc cccttctgca   84960
gggcccagct catcccccct ctcctccctc tgctctcctc tcgtcgcctc tacgggaaat   85020
ccgggactca gcagtaaccc tcaggaagca gggcccaggc gccgtttaat aggaggcttc   85080
ctcacaatga aacttttaga aagccttgac tacaatgatg accttggtgt ggctgtgaac   85140
actgtcagct cccacagctg ctgcagcaaa aaatgtccat agacagggtg ggggcccggg   85200
gtcgtctgct gtcctgctca gcccacagca cgcatggagg atctgaggtg ccacacctga   85260
cgcccaggcc agaacatgcc tccctccagg gtgacctgcc atgtcctgca ttgctggagg   85320
gacaggggca gcctatgagg atctggggcc aggagatgaa tcctattaac ccagaggaaa   85380
actaacagga cccaagcacc ctccccgttg aagctgacct gcccagaggg gcctgggccc   85440
accccacaca ccggggcgga atgtgtacag gcccggtct  ctgtgggtgt tccgctaact   85500
ggggctccca gtgctcaccc cacaactaaa gcgagcccca gcctccagag cccccgaagg   85560
agatgccgcc cacaagccca gcccccatcc aggaggcccc agagctcagg gcgccggggc   85620
agattctgaa cagccccgag tcacggtggg tacaactgga acgaccaccg tgagaaaaac   85680
tgtgtccaaa actgtctcct ggccctgct  ggaggccgcg ccagagaggg gagcagccgc   85740
cccgaaccta ggtcctgctc agctcacacg accccccagca cccagagcac aacgagtcc   85800 ccattgaatg gtgaggacgg ggaccagggc tccagggggt catggaaggg gctggacccc   85860
atcctactgc tatggtccca gtgctcctgg ccagaactga ccctaccacc gacaagagtc   85920
cctcagggaa acggggtca  ctggcacctc ccagcatcaa cccaggcag  cacaggcata   85980 aaccccacat ccagagccga ctccaggagc agagacaccc cagtaccctg ggggacaccg   86040
```

```
accctgatga ctcccccactg gaatccaccc cagagtccac caggaccaaa gacccccgccc   86100 ctgtctctgt ccctcactca ggacctgctg cggggcgggc catgagacca gactcgggct   86160
tagggaacac cactgtggcc ccaacctcga ccaggccaca ggcccttcct tcctgccctg   86220
cggcagcaca gactttgggg tctgtgcaga gaggaatcac agaggcccca ggctgaggtg   86280 gtggggtgg aagacccca ggaggtggcc cacttccctt cctcccagct ggaacccacc   86340
atgaccttct taagataggg gtgtcatccg aggcaggtcc tccatggagc tcccttcagg   86400
ctcctccccg gtcctcacta ggcctcagtc ccggctgcgg gaatgcagcc accacaggca   86460
caccaggcag cccagaccca gccagcctgc agtgcccaag cccacattct ggagcagagc   86520
aggctgtgtc tgggagagtc tgggctcccc accgccccccc cgcacacccc acccacccct   86580
gtccaggccc tatgcaggag ggtcagagcc cccatgggg tatggactta gggtctcact   86640
cacgtggctc ccctcctggg tgaaggggtc tcatgcccag atccccacag cagagctggt   86700
caaaggtgga ggcagtggcc ccagggccac cctgacctgg accctcaggc tcctctagcc   86760
ctggctgccc tgctgtccct gggaggcctg gactccacca gaccacaggt ccagggcacc   86820
gcccataggt gctgcccaca ctcagttcac aggaagaaga taagctccag accccccaaga  86880 ctgggacctg ccttcctgcc accgcttgta gctccagacc tccgtgcctc ccccgaccac   86940
ttacacacgg gccaggggagc tgttccacaa agatcaaccc caaaccggga ccgcctggca   87000
ctcgggccgc tgccacttcc ctctccattt gttcccagca cctctgtgct ccctccctcc   87060
tccctccttc aggggaacag cctgtgcagc ccctccctgc accccacacc ctggggaggc   87120
ccaaccctgc ctccagccct ttctcccccg ctgctcttcc tgcccatcca gacaaccctg   87180
gggtcccatc cctgcagcct acaccctggt ctccacccag acccctgtct ctccctccag   87240
acacccctcc caggccaacc ctgcacatgc aggccctccc cttttctgct gccagagcct   87300
cagtttctac cctctgtgcc taccccctgc ctcctcctgc ccacaactcg agctcttcct   87360
ctcctggggc ccctgagcca tggcactgac cgtgcactcc caccccaca ctgcccatgc    87420 cctcaccttc ctcctggaca ctctgacccc gctcccctct tggacccagc cctggtattt   87480
ccaggacaaa ggctcaccca agtcttcccc atgcaggccc ttgccctcac tgcccggtta   87540
cacggcagcc tcctgtgcac agaagcaggg agctcagccc ttccacaggc agaaggcact   87600
gaaagaaatc ggcctccagc accctgatgc acgtccgcct gtgtctctca ctgcccgcac   87660
ctgcagggag gctcggcact ccctgtaaag acgagggatc caggcagcaa catcatggga   87720
gaatgcaggg ctcccagaca gcccagccct ctcgcaggcc tctcctggga agagacctgc   87780
agccaccact gaacagccac ggagcccgct ggatagtaac tgagtcagtg accgacctgg   87840
agggcagggg agcagtgaac cggagcccag accatagggga cagagaccag ccgctgacat   87900
cccgagcccc tcactggcgg ccccagaaca ccgcgtggaa acagaacaga cccacattcc   87960
cacctggaac agggcagaca ctgctgagcc cccagcacca gccctgagaa acaccaggca   88020
acggcatcag agggggctcc tgagaaagaa aggaggggag gtctccttca ccagcaagta   88080
cttcccttga ccaaaaacag ggtccacgca actcccccag acaaaggag gagcccctg    88140 tacagcactg gctcagagt cctctcccac acacctgag tttcagacaa aaaccccctg    88200
gaaatcatag tatcagcagg agaactagcc agagacagca agaggggact cagtgactcc   88260
cgcggggaca ggaggatttt gtgggggctc gtgtcactgt gaggatattg tagtagtacc   88320
agctgctata cccacagtga cacagcccca ttcccaaagc cctgctgtaa acgcttccac   88380
```

-continued

| | |
|---|---|
| ttctggagct gaggggctgg ggggagcgtc tgggaagtag ggcctagggg tggccatcaa | 88440 |
| tgcccaaaac gcaccagact cccccccaga catcacccca ctggccagtg agcagagtaa | 88500 |
| acagaaaatg agaagcagct gggaagcttg cacaggcccc aaggaaagag ctttggcggg | 88560 |
| tgtgcaagag gggatgcggg cagagcctga gcagggcctt ttgctgtttc tgctttcctg | 88620 |
| tgcagatagt tccataaact ggtgttcaag atcgatggct gggagtgagc ccaggaggac | 88680 |
| agtgtgggaa gggcacaggg aaggagaagc agccgctatc ctacactgtc atctttcaag | 88740 |
| agtttgccct gtgcccacaa tgctgcatca tgggatgctt aacagctgat gtagacacag | 88800 |
| ctaaagagag aatcagtgaa atggatttgc agcacagatc tgaataaatt ctccagaatg | 88860 |
| tggagccaca cagaagcaag cacaaggaaa gtgcctgatg caagggcaaa gtacagtgtg | 88920 |
| taccttcagg ctgggcacag acactctgaa aagccttggc aggaactccc tgcaacaaag | 88980 |
| cagagccctg caggcaatgc cagctccaga gccctccctg agagcctcat gggcaaagat | 89040 |
| gtgcacaaca ggtgtttctc atagcccaa actgagaatg aagcaaacag ccatctgaag | 89100 |
| gaaaacaggc aaataaacga tggcaggttc atgaaatgca aacccagaca gccagaagga | 89160 |
| caacagtgag ggttacaggt gactctgtgg ttgagttcat gacaatgctg agtaattgga | 89220 |
| gtaacaaagg aaagtccaaa aaatactttc aatgtgattt cttctaaata aaatttacag | 89280 |
| ccggcaaaat gaactatctt cttaagggat aaactttcca ctaggaaaac tataaggaaa | 89340 |
| atcaagaaaa ggatgatcac ataaacacag tggtcgttac ttctactggg gaaggaagag | 89400 |
| ggtatgaact gagacacaca gggttggcaa gtctcctaac aagaacagaa caaatacatt | 89460 |
| acagtacctt gaaaacagca gttaaaattc taaattgcaa gaagaggaaa atgcacacag | 89520 |
| ctgtgtttag aaaattctca gtccagcact gttcataata gcaaagacat taacccaggt | 89580 |
| tggataaata aacgatgaca caggcaattg cacaatgata cagacataca ttcagtatat | 89640 |
| gagacattga tgatgtatcc ccaaagaaat gactttaaag agaaaaggcc tgatatgtgg | 89700 |
| tggcactcac ctccctgggc atccccggac aggctgcagg cacactgtgt ggcagggcag | 89760 |
| gctggtacct gctggcagct cctggggcct gatgtggagc aggcacagag ccgtatcccc | 89820 |
| ccgaggacat atacccccaa ggacggcaca gttggtacat tccggagaca agcaactcag | 89880 |
| ccacactccc aggccagagc ccgagaggga cgcccatgca cagggaggca gagcccagct | 89940 |
| cctccacagc cagcagcacc cgtgcagggg ccgccatctg gcaggcacag agcatgggct | 90000 |
| gggaggaggg gcagggacac caggcagggt tggcaccaac tgaaaattac agaagtctca | 90060 |
| tacatctacc tcagccttgc ctgacctggg cctcacctga cctggacctc acctggcctg | 90120 |
| gacctcacct ggcctagacc tcacctctgg gcttcacctg agctcggcct cacctgactt | 90180 |
| ggaccttgcc tgtcctgagc tcacatgatc tgggcctcac ctgacctggg tttcacctga | 90240 |
| cctgggcttc acctgacctg gcctcatct gacctgggcc tcactggcct ggacctcacc | 90300 |
| tggcctgggc ttcacctggc tcaggcctc atctgcacct gctccaggtc ttgctggaac | 90360 |
| ctcagtagca ctgaggctgc aggggctcat ccagggttgc agaatgactc tagaacctcc | 90420 |
| cacatctcag ctttctgggt ggaggcacct ggtggcccag ggaatataaa aagcctgaat | 90480 |
| gatgcctgcg tgatttgggg gcaatttata aacccaaaag gacatggcca tgcagcgggt | 90540 |
| agggacaata cagacagata tcagcctgaa atggagcctc agggcacagg tgggcacgga | 90600 |
| cactgtccac ctaagccagg ggcagacccg agtgtcccg cagtagacct gagagcgctg | 90660 |
| ggcccacagc ctcccctcgg tgcctgcta cctcctcagg tcagccctgg acatcccggg | 90720 |
| tttccccagg cctggcggta ggtttgggt gaggtctgtg tcactgtggt attacgattt | 90780 |

```
ttggagtggt tattataccc acagtgtcac agagtccatc aaaaacccat ccctgggaac    90840
cttctgccac agccctccct gtggggcacc gccgcgtgcc atgttaggat tttgactgag    90900
gacacagcac catgggtatg gtggctaccg cagcagtgca gcccgtgacc caaacacaca    90960
gggcagcagg cacaacagac aagcccacaa gtgaccaccc tgagctcctg cctgccagcc    91020
ctggagacca tgaaacagat ggccaggatt atcccatagg tcagccagac ctcagtccaa    91080
caggtctgca tcgctgctgc cctccaatac cagtccggat ggggacaggg ctggcccaca    91140
ttaccatttg ctgccatccg gccaacagtc ccagaagccc ctccctcaag gctgggccac    91200
atgtgtggac cctgagagcc ccccatgtct gagtaggggc accaggaagg tggggctggc    91260
cctgtgcact gtccctgccc ctgtggtccc tggcctgcct ggccctgaca cctgggcctc    91320
tcctgggtca tttccaagac agaagacatt cccaggacag ctggagctgg gagtccatca    91380
tcctgcctgg ccgtcctgag tcctgcgcct ttccaaacct cacccgggaa gccaacagag    91440
gaatcacctc ccacaggcag agacaaagac cttccagaaa tctctgtctc tctcccagt     91500
gggcaccctc ttccagggca gtcctcagtg atatcacagt gggaacccac atctggatcg    91560
ggactgcccc cagaacacaa gatggccac agggacagcc ccacagccca gcccttccca     91620
gaccccctaaa aggcgtccca cccctgcat ctgccccagg gctcaaactc caggaggact    91680
gactcctgca caccctcctg ccagacatca cctcagcccc tcctggaagg acaggagcg     91740
cgcaagggtg agtcagaccc tcctgccctc gatggcaggc ggagaagatt cagaaaggtc    91800
tgagatcccc aggacgcagc accactgtca atggggggccc cagacgcctg gaccagggcc    91860
tgcgtgggaa aggcctctgg gcacactcag gggcttttttg tgaagggtcc tcctactgtg   91920
tgactacagt aactaccaca gtgatgaacc cagcagcaaa aactgaccgg actcccaagg    91980
tttatgcaca cttctccgct cagagctctc caggatcaga agagccgggc ccaagggttt    92040
ctgcccagac cctcggcctc tagggacatc ttggccatga cagcccatgg gctggtgccc    92100
cacacatcgt ctgccttcaa acaagggctt cagagggctc tgaggtgacc tcactgatga    92160
ccacaggtgc cctggcccct tccccaccag ctgcaccaga ccccgtcatg acagatgccc    92220
cgattccaac agccaattcc tggggccagg aatcgctgta gacaccagcc tccttccaac    92280
acctcctgcc aattgcctgg attcccatcc cggttggaat caagaggaca gcatccccca    92340
ggctcccaac aggcaggact cccacaccct cctctgagag gccgctgtgt tccgtagggc    92400
caggctgcag acagtccccc tcacctgcca ctagacaaat gcctgctgta gatgtcccca    92460
cctggaaaat accactcatg gagccccag ccccaggtac agctgtagag agagtctctg      92520
aggcccctaa gaagtagcca tgcccagttc tgccgggacc ctcggccagg ctgacaggag    92580
tggacgctgg agctgggccc atactgggcc acataggagc tcaccagtga gggcaggaga    92640
gcacatgccg gggagcaccc agcctcctgc tgaccagagg cccgtcccag agcccaggag    92700
gctgcagagg cctctccagg gggacactgt gcatgtctgg tccctgagca gcccccacg     92760
tccccagtcc tgggggcccc tggcacagct gtctggaccc tctctattcc ctgggaagct    92820
cctcctgaca gccccgcctc cagttccagg tgtggttatt gtcagggggt gtcagactgt    92880
ggtggataca gctatggtta ccacagtggt gctgcccata gcagcaacca ggccaagtag    92940
acaggcccct gctgtgcagc cccaggcctc cagctcacct gcttctcctg gggctctcaa    93000
ggctgctgtt ttctgcactc tcccctctgt ggggagggtt ccctcagtgg gagatctgtt    93060
ctcaacatcc cacggcctca ttcctgcaag gaaggccaat ggatgggcaa cctcacatgc    93120
```

```
cgcggctaag atagggtggg cagcctggcg gggacaggac atcctgctgg ggtatctgtc    93180
actgtgccta gtggggcact ggctcccaaa caacgcagtc cttgccaaaa tccccacggc    93240
ctcccccgct aggggctggc ctgatctcct gcagtcctag gaggctgctg acctccagaa    93300
tggctccgtc cccagttcca gggcgagagc agatcccagg ccggctgcag actgggaggc    93360
caccccctcc ttcccagggt tcactgcagg tgaccagggc aggaaatggc ctgaacacag    93420
ggataaccgg gccatccccc aacagagtcc accccctcct gctctgtacc ccgcacccccc   93480 caggccagcc catgacatcc gacaacccca caccagagtc actgcccggt gctgccctag    93540
ggaggacccc tcagccccca ccctgtctag aggactgggg aggacaggac acgccctctc    93600
cttatggttc ccccacctgg ctctggctgg gacccttggg gtgtggacag aaaggacgct    93660
tgcctgattg gccccagga gcccagaact tctctccagg gacccagcc cgagcacccc      93720 cttacccagg acccagccct gcccctcctc ccctctgctc tcctctcatc acccatggg    93780 aatccagaat ccccaggaag ccatcaggaa gggctgaggg aggaagtggg gccactgcac    93840
caccaggcag gaggctctgt ctttgtgaac ccagggaggg gccagcctcc tagagggtat    93900
ggtccaccct gcctatggct cccacagtgg caggctgcag ggaaggacca gggacggtgt    93960
gggggagggc tcagggcccc gcgggtgctc catcttggat gagcctatct ctctcaccca    94020
cggactcgcc cacctcctct tcaccctggc cacacgtcgt ccacaccatc ctaagtccca    94080
cctacaccag agccggcaca gccagtgcag acagaggctg gggtgcaggg gggccgactg    94140
ggcagcttcg gggagggagg aatggaggaa ggggagttca gtgaagaggc cccctcccc    94200 tgggtccagg atcctcctct gggacccccg gatcccatcc cctccaggct ctgggaggag    94260
aagcaggatg ggagaatctg tgcgggaccc tctcacagtg gaatacctcc acagcggctc    94320
aggccagata caaaagcccc tcagtgagcc ctccactgca gtgctgggcc tgggggcagc    94380
cgctcccaca caggatgaac ccagcacccc gaggatgtcc tgccaggggg agctcagagc    94440
catgaaggag caggatatgg gaccccgat acaggcacag acctcagctc cattcaggac    94500
tgccacgtcc tgccctggga ggaaccccctt tctctagtcc ctgcaggcca ggaggcagct    94560
gactcctgac ttggacgcct attccagaca ccagacagag gggcaggccc cccagaacca    94620
gggatgagga cgccccgtca aggccagaaa agaccaagtt gcgctgagcc cagcaaggga    94680
aggtccccaa acaaaccagg aagtttctga aggtgtctgt gtcacagtgg agtatagcag    94740
ctcgtcccac agtgacactc gccaggccag aaaccccatc ccaagtcagc ggaatgcaga    94800
gagagcaggg aggacatgtt taggatctga ggccgcacct gacacccagg ccagcagacg    94860
tctcctgtcc acggcaccct gccatgtcct gcatttctgg aagaacaagg gcaggctgaa    94920
gggggtccag gaccaggaga tgggtccgct ctacccagag aaggagccag gcaggacaca    94980
agccccctcc ccattgaggc tgacctgccc agagggtcct gggcccaccc aacacaccgg    95040
ggcggaatgt gtgcaggcct cggtctctgt gggtgttccg ctagctgggg ctcacagtgc    95100
tcaccccaca cctaaaacga gccacagcct ccggagcccc tgaaggagac cccgcccaca    95160
agcccagccc ccacccagga ggccccagag cacagggcgc cccgtcggat tctgaacagc    95220
cccgagtcac agtgggtata actgaactac ccactgtgag aaaagcttcg tccaaaacgg    95280
tcctctggcc acagtcggag gccccgccag agagggggagc agccaccccca aacccatgtt   95340 ctgccggctc ccatgacccc gtgcacctgg agcccacgg tgtccccact ggatgggagg     95400
acaagggccg ggggctccgg cgggtcgggg caggggcttg atggcttcct tctgccgtgg    95460
ccccattgcc cctggctgga gttgacccctt ctgacaagtg tcctcagaga gtcagggatc   95520
```

| | | | | | |
|---|---|---|---|---|---|
| agtggcacct | cccaacatca | accccacgca | gcccaggcac | aaaccccaca | tccagggcca | 95580 |
| actccaggaa | cagagacacc | ccaataccct | gggggacccc | gaccctgatg | actcccgtcc | 95640 |
| catctctgtc | cctcacttgg | ggcctgctgc | ggggcgagca | cttgggagca | aactcaggct | 95700 |
| taggggacac | cactgtgggc | ctgacctcga | gcaggccaca | gacccttccc | tcctgccctg | 95760 |
| gtgcagcaca | gactttgggg | tctgggcagg | gaggaacttc | tggcaggtca | ccaagcacag | 95820 |
| agccccagg | ctgaggtggc | cccaggggga | accccagcag | gtggcccact | acccttcctc | 95880 |
| ccagctggac | cccatgtctt | ccccaagata | ggggtgccat | ccaaggcagg | tcctccatgg | 95940 |
| agccccttc | aggctcctct | ccagacccca | ctgggcctca | gtccccactc | taggaatgca | 96000 |
| gccaccacgg | gcacaccagg | cagcccaggc | ccagccaccc | tgcagtgccc | aagcccacac | 96060 |
| cctggaggag | agcagggtgc | gtctgggagg | ggctgggctc | cccaccccca | cccccacctg | 96120 |
| cacacccac | ccaccccttgc | ccgggccccc | tgcaggaggg | tcagagcccc | catgggatat | 96180 |
| ggacttaggg | tctcactcac | gcacctcccc | tcctgggaga | aggggtctca | tgcccagatc | 96240 |
| cccccagcag | cgctggtcac | aggtagaggc | agtggcccca | gggccaccct | gacctggccc | 96300 |
| ctcaggctcc | tctagccctg | gctgcccctgc | tgtccctggg | aggcctgggc | tccaccagac | 96360 |
| cacaggtcta | gggcaccgcc | cacactgggg | ccgcccacac | acagctcaca | ggaagaagat | 96420 |
| aagctccaga | cccccaggcc | cgggacctgc | cttgctgcta | cgacttcctg | ccccagacct | 96480 |
| cgttgccctc | ccccgtccac | ttacacacag | gccaggaagc | tgttcccaca | cagaccaacc | 96540 |
| ccagacgggg | accacctggc | actcaggtca | ctgccatttc | cttctccatt | cacttccaat | 96600 |
| gcctctgtgc | ttcctccctc | ctccttcctt | cgggggagca | ccctgtgcag | ctcctccctg | 96660 |
| cagtccacac | cctggggaga | cccgaccctg | cagcccacac | cctggggaga | cctgaccctc | 96720 |
| ctccagccct | ttctccccg | ctgctcttgc | cacccaccaa | gacagccctg | gggtcctgtc | 96780 |
| cctacagccc | ccacccagtt | ctctacctag | acccgtcttc | ctccctctaa | acacctctcc | 96840 |
| caggccaacc | ctacacctgc | aggccctccc | ctccactgcc | aaagaccctc | agtttctcct | 96900 |
| gcctgtgccc | accccgtgc | tcctcctgcc | cacagctcga | gctcttcctc | tcctagggcc | 96960 |
| cctgagggat | ggcattgacc | gtgccctcgc | acccacacac | tgcccatgcc | ctcacattcc | 97020 |
| tcctggccac | tccagcccca | ctcccctctc | aggcctggct | ctggtatttc | tgggacaaag | 97080 |
| ccttacccaa | gtctttccca | tgcaggcctg | ggcccttacc | ctcactgccc | ggttacaggg | 97140 |
| cagcctcctg | tgcacagaag | cagggagctc | agcccttcca | caggcagaag | gcactgaaag | 97200 |
| aaatcggcct | ccagcgcctt | gacacacgtc | tgcctgtgtc | tctcactgcc | cgcacctgca | 97260 |
| gggaggctcg | gcactccctc | taaagacgag | ggatccaggc | agcagcatca | caggagaatg | 97320 |
| cagggctacc | agacatccca | gtcctctcac | aggcctctcc | tgggaagaga | cctgaagacg | 97380 |
| cccagtcaac | ggagtctaac | accaaacctc | cctggaggcc | gatgggtagt | aacggagtca | 97440 |
| ttgccagacc | tggaggcagg | ggagcagtga | gcccgagccc | acaccatagg | gccagaggac | 97500 |
| agccactgac | atcccaagcc | actcactggt | ggtcccacaa | caccccatgg | aaagaggaca | 97560 |
| gacccacagt | cccacctgga | ccagggcaga | gactgctgag | acccagcacc | agaaccaacc | 97620 |
| aagaaacacc | aggcaacagc | atcagagggg | gctctgcgca | aacagaggag | gggaggtctc | 97680 |
| cttccaccagc | aggcgcttcc | cttgaccgaa | gacaggatcc | atgcaactcc | cccaggacaa | 97740 |
| aggaggagcc | ccttgttcag | cactgggctc | agagtcctct | ccaagacacc | cagagtttca | 97800 |
| gacaaaaacc | ccctggaatg | cacagtctca | gcaggagagc | cagccagagc | cagcaagatg | 97860 |

```
gggctcagtg acacccgcag ggacaggagg attttgtggg ggctcgtgtc actgtgagga    97920
tattgtacta atggtgtatg ctatacccac agtgacacag ccccattccc aaagccctac    97980
tgcaaacgca ttccacttct ggggctgagg ggctggggga gcgtctggga aatagggctc    98040
aggggtgtcc atcaatgccc aaaacgcacc agactcccct ccatacatca cacccaccag    98100
ccagcgagca gagtaaacag aaaatgagaa gcaagctggg gaagcttgca caggcccaa     98160
ggaaagagct ttggcgggtg tgtaagaggg gatgcgggca gagcctgagc agggcctttt    98220
gctgtttctg ctttcctgtg cagagagttc cataaactgg tgttcgagat caatggctgg    98280
gagtgagccc aggaggacag cgtgggaaga gcacagggaa ggaggagcag ccgctatcct    98340
acactgtcat ctttcgaaag tttgccttgt gcccacactg ctgcatcatg ggatgcttaa    98400
cagctgatgt agacacagct aaagagagaa tcagtgagat ggatttgcag cacagatctg    98460
aataaattct ccagaatgtg gagcagcaca gaagcaagca cacagaaagt gcctgatgca    98520
aggacaaagt tcagtgggca ccttcaggca ttgctgctgg gcacagacac tctgaaaagc    98580
cctggcagga actccctgtg acaaagcaga accctcaggc aatgccagcc ccagagccct    98640
ccctgagagc ctcatgggca aagatgtgca caacaggtgt ttctcatagc cccaaactga    98700
gagcaaagca aacgtccatc tgaaggagaa caggcaaata aacgatggca ggttcatgaa    98760
atgcaaaccc agacagccac aagcacaaaa gtacagggtt ataagcgact ctggttgagt    98820
tcatgacaat gctgagtaat tggagtaaca agtaaactc  caaaaaatac tttcaatgtg    98880
atttcttcta aataaaattt acaccctgca aaatgaactg tcttcttaag ggatacattt    98940
cccagttaga aaaccataaa gaaaccaag  aaaaggatga tcacataaac acagtggtgg    99000
ttacttctgc tggggaagga agagggtatg aactgagata cacagggtgg gcaagtctcc    99060
taacaagaac agaacgaata cattacagta ccttgaaaac agcagttaaa cttctaaatt    99120
gcaagaagag gaaatgcac  acagttgtgt ttagaaaatt ctcagtccag cactgttcat    99180
aatagcaaag acattaaccc aggtcggata aataagcgat gacacaggca attgcacaat    99240
gatacagaca tatatttagt atatgagaca tcgatgatgt atccccaaat aaacgacttt    99300
aaagagataa agggctgatg tgtggtggca ttcacctccc tgggatcccc ggacaggttg    99360
caggctcact gtgcagcagg gcaggcgggt acctgctggc agttcctggg gcctgatgtg    99420
gagcaagcgc agggccatat atcccggagg acggcacagt cagtgaattc cagagagaag    99480
caactcagcc acactcccca ggcagagccc gagagggacg cccacgcaca gggaggcaga    99540
gcccagcacc tccgcagcca gcaccacctg cgcacgggcc accaccttgc aggcacagag    99600
tgggtgctga gaggaggggc agggacacca ggcagggtga gcacccagag aaaactgcag    99660
acgcctcaca catccacctc agcctcccct gacctggacc tcactggcct gggcctcact    99720
taacctgggc ttcacctgac cttggcctca cctgacttgg acctcgcctg tcccaagctt    99780
tacctgacct gggcctcaac tcacctgaac gtctcctgac ctgggtttaa cctgtcctgg    99840
aactcacctg gccttggctt cccctgacct ggacctcatc tggcctgggc ttcacctggc    99900
ctgggcctca cctgacctgg acctcatctg gcctggacct cacctggcct ggacttcacc    99960
tggcctgggc ttcacctgac ctggacctca cctggcctcg gcctcacct  gcacctgctc   100020
caggtcttgc tggagcctga gtagcactga gggtgcagaa gctcatccag ggttggggaa   100080
tgactctaga agtctcccac atctgacctt tctgggtgga ggcagctggt ggccctggga   100140
atataaaaat ctccagaatg atgactctgt gatttgtggg caacttatga acccgaaagg   100200
acatggccat ggggtgggta gggacatagg gacagatgcc agcctgaggt ggagcctcag   100260
```

-continued

```
gacacaggtg ggcacggaca ctatccacat aagcgaggga tagacccgag tgtccccaca  100320
gcagacctga gagcgctggg cccacagcct cccctcagag ccctgctgcc tcctccggtc  100380
agccctggac atcccaggtt tccccaggcc tggcggtagg tttagaatga ggtctgtgtc  100440
actgtggtat tacgatattt tgactggtta ttataaccac agtgtcacag agtccatcaa  100500
aaacccatgc ctggaagctt cccgccacag ccctccccat ggggccctgc tgcctcctca  100560
ggtcagcccc ggacatcccg ggtttcccca ggctgggcgg taggtttggg gtgaggtctg  100620
tgtcactgtg gtattactat ggttcgggga gttattataa ccacagtgtc acagagtcca  100680
tcaaaaaccc atccctggga gcctcccgcc acagccctcc ctgcagggga ccggtacgtg  100740
ccatgttagg attttgatcg aggagacagc accatgggta tggtggctac cacagcagtg  100800
cagcctgtga cccaaacccg cagggcagca ggcacgatgg acaggcccgt gactgaccac  100860
gctgggctcc agcctgccag ccctggagat catgaaacag atggccaagg tcaccctaca  100920
ggtcatccag atctggctcc gaggggtctg catcgctgct gccctcccaa cgccagtcca  100980
aatgggacag ggacggcctc acagcaccat ctgctgccat caggccagcg atcccagaag  101040
cccctccctc aaggctgggc acatgtgtgg acactgagag ccctcatatc tgagtagggg  101100
caccaggagg gaggggctgg ccctgtgcac tgtccctgcc cctgtggtcc ctggcctgcc  101160
tggccctgac acctgagcct ctcctgggtc atttccaaga cagaagacat tcctggggac  101220
agccggagct gggcgtcgct catcctgccc ggccgtcctg agtcctgctc atttccagac  101280
ctcaccgggg aagccaacag aggactcgcc tcccacattc agagacaaag aaccttccag  101340
aaatccctgc ctctctcccc agtggacacc ctcttccagg acagtcctca gtggcatcac  101400
agcggcctga gatccccagg acgcagcacc gctgtcaata ggggccccaa atgcctggac  101460
cagggcctgc gtgggaaagg cctctggcca cactcgggct ttttgtgaag ggccctcctg  101520
ctgtgtgact acagtaacta ccatagtgat gaacccagtg gcaaaaactg gctggaaacc  101580
caggggctgt gtgcacgcct cagcttggag ctctccagga gcacaagagc cgggcccaag  101640
gatttgtgcc cagaccctca gcctctaggg acacctgggt catctcagcc tgggctggtg  101700
ccctgcacac catcttcctc caaatagggg cttcagaggg ctctgaggtg acctcactca  101760
tgaccacagg tgacctggcc cttccctgcc agctatacca gaccctgtct tgacagatgc  101820
cccgattcca acagccaatt cctgggaccc tgaatagctg tagacaccag cctcattcca  101880
gtacctcctg ccaattgcct ggattcccat cctggctgga atcaagaagg cagcatccgc  101940
caggctccca acaggcagga ctcccgcaca ccctcctctg agaggccgct gtgttccgca  102000
gggccaggcc ctggacagtt cccctcacct gccactagag aaacacctgc cattgtcgtc  102060
cccacctgga aaagaccact cgtggagccc ccagccccag gtacagctgt agagacagtc  102120
ctcgaggccc ctaagaagga gccatgccca gttctgccgg gaccctcggc caggccgaca  102180
ggagtggacg ctggagctgg gcccacactg gccacatag gagctcacca gtgagggcag  102240
gagagcacat gccggggagc acccagcctc ctgctgacca gaggcccgtc ccagagccca  102300
ggaggctgca gaggcctctc cagggagaca ctgtgcatgt ctggtaccta agcagccccc  102360
cacgtcccca gtcctggggg cccctggctc agctgtctgg gccctccctg ctccctggga  102420
agctcctcct gacagccccg cctccagttc caggtgtggt tattgtcagg cgatgtcaga  102480
ctgtggtgga tatagtggct acgattacca cagtggtgcc gcccatagca gcaaccaggc  102540
caagtagaca ggcccctgct gcgcagcccc aggcatccac ttcacctgct tctcctgggg  102600
```

```
ctctcaaggc tgctgtctgt cctctggccc tctgtgggga gggttccctc agtgggaggt    102660
ctgtgctcca gggcagggat gattgagata gaaatcaaag gctggcaggg aaaggcagct    102720
tcccgccctg agaggtgcag gcagcaccac ggagccacgg agtcacagag ccacggagcc    102780
cccattgtgg gcatttgaga gtgctgtgcc cccggcaggc ccagccctga tggggaagcc    102840
tgtcccatcc cacagcccgg gtcccacggg cagcgggcac agaagctgcc aggttgtcct    102900
ctatgatcct catccctcca gcagcatccc ctccacagtg gggaaactga ggcttggagc    102960
accacccggc cccctggaaa tgaggctgtg agcccagaca gtgggcccag agcactgtga    103020
gtacccggc agtacctggc tgcagggatc agccagagat gccaaaccct gagtgaccag     103080
cctacaggag gatccggccc cacccaggcc actcgattaa tgctcaaccc cctgccctgg    103140
agacctcttc cagtaccacc agcagctcag cttctcaggg cctcatccct gcaaggaagg    103200
tcaagggctg ggcctgccag aaacacagca ccctccctag ccctggctaa gacagggtgg    103260
gcagacggct gtggacggga catattgctg gggcatttct cactgtcact tctgggtggt    103320
agctctgaca aaaacgcaga ccctgccaaa atccccactg cctcccgcta ggggctggcc    103380
tggaatcctg ctgtcctagg aggctgctga cctccaggat ggctccgtcc ccagttccag    103440
ggcgagagca gatcccaggc aggctgtagg ctgggaggcc acccctgccc ttgccggggt    103500
tgaatgcagg tgcccaaggc aggaaatggc atgagcacag ggatgaccgg gacatgcccc    103560
accagagtgc gcccttcct gctctgcacc ctgcacccc caggccagcc cacgacgtcc      103620
aacaactggg cctgggtggc agccccaccc agacaggaca gacccagcac cctgaggagg    103680
tcctgccagg gggagctaag agccatgaag gagcaagata tggggccccc gatacaggca    103740
cagatgtcag ctccatccag gaccacccag cccacaccct gagaggaacg tctgtctcca    103800
gcctctgcag gtcgggaggc agctgacccc tgacttggac ccctattcca gacaccagac    103860
agaggcgcag gccccccaga accagggttg agggacgccc cgtcaaagcc agacaaaacc    103920
aaggggtgtt gagcccagca agggaaggcc cccaaacaga ccaggaggtt tctgaaggtg    103980
tctgtgtcac agtggggtat agcagcagct ggtaccacag tgacactcac ccagccagaa    104040
accccattcc aagtcagcgg aagcagagag agcaggagg acacgtttag gatctgagac     104100
tgcacctgac acccaggcca gcagacgtct cccctccagg gcaccccacc ctgtcctgca    104160
tttctgcaag atcaggggcg gcctgagggg gggtctaggg tgaggagatg ggtcccctgt    104220
acaccaagga ggagttaggc aggtcccgag cactctcccc attgaggctg acctgcccag    104280
agagtcctgg gcccacccca cacccgggg cggaatgtgt gcaggcctcg gtctctgtgg     104340
gtgttccgct agctggggct cacagtgctc accccacacc taaaatgagc cacagcctcc    104400
ggagcccccg caggagaccc cgcccacaag cccagccccc acccaggagg ccccagagct    104460
cagggcgccc cgtcggattc cgaacagccc cgagtcacag cgggtataac cggaaccacc    104520
actgtcagaa tagctacgtc aaaaactgtc cagtggccac tgccggaggc cccgccagag    104580
agggcagcag ccactctgat cccatgtcct gccggctccc atgaccccca gcacgcggag    104640
ccccacagtg tccccactgg atgggaggac aagagctggg gattccggcg ggtcggggca    104700
ggggcttgat cgcatccttc tgccgtggct ccagtgcccc tggctggagt tgacccttct    104760
gacaagtgtc ctcagagaga caggcatcac cggcgcctcc caacatcaac cccaggcagc    104820
acaggcacaa accccacatc cagagccaac tccaggagca gagacacccc aatccctgg    104880
gggacccga ccctgatgac ttcccactgg aattcgccgt agagtccacc aggaccaaag     104940
accctgcctc tgcctctgtc cctcactcag gacctgctgc cgggcgaggc cttgggagca    105000
```

```
gacttgggct tagggdacac cagtgtgacc ccgaccttga ccaggacgca gacctttcct  105060
tcctttcctg gggcagcaca gactttgggg tctgggccag gaggaacttc tggcaggtcg  105120
ccaagcacag aggccacagg ctgaggtggc cctggaaaga cctccaggag gtggccactc  105180
cccttcctcc cagctggacc ccatgtcctc cccaagataa gggtgccatc caaggcaggt  105240
gctccttgga gccccattca gactcctccc tggaccccac tgggcctcag tcccagctct  105300
ggggatgaag ccaccacaag caccaggc agcccaggcc cagccaccct gcagtgccca    105360
agcacacact ctggagcaga gcagggtgcc tcgggaggg gctgagctcc ccaccccacc   105420
cccacctgca caccccaccc acccctgccc agcggctctg caggagggtc agagcccac    105480
atggggtatg gacttagggt ctcactcacg tggctcccat catgagtgaa ggggcctcaa  105540
gcccaggttc ccacagcagc gcctgtcgca agtggaggca gaggcccgag gccaccctg    105600
acctggtccc tgaggttcct gcagcccagg ctgccctgct gtccctggga ggcctgggct  105660
ccaccagacc acaggtccag ggcaccgggt gcaggagcca cccacacaca gctcacagga  105720
agaagataag ctccagaccc ccagggccag aacctgcctt cctgctactg cttcctgccc  105780
cagacctggg cgccctcccc cgtccactta cacacaggcc aggaagctgt tcccacacag  105840
aacaacccca aaccaggacc gcctggcact caggtggctg ccatttcctt ctccatttgc  105900
tcccagcgc tctgtcctcc ctggttcctc cttcggggga acagcctgtg cagccagtcc  105960
ctgcagccca caccctgggg agacccaacc ctgcctgggg cccttccaac cctgctgctc  106020
ttactgccca cccagaaaac tctggggtcc tgtccctgca gtccctaccc tggtctccac  106080
ccagacccct gtgtatcact ccagacaccc ctcccaggca aaccctgcac ctgcaggccc  106140
tgtcctcttc tgtcgctaga gcctcagttt ctccccctg tgcccacacc ctacctcctc   106200
ctgcccacaa ctctaactct tcttctcctg gagccctga gccatggcat tgaccctgcc  106260
ctcccaccac ccacagccca tgccctcacc ttcctcctgg ccactccgac ccgccccct   106320
ctcaggccaa gccctggtat ttccaggaca aaggctcacc caagtctttc ccaggcaggc  106380
ctgggctctt gccctcactt cccggttaca cgggagcctc ctgtgcacag aagcagggag  106440
ctcagccctt ccacaggcag aaggcactga agaaatcgg cctccagcac cttgacacac   106500
gtccgcccgt gtctctcact gcccgcacct gcagggaggc tccgcactcc ctctaaagac  106560
aagggatcca ggcagcagca tcacgggaga atgcagggct cccagacatc ccagtcctct  106620
cacaggcctc tcctgggaag agacctgcag ccaccaccaa acagccacag aggctgctgg  106680
atagtaactg agtcaatgac cgacctggag ggcaggggag cagtgagccg gagcccatac  106740
catagggaca gagaccagcc gctgacatcc cgagctcctc aatggtggcc ccataacaca  106800
cctaggaaac ataacacacc cacagcccca cctggaacag ggcagagact gctgagcccc  106860
cagcaccagc cccaagaaac accaggcaac agtatcagag ggggctcccg agaaagagag  106920
gaggggagat ctccttcacc atcaaatgct tcccttgacc aaaaacaggg tccacgcaac  106980
tcccccagga caaaggagga gcccctata cagcactggg ctcagagtcc tctctgagac   107040
accctgagtt tcagacaaca acccgctgga atgcacagtc tcagcaggag aacagaccaa  107100
agccagcaaa agggacctcg gtgacaccag tagggacagg aggattttgt gggggctcgt  107160
gtcactgtga ggatattgta gtggtggtag ctgctactcc cacagtgaca cagacccatt  107220
cccaaagccc tactgcaaac acacccactc ctggggctga ggggctgggg gagcgtctgg  107280
gaagtagggt ccaggggtgt ctatcaatgt ccaaaatgca ccagactccc cgccaaacac  107340
```

```
caccccacca gccagcgagc agggtaaaca gaaaatgaga ggctctggga agcttgcaca 107400
ggccccaagg aaagagcttt ggcgggtgtg caagagggga tgcaggcaga gcctgagcag 107460
ggccttttgc tgtttctgct ttcctgtgca gagagttcca taaactggtg ttcaagatca 107520
gtggctggga atgagcccag gagggcagtc tgtgggaaga gcacagggaa ggaggagcag 107580
ccgctatcct acactgtcat cttttcaaaag tttgccttgt gaccacacta ttgcatcatg 107640
ggatgcttaa gagctgatgt agacacagct aaagagagaa tcagtgagat gaatttgcag 107700
catagatctg aataaactct ccagaatgtg gagcagtaca gaagcaaaca cacagaaagt 107760
gcctgatgca aggacaaagt tcagtgggca ccttcaggca ttgctgctgg gcacagacac 107820
tctgaaaagc cttggcagga tctccctgcg acaaagcaga accctcaggc aatgccagcc 107880
ccagagccct ccctgagagc gtcatgggga aagatgtgca gaacagctga ttatcataga 107940
ctcaaactga gaacagagca aacgtccatc tgaagaacag tcaaataagc aatggtaggt 108000
tcatgcaatg caaacccaga cagccagggg acaacagtag agggctacag gcggctttgc 108060
ggttgagttc atgacaatgc tgagtaattg gagtaacaga ggaaagccca aaaaatactt 108120
ttaatgtgat ttcttctaaa taaaatttac accaggcaaa atgaactgtc ttcttaaggg 108180
ataaactttc ccctggaaaa actacaagga aaattaagaa aacgatgatc acataaacac 108240
agttgtggtt acttctactg gggaaggaag agggtatgag ctgagacaca cagagtcggc 108300
aagtctccaa gcaagcacag aacgaataca ttacagtacc ttgaatacag cagttaaact 108360
tctaaatcgc aagaacagga aaatgcacac agctgtgttt agaaaattct cagtccagca 108420
ctattcataa tagcaaagac attaacccag gttggataaa taatgatga cacaggcaat 108480 tgcacaatga tacagacata catttagtac atgagacatc gatgatgtat ccccaaagaa 108540
atgactttaa agagaaaagg cctgatgtgt ggtggcactc acctccctgg gatccccgga 108600
caggttgcag gcacactgtg tggcagggca ggctggtaca tgctggcagc tcctggggcc 108660
tgatgtggag caagcgcagg gctgtatacc cccaaggatg gcacagtcag tgaattccag 108720
agagaagcag ctcagccaca ctgcccaggc agagcccgag agggacgccc acgtacaggg 108780
aggcagagcc cagctcctcc acagccacca ccacctgtgc acgggccacc accttgcagg 108840
cacagagtgg gtgctgagag gagggcagg gacaccaggc agggtgagca cccagagaaa 108900
actgcagaag cctcacacat ccacctcagc ctccccctgac ctggacctca cctggtctgg 108960
acctcacctg gcctgggcct cacctgacct ggacctcacc tggcctgggc ttcacctgac 109020
ctggacctca cctggcctcc ggcctcacct gcacctgctc caggtcttgc tggaacctga 109080
gtagcactga ggctgcagaa gctcatccag ggttggggaa tgactctgga actctcccac 109140
atctgacctt tctgggtgga ggcatctggt ggccctggga atataaaaag ccccagaatg 109200
gtgcctgcgt gatttggggg caatttatga acccgaaagg acatggccat ggggtgggta 109260
gggacatagg gacagatgcc agcctgaggt ggagcctcag gacacagttg gacgcgggaca 109320 ctatccacat aagcgaggga cagacccgag tgttcctgca gtagacctga gagcgctggg 109380
cccacagcct cccctcggtg ccctgctgcc tcctcaggtc agccctggac atcccgggtt 109440
tccccaggcc agatggtagg tttgaagtga ggtctgtgtc actgtggtat tatgattacg 109500
tttgggggag ttatcgttat acccacagca tcacacggtc catcagaaac ccatgccaca 109560
gccctccccg caggggaccg ccgcgtgcca tgttacgatt ttgatcgagg acacagcgcc 109620
atgggtatgt tggctaccac agcagtgcag cccatgaccc aaacacacag ggcagcaggc 109680
acaatggaca ggcctgtgag tgaccatgct gggctccagc ccgccagccc cggagaccat 109740
```

```
gaaacagatg gccaaggtca ccccacagtt cagccagaca tggctccgtg gggtctgcat 109800
cgctgctgcc ctctaacacc agcccagatg gggacaaggc caaccccaca ttaccatctc 109860
ctgctgtcca cccagtggtc ccagaagccc ctccctcatg gctgagccac atgtgtgaac 109920
cctgagagca ccccatgtca gagtaggggc agcagaaggg cggggctggc cctgtgcact 109980
gtccctgcac ccatggtccc tcgcctgcct ggccctgaca cctgagcctc ttctgagtca 110040
tttctaagat agaagacatt cccggggaca gccggagctg ggcgtcgctc atcccgcccg 110100
gccgtcctga gtcctgcttg tttccagacc tcaccaggga agccaacaga ggactcacct 110160
cacacagtca gagacaaaga accttccaga aatccctgtc tcactcccca gtgggcacct 110220
tcttccagga cattcctcgg tcgcatcaca gcaggcaccc acatctggat caggacggcc 110280
cccagaacac aagatggccc atggggacag ccccacaacc caggccttcc cagacccta 110340 aaaggcgtcc cacccctgc acctgcccca gggctaaaaa tccaggaggc ttgactcccg 110400 catacccctcc agccagacat cacctcagcc ccctcctgga ggggacagga gcccgggagg 110460
gtgagtcaga cccacctgcc ctcgatggca ggcggggaag attcagaaag gcctgagatc 110520
cccaggacga agcaccactg tcaatggggg ccccagacgc ctggaccagg gcctgcgtgg 110580
gaaaggccgc tgggcacact caggggcttt ttgtgaaggc ccctcctact gtgtgactac 110640
ggtgactacc acagtgatga aactagcagc aaaaactggc cggacaccca gggaccatgc 110700
acacttctca gcttggagct ctccaggacc agaagagtca ggtctgaggg tttgtagcca 110760
gaccctcggc ctctagggac accctggcca tcacagcgga tgggctggtg ccccacatgc 110820
catctgctcc aaacaggggc ttcagagggc tctgaggtga cttcactcat gaccacaggt 110880
gccctggccc cttccccgcc agctacaccg aaccctgtcc caacagctgc ccagttcca 110940 acagccaatt cctggggccc agaattgctg tagacaccag cctcgttcca gcacctcctg 111000
ccaattgcct ggattcacat cctggctgga atcaagaggg cagcatccgc caggctccca 111060
acaggcagga ctcccgcaca ccctcctctg agaggccgct gtgttccgca gggccaggcc 111120
ctggacagtt cccctcacct gccactagag aaacacctgc cattgtcgtc cccacctgga 111180
aaagaccact cgtggagccc ccagcccag gtacagctgt agagagactc cccgagggat 111240
ctaagaagga gccatgcgca gttctgccgg gaccctcggc caggccgaca ggagtggaca 111300
ctggagctgg gcccacactg gccacatag gagctcacca gtgagggcag gagagcacat 111360
gccggggagc acccagcctc ctgctgacca gaggcccgtc ccagagccca ggaggctgca 111420
gaggcctctc caggggaca ctgtgcatgt ctggtccctg agcagccccc cacgtcccca 111480
gtcctggggg cccctggcac agctgtctgg accctccctg ttccctggga agctcctcct 111540
gacagccccg cctccagttc caggtgtggt tattgtcagg gggtgtcaga ctgtggtgga 111600
tacagctatg gttaccacag tggtgctgcc catagcagca accaggccaa gtagacaggc 111660
ccctgctgtg cagccccagg cctccacttc acctgcttct cctggggctc tcaaggtcac 111720
tgttgtctgt actctgccct ctgtggggag ggttccctca gtgggaggtc tgttctcaac 111780
atcccagggc ctcatgtctg cacggaaggc caatggatgg gcaacctcac atgccgcggc 111840
taagatgggg tgggcagcct ggcggggggac agtacatact gctggggtgt ctgtcactgt 111900
gcctagtggg gcactggctc ccaaacaacg cagtcctcgc caaaatcccc acagcctccc 111960
ctgctagggg ctggcctgat ctcctgcagt cctaggaggc tgctgacctc cagaatgtct 112020
ccgtccccag ttccagggcg agagcagatc ccaggccggc tgcagactgg gaggccaccc 112080
```

```
cctccttccc agggttcact ggaggtgacc aaggtaggaa atggccttaa cacagggatg   112140
actgcgccat ccccccaacag agtcagcccc ctcctgctct gtaccccgca ccccccaggc   112200
cagtccacga aaaccagggc cccacatcag agtcactgcc tggcccggcc ctgggcgga    112260 cccctcagcc cccaccctgt ctagaggact tgggggaca ggacacaggc cctctcctta    112320
tggttccccc acctgcctcc ggccgggacc cttggggtgt ggacagaaag gacacctgcc   112380
taattggccc ccaggaaccc agaacttctc tccaggacc ccagcccgag cacccccta    112440 cccaggaccc agccctgccc ctcctcccct ctgctctcct ctcatcaccc catgggaatc   112500
cggtatcccc aggaagccat caggaagggc tgaaggagga agcggggccg tgcaccaccg   112560
ggcaggaggc tccgtcttcg tgaacccagg gaagtgccag cctcctagag ggtatggtcc   112620
accctgcctg gggctcccac cgtggcaggc tgcggggaag gaccagggac ggtgtggggg   112680
agggctcagg gccctgcggg tgctcctcca tcttcggtga gcctccccct tcacccaccg   112740
tcccgcccac ctcctctcca ccctggctgc acgtcttcca caccatcctg agtcctacct   112800
acaccagagc cagcaaagcc agtgcagaca aaggctgggg tgcaggggg ctgccagggc    112860 agcttcgggg agggaaggat ggagggaggg gaggtcagtg aagaggcccc cttcccctgg   112920
gtccaggatc ctcctctggg accccggat cccatcccct cctggctctg ggaggagaag    112980
caggatggga gaatctgtgc gggaccctct cacagtggaa tatccccaca gcggctcagg   113040
ccagacccaa aagcccctca gtgagccctc cactgcagtc ctgggcctgg gtagcagccc   113100
ctcccacaga ggacagaccc agcaccccga agaagtcctg ccaggggag ctcagagcca    113160 tgaaagagca ggatatgggg tccccgatac aggcacagac ctcagctcca tccaggccca   113220
ccgggaccca ccatgggagg aacacctgtc tccgggttgt gaggtagctg gcctctgtct   113280
cggaccccac tccagacacc agacagaggg gcaggccccc caaaaccagg gttgagggat   113340
gatccgtcaa ggcagacaag accaaggggc actgacccca gcaagggaag gctcccaaac   113400
agacgaggag gtttctgaag ctgtctgtat cacagtgggg tatagcagtg gctggtacca   113460
cagtgacact cgccaggcca gaaaccccgt cccaagtcag cggaagcaga gagagcaggg   113520
aggacacgtt taggatctga ggccgcacct gacacccagg gcagcagacg tctcccctcc   113580
agggcaccct ccaccgtcct gcgtttcttc aagaatagg gcggcctgag ggggtccagg    113640
gccaggcgat aggtccccctc taccccaagg aggagccagg caggacccga gcaccgtccc   113700
cattgaggct gacctgccca gacgggcctg ggcccacccc acacaccggg gcggaatgtg   113760
tgcaggcccc agtctctgtg ggtgttccgc tagctggggc ccccagtgct caccccacac   113820
ctaaagcgag cccccagcctc cagagccccc taagcattcc ccgcccagca gcccagcccc   113880
tgcccccacc caggaggccc cagagctcag ggcgcctggt cggattctga acagcccga    113940 gtcacagtgg gtataactgg aacgaccacc gtgagaaaaa ctgtgtccaa aactgactcc   114000
tggcagcagt cggaggcccc gccagagagg ggagcagccg gcctgaaccc atgtcctgcc   114060
ggttcccatg acccccagca cccagagccc cacggtgtcc ccgttggata atgaggacaa   114120
gggctggggg ctccggtggt ttgcggcagg gacttgatca catccttctg ctgtggcccc   114180
attgcctctg gctggagttg acccttctga caagtgtcct cagaaagaca gggatcaccg   114240
gcacctccca atatcaaccc caggcagcac agacacaaac cccacatcca gagccaactc   114300
caggagcaga gacaccccaa cactctgggg gaccccaacc gtgataactc cccactggaa   114360 tccgcccag agtctaccag gaccaaaggc cctgccctgt ctctgtccct cactcagggc    114420
ctcctgcagg gcgagcgctt gggagcagac tcggtcttag gggacaccac tgtgggcccc   114480
```

```
aactttgatg aggccactga cccttccttc ctttcctggg gcagcacaga ctttggggtc  114540
tgggcaggga agaactactg gctggtggcc aatcacagag cccccaggcc gaggtggccc  114600
caagaaggcc ctcaggaggt ggccactcca cttcctccca gctggacccc aggtcctccc  114660
caagataggg gtgccatcca aggcaggtcc tccatggagc cccttcaga ctcctcccgg  114720 gaccccactg gacctcagtc cctgctctgg gaatgcagcc accacaagca caccaggaag  114780
cccaggccca gccaccctgc agtgggcaag cccacactct ggagcagagc agggtgcgtg  114840
tgggaggggc taacctcccc acccccacc cccatctgc acacagccac ctaccactgc  114900
ccagaccctc tgcaggaggg ccaagccacc atggggtatg gacttagggt ctcactcacg  114960
tgcctcccct cctgggagaa ggggcctcat gcccagatcc ctgcagcact agacacagct  115020
ggaggcagtg gccccagggc caccctgacc tggcatctaa ggctgctcca gcccagacag  115080
cactgccgtt cctgggaagc ctgggctcca ccagaccaca ggtccagggc acagcccaca  115140
ggagccaccc acacacagct cacaggaaga agataagctc cagacccag ggcgggacct  115200 gccttcctgc caccacttac acacaggcca gggagctgtt cccacacaga tcaaccccaa  115260
accgggactg cctggcacta gggtcactgc catttccctc tccattccct cccagtgcct  115320
ctgtgctccc tccttctggg gaacaccctg tgcagcccct cctgcagcc cacacgctgg  115380 ggagaccca ccctgcctcg ggccttttct acctgctgca cttgccgccc acccaaacaa  115440
ccctgggtac gtgaccctgc agtcctcacc ctgatctgca accagacccc tgtccctccc  115500
tctaaacacc cctcccaggc caactctgca cctgcaggcc ctccgctctt ctgccacaag  115560
agcctcaggt tttcctacct gtgcccaccc cctaacccct cctgcccaca acttgagttc  115620
ttcctctcct ggagcccttg agccatggca ctgaccctac actccacccc acacactgcc  115680
catgccatca ccttcctcct ggacactctg acccgctcc cctccctctc agacccggcc  115740
ctggtatttc caggacaaag gctcacccaa gtcttcccca tgcaggccct tgccctcact  115800
gcctggttac acgggagcct cctgtgcgca gaagcaggga gctcagctct tccacaggca  115860
gaaggcactg aaagaaatca gcctccagtg ccttgacaca cgtccgcctg tgtctctcac  115920
tgcctgcacc tgcagggagg ctccgcactc cctctaaaga tgagggatcc aggcagcaac  115980
atcacgggag aatgcagggc tcccagacag cccagccctc tcgcaggcct ctcctgggaa  116040
gagacctgca gccaccactg aacagccacg gaggtcgctg gatagtaacc gagtcagtga  116100
ccgacctgga gggcagggga gcagtgaacc ggagcccata ccatagggac agagaccagc  116160
cgctaacatc ccgagcccct cactggcggc cccagaacac cccgtggaaa gagaacagac  116220
ccacagtccc acctggaaca gggcagacac tgctgagccc ccagcaccag ccccaagaaa  116280
cactaggcaa cagcatcaga gggggctcct gagaaagaga ggaggggagg tctccttcac  116340
catcaaatgc ttcccttgac caaaaacagg gtccacgcaa ctcccccagg acaaaggagg  116400 agcccctgt acagcactgg gctcagagtc ctctctgaga caggctcagt ttcagacaac  116460
aacccgctgg aatgcacagt ctcagcagga gagccaggcc agagccagca agaggagact  116520
cggtgacacc agtctcctgt agggacagga ggattttgtg ggggttcgtg tcactgtgag  116580
catattgtgg tggtgactgc tattcccaca gtgacacaac cccattccta aagccctact  116640
gcaaacgcac ccactcctgg gactgagggg ctggggagc gtctgggaag tatggcctag  116700
gggtgtccat caatgcccaa aatgcaccag actctcccca agacatcacc ccaccagcca  116760
gtgagcagag taaacagaaa atgagaagca gctgggaagc ttgcacaggc cccaaggaaa  116820
```

```
gagctttggc aggtgtgcaa gaggggatgt gggcagagcc tcagcagggc cttttgctgt  116880
ttctgctttc ctgtgcagag agttccataa actggtattc aagatcaatg ctgggagtg  116940 agcccaggag gacagtgtgg gaagagcaca gggaaggagg agcagccgct atcctacact  117000
gtcatctttt gaaagtttgc cctgtgccca caatgctgca tcatgggatg cttaacagct  117060
gatgtagaca cagctaaaga gagaatcagt gaaatgcatt tgcagcacag atctgaataa  117120
atcctccaga atgtggagca gcacagaagc aagcacacag aaagtgcctg atgccaaggc  117180
aaagttcagt gggcaccttc aggcattgct gctgggcaca gacactctga aaagcactgg  117240
caggaactgc ctgtgacaaa gcagaaccct caggcaatgc cagccctaga gcccttcctg  117300
agaacctcat gggcaaagat gtgcagaaca gctgtttgtc atagccccaa actatggggc  117360
tggacaaagc aaacgtccat ctgaaggaga acagacaaat aaacgatggc aggttcatga  117420
aatgcaaact aggacagcca gaggacaaca gtagagagct acaggcggct ttgcggttga  117480
gttcatgaca atgctgagta attggagtaa cagaggaaag cccaaaaaat acttttaatg  117540
tgatttcttc taaataaaat ttacacccgg caaaatgaac tatcttctta agggataaac  117600
tttcccctgg aaaaactata aggaaaatca agaaaacgat gatcacataa acacagtggt  117660
ggttacttct actggggaag gaagagggta tgagctgaga cacacagagt cggcaagtct  117720
cctaacaaga acagaacaaa tacattacag taccttgaaa acagcagtta aacttctaaa  117780
tcgcaagaag aggaaaatgc acacacctgt gtttagaaaa ttctcagtcc agcactgttc  117840
ataatagcaa agacattaac ccaggttgga taaataagcg atgacacagg caattgcaca  117900
atgatacaga catacattca gtatatgaga catcgatgat gtatccccaa agaaatgact  117960
ttaaagagaa aaggcctgat gtgtggtggc aatcacctcc ctgggcatcc ccggacaggc  118020
tgcaggctca ctgtgtggca gggcaggcag gcacctgctg gcagctcctg gggcctgatg  118080
tggagcaggc acagagctgt atatccccaa ggaaggtaca gtcagtgcat tccagagaga  118140
agcaactcag ccacactccc tggccagaac ccaagatgca cacccatgca cagggaggca  118200
gagcccagca cctccgcagc caccaccacc tgcgcacggg ccaccacctt gcaggcacag  118260
agtgggtgct gagaggaggg gcagggacac caggcagggt gagcacccag agaaaactgc  118320
agaagcctca cacatccacc tcagcctccc ctgacctgga cctcacctgg cctgggcctc  118380
acctgacctg gacctcacct ggcctgggct tcacctggcc tgggcttcac ctgacctgga  118440
cctcacctgg cctcgggcct cacctggcct gggcttcacc tggcctgggc ttcacctgac  118500
ctggacctca cctggcctgg gcctcacctg acctggacct cacctggcct gggcttcacc  118560
tggcctgggc ttcacctggc ctgggcttca cctgacctgg acctcacctg gcctgggctt  118620
cacctgacct ggacctcacc tggcctcggg cctcacctgc acctgctcca ggtcttgctg  118680
gagcctgagt agcactgagg ctgtagggac tcatccaggg ttggggaatg actctgcaac  118740
tctcccacat ctgaccttc tgggtggagg cacctggtgg cccagggaat ataaaaagcc  118800
ccagaatgat gcctgtgtga tttggggca atttatgaac ccgaaaggac atggccatgg  118860
ggtgggtagg gacagtaggg acagatgtca gcctgaggtg aagcctcagg acacaggtgg  118920
gcatggacag tgtccaccta agcgagggac agacccgagt gtccctgcag tagacctgag  118980
agcgctgggc ccacagcctc cctcggggc cctgctgcct cctcaggtca gccctggaca  119040
tcccgggttt cccaggcct ggcggtaggt ttgaagtgag gtctgtgtca ctgtggtatt  119100
actatgatag tagtggttat tactaccaca gtgtcacaga gtccatcaaa aactcatgcc  119160
tgggagcctc ccaccacagc cctccctgcg ggggaccgct gcatgccgtg ttaggatttt  119220
```

```
gatcgaggac acggcgccat gggtatggtg gctaccacag cagtgcagcc catgacccaa   119280
acacacgggg cagcagaaac aatggacagg cccacaagtg accatgatgg gctccagccc   119340
accagcccca gagaccatga aacagatggc caaggtcacc ctacaggtca tccagatctg   119400
gctccaaggg gtctgcatcg ctgctgccct cccaacgcca aaccagatgg agacagggcc   119460
ggccccatag caccatctgc tgccgtccac ccagcagtcc cggaagcccc tccctgaacg   119520
ctgggccacg tgtgtgaacc ctgcgagccc cccatgtcag agtaggggca gcaggagggc   119580
ggggctggcc ctgtgcactg tcactgcccc tgtggtccct ggcctgcctg gccctgacac   119640
ctgagcctct cctgggtcat ttccaagaca ttcccaggga cagccggagc tgggagtcgc   119700
tcatcctgcc tggctgtcct gagtcctgct catttccaga cctcaccagg gaagccaaca   119760
gaggactcac ctcacacagt cagagacaac gaaccttcca gaaatccctg tttctctccc   119820
cagtgagaga aaccctcttc cagggtttct cttctctccc accctcttcc aggacagtcc   119880
tcagcagcat cacagcggga acgcacatct ggatcaggac ggcccccaga acacgcgatg   119940
gcccatgggg acagcccagc ccttcccaga cccctaaaag gtatcccac cttgcacctg   120000 ccccagggct caaactccag gaggcctgac tcctgcacac cctcctgcca gatatcacct   120060 cagcccctc ctggagggga caggagcccg ggagggtgag tcagacccac ctgccctcaa   120120
tggcaggcgg ggaagattca gaaaggcctg agatccccag gacgcagcac cactgtcaat   120180
gggggcccca gacgcctgga ccagggcctg tgtgggaaag gcctctggcc acactcaggg   120240 gcttttgtg aagggccctc ctgctgtgtg actacggtgg taactcccac agtgatgaaa   120300
ccagcagcaa aaactgaccg gactcgcagg gtttatgcac acttctcggc tcggagctct   120360
ccaggagcac aagagccagg cccgagggtt tgtgcccaga ccctcggcct ctagggcacac   120420 ccgggccatc ttagccgatg ggctgatgcc ctgcacaccg tgtgctgcca aacagggct   120480 tcagagggct ctgaggtgac ttcactcatg accacaggtg ccctggtccc ttcactgcca   120540
gctgcaccag accctgttcc gagagatgcc ccagttccaa aagccaattc ctggggccgg   120600
gaattactgt agacaccagc ctcattccag tacctcctgc caattgcctg gattcccatc   120660
ctggctggaa tcaagagggc agcatccgcc aggctcccaa caggcaggac tcccacacac   120720
cctcctctga gaggccgctg tgttccgcag ggccaggccg cagacagttc ccctcacctg   120780
cccatgtaga aacacctgcc attgtcgtcc ccacctggca aagaccactt gtggagcccc   120840
cagccccagg tacagctgta gagagagtcc tcgaggcccc taagaaggag ccatgcccag   120900
ttctgccggg accctcggcc aggccgacag gagtggacgc tggagctggg cccacactgg   120960
gccacatagg agctcaccag tgagggcagg agagcacatg ccggggagca cccagcctcc   121020
tgctgaccag agaccgtcc cagagcccag gaggctgcag aggcctctcc aggggacac   121080 agtgcatgtc tggtccctga gcagccccca ggctctctag cactgggggc ccctggcaca   121140
gctgtctgga ccctccctgt tccctgggaa gctcctcctg acagcccgc ctccagttcc   121200 aggtgtggtt attgtcaggg ggtgccaggc cgtggtagag atggctacaa ttaccacagt   121260
ggtgccgccc atagcagcaa ccaggccaag tagacagacc cctgccacgc agccccaggc   121320
ctccagctca cctgcttctc ctggggctct caaggctgct gtctgccctc tggccctctg   121380
tggggagggt tccctcagtg ggaggtctgt gctccagggc agggatgact gagatagaaa   121440
tcaaaggctg gcagggaaag gcagcttccc gccctgagag gtgcaggcag caccacagag   121500
ccatggagtc acagagccac ggagccccca gtgtgggcgt gtgagggtgc tgggctcccg   121560
```

```
gcaggcccag ccctgatggg gaagcctgcc ccgtcccaca gcccaggtcc ccaggggcag   121620
caggcacaga agctgccaag ctgtgctcta cgatcctcat ccctccagca gcatccactc   121680
cacagtgggg aaactgagcc ttggagaacc acccagcccc ctggaaacaa ggcggggagc   121740
ccagacagtg ggcccagagc actgtgtgta tcctggcact aggtgcaggg accacccgga   121800
gatccccatc actgagtggc cagcctgcag aaggacccaa ccccaaccag gccgcttgat   121860
taagctccat cccctgtcc tgggaacctc ttcccagcgc caccaacagc tcggcttccc   121920
aggccctcat ccctccaagg aaggccaaag ctgggcctg ccaggggcac agtaccctcc   121980
cttgccctgg ctaagacagg gtgggcagac ggctgcagat aggacatatt gctggggcat   122040
cttgctctgt gactactggg tactggctct caacgcagac cctaccaaaa tccccactgc   122100 ctccctgct aggggctggc ctggtctcct cctgctgtcc taggaggctg ctgacctcca   122160
ggatggcttc tgtccccagt tctagggcca gagcagatcc caggcaggct gtaggctggg   122220
aggccacccc tgtccttgcc gaggttcagt gcaggcaccc aggacaggaa atggcctgaa   122280
cacagggatg actgtgccat gccctaccta agtccgcccc tttctactct gcaacccca   122340 ctccccaggt cagcccatga cgaccaacaa cccaacacca gagtcactgc ctggccctgc   122400
cctggggagg acccctcagc ccccaccctg tctagaggag ttgggggac aggacacagg   122460 ctctctcctt atggttcccc cacctggctc ctgccgggac ccttggggtg tggacagaaa   122520
ggacgcctgc ctaattggcc cccaggaacc cagaacttct ctccagggac cccagcccga   122580
gcaccccctt acccaggacc cagccctgcc cctcctcccc tctgctctcc tctcatcact   122640
ccatgggaat ccagaatccc caggaagcca tcaggaaggg ctgaaggagg aagcgggcc   122700 gctgcaccac cgggcaggag gctccgtctt cgtgaaccca gggaagtgcc agcctcctag   122760
agggtatggt ccaccctgcc tggggctccc accgtggcag gctgcgggga aggaccaggg   122820
acggtgtggg ggagggctca gggccctgca ggtgctccat cttggatgag cccatccctc   122880
tcacccaccg acccgcccac ctcctctcca ccctggccac acgtcgtcca caccatcctg   122940
agtcccacct acaccagagc cagcagagcc agtgcagaca gaggctgggg tgcaggggg   123000 ccgccagggc agctttgggg agggaggaat ggaggaaggg gaggtcagtg aagaggcccc   123060
cctcccctgg gtctaggatc cacctttggg accccggat cccatcccct ccaggctctg   123120
ggaggagaag caggatggga gattctgtgc aggaccctct cacagtgaa tacctccaca   123180 gcggctcagg ccagatacaa aagcccctca gtgagccctc cactgcagtg cagggcctgg   123240
gggcagcccc tcccacagag gacagaccca gcacccgaa gaagtcctgc cagggggagc   123300
tcagagccat gaaggagcaa gatatgggga ccccaatact ggcacagacc tcagctccat   123360
ccaggcccac caggacccac catgggtgga acacctgtct ccggcccctg ctggctgtga   123420
ggcagctggc ctctgtctcg gaccccatt ccagacacca gacagaggga caggccccc   123480 agaaccagtg ttgagggaca cccctgtcca gggcagccaa gtccaagagg cgcgctgagc   123540
ccagcaaggg aaggccccca aacaaaccag gaggtttctg aagctgtctg tgtcacagtc   123600
gggtatagca gcggctacca caatgacact gggcaggaca gaaaccccat cccaagtcag   123660
ccgaaggcag agagagcagg caggacacat ttaggatctg aggccacacc tgacactcaa   123720
gccaacagat gtctcccctc cagggcgccc tgccctgttc agtgttcctg agaaaacagg   123780
ggcagcctga ggggatccag ggccaggaga tgggtcccct ctaccccgag gaggagccag   123840
gcgggaatcc cagcccctc cccattgagg ccatcctgcc cagaggggcc cggacccacc   123900
ccacacaccc aggcagaatg tgtgcaggcc tcaggctctg tgggtgccgc tagctgggc   123960
```

```
tgccagtcct caccccacac ctaaggtgag ccacagccgc cagagcctcc acaggagacc   124020
ccacccagca gcccagcccc tacccaggag gccccagagc tcagggcgcc tgggtggatt   124080
ctgaacagcc ccgagtcacg gtgggtatag tgggagctac taccactgtg agaaaagcta   124140
tgtccaaaac tgtctcccgg ccactgctgg aggcccagcc agagaaggga ccagccgccc   124200
gaacatacga ccttcccaga cctcatgacc cccagcactt ggagctccac agtgtcccca   124260
ttggatggtg aggatggggg ccggggccat ctgcacctcc caacatcacc cccaggcagc   124320
acaggcacaa accccaaatc cagagccgac accaggaaca cagacacccc aatacccctgg  124380 gggaccctgg ccctggtgac ttcccactgg gatccacccc cgtgtccacc tggatcaaag   124440
accccaccgc tgtctctgtc cctcactcag ggcctgctga ggggcgggtg ctttggagca   124500
gactcaggtt taggggccac cattgtgggg cccaacctcg accaggacac agattttttct  124560 ttcctgccct ggggcaacac agactttggg gtctgtgcag ggaggacctt ctggaaagtc   124620
accaagcaca gagccctgac tgaggtggtc tcaggaagac ccccaggagg gggcttgtgc   124680
cccttcctct catgtggacc ccatgccccc caagataggg gcatcatgca gggcaggtcc   124740
tccatgcagc caccactagg caactccctg gcgccggtcc ccactgcgcc tccatcccgg   124800
ctctggggat gcagccacca tggccacacc aggcagcccg ggtccagcaa ccctgcagtg   124860
cccaagccct tggcaggatt cccagaggct ggagcccacc cctcctcatc cccccacacc   124920
tgcacacaca cacctacccc ctgcccagtc ccctccagg agggttggag ccgcccatag   124980
ggtgggggct ccaggtctca ctcactcgct tcccttcctg ggcaaaggag cctcgtgccc   125040 cggtccccc tgacggcgct gggcacaggt gtgggtactg ggcccaggg ctcctccagc    125100 cccagctgcc ctgctctccc tgggaggcct gggcaccacc agaccaccag tccagggcac   125160
agccccaggg agccgcccac tgccagctca caggaagaag ataagcttca gaccctcagg   125220
gccgggagct gccttcctgc cacccctttcc tgccccagac ctccatgccc tcccccaacc  125280
acttacacac aagccaggga gctgtttcca cacagttcaa ccccaaacca ggacggcctg   125340
gcactcgggt cactgccatt tctgtctgca ttcgctccca gcgcccctgt gttccctccc   125400
tcctccctcc ttcctttctt cctgcattgg gttcatgccg cagagtgcca ggtgcaggtc   125460
agccctgagc ttggggtcac ctcctcactg aaggcagcct cagggtgccc aggggcaggc   125520
agggtggggg tgaggcttcc agctccaacc gctccactag ccgagactaa ggaagtgaga   125580
ggcagccaga aatccagacc attccatagc aaatggattt cattaaagtt accagacttc   125640
agtgtaagta acatgagccc catgcacaac aatcccttat gaaggggaag tcagtgtcgc   125700
ctcggatttc ttgaaaaaca caaaaactta tcaatgcctg taaaagtctg ttggaaagaa   125760
aatatgattc aagaatgtta tgcccaacaa agctggcata ttttctaccc ggacacactc   125820
agggaatgtg gtcccttgag tgcttctctc actgcgtaaa tcctacgtgg tgtttaagca   125880
tattcataaa tgtgtatgtc tatttttatg tgtaagatgg ttcatttta tttatttat    125940 tcaatatgta caataaagaa tattgacaaa taggctggac atggtggctc ccacctgtaa   126000
tcccagccct ttgggaggcc gaggcgggca gatcacctga ggtctggagt tcgagaccag   126060
cctggccaac atgatgaaaa cccatctcta ctaaaaatac aaagattagc caggcatggt   126120
ggtgcatgcc tgtaatccca gccactcagg aggctgagac aggagaaatg cgtgaacccg   126180
gaaggcggag gttgcagtga gccgagatca caccactgca ctccagcctg gcgacagagc   126240
aagattccat ctcaaaaaaa aaaaaagaca aagaaatttg tttttttgaa taaagacaaa   126300
```

```
tttcatcaca cgaagataaa gatgcaaagc tccagacagg aaggcacgga cagcacagtg   126360
aagcccggag cgggcgctgg ggggccaggg gcatggcggg ggtgccagcg tctctcggtt   126420
cctaccatgg ccactccagc ctgtgttctc acgaggatgg ctgtgcaatg ctaggagcgt   126480
gttcgaagct ctagggcaac cactggaagt gaggctgagg agcagagccc agaggcccgt   126540
ggagctgatg aaagaaagc tggagaaagt gtttgctgcc tcccaacatg gtaagaaaag    126600
atagaaagag agagcacacg gcaaagggag cttgctgagg gactctttac aatggcttgc   126660
acagagctca gggggtctgg gaggctaggg ccctgcgcag ggcagtcacc ccagcctgct   126720
gaccaaggtt tgctgcaggc agctctgggg gtggttgagg cgcggtccct ggagccaccc   126780
ctcaagggaa cgaggcagca gagtgggcca aggcccaggt cggctgcaag gctgcccagg   126840
acttggggtc cttacatcag cagccactga tgcagctggc ccagagagag gcgccgagca   126900
ggttgcctcc aggggacaaa ccaggtcgga gagggtgagg cagtggatgg agccacaaca   126960
accccgggca cgggtgacac gcacgttcat gcacatctga cccttcctcc ctcaccaaac   127020 aggtcccccct gccttcccca tggttgcgaa aaagcaaaat gtagacgttt tttcttttt    127080 aattcatgtt ttaattgaca aatgaagccg tatatattta ttgtgtacaa catgatgctt   127140
taaaatatgt atacatcgtg gaacagcaac gttgagctaa tttaacacgc attacttcac   127200
atacttgtca tcttttgtgg cgagaatgct taaaatccac tctcttagta ttttttaaga   127260
atgcaataca ttgttgtcaa ctgtggtcac cgtcatgcat agccaagctc ccgacctcac   127320
cctcctgcca gctcaggctg tgcatccttt caccagcatc ccccacccccg gccctggcc   127380 ctggtaacta ccactctata ctctacgtat gagttcagct ttttaagatt ccacagatga   127440
atgagatcat acagtatttg ctttctatgc ctggcttatt ttagttaaca cactgtcctc   127500
cagatccatc cgttgttgca aatgacaggg tttcattctt tttaaagtct aaagagtatt   127560
ccattgtgtc aatggaccctc atttgctttta tccatgcatc aactatggac atttaggttg   127620
attccatttc ttagctgttg tggatggtgc tgcagtaaac atggggctgc agatgtctct   127680
tcaacatact gacatcatgt cctttggata aataccccagt agtgggatcg ctggatcaca   127740
atgtacagtt ttttttttaa tggaaacttt cattttttgg tgaaattagg aaaacagata   127800 aacccacag aatccaaaat atatgtgaag atgccaaaaa cagttgacat tgggcagagg    127860
tcacatggaa ggaagtgaat acatgacggg gtgtgagggc ccagaggcag ctgaaatacg   127920 cttctaaac acaaggacct cttctgagag ggcagaagtt ttatcctgca catgcaatga    127980
ccagcacagc taaaatacac tttctaaaca tgaggacctc ttctgagagg gcagcttat   128040 cctgcaaatg caatgaccag cacaggaccc agaataaaga gagttgccag cggacgcctg   128100
gtgtccatgt gtccaggtga gttcgagatg cggacggcgc tggccagcca gtcacaccct   128160
aagtcaatct gctgcatgca tttgtccttg ccacagcaga aaacgagaaa gcctttgggc   128220
tgcaaagctt cacaggctcc tcttctcccg actccatgga aacagctaca aagagcaggc   128280
ccagtagagc ttaattcatg aaaatgagta ataaacttga actggaacag tatcgacttt   128340
ttagaaacgg cagcaaagtg tataaaaaat attcaccaga acaatatttc caaacgatga   128400
gatgagaatt tcagccaagt aatcctccat ggatagaaaa taatgaaggg attggattta   128460
tgaaggaaaa tcatggagct caaatacaag aaaagagaat caaaaatgaa caggaggaga   128520
taaaatatgg tttggccaaa gttacaaaat aaatttttta aaaacccttc atcatggcaa   128580
gtagaaagag cgagaggaaa aacagatccc gtggaagaca caaataggac atggggagaa   128640
aaatgaatga gatgaaacag agcagaaata aaatttacg gaactaaaga caagtgatct    128700
```

```
gaacctgcct ggggcctggg ggacctcgcc accctgaagg gaaagaacat gcctggctgg  128760
ctttgccacc tgctcattgc agagcccac  agcttgcaac aaacataggc ggtagccagg  128820
gagtggttac agcaggcctt gagcaagacc cagtgttgtg ctgacttcag gtctgaccca  128880
gcactgtcat agtggtggtg tccatagtgg tagtgggggt gcttgtgtca ctccaccccc  128940
atctccagga ggctcagaac agacagagag agactccatt tgtttgggag aaagtaaggg  129000
atgagaacaa gagtctctgc ctggtaatcc agagaattat tctagatctt ggccaagatt  129060
atcaaagcag tacctctatg agtcttttgg gcttggagtc cccctaaagc agatatagct  129120
aagatcacac cacccaagtc cttttgaata tgtgggaaga cttcccaagg acaggagcaa  129180
acaaacaagc ccagactgca aaaaacaag  ccgagactgc aataaacacc tcactcttca  129240
atgcccaggc actgaagaac atctcctagc agcaacacca tccaggaaaa catgcctca   129300 accagtgaac taaataaggc ccagggacc  agtctcggag aaatagaggt atgttatctt  129360
tcagagaatt caaagtagct tgttgagga  aactcaaaga aattcaagat aacacagtga  129420
aggaattcag aatcctatcc gataaattta acagagattg aagcaattaa aaagaattaa  129480
gcagaaatta tggagctgaa aaatgcaatt ggcatactga aaatgcatc  agagtatttt  129540 catagcctca tatatcaagt agaagaaaga attagtgagc ttgaaaacag gctatttgga  129600
aaagcacgat aaaaggagac aaaagagaaa agaataaata acaatgaagc atatctacag  129660
gatctagaaa atagcctcaa aaggccaaat ctaagaatta ttagccttaa agaggaggta  129720
gagaaagagg gatggagagt ttattcaaag ggataataac agaaaacttc ccaaacctag  129780
agaaagatat caatatccaa atgcaagaag gatgtagtac accaaggaga tttaatgcaa  129840
agaagactac ctcaaggcat tcaatactca aactcccata tgacaaggac tttaaaaaga  129900
tcctaaaagc agcaaaagaa aagaaatgaa taaaatacta tggagctcca atatgtctgg  129960
cagcagactt ttcagtgaag actttatatg ccaggagaga gtgtcataat ggatttaaag  130020
tgctgaagga aaaaactttt accctcgaac agtatagctg gtgaaattat ccttcaaaca  130080
tgaaggagaa ataatttgtt tccagacaaa tgttgaggga tttcatgaac accagacctg  130140
tcttttaaga aatgctaaag ggagtacttc aatcagaaag aaacacgtta gtgaacaata  130200
agaaatcatc tgaaggcaca aaactccaccg gtaatagtaa gtacacagaa aaacacagaa  130260
tattataaca ctgtaactgt ggtgtgtaaa ctccttttgt ttgtttgttt gtttgtttgt  130320 ttgttttgt  ttttagacgg agttttgctc cagcccaggc tggagtgcaa tggcacaatc  130380
tcagctcact gcaacttcca cctcccgggt tcaagcaatt ctcctgcctc agcctcccaa  130440
gtagctggga ttacaggcat gtgctaccat gtccagctaa ttttgtattt tagtagagac  130500
ggtgtttcac catgttggtc aggctagcct tatcttgagt agaaaaacta atgatgaag   130560 caatgaaaaa taataactac aactttcaa  gacatagtac aataagatat aaatcataac  130620
aaaaagttaa aaggtggagg gatgaagtta aggcatagag tctttattag ttttcttttt  130680
acttgtctgt ttatgcaaac agtgttaagt tgtcatcagt ttaaataat  gggtcataag  130740 atactatttg caagcctcat ggtaacgtca aaccaaaagc aatacaacag atacacaaaa  130800
aacaaaaagc aagaagctaa attacgtcat cagagaaaat caccttcact aaaaggaaga  130860
cggagaaaag aatgaagaga gagaagacca aaagcaaata gcaatatggc aggagtaagt  130920
ccttacttat caataatacc attgaatgta aatggactaa actctccaat caaaagacat  130980
agagtggctg aatcaattaa agaaaaaaca agacccattg atctgttgtc cacaagaaac  131040
```

```
acactttatc tataaagaca cacatagact gaaaacaaag ggatggaaaa agatactcca    131100
cgccaatgga aaccaaagaa agagcaggag tagctacact tatatcaggc aaaatagatt    131160
tcaagacaaa aactataaga agagacaagg tcactaatga taaacaggtc aattcagcaa    131220
gaggatataa caattgtaaa tatatatgca cccaatgctg gagcacccag atatataaag    131280
caagtattta ctagagctaa agagagaaat agactccaat gcaataatag ctggagattt    131340
caacatccca cttctcaacat tgaacagatc ctccagatag aaaatcaaca agaaatatt    131400
ggacttaatc tgcactatcg accaaatgga tctaacagat atttacagaa catttcatcc    131460
aacagctgca gaacacacat tcttttcctc agcacataga tcattctcaa ggatagacca    131520
tatgttgggt cacaaaacaa gttttaaaat attcaaatac attgaaataa tatcaagcat    131580
cttctgtgac cacaatggac taaaactaga aatcaataac aagaggaatt ttggaaacta    131640
tataaatata tggaaattaa tgaatgctga gtgggtcaat gaagcaatta agaaggaaac    131700
tgaaattttt cttggaacga atgatcatgg aaacagaaaa taccaaaacc tatgggatac    131760
agcaaaagca gtactaagag ggaagtttac agctacaaat gcttacatta aaaagaaga    131820
aaaacttcaa taaaaaaacc taacaatgca tcttaaagaa ctagaaaagc aagaggaaat    131880
caaatccaaa attagtagaa gaaaacagta aaggtcagag cagaaataag taaaattgaa    131940
atgaagaaaa caatacaaaa gatcaataaa acaacaggtt gttttcttga aaagttaaac    132000
aaaattgaca aaccttttagc cagactaaga aaaaagaca gaagatccaa ataaataaaa    132060
tcagagatga aaaaggtgac attacaactt acaccacaga aattcaaagg atcattagtg    132120
gctactataa gcaactatat gccaataaat tggaaaatct agaagaaatg cagaaattcc    132180
tagacacata caacctccca agattaaacc aagaagaaat tcaaaacctg aacagactga    132240
taacaagtaa tgagatcaaa gccgtaataa aaagcctccc agtaaagaga agcccaggac    132300
ccgacggctt cactgctgaa ttctaccaaa catttaaagt agaactaata ccaatcctac    132360
tcaaactatt ccaaaaaata gaggtggaag gaatacttca aaactcatta tacgaggcca    132420
gtattaacct gacaccaaaa ctagacaaag acacatgaaa aaagaaaac tacaggccaa    132480
tatgtctgat gaatattgac acaaaaatcc tcaacaaaat actagcaaac caaattcaac    132540
tacacattag aaagttcact catcatgacc aagtggaatt tatctaactt gggatgcaaa    132600
gatggttcaa catatgcaaa tcaatcaatg tgatacatca tatcaacaga atgaacaaca    132660
aaaccatttt gatcatttaa ttgatactga aaaagcattt gataaaattc aacattcctt    132720
cataataaaa attctcttct atactaggta caaaagaaac ttacctcaac ataataaagc    132780
catatatgac agtcccacag tatgatacta aatgaggaaa aactgagagc ctttcctcta    132840
cgatctggaa catgacaaag atgcccactt tcatcactgt tattcaacat agtactggaa    132900
gtcctagctg gagcgatcag acaagagaaa gatataaaag acatccaaat tggaaggaa     132960
taagtcaaat tatcctcatt tgcatatggt atgatcttct atttagagct aactaaagac    133020
tccaccaaaa aaagttatta gaactgacga acaaattcag taaagctgca ggatacaaaa    133080
tcaacataca aaaatcagta gcatttctat atgccaacaa tgaccaatgt gaaaagaaa     133140
ttaaaaagta accctatttta caataaccac aaataaacac ctaggaatta accaagagg    133200
taaaagattt ctgtaatgaa aactataaaa cactgatgaa agaaattgaa gagtacacca    133260
aaaaatggaa agcaattgca tgttcatgga ttagaagaat cagtgttgtt ataatgtcca    133320
tactatccaa agcaatctac agattcaatg caatccttat caaatacca atgacatcat     133380
tcacagaaat agaaaaaaaa aatcctaaaa tttacgtgga accacaaaga cccagaatag    133440
```

```
ccaaagctct cctaagcaaa aagaacgaaa ctgtaggaat gacattgcct gtcttcaaat  133500
tctactacag agctatagat agtaaccaaa acagcgtggt actggcataa aaacagacac  133560
agagacaaac agaacaaaat ttaaaaaccc agaaataaat ccacacacct acagcaaatt  133620
catttttgac aaagttgcca agaacatact ctggggaata gataatgata tctcttcaat  133680
aaatagtgtg gggaaaactg gatatccata tacataacag tgaaactaga cccctctctc  133740
tctcactata tacaaaaatc aaatcaaaat tgtttaagga cttaaatcta agacctcata  133800
ctatgaaacc actgcaagac aaccttggcg gaaactctcc aagacatcag tccaggcaaa  133860
gatttcttga gtaatatccc acaagcacag acaaccaaag caaaaatgga caaatgggat  133920
cacatcaagt taaaaagctt ctgcacagta agggaaacaa ccaacaaaat gaagagacaa  133980
cccacagaat gggagaaaat atttgaaaaa tacccatctg gcaagggatt aaaaaccaga  134040
atatatgcag aatatataag gagctcaaac agtgctatag aaaaaaaaat ctaataatct  134100
gatttaaaaa tgggaaaaat gttagaatag acatttctta aaataagaca tacagatggc  134160
aaaccgacat ggaacggtgc tcaacatcat ggattatcac agaaacacaa tcaatcaaaa  134220
ctaaaactaa aatgtgctat catctcaccc cagttaaaat ggctgatatc cagaagacag  134280
gcaataacaa atgctggcaa ggatgtgggg aaaagggagc ccccatacac tgttgctggg  134340
attgtaaatt agtacaacca ctgtggagag cagcatgaaa gttcctcaaa aaactgaaag  134400
aaagctacca taggatccag caatcccact gctgtgtata tactacaaaa gaaaggaagt  134460
cagtatatga agaggtatct gcactcccat gtttgttgca gccctgttca caacagccaa  134520
gatttggaag caacctaagt gtccatcagc agttgaatgt ataagaaaaa tgtggtgcat  134580
atacacaatg gagtattatt caataataaa aaggaatgag attgagtcat ttgcaacaac  134640
atggatggaa ctggagatca ttatgtgaag tgaaataagc caggcacaga aagacaaaca  134700
ttacaatgtt cttacttatt aatgagatct aaaaatcaaa acaattgcac ccatgttcat  134760
aaagagtaaa aggatggtta ccagatgctg agaacggtgg tggggggata gggaaaggtg  134820
gcagtggtta acgggtacaa aaaaatagaa agaatgaata agacttgcta cttgatagca  134880
cagcaaggtg gctatagtca gtaatttagt tgtatatttt taataatgaa aggtgtataa  134940
ttggattgtt tctaacacaa aggataatgc ttaagaggat ggataccccca ttttccatga  135000 tgtgattatt tcacattgca cgcctagatc aaaacatcca atgtaccccca taatatata  135060 catcttctat gtacccataa aaattctgta aaataaaata tataaaaaga ggtgacagat  135120
atggaagaca ggcaaagaag agacgacatc cacataatcc gagtacctaa gaaagaatgg  135180
agtccagtgc atctcaggag ccaccattct aagccaattt tctctggttc tctcagtcac  135240
cctaccaata cgtgggcaat cttgttttat ttcaggatag agttttttgaa attatagatt  135300 taagtatgct ttctgttcta ttacttttgg taattaattt tagaaagaac taatttgggc  135360
acaaatttga aaaaattcta aatccaaaaa aaaaagaaa aaacacaca cacaatcatc  135420 tataagggg atgatgacca gtcctagatt tctcaccagc cacattcaag atcagtaaat  135480
ggtaggacaa aacctgtagg gtccttaagg gggaaagaag tagtggatag tccagagtct  135540
atatacagcc aactgttctt gaagaaaaaa ggctgctgaa aaggagttcc aaacattcta  135600
taatccataa tctcatgatg aaactactag aggaagacca ccagccatca aaggtgcttt  135660
ggagaaccca gggccaagaa ccaaaagtaa atattaagtg tccttaactg cgagactaag  135720
atagaaatga ctgtggggga ccatgtggcc tcaacagagg tgaaatggtg tctgcctgac  135780
```

```
aaagtggaca ttttacaatg atcaaaacac agaatatgag atagagagca cttctgaatt   135840
actgcctcac tccaaataac tctcagccaa aggacttcag taaaaccaaa ttgggcatat   135900
tagacagtac aaacaaattc taagaaaata atattactga ttacaatcac atgatgctag   135960
agatggaggg gaaaaggaag aggaaaccag gtaatttcat actcgtatat agtaaagaac   136020
taaagtacat tgtccaaaga agaacaaaga atattttgga aagttataaa ggtagccact   136080
acacatagaa gatagcaaag aacaagaaaa cttaagatgg aaaactttt ggaagcataa    136140 gaatagaaaa tataaactac taagataaga ttgaagccaa acagatctat gaaaacaaca   136200
aacatcaatg gccttaactt gcctattaaa aggaagagac tttcaaattg gaccacaaga   136260
taaaacccaa ctctatatag catatgagta ttacacacaa aatgggaaaa gctgaaaaaa   136320
cttgggcaaa attcacccca agcaaattcc actgtttcct ttgggacaaa atgccaagct   136380
ccatgccagg gaagatgatt ctcctcagac cttctcctca ctctcccagt cctcttaggg   136440
aaggaattgg gtgttagagg agggagactc tgtcgattat cagctgaagc agtggtgtgc   136500
tcctgcgttg cttctgacct gggaaatgaa gcagcaagac tctttctgct gtgtctttgc   136560
ccagaagggc catcccccca gagcagagta cccaggccgg caggagcagt ggtggaagcg   136620
tggaaaccac gtctcctaca gcagagacca tcagaagcgg agcctcgggt ataagggaaa   136680
caacgcgttc tccctaacct gggagtgaca gacagcgtca ttcctcacag tgataccctg   136740
tgttctagcc atctggccca tgacagagcc agcccagagc cagcccagag ccagcccctc   136800
accatcctgg agcctggcca gctcgccaag ctgcaccata ggcctggaag gcgtggagac   136860
ctgcggcagt gccctgtcct cccgtgaggc ctgccatccc tgccaggggt cgcctctggc   136920
ttctccttct ccaggaccgc acggtccaga ggctcagtgc ctggagtagg tgttgcctcc   136980
ctgcttctag gcccagaccc tcccttgttc ctgaccccgg gcctttccct ctggcttgga   137040
catccagggc cctgtctcag ctggggagct gctcctgctc aaggactgtc ttccgcggga   137100
tcgaaaggcc gcgtcctgaa caatgcgtgg gccacgtaag cggagcaggc tctaaaggcc   137160
gcgtcctaaa cagtgcgtgg gccacgtgag cggagcaggc tctaaaggcc gcgtcctaaa   137220
cagtgcgtgg gccacgtgag cggagcaggc tctaaaggcc gcgtcctaaa cagtgcgtgg   137280
gccacgtgag cggagcaggc tctaaaggcc gcgtcctaaa cagtgcgtgg gccacgtgag   137340
cggagcaggc tctaaaggcc gcgtcctaaa cagtgcgtgg gccacgtgag cggagcaggc   137400
tctaaaggcc gcgtcctaaa cagtgcgtgg gccacgtgag cggagcaggc tctaaaggcc   137460
gcgtcctaaa cagtgcgtgg gccacgtgag cggagcaggc tctaaaggcc gcgtcctaaa   137520
cagtgcgtgg gccacgtgag cggagcaggc tctaaaggcc gcgtcctaaa cagtgcgtgg   137580
gccacgggag cggagcagac tctaaaggcc gcgtcctaaa cagtgtgtgg gccacgtgag   137640
cggagcgccc tctccactgc cctcggggcc gcagctccca gctcagctcc cagccctgct   137700
cagggcagcc aggccaggag gtaccatcca ggctaagtga ccctcagggg gacaggtgc    137760 cccaggagat gccagctgtt gggagaggct ggggaccaa ctcgacctgg cctgtgggcc    137820
ctgccctggc cacccattgt aggatccagc cgccacgcct gtgacactcg tgtgctttcc   137880
ctggtgtgtg cttgtggcag gtggggcag agggtcctca ggcagagag ccactccccc     137940 agcgccagac caccctcttc ctcactcccc cacctcaccc cctcacaggt gcctcccagg   138000
ccatcagggc ccaaccaccc ctaaacaaat gggttctcgg cccctcgtgg ctggaggtgg   138060
gttctctcac cattcccagc ctaagactcc atcccatgc tggcagctgt tcaaccatgt    138120
ctagagagat ccactgtccc agacagcacc tcagggtccc ccgtcctgcc tggaaccctg   138180
```

```
taggaaactc cacaaaccgc cgccattctg tccacacccc tacaggagcc ccaaccctct 138240
ccccacatcc aggcttccct cccagacccc tcatccctgc ccgcacggtg cctgagggg  138300 ccttcttggg cagcgcctaa gcaagccccc agcaccttc  ggccccttca aggcacacag 138360
gccccctttc cacccagcct caggaaacca cctgtgtcct ccaacgacag gtcccagcct 138420
cccagccttt gccttgcctg ttcctctccc tggaactctg ccccgacaca gaccctcccc 138480
agcaagcccg caggggcacc tcccctgccc ccagacaccc tgtgcccgtc agttcatccc 138540
cagcagaggc cctcaccagg cacaccccca tgctcacacc tggccccagg cctcagcctc 138600
cctgagggcc ccacccagcc cgcgtctggc cagtggtgcg tgcaaagccc ctcacccaga 138660
ctcggcggaa ggcagccagt gcaggcctgg ggagggctc  tccttagacc accttgcacc 138720
ttccctggca cccaccatgg gaagagctga gactcactga ggaccagctg aggctcagag 138780
aagggaccca gcactggtgg acacgcaggg agcccacgcc agggcgccgt ggtgagtgag 138840
gcccagtgcc acccactgag gcctcccgtt cagtgggacg acggtgaaca ggtggaacca 138900
accaggcaac ccccgccggg ccccacagac gggatcagag caggaaaggc ttcctgcccc 138960
tgcaggccag cgaggagccc tggcgggggc cgtggccctc caggcgagga ggctcccctg 139020
gccaccgcca cccgggccctc tctgctgctg ggaaaacaag tcagaaagca agtggatgag 139080
aggtggcgtg acagacccag cttcagatct gctctaattt acaaaagaaa aggaaaaaca 139140
cacttggcag ccttcagcac tctaatgatt cttaacagca gcaaattatt ggcacaagac 139200
tccagagtga ctgcagggt  tgagggctgg ggtctcccac gtgttttggg gctaacagcg 139260
gaagggagag cactggcaaa ggtgctgggg gccctggac  ccgacccgcc ctggagaccg 139320
cagccacatc agccccccagc cccacaggcc ccctaccagc cgcagggttt tggctgagct 139380
gagaaccact gtgctaactg gggacacagt gattggcagc tctacaaaaa ccatgctccc 139440
ccggaccccc gggctgtggg tttctgtagc ccctggctca gggctgactc accgtggctg 139500
aatacttcca gcactgggc  cagggcaccc tggtcaccgt ctcctcaggt gagtctgctg 139560
tctggggata gcggggagcc aggtgtactg ggccaggcaa gggctttggc ttcagacttg 139620
gggacaggtg ctcagcaaag gaggtcggca ggagggcgga gggtgtgttt ttgtatggga 139680
gaagcaggag ggcagaggct gtgctactgg tacttcgatc tctggggccg tggcaccctg 139740
gtcactgtct cctcaggtga gtcccactgc agccccctcc cagtcttctc tgtccaggca 139800
ccaggccagg tatctggggt ctgcagccgg cctgggtctg gcctgaggcc acaccagctg 139860
ccatccctgg ggtctccgcc atgggctgca tgccagagcc ctgctgtcac ttagccctgg 139920
ggccagctgg agcccccaag gacaggcagg gaccccgctg ggcttcagcc ccgtcaggga 139980
ccctccacag gtagcaagca ggccgagggc agggacggga aggagaagtt gtgggcagag 140040
cctgggctgg ggctgggcgc tggctgttca tgtgccgggg accaggcctg cgctttagtg 140100
tggctacaag tgcttggagc actggggcca gggcagcccg gccaccgtct ccctgggaac 140160
gtcacccctc cctgcctggg tctcagcccg ggggtctgtg tggctgggga cagggacgcc 140220
ggctgcctct gctctgtgct tgggccatgt gacccattcg agtgtcctgc acgggcacag 140280
gtttgtgtct gggcaggaac agggactgtg tccctgtgtg atgcttttga tatctggggc 140340
caagggacaa tggtcaccgt ctcttcaggt aagatggctt tccttctgcc tcctttctct 140400
gggcccagcg tcctctgtcc tggagctggg agataatgtc cggggctcc  ttggtctgcg 140460 ctgggccatg tggggccctc cggggctcct ttctccggctg tttgggacca cgttcagcag 140520
```

```
aaggcctttc tttgggaact gggactctgc tgctggggca aagggtgggc agagtcatgc   140580
ttgtgctggg gacaaaatga ccttgggaca cggggctggc tgccacggcc ggcccgggac   140640
agtcggagag tcaggttttt gtgcacccct taatgggcc tcccacaatg tgactacttt    140700
gactactggg gccagggaac cctggtcacc gtctcctcag gtgagtcctc acaacctctc   140760
tcctgcttta actctgaagg gttttgctgc attttttgggg ggaaataagg gtgctgggtc  140820
tcctgccaag agagcccgg agcagcctgg ggggctcagg aggatgccct gaggcaacag    140880
cggccacaca gacgagggc aagggctcca gatgctcctt cctcctgagc ccagcagcac    140940
gggtctctct gtggccaggg ccaccctagg cctctgggt ccaatgccca caaccccccg    141000
ggccctcccc gggctcagtc tgagagggtc ccagggacgt agcggggcgc cagttcttgc   141060
ctggggtcct ggcattgttg tcacaatgtg acaactggtt cgacccctgg ggccagggaa   141120
ccctggtcac cgtctcctca ggtgagtcct caccaccccc tctctgagtc cacttaggga   141180
gactcagctt gccagggtct cagggtcaga gtcttggagg cattttggag gtcaggaaag   141240
aaagccgggg agagggaccc ttcgaatggg aacccagcct gtcctcccca agtccggcca   141300
cagatgtcgg cagctggggg gctccttcgg ctggtctggg gtgacctctc tccgcttcac   141360
ctggagcatt ctcagggct gtcgtgatga ttgcgtggtg ggactctgtc ccgctccaag    141420
gcacccgctc tctgggacgg gtgcccccg gggttttgg actcctgggg gtgacttagc    141480
agccgtctgc ttgcagttgg acttcccagg ccgacagtgg tctggcttct gaggggtcag   141540
gccagaatgt ggggtacgtg ggaggccagc agagggttcc atgagaaggg caggacaggg   141600
ccacggacag tcagcttcca tgtgacgccc ggagacagaa ggtctctggg tggctgggtt   141660
tttgtggggt gaggatggac attctgccat tgtgattact actactacta cggtatggac   141720
gtctggggcc aagggaccac ggtcaccgtc tcctcaggta agaatggcca ctctagggcc   141780
tttgttttct gctactgcct gtggggtttc ctgagcattg caggttggtc ctcggggcat   141840
gttccgaggg gacctgggcg gactggccag gaggggacgg gcactggggt gccttgagga   141900
tctgggagcc tctgtggatt ttccgatgcc tttggaaaat gggactcagg ttgggtgcgt   141960
ctgatggagt aactgagcct ctagactgag cattgcagac taatcttgga tatttgtccc   142020
tgagggagcc ggctgagaga agttgggaaa taaactgtct agggatctca gagcctttag   142080
gacagattat ctccacatct ttgaaaaact aagaatctgt gtgatggtgt tggtggagtc   142140
cctggatgat gggataggga cttttggaggc tcatttgagg gagatgctaa acaatccta   142200 tggctggagg gatagttggg gctgtagttg gagattttca gttttttagaa taaaagtatt  142260 agctgcggaa tatacttcag gaccacctct gtgacagcat ttatacagta tccgatgcat  142320
agggacaaag agtggagtgg ggcactttct ttagatttgt gaggaatgtt ccacactaga   142380
ttgtttaaaa cttcatttgt tggaaggaga gctgtcttag tgattgagtc aagggagaaa   142440
ggcatctagc ctcggtctca aagggtagt tgctgtctag agaggtctgg tggagcctgc    142500
aaaagtccag ctttcaaagg aacacagaag tatgtgtatg gaatattaga agatgttgct   142560
tttactctta agttggttcc taggaaaaat agttaaatac tgtgacttta aatgtgaga    142620 gggttttcaa gtactcattt ttttaaatgt ccaaaattct tgtcaatcag tttgaggtct   142680
tgtttgtgta gaactgatat tacttaaagt ttaaccgagg aatgggagtg aggctctctc   142740
ataacctatt cagaactgac ttttaacaat aataaattaa gtttcaaata tttttaaatg   142800
aattgagcaa tgttgagttg gagtcaagat ggccgatcag aaccagaaca cctgcagcag   142860
ctggcaggaa gcaggtcatg tggcaaggct atttggggaa gggaaaataa aaccactagg   142920
```

```
taaacttgta gctgtggttt gaagaagtgg ttttgaaaca ctctgtccag ccccaccaaa   142980
ccgaaagtcc aggctgagca aaacaccacc tgggtaattt gcatttctaa aataagttga   143040
ggattcagcc gaaactggag aggtcctctt ttaacttatt gagttcaacc ttttaatttt   143100
agcttgagta gttctagttt ccccaaactt aagtttatcg acttctaaaa tgtatttaga   143160
attcattttc aaaattaggt tatgtaagaa attgaaggac tttagtgtct ttaatttcta   143220
atatatttag aaaacttctt aaaattactc tattattctt ccctctgatt attggtctcc   143280
attcaattct tttccaatac ccgaagcatt tacagtgact tgttcatga tcttttttag    143340 ttgtttgttt tgccttacta ttaagacttt gacattctgg tcaaaacggc ttcacaaatc   143400
tttttcaaga ccactttctg agtattcatt ttaggagaaa gactttttt ttaaatgaat    143460 gcaattatct agacttattt cagttgaaca tgctggttgg tggttgagag gacactcagt   143520
cagtcagtga cgtgaagggc ttctaagcca gtccacatgc tctgtgtgaa ctccctctgg   143580
ccctgcttat tgttgaatgg gccaaaggtc tgagaccagg ctgctgctgg gtaggcctgg   143640
actttgggtc tcccacccag acctgggaat gtatggttgt ggcttctgcc acccatccac   143700
ctggctgctc atggaccagc cagcctcggt ggctttgaag gaacaattcc acacaaagac   143760
tctggacctc tccgaaacca ggcaccgcaa atggtaagcc agaggcagcc acagctgtgg   143820
ctgctgctct taaagcttgt aaactgtttc tgcttaagag ggactgagtc ttcagtcatt   143880
gctttagggg gagaaagaga catttgtgtg tcttttgagt accgttgtct gggtcactca   143940
catttaactt tccttgaaaa actagtaaaa gaaaaatgtt gcctgttaac caataatcat   144000
agagctcatg gtactttgag gaaatcttag aaagcgtgta tacaattgtc tggaattatt   144060
tcagttaagt gtattagttg aggtactgat gctgtctcta cttcagttat acatgtgggt   144120
ttgaattttg aatctattct ggctcttctt aagcagaaaa tttagataaa atggatacct   144180
cagtggtttt taatggtggg tttaatatag aaggaattta aattggaagc taatttagaa   144240
tcagtaagga gggacccagg ctaagaaggc aatcctggga ttctggaaga aaagatgttt   144300 ttagtttttta tagaaaacac tactacattc ttgatctaca actcaatgtg gtttaatgaa   144360
tttgaagttg ccagtaaatg tacttcctgg ttgttaaaga atggtatcaa aggacagtgc   144420
ttagatccga ggtgagtgtg agaggacagg ggctggggta tggatacgca gaaggaaggc   144480
cacagctgta cagaattgag aaagaataga gacctgcagt tgaggccagc aggtcggctg   144540
gactaactct ccagccacag taatgaccca gacagagaaa gccagactca taaagcttgc   144600
tgagcaaaat taagggaaca aggttgagag ccctagtaag cgaggctcta aaaagcacag   144660
ctgagctgag atgggtgggc ttctctgagt gcttctaaaa tgcgctaaac tgaggtgatt   144720
actctgaggt aagcaaagct gggcttgagc caaaatgaag tagactgtaa tgaactggaa   144780
tgagctgggc cgctaagcta aactaggctg gcttaaccga gatgagccaa actggaatga   144840
acttcattaa tctaggttga atagagctaa actctactgc ctacactgga ctgttctgag   144900
ctgagatgag ctggggtgag ctcagctatg ctacgctgtg ttggggtgag ctgatctgaa   144960
atgagatact ctggagtagc tgagatgggg tgagatgggg tgagctgagc tgggctgagc   145020
tagactgagc tgagctaggg tgagctgagc tgggtgagct gagctaagct ggggtgagct   145080
gagctgagct tggctgagct agggtgagct gggctgagct ggggtgagct gagctgagct   145140
ggggtaagct gggatgagct ggggtgagct gagctgagct ggagtgagct gagctgggct   145200
gagctggggt gagctgggct gagctgggct gagctgggct gagctggggt gagctgagct   145260
```

```
ggggtgagct gagctgagct ggggtgagct gagctgagct ggggtgagct ggggtgagct   145320
gagctggggt gagctgagct gagctggggt gagctgagct ggggtgagct gagctgagct   145380
ggggtgagct gagctgagct gagctgagct gagctggggt gagctgagct gagctgagct   145440
ggggtgagct ggggtgagct gagctgagct ggagtgagct gagctgggct gagctggggt   145500
gagctgggct gagctggggt gagctgagct gagctgagct gagctggggt gagctgagct   145560
gagctggggt gagctgagct ggggtgagct gggctgagct gagctgagct gagctgagct   145620
gagctgagct gagctgagct gagctgagct gagctgagct gagctgagct gagctgagct   145680
ggggtgagct gagctgagct gggctgagct ggggtgagct gggctgagct gggctgagct   145740
gggctgagct ggggtgagct gagctggggt gagctgagct gagctgggct gagctgagct   145800
gagctggggt gagctgagct gagctggggt gagctgagct gagctgagct ggggtgagct   145860
gagctgagct gggctgagca gggctgagct ggggtgagct gagctgagct ggggtgagct   145920
gggctgagct gggctgagct gagctgagct gggctgagct gggctgagct gggctgagct   145980
gggctgagct gggctgagct ggggtgagct gagctggggt gagctggggt gagctgagct   146040
ggggtgagct gagctggggt gagctgagct gagctggggt gagctgagct ggggtgagct   146100
gagctgagct ggggtgagct gagctgagct ggggtgagct gagctagggt gaactgggct   146160
gggtgagctg gagtgagctg agctgaggtg aactggggtg agccgggatg ttttgagttg   146220
agctggggta agatgagctg aactggggta aactgggatg agctgtggtg agcggagctg   146280
gattgaactg agctgtgtga gctgagctgg ggtcagctga gcaagagtga gtagagctgg   146340
ctggccagaa ccagaatcaa ttaggctaag tgagccagat tgtgctggga tcagctgtac   146400
tcagatgagc tgggatgagg taggctggga tgagctgggc tagctgacat ggattatgtg   146460
aggctgagct agcatgggct ggcctagctg atgagctaag cttgaatgag cggggctgag   146520
ctggactcag atgtgctaga ctgagctgta ctggatgatc tggtgtaggg tgatctggac   146580
tcaactgggc tggctgatgg gatgcgccag gttgaactag gctcagataa gttaggctga   146640
gtagggcctg gttgagatgg ttcgggatga gctgggaaaa gatggactcg gaccatgaac   146700
tgggctgagc tgggttggga gaccatgaat tgagctgaac tgagtgcagc tgggataaac   146760
tgggttgagc taagaataga ctacctgaat tgtgccaaac tcggctggga tcaattggaa   146820
attatcagga tttagatgag ccggactaaa ctatgctgag ctggactggt tggatgtgtt   146880
gaactggcct gctgctgggc tggcatagct gagttgaact aaatgagga aggctgagca   146940
aggctagcct gcttgcatag agctgaactt tagcctagcc tgagctggac cagcctgagc   147000
tgagtaggtc taaactgagt taaaaatcaa cagggataat ttaacagcta atttaacaag   147060
cctgaggtct gagattgaat gagcagagct gggatgaact gaatgagttt caccaggcct   147120
ggaccagtta ggctaggacc tcgttctata gaggcagact gtgtgctaca gtggagtttc   147180
aagatgattc catgagtcct ccccgccccc aacataaccc accttcctcc taccctacac   147240
gcctgtctgg tgtgtaaatc ccagctttgt gtgctgatac agaagcctga gcccctcccc   147300
cacctccacc tacctattac tttgggatga gaatagttct cccagccagt gtctcagagg   147360
gaagccaagc aggacaggcc caaggctact tgagaagcca ggatctaggc ctctccctga   147420
gaacgggtgt tcatgcccct agagttggct gaagggccag atccacctac tctagaggca   147480
tctctccctg tctgtgaagg cttccaaagt cacgttcctg tggctagaag gcagctccat   147540
agccctgcta cagtttcgtc ctgtatacca ggttcaccta ctaccatatc tagccctgcc   147600
tgccttaaga gtagcaacaa ggaaatagca gggtgtagag ggatctcctg tctgacagga   147660
```

```
ggcaagaaga cagattctta cccctccatt tctcttttat ccctctctgg tcctcagaga 147720
gtcagtcctt cccaaatgtc ttcccccctcg tctcctgcga gagcccctg tctgataaga 147780
atctggtggc catgggctgc ctggcccggg acttcctgcc cagcaccatt tccttcacct 147840
ggaactacca gaacaacact gaagtcatcc agggtatcag aaccttccca acactgagga 147900
caggggcaa gtacctagcc acctcgcagg tgttgctgtc tcccaagagc atccttgaag 147960
gttcagatga atacctggta tgcaaaatcc actacggagg caaaaacaaa gatctgcatg 148020
tgcccattcc aggtaagaac caaaccctcc cagcagggt gcccaggccc aggcatggcc 148080
cagagggagc agcggggtgg ggcttaggcc aagctgagct cacaccttga cctttcattc 148140
cagctgtcgc agagatgaac cccaatgtaa atgtgttcgt cccaccacgg gatggcttct 148200
ctggccctgc accacgcaag tctaaactca tctgcgaggc cacgaacttc actccaaaac 148260
cgatcacagt atcctggcta aaggatggga agctcgtgga atctggcttc accacagatc 148320
cggtgaccat cgagaacaaa ggatccacac cccaaaccta caaggtcata agcacactta 148380
ccatctctga aatcgactgg ctgaaccctga atgtgtacac ctgccgtgtg atcacaggg 148440
gtctcaccttt cttgaagaac gtgtcctcca catgtgctgc cagtgagtgg cctgggctaa 148500
gcccaatgcc tagccctccc agattaggga agtcctccta caattatggc caatgccacc 148560
cagacatggt catttgctcc ttgaactttg gctccccaga gtggcaagg acaagaatga 148620
gcaataggca gtagaggggt gagaatcagc tggaaggacc agcatcttcc cttaagtagg 148680
tttgggggat ggagactaag ctttttttcca acttcacaac tagatatgtc ataacctgac 148740
acagtgttct cttgactgca ggtccctcca cagacatcct aaccttcacc atccccccct 148800
cctttgccga catcttcctc agcaagtccg ctaacctgac ctgtctggtc tcaaacctgg 148860
caacctatga aaccctgaat atctcctggg cttctcaaag tggtgaacca ctggaaacca 148920
aaattaaaat catggaaagc cctcccaatg gcaccttcag tgctaagggt gtggctagtg 148980
tttgtgtgga agactggaat aacaggaagg aatttgtgcg tactgtgact cacagggatc 149040
tgccttcacc acagaagaaa ttcatctcaa aacccaatgg taggtatccc cccttccctt 149100
cccctccaat tgcaggaccc ttcctgtacc tcatagggag ggcaggtcct cttccaccct 149160
atcctcacta ctgtcttcat ttacagaggt gcacaaacat ccacctgctg tgtacctgct 149220
gccaccagct cgtgagcaac tgaacctgag ggagtcagcc acagtcacct gcctggtgaa 149280
gggcttctct cctgcagaca tcagtgtgca gtggcttcag agagggcaac tcttgcccca 149340
agagaagtat gtgaccagtg ccccgatgcc agagcctggg gccccaggct tctactttac 149400
ccacagcatc ctgactgtga cagaggagga atggaactcc ggagagacct atacctgtgt 149460
tgtaggccac gaggccctgc cacacctggt gaccgagagg accgtggaca agtccactgg 149520
taaacccaca ctgtacaatg tctccctgat catgtctgac acaggcggca cctgctattg 149580
accatgctag cgctcaacca ggcaggccct gggtgtccag ttgctctgtg tatgcaaact 149640
aaccatgtca gagtgagatg ttgcatttta taaaaattag aaataaaaaa aatccattca 149700
aacgtcactg gttttgatta tacaatgctc atgcctgctg agacagttgt gttttgcttg 149760
ctctgcacac accctgcata cttgcctcca ccctggccct tcctctacct tgccagtttc 149820
ctccttgtgt gtgaactcag tcaggcttac aacagacaga gtatgaacat gcgattcctc 149880
cagctacttc tagatatatg gctgaaagct tgcatgcctg caggtcgact ctagaggatc 149940
cccgggtacc gagctcgaat tcgccctata gtgagtcgta ttacaattca ctggccgtcg 150000
```

-continued

```
ttttacaacg tcgtgactgg gaaaaccctg gcgttaccca acttaatcgc cttgcagcac   150060
atcccccttt cgccagctgg cgtaatagcg aagaggcccg caccgatcgc ccttcccaac   150120
agttgcgcag cctgaatggc gaatggcgcc tgatgcggta ttttctcctt acgcatctgt   150180
gcggtatttc acaccgcata tggtgcactc tcagtacaat ctgctctgat gccgcatagt   150240
taagccagcc ccgacacccg ccaacacccg ctgacgcgaa ccccttgc               150288
```

<210> SEQ ID NO 71
<211> LENGTH: 23
<212> TYPE: DNA
<213> ORGANISM: Artificial Sequence
<220> FEATURE:
<223> OTHER INFORMATION: synthetic

<400> SEQUENCE: 71
ggaaggtgtg cacaccgctg gac                                          23

<210> SEQ ID NO 72
<211> LENGTH: 23
<212> TYPE: DNA
<213> ORGANISM: Artificial Sequence
<220> FEATURE:
<223> OTHER INFORMATION: synthetic

<400> SEQUENCE: 72
ggaaggtgtg cacaccactg gac                                          23

<210> SEQ ID NO 73
<211> LENGTH: 23
<212> TYPE: DNA
<213> ORGANISM: Artificial Sequence
<220> FEATURE:
<223> OTHER INFORMATION: synthetic

<400> SEQUENCE: 73
ggaaggtgtg cacactgctg gac                                          23

<210> SEQ ID NO 74
<211> LENGTH: 23
<212> TYPE: DNA
<213> ORGANISM: Artificial Sequence
<220> FEATURE:
<223> OTHER INFORMATION: synthetic

<400> SEQUENCE: 74
agactgtgcg cacaccgctg gac                                          23

<210> SEQ ID NO 75
<211> LENGTH: 22
<212> TYPE: DNA
<213> ORGANISM: Artificial Sequence
<220> FEATURE:
<223> OTHER INFORMATION: synthetic

<400> SEQUENCE: 75
tcttatcaga caggggctc tc                                            22

<210> SEQ ID NO 76
<211> LENGTH: 22
<212> TYPE: DNA
<213> ORGANISM: Artificial Sequence
<220> FEATURE:
<223> OTHER INFORMATION: synthetic

<400> SEQUENCE: 76

-continued aagaagcaca cgactgaggc ac        22

<210> SEQ ID NO 77
<211> LENGTH: 22
<212> TYPE: DNA
<213> ORGANISM: Artificial Sequence
<220> FEATURE:
<221> NAME/KEY: variation
<222> LOCATION: (12)...(12)
<223> OTHER INFORMATION: w = a or t
<220> FEATURE:
<223> OTHER INFORMATION: synthetic

<400> SEQUENCE: 77
agtggataga cwgatggggg tg        22

<210> SEQ ID NO 78
<211> LENGTH: 22
<212> TYPE: DNA
<213> ORGANISM: Artificial Sequence
<220> FEATURE:
<223> OTHER INFORMATION: synthetic

<400> SEQUENCE: 78
agtggataga ccgatggggc tg        22

<210> SEQ ID NO 79
<211> LENGTH: 22
<212> TYPE: DNA
<213> ORGANISM: Artificial Sequence
<220> FEATURE:
<223> OTHER INFORMATION: synthetic

<400> SEQUENCE: 79
aagggataga cagatggggc tg        22

<210> SEQ ID NO 80
<211> LENGTH: 22
<212> TYPE: DNA
<213> ORGANISM: Artificial Sequence
<220> FEATURE:
<223> OTHER INFORMATION: synthetic

<400> SEQUENCE: 80
ggaagacatt tgggaaggac tg        22

<210> SEQ ID NO 81
<211> LENGTH: 22
<212> TYPE: DNA
<213> ORGANISM: Artificial Sequence
<220> FEATURE:
<223> OTHER INFORMATION: synthetic

<400> SEQUENCE: 81
ggaagatgga tacagttggt gc        22